(12) United States Patent
Jain et al.

(10) Patent No.: US 12,217,036 B2
(45) Date of Patent: *Feb. 4, 2025

(54) AUTOMATING INTERACTIONS FOR HEALTH DATA COLLECTION AND PATIENT ENGAGEMENT

(71) Applicant: VigNet Incorporated, Fairfax, VA (US)

(72) Inventors: Praduman Jain, Fairfax, VA (US); Dave Klein, Oakton, VA (US); Neeta Jain, Fairfax, VA (US); Yue Cao, Vienna, VA (US)

(73) Assignee: VigNet Incorporated, Fairfax, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/947,064

(22) Filed: Sep. 16, 2022

(65) Prior Publication Data
US 2023/0017196 A1    Jan. 19, 2023

Related U.S. Application Data

(60) Continuation-in-part of application No. 17/036,426, filed on Sep. 29, 2020, now Pat. No. 11,467,813,
(Continued)

(51) Int. Cl.
*G06F 8/61* (2018.01)
*G06F 3/04817* (2022.01)
(Continued)

(52) U.S. Cl.
CPC ............ *G06F 8/60* (2013.01); *G06F 3/04817* (2013.01); *G06F 3/04842* (2013.01); *G06F 8/61* (2013.01);
(Continued)

(58) Field of Classification Search
None
See application file for complete search history.

(56) References Cited

U.S. PATENT DOCUMENTS

| 5,545,186 A | 8/1996 | Olson et al. |
| 5,547,878 A | 8/1996 | Kell |

(Continued)

FOREIGN PATENT DOCUMENTS

| AU | 2014213012 | 1/2014 |
| CN | 106384321 | 2/2017 |

(Continued)

OTHER PUBLICATIONS

US 11,270,599 B1, 03/2022, Jain et al. (withdrawn)
(Continued)

*Primary Examiner* — Marina Lee
(74) *Attorney, Agent, or Firm* — Fish & Richardson P.C.

(57) ABSTRACT

In some implementations, a system enables an administrator to customize a set of rules to dynamically adjust the configuration and output of an application provided to users. A configuration interface for setting rules that dynamically adjust output of an application is provided. Data indicating one or more rules are received through the configuration interface. Activity data indicating user interaction with the application or sensor data for at least some of a plurality of users of the application are then received from multiple client devices. A determination relating to the activity data satisfying at least one condition or trigger is then made. Instructions to adjust output of the application according to one or more system actions of the one or more rules are then communicated to client devices associated with the users in the first subset of the plurality of users.

20 Claims, 43 Drawing Sheets

Related U.S. Application Data which is a continuation of application No. 16/847,428, filed on Apr. 13, 2020, now Pat. No. 11,314,492, which is a continuation of application No. 15/858,165, filed on Dec. 29, 2017, now Pat. No. 10,705,816, which is a division of application No. 15/040,635, filed on Feb. 10, 2016, now Pat. No. 9,858,063, application No. 17/947,064, filed on Sep. 16, 2022 is a continuation-in-part of application No. 17/037,898, filed on Sep. 30, 2020, now Pat. No. 11,487,531, which is a continuation of application No. 16/702,631, filed on Dec. 4, 2019, now Pat. No. 11,321,082, which is a continuation of application No. 15/841,540, filed on Dec. 14, 2017, now Pat. No. 10,587,729, which is a continuation of application No. 15/337,222, filed on Oct. 28, 2016, now Pat. No. 9,848,061, application No. 17/947,064, filed on Sep. 16, 2022 is a continuation-in-part of application No. 17/092,842, filed on Nov. 9, 2020, now Pat. No. 11,595,498, which is a continuation of application No. 16/120,083, filed on Aug. 31, 2018, now Pat. No. 11,159,643, which is a continuation of application No. 15/382,126, filed on Dec. 16, 2016, now Pat. No. 10,069,934, application No. 17/947,064, filed on Sep. 16, 2022 is a continuation-in-part of application No. 17/076,056, filed on Oct. 21, 2020, now Pat. No. 11,675,971, which is a continuation of application No. 16/808,448, filed on Mar. 4, 2020, now Pat. No. 11,244,104, which is a continuation of application No. 15/935,276, filed on Mar. 26, 2018, now Pat. No. 10,621,280, which is a division of application No. 15/279,845, filed on Sep. 29, 2016, now Pat. No. 9,928,230, application No. 17/947,064, filed on Sep. 16, 2022 is a continuation-in-part of application No. 17/082,428, filed on Oct. 28, 2020, now Pat. No. 11,450,223, which is a continuation of application No. 16/783,273, filed on Feb. 6, 2020, now Pat. No. 11,127,308, which is a continuation of application No. 15/694,372, filed on Sep. 1, 2017, now Pat. No. 10,565,892, which is a continuation of application No. 15/152,411, filed on May 11, 2016, now Pat. No. 9,753,618.

(51) Int. Cl.

| | | |
|---|---|---|
| *G06F 3/04842* | (2022.01) | |
| *G06F 8/60* | (2018.01) | |
| *G16H 40/63* | (2018.01) | |
| *G16H 40/67* | (2018.01) | |
| *H04L 67/00* | (2022.01) | |
| *H04L 67/01* | (2022.01) | |
| *H04L 67/025* | (2022.01) | |
| *H04L 67/06* | (2022.01) | |
| *H04L 67/125* | (2022.01) | |
| *H04L 67/53* | (2022.01) | |
| *G06F 8/38* | (2018.01) | |
| *G16H 10/20* | (2018.01) | |
| *G16H 10/60* | (2018.01) | |
| *G16H 40/40* | (2018.01) | |
| *H04L 41/0803* | (2022.01) | |

(52) U.S. Cl.
CPC .......... *G16H 40/63* (2018.01); *G16H 40/67* (2018.01); *H04L 67/01* (2022.05); *H04L 67/025* (2013.01); *H04L 67/06* (2013.01); *H04L 67/125* (2013.01); *H04L 67/34* (2013.01); *H04L 67/53* (2022.05); *G06F 8/38* (2013.01); *G16H 10/20* (2018.01); *G16H 10/60* (2018.01); *G16H 40/40* (2018.01); *H04L 41/0803* (2013.01)

(56) References Cited

U.S. PATENT DOCUMENTS

| | | |
|---|---|---|
| 6,019,777 A | 2/2000 | Mackenzie |
| 6,029,144 A | 2/2000 | Barrett et al. |
| 6,029,195 A | 2/2000 | Herz |
| 6,039,688 A | 3/2000 | Douglas et al. |
| 6,260,022 B1 | 7/2001 | Brown |
| 6,269,339 B1 | 7/2001 | Silver |
| 6,321,172 B1 | 11/2001 | Jakob et al. |
| 6,514,200 B1 | 2/2003 | Khouri |
| 6,663,846 B1 | 12/2003 | McCombs et al. |
| 6,828,992 B1 | 12/2004 | Freeman |
| 6,879,970 B2 | 4/2005 | Shiffman et al. |
| 6,904,408 B1 | 6/2005 | McCarthy |
| 6,907,375 B2 | 6/2005 | Guggari |
| 7,054,782 B2 | 5/2006 | Hartlaub |
| 7,076,534 B1 | 7/2006 | Cleron et al. |
| 7,086,007 B1 | 8/2006 | Bushey |
| 7,251,609 B1 | 7/2007 | McAlindon et al. |
| 7,330,717 B2 | 2/2008 | Gidron et al. |
| 7,415,447 B2 | 8/2008 | Shiffman et al. |
| 7,447,643 B1 | 11/2008 | Olson et al. |
| 7,752,059 B2 | 7/2010 | Sweeney et al. |
| 7,761,800 B2 | 7/2010 | Chaudhri et al. |
| 7,809,802 B2 | 10/2010 | Lerman et al. |
| 7,827,478 B2 | 11/2010 | Farr et al. |
| 7,827,495 B2 | 11/2010 | Bells et al. |
| 7,853,455 B2 | 12/2010 | Brown |
| 7,935,613 B2 | 5/2011 | Gizewski |
| 7,953,613 B2 | 5/2011 | Gizewski |
| 8,056,100 B2 | 11/2011 | Herz et al. |
| 8,060,553 B2 | 11/2011 | Mamou |
| 8,065,180 B2 | 11/2011 | Hufford et al. |
| 8,078,596 B2 | 12/2011 | McAllister et al. |
| 8,078,956 B1 | 12/2011 | Feldman |
| 8,180,688 B1 | 5/2012 | Velummylum et al. |
| 8,224,959 B2 | 7/2012 | Kirwan et al. |
| 8,239,918 B1 | 8/2012 | Cohen |
| 8,302,020 B2 | 10/2012 | Louch et al. |
| 8,347,263 B1 | 1/2013 | Offer |
| 8,380,531 B2 | 2/2013 | Paty et al. |
| 8,433,605 B2 | 4/2013 | Hufford et al. |
| 8,533,029 B2 | 9/2013 | Hufford et al. |
| 8,566,175 B1 | 10/2013 | Nguyen et al. |
| 8,584,082 B2 | 11/2013 | Baird et al. |
| 8,667,487 B1 | 3/2014 | Boodman et al. |
| 8,775,415 B2 | 7/2014 | Jeon et al. |
| 8,799,666 B2 | 8/2014 | Kesanupalli et al. |
| 8,805,759 B1 | 8/2014 | Cha et al. |
| 8,849,610 B2 | 9/2014 | Molettiere |
| 8,850,304 B2 | 9/2014 | Ye et al. |
| 8,978,106 B2 | 3/2015 | Swamy et al. |
| 8,990,250 B1 | 3/2015 | Chowdry et al. |
| 8,997,038 B2 | 3/2015 | Becker |
| 9,134,964 B2 | 9/2015 | Hirsch |
| 9,135,445 B2 | 9/2015 | Kay et al. |
| 9,170,800 B2 | 10/2015 | Lang |
| 9,183,365 B2 | 11/2015 | Taveau et al. |
| 9,203,911 B2 | 12/2015 | Krishnaswamy et al. |
| 9,256,698 B2 | 2/2016 | Vincent, III |
| 9,361,011 B1 | 6/2016 | Burns |
| 9,426,433 B1 | 8/2016 | Mazzarella |
| 9,461,972 B1 | 10/2016 | Mehta |
| 9,542,649 B2 | 1/2017 | Su |
| 9,715,370 B2 | 7/2017 | Friedman |
| 9,753,618 B1 | 9/2017 | Jain et al. |
| 9,753,988 B2 | 9/2017 | McGilliard |
| 9,760,343 B2 | 9/2017 | Noens et al. |
| 9,824,606 B2 | 11/2017 | Basson et al. |
| 9,844,725 B1 | 12/2017 | Durkin |
| 9,848,061 B1 | 12/2017 | Jain et al. |
| 9,858,063 B2 | 1/2018 | Jain et al. |

(56) References Cited

U.S. PATENT DOCUMENTS

| | | |
|---|---|---|
| 9,918,664 B2 | 3/2018 | Blahnik et al. |
| 9,928,230 B1 | 3/2018 | Jain et al. |
| 9,940,454 B2 | 4/2018 | Richardson et al. |
| 9,942,358 B2 | 4/2018 | Babu et al. |
| 9,983,775 B2 | 5/2018 | Jain et al. |
| 10,002,199 B2 | 6/2018 | Matamala et al. |
| 10,007,501 B1 | 6/2018 | Zhang et al. |
| 10,055,745 B2 | 8/2018 | Carlson et al. |
| 10,063,996 B2 | 8/2018 | Clark et al. |
| 10,068,270 B1 | 9/2018 | Kay et al. |
| 10,068,422 B2 | 9/2018 | Gadher et al. |
| 10,069,934 B2 | 9/2018 | Jain et al. |
| 10,095,688 B1 | 10/2018 | Jain et al. |
| 10,152,761 B2 | 12/2018 | Kress et al. |
| 10,202,769 B2 | 2/2019 | Gya |
| 10,205,769 B2 | 2/2019 | Sehgal |
| 10,241,772 B1 | 3/2019 | Ning et al. |
| 10,248,401 B1 | 4/2019 | Chen et al. |
| 10,304,000 B2 | 5/2019 | Birnbaum et al. |
| 10,311,478 B2 | 6/2019 | Dai et al. |
| 10,346,900 B1 | 7/2019 | Wilson |
| 10,482,135 B2 | 11/2019 | Rychikhin |
| 10,521,557 B2 | 12/2019 | Jain et al. |
| 10,565,892 B1 | 2/2020 | Jain et al. |
| 10,565,894 B1 | 2/2020 | Jain et al. |
| 10,587,729 B1 * | 3/2020 | Jain .................. G06F 3/0481 |
| 10,621,280 B2 | 4/2020 | Jain et al. |
| 10,705,816 B2 | 7/2020 | Jain et al. |
| 10,733,116 B2 | 8/2020 | Litichever et al. |
| 10,733,266 B2 | 8/2020 | Whitehurst |
| 10,756,957 B2 | 8/2020 | Jain et al. |
| 10,762,990 B1 | 9/2020 | Jain et al. |
| 10,775,974 B2 | 9/2020 | Schilling et al. |
| 10,776,739 B2 | 9/2020 | Blahnik |
| 10,796,549 B2 | 10/2020 | Roberts et al. |
| 10,915,306 B2 | 2/2021 | Jain |
| 10,938,651 B2 | 3/2021 | Jain et al. |
| 11,056,242 B1 | 7/2021 | Jain et al. |
| 11,061,798 B1 | 7/2021 | Jain et al. |
| 11,062,083 B1 | 7/2021 | Hitchcock et al. |
| 11,082,487 B1 | 8/2021 | Jain et al. |
| 11,102,304 B1 | 8/2021 | Jain et al. |
| 11,127,308 B2 | 9/2021 | Jain et al. |
| 11,159,643 B2 | 10/2021 | Jain |
| 11,244,104 B1 | 2/2022 | Jain et al. |
| 11,314,492 B2 | 4/2022 | Jain et al. |
| 11,321,062 B2 | 5/2022 | Jain et al. |
| 11,321,082 B2 | 5/2022 | Jain et al. |
| 11,340,878 B2 | 5/2022 | Jain et al. |
| 11,409,417 B1 | 8/2022 | Schilling et al. |
| 11,450,223 B1 | 9/2022 | Jain et al. |
| 11,450,224 B1 | 9/2022 | Jain et al. |
| 11,467,813 B2 | 10/2022 | Jain et al. |
| 11,474,800 B2 | 10/2022 | Jain et al. |
| 11,487,531 B2 | 11/2022 | Jain et al. |
| 11,501,060 B1 | 11/2022 | Jain et al. |
| 11,507,737 B1 | 11/2022 | Jain et al. |
| 11,520,466 B1 | 12/2022 | Schilling et al. |
| 11,595,498 B2 | 2/2023 | Jain et al. |
| 11,664,099 B1 | 5/2023 | Jain et al. |
| 11,675,971 B1 | 7/2023 | Jain et al. |
| 11,954,470 B2 | 4/2024 | Jain et al. |
| 2001/0019338 A1 | 9/2001 | Roth |
| 2002/0022973 A1 | 2/2002 | Sun |
| 2002/0035486 A1 | 3/2002 | Huyn |
| 2002/0099570 A1 | 7/2002 | Knight |
| 2002/0143595 A1 | 10/2002 | Frank et al. |
| 2002/0157091 A1 | 10/2002 | DeMello et al. |
| 2003/0065669 A1 | 4/2003 | Kahn et al. |
| 2003/0078960 A1 | 4/2003 | Murren et al. |
| 2003/0130871 A1 | 7/2003 | Rao et al. |
| 2003/0229522 A1 | 12/2003 | Thompson et al. |
| 2004/0073868 A1 | 4/2004 | Easter et al. |
| 2004/0122715 A1 | 6/2004 | McAuliffe |
| 2004/0172447 A1 | 9/2004 | Miller |
| 2004/0203755 A1 | 10/2004 | Brunet et al. |
| 2004/0210457 A1 | 10/2004 | Sameh |
| 2004/0216054 A1 | 10/2004 | Matthews |
| 2005/0050320 A1 | 3/2005 | Wassmann et al. |
| 2005/0055687 A1 | 3/2005 | Mayer |
| 2005/0071752 A1 | 3/2005 | Marlatt |
| 2005/0086587 A1 | 4/2005 | Balz |
| 2005/0144072 A1 | 6/2005 | Perkowski et al. |
| 2005/0165626 A1 | 7/2005 | Karpf |
| 2005/0186550 A1 | 8/2005 | Gillani |
| 2005/0246304 A1 | 11/2005 | Knight et al. |
| 2006/0004603 A1 | 1/2006 | Peterka et al. |
| 2006/0004680 A1 * | 1/2006 | Robarts .................. G06F 16/40 |
| | | 706/46 |
| 2006/0041452 A1 | 2/2006 | Kukarni |
| 2006/0107219 A1 | 5/2006 | Ahya |
| 2006/0184493 A1 | 8/2006 | Shiffman et al. |
| 2006/0205564 A1 | 9/2006 | Peterson |
| 2006/0206861 A1 | 9/2006 | Shenfield |
| 2006/0282516 A1 | 12/2006 | Taylor |
| 2007/0021984 A1 | 1/2007 | Brown |
| 2007/0033273 A1 | 2/2007 | White |
| 2007/0072156 A1 | 3/2007 | Kaufman et al. |
| 2007/0136093 A1 | 6/2007 | Rankin et al. |
| 2007/0179361 A1 | 8/2007 | Brown et al. |
| 2007/0250429 A1 | 10/2007 | Walser et al. |
| 2007/0281285 A1 | 12/2007 | Jayaweera |
| 2008/0005679 A1 | 1/2008 | Rimas-Ribikauskas |
| 2008/0010254 A1 | 1/2008 | Settimi |
| 2008/0021287 A1 | 1/2008 | Woellenstein et al. |
| 2008/0034314 A1 | 2/2008 | Louch et al. |
| 2008/0077865 A1 | 3/2008 | Hiles et al. |
| 2008/0126110 A1 | 5/2008 | Haeberle |
| 2008/0127040 A1 | 5/2008 | Barcellona |
| 2008/0140444 A1 | 6/2008 | Karkanias |
| 2008/0177638 A1 | 7/2008 | Butler |
| 2008/0201174 A1 | 8/2008 | Ramasubramanian |
| 2008/0242221 A1 | 10/2008 | Shapiro et al. |
| 2008/0243038 A1 | 10/2008 | Bennett |
| 2008/0254429 A1 | 10/2008 | Woolf et al. |
| 2008/0261191 A1 | 10/2008 | Woolf et al. |
| 2008/0301118 A1 | 12/2008 | Chien |
| 2008/0311968 A1 | 12/2008 | Hunter |
| 2009/0023555 A1 | 1/2009 | Raymond |
| 2009/0024944 A1 | 1/2009 | Louch |
| 2009/0035733 A1 | 2/2009 | Meiter |
| 2009/0043689 A1 | 2/2009 | Yang |
| 2009/0049389 A1 * | 2/2009 | Kuzmanovic ........... G06F 9/451 |
| | | 715/745 |
| 2009/0076856 A1 | 3/2009 | Darby et al. |
| 2009/0094052 A1 | 4/2009 | James et al. |
| 2009/0119678 A1 | 5/2009 | Shih |
| 2009/0150814 A1 | 6/2009 | Eyer |
| 2009/0156190 A1 | 6/2009 | Fisher |
| 2009/0163182 A1 | 6/2009 | Gatti |
| 2009/0164474 A1 | 6/2009 | Noumeir |
| 2009/0172002 A1 | 7/2009 | Bathiche |
| 2009/0248883 A1 | 10/2009 | Suryanarayana et al. |
| 2009/0249359 A1 | 10/2009 | Caunter et al. |
| 2009/0276771 A1 | 11/2009 | Nickolov et al. |
| 2010/0036681 A1 | 2/2010 | Naik et al. |
| 2010/0041378 A1 | 2/2010 | Aceves |
| 2010/0082367 A1 | 4/2010 | Hains et al. |
| 2010/0088245 A1 | 4/2010 | Harrison et al. |
| 2010/0122286 A1 | 5/2010 | Begeja |
| 2010/0131482 A1 | 5/2010 | Linthicum |
| 2010/0138239 A1 | 6/2010 | Reicher et al. |
| 2010/0179833 A1 | 7/2010 | Roizen et al. |
| 2010/0211941 A1 | 8/2010 | Roseborough |
| 2010/0218132 A1 | 8/2010 | Soni et al. |
| 2010/0235889 A1 | 9/2010 | Chu et al. |
| 2010/0250258 A1 | 9/2010 | Smithers et al. |
| 2010/0250341 A1 | 9/2010 | Hauser |
| 2010/0262664 A1 | 10/2010 | Brown |
| 2010/0325144 A1 | 12/2010 | Fischer et al. |
| 2010/0333037 A1 | 12/2010 | Pavlovski |
| 2011/0066934 A1 | 3/2011 | Treisman |
| 2011/0112852 A1 | 5/2011 | Ware et al. |
| 2011/0126119 A1 | 5/2011 | Young |

(56) References Cited

U.S. PATENT DOCUMENTS

| | | |
|---|---|---|
| 2011/0145747 A1 | 6/2011 | Wong et al. |
| 2011/0166628 A1 | 7/2011 | Jain |
| 2011/0167133 A1 | 7/2011 | Jain |
| 2011/0173308 A1 | 7/2011 | Gutekunst |
| 2011/0184748 A1 | 7/2011 | Fierro et al. |
| 2011/0200979 A1 | 8/2011 | Benson |
| 2011/0218407 A1 | 9/2011 | Haberman |
| 2011/0288900 A1 | 11/2011 | McQueen et al. |
| 2011/0295986 A1 | 12/2011 | Ferris et al. |
| 2011/0307331 A1 | 12/2011 | Richard |
| 2012/0003931 A1 | 1/2012 | Eisinger et al. |
| 2012/0035954 A1 | 2/2012 | Yeskel |
| 2012/0036220 A1 | 2/2012 | Dare |
| 2012/0047029 A1 | 2/2012 | Veres et al. |
| 2012/0060922 A1 | 3/2012 | Wadia et al. |
| 2012/0072232 A1 | 3/2012 | Frankham et al. |
| 2012/0084399 A1 | 4/2012 | Scharber et al. |
| 2012/0084848 A1 | 4/2012 | Kim |
| 2012/0089521 A1 | 4/2012 | Abrevaya et al. |
| 2012/0102050 A1 | 4/2012 | Button |
| 2012/0143694 A1 | 6/2012 | Zargahi |
| 2012/0143697 A1 | 6/2012 | Chopra |
| 2012/0215639 A1 | 8/2012 | Ramer et al. |
| 2012/0260294 A1 | 10/2012 | Reichardt et al. |
| 2012/0266251 A1 | 10/2012 | Birtwhistle |
| 2012/0272156 A1 | 10/2012 | Kerger |
| 2013/0060922 A1 | 3/2013 | Koponen |
| 2013/0085744 A1 | 4/2013 | Arias |
| 2013/0085858 A1 | 4/2013 | Sim et al. |
| 2013/0103749 A1 | 4/2013 | Werth et al. |
| 2013/0110565 A1 | 5/2013 | Means |
| 2013/0145024 A1 | 6/2013 | Cao |
| 2013/0145457 A1 | 6/2013 | Papkipos et al. |
| 2013/0151710 A1 | 6/2013 | D'souza |
| 2013/0166494 A1 | 6/2013 | Davis |
| 2013/0173413 A1 | 7/2013 | Page et al. |
| 2013/0179472 A1 | 7/2013 | Junqua |
| 2013/0198694 A1 | 8/2013 | Rahman et al. |
| 2013/0212487 A1 | 8/2013 | Cote |
| 2013/0238686 A1 | 9/2013 | O'Donoghue |
| 2013/0283188 A1 | 10/2013 | Sanghvi |
| 2013/0326375 A1 | 12/2013 | Barak et al. |
| 2013/0329632 A1 | 12/2013 | Buyukkoc |
| 2014/0017648 A1 | 1/2014 | Williams et al. |
| 2014/0019480 A1 | 1/2014 | Rychikhin |
| 2014/0026113 A1 | 1/2014 | Farooqi |
| 2014/0033171 A1 | 1/2014 | Lorenz |
| 2014/0052681 A1 | 2/2014 | Nitz et al. |
| 2014/0068006 A1 | 3/2014 | Singhal |
| 2014/0088995 A1 | 3/2014 | Damani |
| 2014/0100883 A1 | 4/2014 | Hamilton |
| 2014/0101628 A1 | 4/2014 | Almog |
| 2014/0109072 A1 | 4/2014 | Lang et al. |
| 2014/0109115 A1 | 4/2014 | Low |
| 2014/0109177 A1 | 4/2014 | Barton et al. |
| 2014/0156645 A1 | 6/2014 | Brust |
| 2014/0156823 A1 | 6/2014 | Liu |
| 2014/0157171 A1 | 6/2014 | Brust et al. |
| 2014/0173405 A1 | 6/2014 | Ferrara |
| 2014/0176955 A1 | 6/2014 | Rao |
| 2014/0181715 A1 | 6/2014 | Axelrod |
| 2014/0186810 A1 | 7/2014 | Falash |
| 2014/0187228 A1 | 7/2014 | Fisher |
| 2014/0206391 A1 | 7/2014 | Perotti |
| 2014/0240122 A1 | 8/2014 | Roberts |
| 2014/0257058 A1 | 9/2014 | Clarysse et al. |
| 2014/0258827 A1 | 9/2014 | Gormish |
| 2014/0273913 A1 | 9/2014 | Michel |
| 2014/0278536 A1 | 9/2014 | Zhang |
| 2014/0282061 A1 | 9/2014 | Wheatley et al. |
| 2014/0288955 A1 | 9/2014 | Zhou et al. |
| 2014/0309868 A1 | 10/2014 | Ricci |
| 2014/0317595 A1 | 10/2014 | Kilby |
| 2014/0344208 A1 | 11/2014 | Ghasemzadeh et al. |
| 2014/0344397 A1 | 11/2014 | Kostof |
| 2014/0358482 A1 | 12/2014 | Sehgal |
| 2014/0365961 A1 | 12/2014 | Lefor et al. |
| 2015/0006214 A1 | 1/2015 | Lavoie et al. |
| 2015/0012301 A1 | 1/2015 | Weschler et al. |
| 2015/0019342 A1 | 1/2015 | Gupta |
| 2015/0025917 A1 | 1/2015 | Stempora |
| 2015/0025997 A1 | 1/2015 | Tilenius |
| 2015/0056589 A1 | 2/2015 | Zhang et al. |
| 2015/0074635 A1 | 3/2015 | Margiotta |
| 2015/0088955 A1 | 3/2015 | Hendrick et al. |
| 2015/0089224 A1 | 3/2015 | Beckman |
| 2015/0106369 A1 | 4/2015 | Nolan et al. |
| 2015/0106449 A1 | 4/2015 | Cherry |
| 2015/0120846 A1 | 4/2015 | Volach |
| 2015/0135160 A1 | 5/2015 | Gauvin |
| 2015/0143470 A1 | 5/2015 | Stiekes |
| 2015/0148061 A1 | 5/2015 | Koukoumidis |
| 2015/0149390 A1 | 5/2015 | Brdiczka et al. |
| 2015/0154002 A1 | 6/2015 | Weinstein et al. |
| 2015/0163121 A1 | 6/2015 | Mahaffey |
| 2015/0178473 A1 | 6/2015 | Hufford et al. |
| 2015/0178474 A1 | 6/2015 | Hufford et al. |
| 2015/0182861 A1 | 7/2015 | Winter et al. |
| 2015/0199490 A1 | 7/2015 | Iancu |
| 2015/0212714 A1 | 7/2015 | Hua |
| 2015/0213197 A1 | 7/2015 | Brennan et al. |
| 2015/0220233 A1 | 8/2015 | Kok et al. |
| 2015/0256689 A1 | 9/2015 | Erkkila et al. |
| 2015/0286802 A1 | 10/2015 | Kansara |
| 2015/0294090 A1 | 10/2015 | Kodiyan |
| 2015/0347784 A1 | 12/2015 | Keen |
| 2015/0370228 A1 | 12/2015 | Kohn |
| 2016/0021040 A1 | 1/2016 | Frei |
| 2016/0058287 A1 | 3/2016 | Dyell |
| 2016/0085754 A1 | 3/2016 | Gifford et al. |
| 2016/0092339 A1 | 3/2016 | Straub |
| 2016/0124930 A1 | 5/2016 | Dhawan |
| 2016/0147955 A1 | 5/2016 | Shah |
| 2016/0165409 A1 | 6/2016 | Bulut et al. |
| 2016/0196389 A1 | 7/2016 | Moturu et al. |
| 2016/0203663 A1 | 7/2016 | Proctor |
| 2016/0209920 A1 | 7/2016 | Mastandrea |
| 2016/0217118 A1 | 7/2016 | Singh |
| 2016/0234624 A1 | 8/2016 | Riva et al. |
| 2016/0261425 A1 | 9/2016 | Horton |
| 2016/0261528 A1 | 9/2016 | Blahnik |
| 2016/0300570 A1 | 10/2016 | Gustafson et al. |
| 2016/0314110 A1 | 10/2016 | Corcoran |
| 2016/0357794 A1 | 12/2016 | Liang et al. |
| 2016/0357944 A1 | 12/2016 | Iyer et al. |
| 2016/0359880 A1 | 12/2016 | Pang et al. |
| 2016/0359915 A1 | 12/2016 | Gupta et al. |
| 2017/0000422 A1 | 1/2017 | Moturu et al. |
| 2017/0024546 A1 | 1/2017 | Schmidt |
| 2017/0034649 A1 | 2/2017 | Dotan-Cohen et al. |
| 2017/0039324 A1 | 2/2017 | Francois et al. |
| 2017/0048215 A1 | 2/2017 | Straub |
| 2017/0049374 A1 | 2/2017 | Eldardiry et al. |
| 2017/0068006 A1 | 3/2017 | Forgues et al. |
| 2017/0083837 A1 | 3/2017 | Berlandier |
| 2017/0097743 A1 | 4/2017 | Hameed et al. |
| 2017/0124276 A1 | 5/2017 | Tee |
| 2017/0132395 A1 | 5/2017 | Futch |
| 2017/0132396 A1 | 5/2017 | Bechtold et al. |
| 2017/0169343 A1 | 6/2017 | Kirkham et al. |
| 2017/0176955 A1 | 6/2017 | Rao et al. |
| 2017/0181698 A1 | 6/2017 | Wiedenhoefer et al. |
| 2017/0118159 A1 | 7/2017 | Ratiu et al. |
| 2017/0201425 A1 | 7/2017 | Marinelli |
| 2017/0228229 A1 | 8/2017 | Jain et al. |
| 2017/0231528 A1 | 8/2017 | Nathan |
| 2017/0249435 A1 | 8/2017 | Lancelot |
| 2017/0257450 A1 | 9/2017 | Rao |
| 2017/0286389 A1 | 10/2017 | Ceneviva |
| 2017/0286605 A1 | 10/2017 | Wong et al. |
| 2017/0300538 A1 | 10/2017 | Seuss et al. |
| 2017/0303187 A1 | 10/2017 | Crouthamel |
| 2017/0308680 A1 | 10/2017 | Efros et al. |
| 2017/0323064 A1 | 11/2017 | Bates |

(56) References Cited

U.S. PATENT DOCUMENTS

| | | |
|---|---|---|
| 2017/0329483 A1 | 11/2017 | Jann et al. |
| 2017/0329500 A1 | 11/2017 | Grammatikakis et al. |
| 2017/0330297 A1 | 11/2017 | Cronin et al. |
| 2017/0344895 A1 | 11/2017 | Roy |
| 2017/0358242 A1 | 12/2017 | Thompson |
| 2017/0372442 A1 | 12/2017 | Mejias |
| 2017/0374178 A1 | 12/2017 | Sharma et al. |
| 2018/0046780 A1 | 2/2018 | Graiver et al. |
| 2018/0060500 A1 | 3/2018 | Ni et al. |
| 2018/0089159 A1 | 3/2018 | Jain et al. |
| 2018/0090229 A1 | 3/2018 | Sanyal |
| 2018/0108272 A1 | 4/2018 | Ahmad et al. |
| 2018/0114596 A1 | 4/2018 | Churchwell et al. |
| 2018/0121187 A1 | 5/2018 | Jain et al. |
| 2018/0122509 A1 | 5/2018 | Christiansson |
| 2018/0144100 A1 | 5/2018 | Chalas et al. |
| 2018/0150523 A1 | 5/2018 | Shiffman et al. |
| 2018/0176331 A1 | 6/2018 | Jain et al. |
| 2018/0197624 A1 | 7/2018 | Robaina |
| 2018/0206775 A1 | 7/2018 | Saria et al. |
| 2018/0210870 A1 | 7/2018 | Jain et al. |
| 2018/0277243 A1 | 9/2018 | Qing et al. |
| 2018/0286509 A1 | 10/2018 | Shah |
| 2018/0341378 A1 | 11/2018 | Morrow |
| 2018/0349516 A1 | 12/2018 | Dutta et al. |
| 2018/0350451 A1 | 12/2018 | Ohnemus et al. |
| 2018/0365316 A1 | 12/2018 | Liang et al. |
| 2019/0002982 A1 | 1/2019 | Wang |
| 2019/0026663 A1 | 1/2019 | Homeyer et al. |
| 2019/0043619 A1 | 2/2019 | Vaughan |
| 2019/0068753 A1 | 2/2019 | Jain et al. |
| 2019/0198172 A1 | 6/2019 | Nelson |
| 2019/0201123 A1 | 7/2019 | Shelton |
| 2019/0207814 A1 | 7/2019 | Jain |
| 2019/0306093 A1 | 10/2019 | Schilling et al. |
| 2019/0320310 A1 | 10/2019 | Horelik |
| 2019/0325204 A1 | 10/2019 | Purandare et al. |
| 2019/0361579 A1 | 11/2019 | Srivastava |
| 2020/0005417 A1 | 1/2020 | Agasi et al. |
| 2020/0035341 A1 | 1/2020 | Kain et al. |
| 2020/0050330 A1 | 2/2020 | Schilling et al. |
| 2020/0082918 A1 | 3/2020 | Simhon |
| 2020/0106863 A1 | 4/2020 | Jain |
| 2020/0131581 A1 | 4/2020 | Jain et al. |
| 2020/0175886 A1 | 6/2020 | Jain et al. |
| 2020/0203012 A1 | 6/2020 | Kamath et al. |
| 2020/0241859 A1 | 7/2020 | Jain et al. |
| 2020/0241860 A1 | 7/2020 | Jain et al. |
| 2020/0243167 A1 | 7/2020 | Will et al. |
| 2020/0250508 A1 | 8/2020 | De Magalhaes |
| 2020/0267110 A1 | 8/2020 | Nolan et al. |
| 2020/0278852 A1 | 9/2020 | Jain et al. |
| 2020/0279622 A1 | 9/2020 | Heywood et al. |
| 2020/0303074 A1 | 9/2020 | Mueller-Wolf |
| 2020/0336450 A1 | 10/2020 | Gao et al. |
| 2020/0348919 A1 | 11/2020 | Jain |
| 2020/0356353 A1 | 11/2020 | Jain |
| 2020/0364588 A1 | 11/2020 | Knox |
| 2021/0026615 A1 | 1/2021 | Jain |
| 2021/0026626 A1 | 1/2021 | Jain |
| 2021/0050105 A1 | 2/2021 | Randhawa et al. |
| 2021/0058490 A1 | 2/2021 | Jain |
| 2022/0382538 A1 | 12/2022 | Jain et al. |

FOREIGN PATENT DOCUMENTS

| | | |
|---|---|---|
| EP | 2851820 | 3/2015 |
| EP | 2545468 | 1/2016 |
| WO | WO1995012812 | 5/1995 |
| WO | WO 2011112556 | 9/2011 |
| WO | WO2012078753 | 6/2012 |
| WO | WO2013144769 | 10/2013 |
| WO | WO2014117223 | 8/2014 |

OTHER PUBLICATIONS

[No Author Listed] [online], "AirWatch Enterprise Mobility Management Demo," Jul. 22, 2014, retrieved on Apr. 21, 2022, retrieved from URL <https://www.youtube.com/watch?v=ucVln41-tgk>, 14 pages.

[No Author], "Methods for JITAIs Just in Time Adaptive Intervention," Apr. 22, 2016, retrieved on Nov. 9, 2016, retrieved from URL<https://community.isr.umich.edu/public/Default.aspx?alias=community.isr.umi ch.edu/public/jitai&>, 1 page.

addiction-ssa.org [online], "Ecological momentary assessment," Jul. 2015, retrieved on May 12, 2017, retrieved from URL <https://www.addiction-ssa.org/commentary/emerging-research-methods-series-ecological-momentary-assessment>, 3 pages.

alphr.com [online], "How to Write A Chrome Extension," Nov. 22, 2010, retrieved on Oct. 21, 2022, retrieved from URL<https://www.alphr.com/tutorials/363031/how-to-write-a-chrome-extension/>, 12 pages.

Conner, "Experience Sampling and Ecological Momentary Assessment with Mobile Phones," 2015, retrieved on May 3, 2017, retrieved from URL<http://www.otago.ac.nz/psychology/otago047475.pdf>, 4 pages.

dev.opera.com [online], "Extension Templates and Samples", Feb. 17, 2016, retrieved on Oct. 20, 2022, retrieved from URL<https://dev.opera.com/extensions/extension-samples/>, 5 pages.

ditoweb.com [online], "What is the Google Chrome Web Store?", published in Aug. 2012, retrieved on Oct. 18, 2021, retrieved from URL<https://www.ditoweb.com/2012/08/what-is-google-chrome-web-store/>, 8 pages.

edsurge.com [online], "Extensions, Add-Ons and Apps, Oh My! How to Utilize Google in Your Classroom," Oct. 13, 2014, retrieved on Oct. 21, 2022, retrieved from URL<https://www.edsurge.com/news/2014-10-13-extensions-add-ons-and-apps-oh-my-how-to-utilize-google-in-your-classroom>, 5 pages.

EP Search Report in European Appln. No. 17706938.2, dated Nov. 6, 2019, 9 pages.

Final Office Action in U.S. Appl. No. 15/040,635, dated Apr. 13, 2017, 13 pages.

Final Office Action in U.S. Appl. No. 15/152,411, dated Mar. 17, 2017, 18 pages.

Final Office Action in U.S. Appl. No. 16/120,083, dated Jan. 13, 2021, 17 pages.

Final Office Action in U.S. Appl. No. 17/092,842, dated Mar. 29, 2022, 19 pages.

Final Office Action in U.S. Appl. No. 15/858,165, dated Nov. 6, 2019, 13 pages.

Final Office Action in U.S. Appl. No. 17/076,056, dated Jan. 21, 2022, 38 pages.

Final Office Action in U.S. Appl. No. 17/088,076, dated Jan. 19, 2022, 32 pages.

ghacks.net [online], "The Best Way to Find New Extensions on the Chrome Web Store", published on May 12, 2014, retrieved on Oct. 18, 2021, retrieved from URL<https://www.ghacks.net/2014/05/12/best-way-find-new-extensions-chrome-web-store/>, 6 pages.

Goldsack et al., "Verification, analytical validation and clinical validation (V3): the foundation of determining fit-for-purpose for Biometric Monitoring Technologies (BioMeTs)", NPJ Digital Medicine, Apr. 14, 2020, 3(55):1-15.

groovypost.com [online], "How Safe is it to Download Chrome Extensions", published on Mar. 4, 2011, retrieved on Oct. 18, 2021, retrieved from URL<https://www.groovypost.com/howto/reviews/chrome-extensions-privacy- security/>, 7 pages.

Henze et al., "Push the study to the App store: evaluating off-screen visualizations for maps in the android market," Proceedings of the 12th Conference on Human-Computer Interaction with Mobile Devices and Services, Sep. 2010, pp. 373-374.

Heron, "Ecological Momentary Intervention [EMI]: Incorporating mobile technology into a disordered eating treatment program for college women," Psychology—Dissertations, Syracuse University, Jul. 2011, 24 pages.

(56) References Cited

OTHER PUBLICATIONS hub.jhu.edu [online], "Johns Hopkins Researchers to Use Apple Watch Data to Study Epilepsy," Oct. 15, 2015, retrieved on Mar. 30, 2020, retrieved from URL<https://hub.jhu.edu/2015/10/15/apple-watch-epiwatch/>, 3 pages.

International Preliminary Report on Patentability in International Appln No. PCT/US2017/017480, dated Aug. 23, 2018, 13 pages.

International Search Report and Written Opinion in International Appln. No. PCT/US2017/017480, dated May 17, 2017, 19 pages.

Khanacademy.org, [online] "Khan Academy," Available on or before Nov. 2, 2012, retrieved on Oct. 26, 2022, retrieved from URL<http://web.archive.org/web/20111202083549/http://www.khanacademy.org/>, 20 pages.

Kotsiantis, "Supervised Machine Learning: A Review of Classification Techniques", Informatica 31, Jul. 2007, pp. 249-268.

Lunn et al., "Using Mobile Technology to Engage Sexual and Gender Minorities in Clinical Research," PLOS ONE, May 2, 2019, 14(5):1-19.

macstories.net [online], "Apple's ResearchKit: Our Complete Overview," Mar. 9, 2015, retrieved on Mar. 30, 2020, retrieved from URL<https://www.macstories.net/news/apples-researchkit-our-complete-overview/>, 10 pages.

makeuseof.com [online], "How Safe Is The Chrome Web Store Anyway?" Apr. 10, 2015, retrieved on Oct. 26, 2022, retrieved from URL<https://www.makeuseof.com/tag/secure-chrome-web-store-anyway/>, 19 pages.

Non-Final Office Action in U.S. Appl. No. 15/040,635, dated Dec. 30, 2016, 12 pages.

Non-Final Office Action in U.S. Appl. No. 15/040,635, dated Jul. 8, 2016, 12 pages.

Non-Final Office Action in U.S. Appl. No. 15/067,046, dated Nov. 1, 2016, 23 pages.

Non-Final Office Action in U.S. Appl. No. 15/152,411, dated Dec. 7, 2016, 12 pages.

Non-Final Office Action in U.S. Appl. No. 15/279,845, dated Apr. 21, 2017, 11 pages.

Non-Final Office Action in U.S. Appl. No. 15/337,222, dated Mar. 23, 2017, 14 pages.

Non-Final Office Action in U.S. Appl. No. 15/382,126, dated Mar. 17, 2017, 17 pages.

Non-Final Office Action in U.S. Appl. No. 17/076,056, dated Jul. 21, 2021, 18 pages.

Non-Final Office Action in U.S. Appl. No. 17/088,076, dated Jul. 21, 2021, 21 pages.

Non-Final Office Action in U.S. Appl. No. 17/092,842, dated Sep. 27, 2021, 22 pages.

Non-Final Office Action in U.S. Appl. No. 15/858,165, dated Apr. 3, 2019, 14 pages.

Non-Final Office Action in U.S. Appl. No. 16/847,428, dated Sep. 15, 2020, 23 pages.

Non-Final Office Action in U.S. Appl. No. 16/847,452, dated Sep. 16, 2020, 23 pages.

Non-Final Office Action in U.S. Appl. No. 16/877,187, dated Jul. 20, 2020, 29 pages.

Non-Final Office Action in U.S. Appl. No. 16/877,187, dated May 5, 2021, 28 pages.

Non-Final Office Action in U.S. Appl. No. 16/942,822, dated Jul. 21, 2021, 22 pages.

Non-Final Office Action in U.S. Appl. No. 17/036,426, dated Aug. 3, 2021, 23 pages.

Non-Final Office Action in U.S. Appl. No. 17/076,056, dated Jul. 21, 2022, 23 pages.

Non-Final Office Action in U.S. Appl. No. 17/244,131, dated Jan. 19, 2022, 30 pages.

Non-Final Office Action in U.S. Appl. No. 16/702,631, dated Apr. 16, 2021, 48 pages.

Non-Final Office Action in U.S. Appl. No. 17/037,898, dated Nov. 26, 2021, 56 pages.

Notice of Allowance in U.S. Appl. No. 16/808,448, dated Oct. 1, 2021, 7 pages.

Notice of Allowance in U.S. Appl. No. 16/847,428, dated Jan. 5, 2022, 17 pages.

Notice of Allowance in U.S. Appl. No. 16/877,187, dated Sep. 22, 2021, 8 pages.

Notice of Allowance in U.S. Appl. No. 16/702,631, dated Dec. 22, 2021, 24 pages.

Obgyn.com [online], "Neural Networks", 2002, retrieved on Apr. 14, 2014, retrieved from URL<http://www.obgyn.cam.ac.uk/cam-only/statsbook/stneunet.html>, 34 pages.

Rabelo et al., "Development of a real-time learning scheduler using reinforcement learning concepts", Proceedings of the 1994 9th IEEE International Symposium on Intelligent Control, 1994, pp. 291-296.

Runyan et al., "Virtues, ecological momentary assessment/intervention and smartphone technology," Frontiers in Psychology, May 6, 2015, 6:481, 24 pages.

sbir.cancer.gov [online], "322 Real-Time Integration of Sensor and Self-Report Data for Clinical and Research Applications", Jun. 24, 2015, retrieved on Oct. 18, 2021, retrieved from URL<https://sbir.cancer.gov/funding/contracts/pastcontracts/322>, 3 pages.

sbir.cancer.gov [online], "340 Validation of Mobile Technologies for Clinical Assessment, Monitoring and Intervention", Jun. 24, 2015, retrieved on Oct. 18, 2021, retrieved from URL<https://sbir.cancer.gov/funding/contracts/pastcontracts/340>, 3 pages.

sbir.cancer.gov [online], "NIH/NCI 342: Validation of Mobile Technologies for Clinical Assessment, Monitoring and Intervention", Jul. 24, 2015, retrieved on Oct. 18, 20121, retrieved from URL<https://sbir.cancer.gov/funding/contracts/nihnci342>, 4 pages.

Schilit et al., "Context-aware computing applications," Proceedings of Mobile Computing Systems and Applications, Dec. 8, 1994, pp. 85-90.

scientificamerican.com [online], "Apple's First 5 Health ResearchKit Apps in Brief," Jul. 1, 2015, retrieved on Oct. 20, 2022, retrieved from URL<https://www.scientificamerican.com/article/pogue-apples-first-5-health-researchkit-apps-in-brief/>, 3 pages.

sitepoint.com [online], "How to Create a Chrome Extension in 10 Minutes Flat", Apr. 8, 2015, retrieved on Oct. 20, 2022, retrieved from URL<https://www.sitepoint.com/create-chrome-extension-10-minutes-flat/>, 12 pages.

smallbusiness.chron.com [online], "What Is The Chrome Web Store", Oct. 6, 2011, retrieved on Oct. 20, 2022, retrieved from URL<https://smallbusiness.chron.com/chrome-store-26652.html>, 6 pages.

Taivan et al., "Application Diversity in Open Display Networks," Proceedings of the International Symposium on Pervasive Displays, Jun. 2014, pp. 68-73.

techcrunch.com [online], "Google Gives Chrome Web Store a Welcome New Lick of Paint," Oct. 15, 2011, retrieved on Oct. 20, 2022, retrieved from URL<https://techcrunch.com/2011/10/25/google-gives-chrome-web-store-a-welcome-new-lick-of-paint/>, 11 pages.

West et al., "There's an App for That: Content Analysis of Paid Health and Fitness Apps," Journal of Medical Internet Research, May-Jun. 2012, 14(3): e72, 12 pages.

youtube.com [online], "Airwatch Laptop Management Demo," Oct. 3, 2014, retrieved on Oct. 21, 2022, retrieved from URL<https://www.youtube.com/watch?v=3gHfmdVZECM>, 1 page.

Advisory Action in U.S. Appl. No. 15/729,845, dated Nov. 30, 2017, 3 pages.

Corrected Notice of Allowance in U.S. Appl. No. 16/808,448, filed Dec. 22, 2021, 3 pages.

Corrected Notice of Allowance in U.S. Appl. No. 17/244,131, dated Aug. 9, 2022, 3 pages.

Notice of Allowance in U.S. Appl. No. 15/279,845, dated Jan. 29, 2018, 6 pages.

Notice of Allowance in U.S. Appl. No. 15/935,276, dated Dec. 13, 2019, 5 pages.

Notice of Allowance in U.S. Appl. No. 16/808,448, dated Dec. 7, 2021, 8 pages.

Notice of Allowance in U.S. Appl. No. 16/942,833, mailed on Mar. 30, 2022, 12 pages.

Notice of Allowance in U.S. Appl. No. 17/036,426, mailed on Mar. 15, 2022, 9 pages.

(56) References Cited

OTHER PUBLICATIONS

Notice of Allowance in U.S. Appl. No. 17/076,056, dated Feb. 1, 2023, 6 pages.
Notice of Allowance in U.S. Appl. No. 17/088,076, dated Jul. 5, 2022, 5 pages.
Notice of Allowance in U.S. Appl. No. 17/244,131, dated Jul. 7, 2022, 6 pages.
Office Action in U.S. Appl. No. 17/968,442, mailed on Jan. 26, 2024, 26 pages.
Office Action in U.S. Appl. No. 15/279,845, dated Sep. 8, 2017, 14 pages.
Office Action in U.S. Appl. No. 15/935,276, dated May 2, 2019, 9 pages.
Office Action in U.S. Appl. No. 16/808,448, dated Apr. 6, 2021, 15 pages.
Office Action in U.S. Appl. No. 17/076,056, dated Jan. 21, 2022, 20 pages.
Restriction Requirement in U.S. Appl. No. 15/729,845, dated Dec. 1, 2016, 6 pages.

\* cited by examiner

| RULE | TRIGGER(S) | CONDITION(S) | ACTION |
|---|---|---|---|
| PROGRAM RULE 1 | PROGRAM MODULE A: WHEN A USER REACHES PERSONAL WEEKLY ACTIVE MINIMUM GOAL | PERIOD = 1<br>TRACK = DOG WALKING<br>LEVEL = MODERATE | - DELIVER VIDEO 1 FOLLOWED BY ASSESSMENT 1 TO USER DEVICE<br>- DELIVER EMAIL 1 TO EMAIL ADDRESS |
| PROGRAM RULE 2 | PROGRAM MODULE A: WHEN A USER REACHES PERSONAL WEEKLY ACTIVE MINIMUM GOAL | PERIOD = 1<br>TRACK = DOG WALKING<br>LEVEL = VIGOROUS | - DELIVER VIDEO 2 FOLLOWED BY ASSESSMENT 2 TO USER DEVICE<br>- DELIVER EMAIL 2 TO EMAIL ADDRESS |
| PROGRAM RULE 3 | PROGRAM MODULE A: WHEN A USER REACHES PERSONAL WEEKLY ACTIVE MINIMUM GOAL | PERIOD = 2<br>TRACK = DOG WALKING<br>PREVIOUS LEVEL = MODERATE<br>LEVEL = MODERATE | DELIVER RANDOM CONTENT ITEM FROM CATEGORY A OF CONTENT LIST |
| PROGRAM RULE 4 | PROGRAM MODULE A: WHEN A USER REACHES PERSONAL WEEKLY ACTIVE MINIMUM GOAL | PERIOD = 2<br>TRACK = DOG WALKING<br>PREVIOUS LEVEL = VIGOROUS<br>LEVEL = MODERATE | DELIVER RANDOM CONTENT ITEM FROM CATEGORY B OF CONTENT LIST |

USER: 36 YEAR OLD WOMAN; NO HISTORY OF PERFORMANCE RUNNING

PROGRAM: MARATHON PREPARATION

PERFORMANCE CATEGORY: INCREASE USER'S PROGRAM ADHERENCE

PRIOR PERFORMANCE: +15 MIN OVER TARGET PERFORMANCE; SENSOR DATA INDICATING REPEATED STOPPING

TIME: 2 DAYS INTO PROGRAM

PRIOR PERFORMANCE: -5 MIN OVER TARGET PERFORMANCE; SENSOR DATA INDICATING EXCEPTIONAL PERFORMANCE

TIME: 3 WEEKS INTO PROGRAM

PRIOR PERFORMANCE: NO EXERCISE IN LAST 2 WEEKS; LIMITED INTERACTION ON APPLICATION

TIME: 3 MONTHS INTO PROGRAM

2110a — WATCH THIS VIDEO ABOUT BEST RUNNING TECHNIQUES:

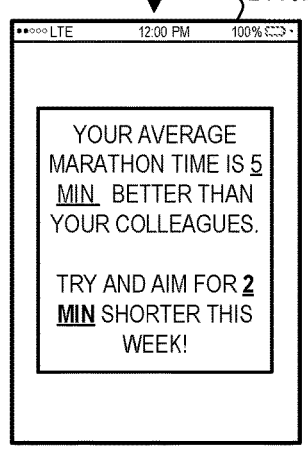

2110b — YOUR AVERAGE MARATHON TIME IS 5 MIN BETTER THAN YOUR COLLEAGUES. TRY AND AIM FOR 2 MIN SHORTER THIS WEEK!

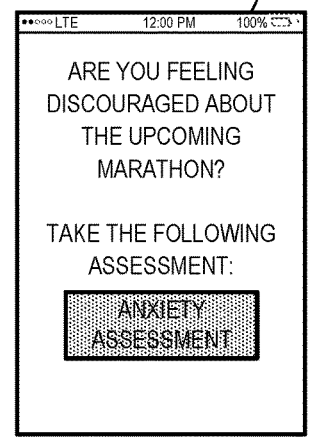

2110c — ARE YOU FEELING DISCOURAGED ABOUT THE UPCOMING MARATHON? TAKE THE FOLLOWING ASSESSMENT: ANXIETY ASSESSMENT

CONTENT TYPE: VIDEO
COMMUNICATION TYPE: ENCOURAGEMENT

CONTENT TYPE: TEXT MESSAGE
COMMUNICATION TYPE: USER CHALLENGE

CONTENT TYPE: USER SURVEY
COMMUNICATION TYPE: REASSURANCE / USER EVALUATION

```
┌─────────────────────────────────────────────────┐
│      FORM A – PERFORMANCE ANALYSIS              │
│           FOR ELECTRONIC FORM                   │
├─────────────────────────────────────────────────┤
│  OVERALL COMPLETION RATE: 82%                   │
├─────────────────────────────────────────────────┤
│        > 50 YEARS OLD      62%                  │
│        < 50 YEARS OLD      96%                  │
├─────────────────────────────────────────────────┤
│  AVERAGE TIME SPENT: 7 MIN                      │
├─────────────────────────────────────────────────┤
│        > 50 YEARS OLD      11 MIN               │
│        < 50 YEARS OLD      3 MIN                │
├─────────────────────────────────────────────────┤
│  SUGGESTED FORM UPDATES                         │
├─────────────────────────────────────────────────┤
│      > 50 YEARS OLD    REDUCE FORM COMPLEXITY   │
│      < 50 YEARS OLD    MAINTAIN CURRENT FORM    │
└─────────────────────────────────────────────────┘
```

2812 — Overall completion rate section
2814 — Average time spent section
2816 — Suggested form updates section

FIG. 28

AUTOMATING INTERACTIONS FOR HEALTH DATA COLLECTION AND PATIENT ENGAGEMENT

This application is a continuation-in-part of U.S. application Ser. No. 17/036,426, filed on Sep. 29, 2020, now U.S. Pat. No. 11,467,813, which is a continuation of U.S. application Ser. No. 16/847,428, filed Apr. 13, 2020, now U.S. Pat. No. 11,314,492, which is a continuation of U.S. application Ser. No. 15/858,165, filed Dec. 29, 2017, now U.S. Pat. No. 10,705,816, which is a divisional of U.S. application Ser. No. 15/040,635, filed Feb. 10, 2016, now U.S. Pat. No. 9,858,063, all of which are hereby incorporated by reference in their entirety.

This application is a continuation-in-part of U.S. patent application Ser. No. 17/037,898, filed on Sep. 30, 2020, now U.S. Pat. No. 11,487,531, which is a continuation of U.S. patent application Ser. No. 16/702,631, filed Dec. 4, 2019, now U.S. Pat. No. 11,321,082, which is a continuation of U.S. patent application Ser. No. 15/841,540, filed Dec. 14, 2017, now U.S. Pat. No. 10,587,729, which is a continuation of U.S. patent application Ser. No. 15/337,222, filed Oct. 28, 2016, now U.S. Pat. No. 9,848,061, all of which are hereby incorporated by reference in their entirety.

This application is a continuation-in-part of U.S. application Ser. No. 17/082,428, filed on Oct. 28, 2020, now U.S. Pat. No. 11,450,223, which is a continuation of U.S. application Ser. No. 16/783,273, filed Feb. 6, 2020, now U.S. Pat. No. 11,127,308, which is a continuation of U.S. application Ser. No. 15/694,372, filed Sep. 1, 2017, now U.S. Pat. No. 10,565,892, which is a continuation of U.S. application Ser. No. 15/152,411, filed May 11, 2016, now U.S. Pat. No. 9,753,618, all of which are hereby incorporated by reference in their entirety.

This application is a continuation-in-part of U.S. application Ser. No. 17/092,842, filed on Nov. 9, 2020, now U.S. Pat. No. 11,595,498, which is a continuation of U.S. application Ser. No. 16/120,083, filed on Aug. 31, 2018, now U.S. Pat. No. 11,159,643, which is a continuation of U.S. Application Ser. No. 15/382,126, filed Dec. 16, 2016, now U.S. Pat. No. 10,069,934, all of which are hereby incorporated by reference in their entirety.

This application is a continuation-in-part of U.S. application Ser. No. 17/076,056, filed on Oct. 21, 2020, now U.S. Pat. No. 11,675,971, which is a continuation of U.S. application Ser. No. 16/808,448, filed Mar. 4, 2020, now U.S. Pat. No. 11,244,104 which is a continuation of U.S. application Ser. No. 15/935,276, filed Mar. 26, 2018, now U.S. Pat. No. 10,621,280, which is a is a divisional of U.S. application Ser. No. 15/279,845, filed Sep. 29, 2016, now U.S. Pat. No. 9,928,230, all of which are hereby incorporated by reference in their entirety.

GOVERNMENT LICENSE RIGHTS

This invention was made with government support under grant numbers HHSN261201300056C and HHSN261201500013C awarded by the National Institutes of Health. The government has certain rights in the invention.

FIELD

This specification generally describes technology related to publishing customized application modules.

BACKGROUND

Applications for computers, mobile devices, and other devices can provide useful functionality to users. However, it can be very costly and time consuming to create, distribute, and maintain an application.

Typically, it is very difficult for organizations to create and distribute mobile applications and other solutions that can meet the needs of their members. Different organizations have widely varying health policies. For example, different organizations may have different insurance options and health goals for their members. Similarly, individuals have widely varying healthcare needs.

SUMMARY

Various techniques for creating and using software applications are discussed herein. The details of one or more implementations are set forth in the accompanying drawings and the description below. Other potential features and advantages will become apparent from the description, the drawings, and the claims.

BRIEF DESCRIPTION OF THE DRAWINGS

FIG. 15 is a diagram that illustrates examples of rules that can be used to adjust content associated with a program.

FIG. 21 is a diagram that illustrates examples of different communications that are provided in response to user actions on an application.

FIG. 28 is a diagram that illustrates an example of a performance analysis report for an electronic form.

In the drawings, like reference numbers represent corresponding parts throughout.

DETAILED DESCRIPTION

This application includes five separate sections: (1) FIGS. 1-6B and corresponding description, (2) FIGS. 7A-11 and corresponding description, (3) FIGS. 12A-17 and corresponding description, (4) FIGS. 18A-22 and corresponding description, and (5) FIGS. 23-29B and corresponding description. Each of these five sections of the application describes a separate set of embodiments. Each of these five sections of the application is self-contained and independent, and does not refer to and should not be interpreted based on the content of the other sections.

Section 1

Figure 1:
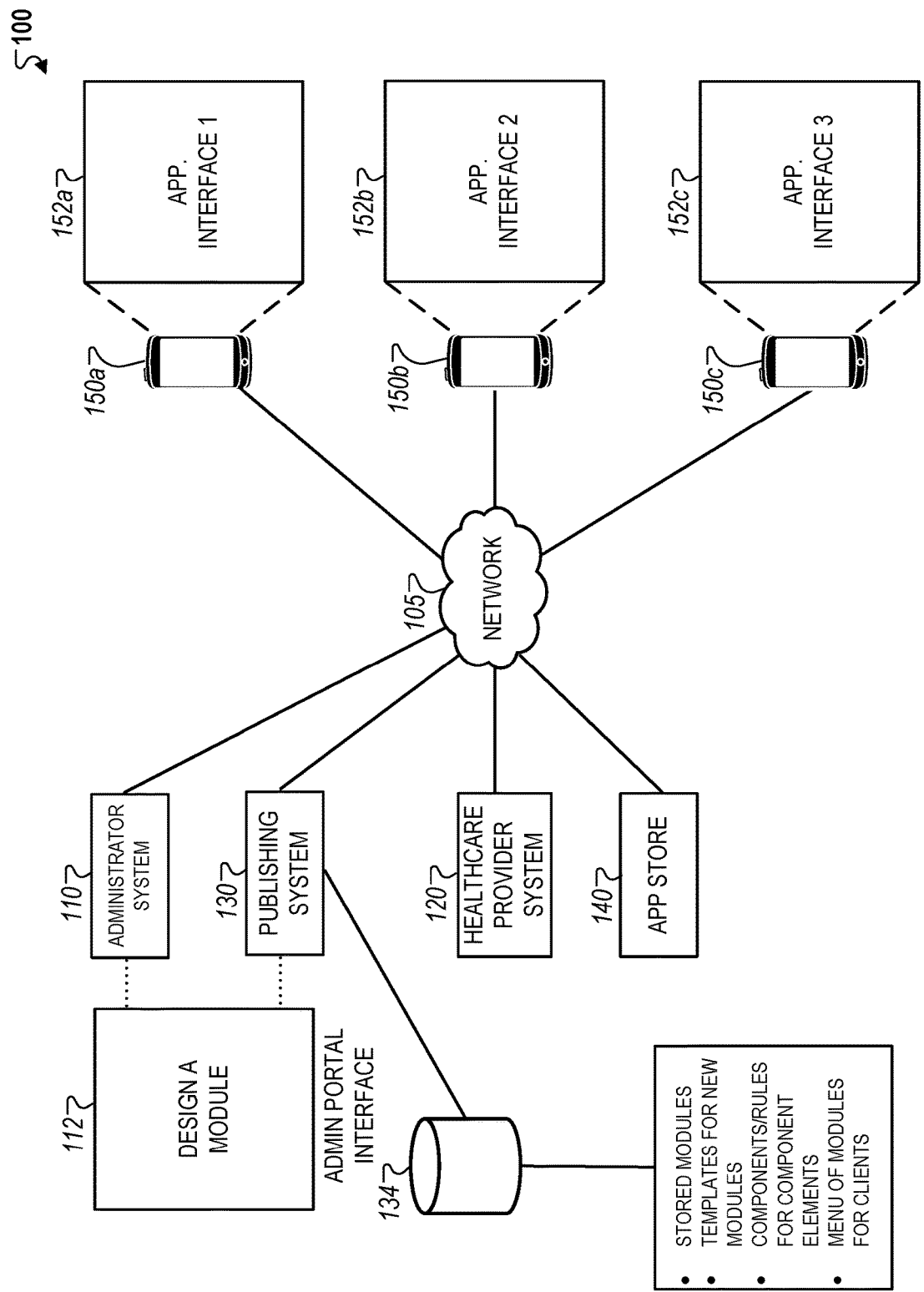
FIG. 1 is a diagram that illustrates an example of a publishing system.

FIG. 1 is a diagram that illustrates an example of a publishing system 100. The system 100 can include an administrator system 110, a healthcare provider system 120, a publishing system 130, an app store 140, and one or more user devices 150a, 150b, 150c connected over a network 105. The administrator system 110 can access an admin portal 112 provided by the publishing system 130. The publishing system 130 can include a repository 134 for storing content and information associated with the publishing system 100, such as templates for creating new modules and previously-created custom modules and associated content. In addition, each of the user devices 150a, 150b, and 150c can display user interfaces 152a, 152b, and 152c, respectively, to a set of different users associated with each of the user devices.

In some implementations, a system provides a platform that allows efficient creation and distribution of customized program modules to users. Individual users can download a single application from a server for an application store or marketplace. Separately, a publishing system provides modules for the application that define different sets of functionality and different user experiences. Various organizations can use the publishing system to quickly create and customize a program module to meet their needs, based on predetermined templates offered by the publishing system. For example, the publishing system allows an organization to customize the module templates to use the organization's own name, logo, media, and other branding assets. Organizations can also select which aspects of the application will be made available to the user and in what manner. By creating a custom module, an organization can define a unique, branded user experience for an application, e.g., for a mobile device such as a smartphone or tablet computer, without requiring the organization to invest the time and effort to code, test, publish, and maintain an application.

When a user downloads and installs the application associated with the publishing system, the user can select and download an appropriate customized module. The module can include a variety of elements that adjust the user's experience. For example, a module can include custom content from the organization that customized it, as well as interactive elements, media, and features from the template used to generate the module. After downloading the module, the application may reconfigure its interface as directed by the module, as if the organization that customized the module had provided the user a customized, stand-alone application.

In some implementations, organizations may use the publishing system to customize modules that enhance the wellbeing of users. For example, an organization may provide various modules that support health initiatives of a company. Using the publishing system, the employer may select module templates for various aspects of wellbeing, such as general fitness, weight loss, diabetes management, and so on. The module templates may include clinically validated information and recommendations tailored for a specific medical condition or health goal. This template information provides the employer effective, validated techniques to improve a user's health, without requiring the employer to invest in research to identify appropriate user experiences supporting health. The employer may customize the template, for example, specifying additional goals or incentives specific to the employer, as well as health insurance information that is applicable for the employer. Additionally, the employer may include the employer's name, logo, and other content, so that once the module is downloaded and incorporated into the application, the application may appear as if it were a fully customized application from the employer. In a similar manner, health insurance companies, doctors and hospitals, government entities, and other organizations may all create their own respective customized modules to be published.

In some implementations, customized health management modules can be used to provide organization-specific information on user interfaces of mobile applications from a third-party application store. The customized health management modules can be published by a publishing system that supports data collection and monitoring processes associated with health management programs provided by multiple healthcare providers. The customized health management modules can be used to integrate various types of information from different entities associated with healthcare services such as insurance companies, providers, pharmacies, and patients into a common platform with limited costs of implementation for organizations that provide modules through the publishing system.

In one general aspect, a computer-implemented method includes: providing, by a server system, a user interface for designing a health management module, the user interface identifying a plurality of health management module templates; receiving, by the server system, data indicating a user input received through the user interface that selects of one of the plurality of module templates; receiving, by the server system, customization parameters that customize the selected module template for a particular organization; generating, by the server system, a customized health management module for the particular organization based on the selected template and the customization parameters; and publishing, by the server system, the customized health management module for the particular organization, the customized health management module including instructions that configures an application provided by a third-party application store.

Implementations can include one or more optional features. For instance, in some implementations, each of the particular organization, an operator of the third-party application store, and the provider of the application are independent entities.

In some implementations, the plurality of health management module templates include multiple templates corresponding to different medical conditions, each of the multiple templates including clinical information for the corresponding medical condition.

In some implementations, the user interface for designing the health management module additionally identifies a set of interactivity settings.

In some implementations, the customization parameters specify one or more access conditions for the customized health management module for the particular organization.

In some implementations, the customization parameters include information identifying healthcare initiatives provided by the particular organization.

In some implementations, generating the customized health management module for the particular organization includes: identifying a module template based on user input; associating media content for the particular organization; and defining one or more user interaction settings for the customized health management module.

In some implementations, publishing the customized health management module for the particular organization includes providing the customized health management module over a network for access by the application provided by the third-party application store.

In some implementations, publishing the customized health management module for the particular organization includes: receiving, by the server system and from a client device having the application from the third party application store installed, a request for the customized health management module for the particular organization; and in response to receiving the request for the customized health management module for the particular organization, transferring, over a network, the customized health management module to the client device that has previously installed the application from the third-party application store such that the customized health management module performs a set of operations to adjust the application on the client device.

In some implementations, the customized health management module includes one or more tracking modules, the one or more tracking modules configured to initiate monitoring and reporting of predetermined content items associated with the application provided by the third party application store according to predetermined conditions specified by the customized health management module.

In some implementations, the customization parameters that customize the selected module template specify branding items, associated with the particular organization, to be displayed on the customized health management module.

In some implementations, the customization parameters that customize the selected module template specify interaction rules that specify techniques for submitting information on a user interface of the application provided by the third party application store.

In some implementations, generating the customized health management module for the particular organization includes: determining one or more healthcare providers that are supported by the particular organization to provide healthcare services; and generating the customized health management module to include information associated with the one or more healthcare providers that are supported by the particular organization to provide healthcare services.

In another general aspect, a computer-implemented method includes: installing, at an electronic device, an application downloaded over a computer network from an application store provided by a first server system; after installing the application, displaying, at the electronic device, a list of health management modules provided by a second server system that is independent of the first server system; providing, by the electronic device and to the second server system, data indicating one of the listed health management modules that was selected by a user of the electronic device; receiving, by the electronic device and from the second server system, the selected health management module; and installing, by the electronic device, the received health management module to modify the application to interact with the user according to the received health management module.

In some implementations, providing the data indicating one of the listed health management modules that was selected by the user of the electronic device includes information of a particular organization associated with the one of the listed health management modules that was selected by the user of the electronic device, and receiving the selected health management module includes receiving a list of health management modules that correspond to the particular organization.

In some implementations, installing the received health management module to modify the application includes: storing the received health management module on the electronic device; and designating the received health management module as a health management module to be displayed on the application during a subsequent application session.

In some implementations, modifying the application to interact with the user includes at least one of adjusting the user interface of the application, or adjusting tracking and reporting operations associated with the application.

In some implementations, the computer-implemented method for installing the received health management module includes modifying the application based on a set of instructions within the received health management module, the set of instructions enabling one or more functions of the application during a subsequent application session.

In some implementations, the application provided by the third-party application store is configured according to a local application configuration.

In some implementations, the computer-implemented method for installing the received health management module includes, after installing the received health management module, receiving, from the second server system, data indicating one or more updates to the received health management module.

In general, the discussion of FIGS. 1-6B describes systems and methods for generating and publishing customized program modules that adjust a user experience provided by an application. The customized module can include data that directs the application how to use and display various capabilities already existing in the application. In some implementations, the publishing system provides customized health management modules that enable client organizations to provide customized information to users through a single publishing platform. The publishing system allows client organizations to provide their members the benefits of customized applications without incurring the significant costs associated with developing and distributing a new application for each organization.

The publishing system can provide a publishing platform for generating and distributing customized health management modules. A client organization can use the publishing platform provided by the publishing system to distribute a health management module to users. In addition, a healthcare provider can also provide information that is used in the health management modules. Finally, a user can be an end-user that installs a mobile application from a third-party app store on a user device, and then downloads one of the customized health management modules provided by the publishing system.

With respect to FIGS. 1-6B, a "health management module" refers to a set of computer-implemented code or instructions that define a user experience associated with a mobile application. The health management module can indicate specific features of an application that a particular client organization selected to expose to the user. When downloaded and stored on a user device, the module configures the associated mobile application to provide custom content and interactions selected by the client organization. When the user subsequently runs the application, the application retains the configuration, appearance, and interactivity specified by the previously downloaded module. Using a customized module, the client organization can provide the user the experience of a native mobile application without the need for the client organization to code and register an application with an app store (e.g., the Apple App Store, or Google Play for Android Apps, etc.). The health management module can also include or refer to various content items such as media, forms, and user interface parameters that include customized logos and branding for a client organization. In addition, the health management module enables the user and the client organization to perform specific types of data tracking and reporting according to a user's specific medical needs, or the priorities of the client organization (e.g., to encourage and reward exercise, or to promote quitting smoking, etc.). In this regard, the health management module can be customized to the goals of the client organization, the user, or both.

Several different actors interact with the publishing system discussed with respect to FIGS. 1-6B, for example, (a) a "client organization," (b) an "administrator," (c) a "healthcare provider," and (d) a "user" (or "patient"). A "client organization" refers to an organization that uses the services of the publishing system to distribute a module for the organization. For instance, the client organization can be an employer that provide healthcare insurance or other health management programs to employees. When using the publishing system, the client organization can provide organization-specific information such as logos, promotional content, or specific healthcare initiatives to the publishing system to display to users that use the customized module.

With respect to FIGS. 1-6B, an "administrator" refers to an entity or individual that interacts with an administrator portal of the publishing system to create a customized healthcare module. In some instances, the administrator is an employee or representative of the client organization that manages and updates the customized module. For instance, the administrator can use an administrator portal of the publishing system to select from various options and provide specifications for a desired module. Additionally, the administrator may identify a list of users that are eligible to receive the module, data indicating applicable healthcare providers or insurance plans, access privileges associated with particular features of the health management modules, or custom content for health management modules.

With respect to FIGS. 1-6B, a "healthcare provider" refers to individuals, institutions, or organizations that provide healthcare services to users. In some instances, the healthcare provider can be an individual health professional such as a physician, or an entity such as a hospital that provides preventative, curative, or rehabilitative programs for users, or a health insurance provider. Healthcare providers can use a provider portal to interact with the publishing system, both to submit information that is accessed through appropriate modules and to receive information from users of certain modules to use in enhancing treatment. As an example, healthcare providers may submit health-related information such as electronic health records, treatment program information, or promotional material. This information may be general for a group of users (e.g., for all users who have a particular insurance plan) or specific to individual users. In some instances, the information submitted on the provider portal can be compiled into a set of module information that is used to personalize the display and operation of the customized health management modules to the provider.

With respect to FIGS. 1-6B, a "user" or "patient" refers to an individual that uses a mobile application and one or more customized modules. In some instances, the user receives healthcare-related services from the healthcare provider. For instance, the user can use a mobile application that is customized using a healthcare module created on behalf of the user's employer, the user's insurance company, or another entity.

In more detail, the administrator system 110 can be a computing system used by an administrator of a client organization that uses the publishing system 130 to create and distribute a customized module. The administrator system 110 can access an administrator portal 112 that is provided by the publishing system 130. The administrator portal 112 can be used by the administrator to create or update a set of module specifications that configure a health management modules for a specific client organization. In addition, the administrator portal 112 can be used to identify which users are eligible for the customized module. Also, the admin portal can also be used to configure a payment gateway that is used in financial transactions associated with the client organization.

The admin portal 112 can also be used to create accounts for providers that are associated with a client organization. For example, the providers can be healthcare insurers and/or healthcare providers that accept the health insurance plans that are provided to employees of the client organization.

The healthcare provider system 120 can be a computing system that includes information related to one or more healthcare providers. The healthcare provider system 120 can access a provider portal provided by the publishing system 130 to submit patient and provider information that is relevant to treatment programs created in the admin portal 112. For example, a provider can submit medical histories, immunization records, previous consultation reports, and/or procedure charts for a particular user through the provider portal, which can then be associated with specific treatment programs for the particular user. In addition, the provider portal can be used by providers to periodically update patient and provider information such that the data within the application ecosystem of the system 110 is up-to-date and accurate.

The publishing system 130 can be a remote server that aggregates information provided by administrators on the admin portal 112 and by providers on the healthcare provider portal 122, and generates customized health management modules based on the information provided. For instance, as described more particularly with respect to FIG. 2A, the publishing system 130 can use the module specifications received from the admin portal and the module information received from the healthcare provider portal 122 to generate customization instructions that customize a module for a particular organization. The publishing system 130 also includes the repository 134, which can store related information of the system 100. For example, as depicted in FIG. 1, the repository 134 can include stored modules for other client organizations, templates for new health management modules, components or rules for components or elements to be included within health management modules, or lists of available modules for the user.

The app store 140 can be a mobile application store associated with the particular operating system of the user devices 150a, 150b, and 150c. The app store 140 can be operated by an entity that is independent of the client organization and its associated administrator, the healthcare provider, and the publishing system. In particular, an application associated with the publishing system may be provided by a server for an app store, but the publishing system 130 may independently provide modules that are subsequently downloaded after the application is installed. For instance, the app store 140 can be operated by a third party mobile device manufacturer or a third party software vendor that provides software development toolkits to design mobile applications on the mobile operating systems of the user devices 150a, 150b, 150c. Examples of app stores include the Apple App Store, the Google Play app store for Android devices, and the Amazon.com app store. In some instances, different app stores 140 can be used with different mobile operating systems of the user devices 150b, and 150c. In such instances, a mobile application of the publishing system 100 can be designed for multiple mobile operating systems.

The app store 140 can be used by users to install a mobile application associated with the system 100 onto the user devices 150a, 150b, and 150c. For instance, the same mobile application can display the interfaces 152a, 152b, and 152c to users of the user devices 150a, 150b, and 150c. In addition, as described more particularly with respect to FIG. 2A, the mobile application can periodically receive data from the publishing system 130 that include instructions to adjust the interfaces 152a, 152b, and 152c according to the customized health management modules. The instructions can different for each user device, according to the different modules installed, the different healthcare providers associated, and the user's individual health needs. As a result, the interfaces 152a, 152b, and 152c may provide information tailored for each user's organization, and in some instances, user-specific information.

The user devices 150a, 150b, 150c can be any type of electronic device that is capable of running third party mobile applications from the app store 140. For instance, the user devices 150a, 150b, 150c can be one or more of a smart phone, a laptop computing device, a tablet computing device, a watch or other connected wearable device, or other types of network-enabled computing devices. In addition, the user devices 150a, 150b, 150c can be associated with different users such that each device is used for different treatment programs. In some instances, the user devices 150a, 150b, 150c can additionally store an installed mobile application that enables the user devices to exchange communications with the publishing system 130 and receive a set of customization instructions that configure the interfaces 152a, 152b, and 152c.

Figure 2A:
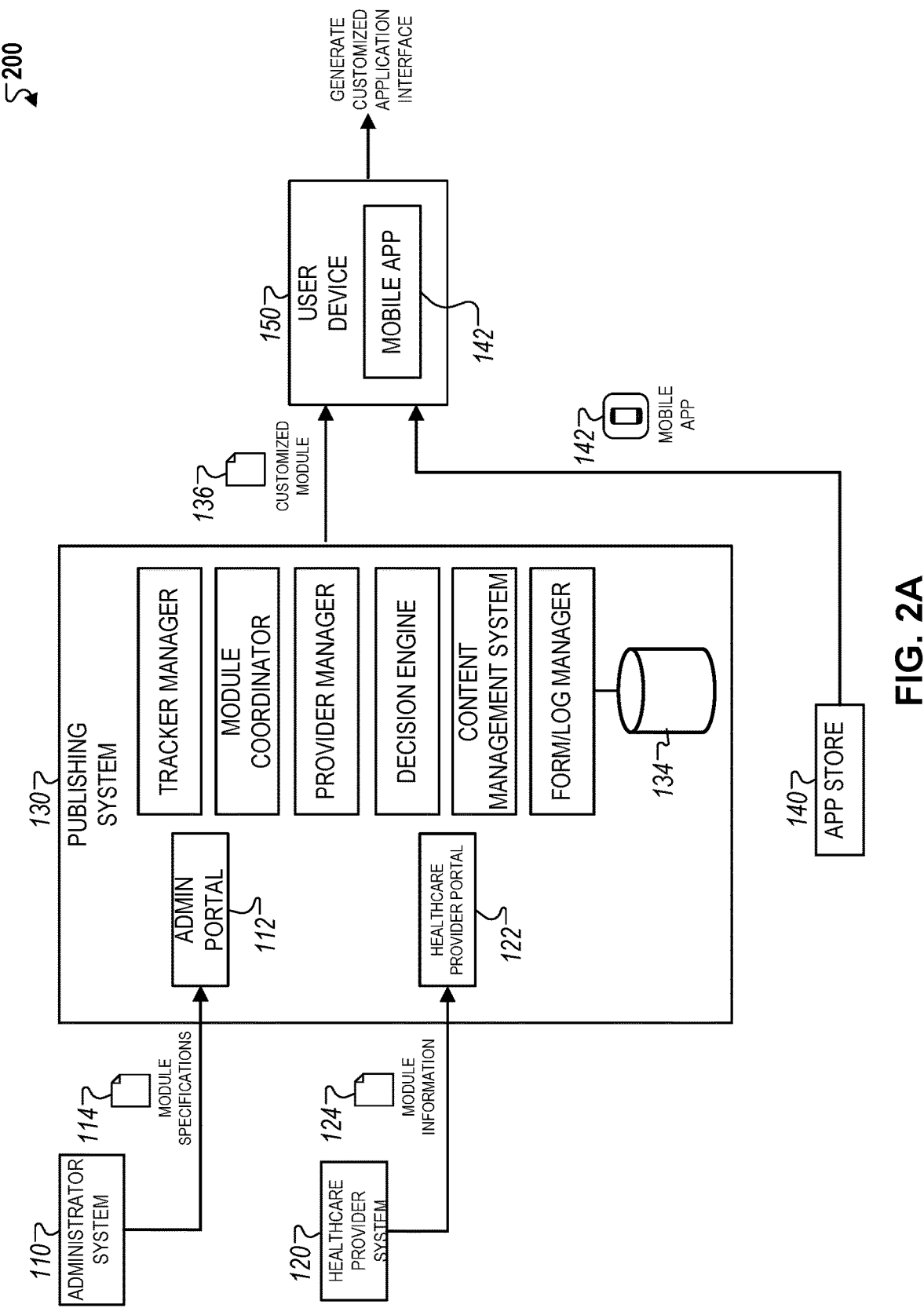
FIG. 2A is a diagram that illustrates an example of a process for publishing a customized module to a user device.

FIG. 2A is a diagram that illustrates an example of a process 200 for publishing a customized health management module to a user device 150. In general, the process 200 can be used to customize health management modules based on health-related associated with particular treatment programs that a user of the user device 150 is enrolled in, health-related information submitted by providers, and module specifications created by a system administrator. In this regard, the process 200 can be used by a plurality of entities within an application ecosystem, as described with respect to FIG. 1, to provide a set of customized health management modules can include provider-specific, client organization-specific, and user-specific information to the user device 150.

The process 200 initially starts when the administrator system 110 transmits module specifications 114 to the publishing system 130. As described above, the module specifications 114 can include account information for client organizations, providers, and/or users, access control lists specifying account privileges for features associated with customized health management modules, or client organizational frameworks that link client organizations to a list of available providers and treatment programs that are offered to users. The module specifications 114 can be inputted and/or updated by an administrator using the admin portal 112 as described with respect to FIG. 1. In some implementations, the module specifications 114 can also include access credentials associated with a provider or a user. For example, the access credentials can be based on a code such as a value from a quick reader (QR) code, a personal identifier number (PIN), or a user-selectable password that is associated with the mobile application 142.

In addition to the administrator system 110 transmitting the module specifications 114, the healthcare provider system 120 transmits module information 122 to the publishing system 130. As described previously, the module information 122 can include health-related information associated with client organizations such as policy information for health insurance provides associated with an employer. The module information 122 can also include a list of providers that accept the particular types of health insurance provided to employees by an employer. In some instances, the module information 122 can include client organization-specific information that is used to customize the appearance of the health management modules for the client organization. For example, in such instances, the module information 122 can include proprietary information, marketing or branding information associated with the organization, healthcare initiatives that are offered by the client organization, or treatment programs that are offered as services by associated providers to the users. In each of these examples, the module information 122 is used to gather client organization-specific information that is then used to generate a customized health management module that includes published information that is unique to the client organization.

After receiving the module specifications 114 and the module information 122, the publishing system 130 can execute a set of computer-implemented procedures to generate the customized module 136. For instance, the publishing system 130 can include a set of dedicated software modules that perform a set of particular actions based on the data submitted on the administrator portal 112 and the healthcare provider portal 122.

As depicted in FIG. 2A, the publishing system 130 can include a tracker manager that creates and manages trackers associated with treatment programs provided to users based on data submitted on the healthcare provider portal 122. For example, the trackers can monitor treatment milestones for a patient undergoing recovery after an operation based on the type of procedure performed.

The publishing system can also include a module coordinator that processes operations related to multiple customized health management modules for a provider or a client organization. For instance, the module coordinator can assign relative importance to individual health management modules such that certain health management modules that provide life-critical information to users can be prioritized over recreational health management modules. In other instances, the module coordinator can create and adjust update schedules for individual health management modules that determine how often each of the individual health management modules are periodically customized.

The module coordinator can also process incoming signal transmissions from different components of the publishing system 130 and generate instructions to perform particular activities by the publishing system 130. For instance, the module coordinator can receive module-specific content from the content manager and determine instructions to generate a customized health management module that includes the module-specific content. The module coordinator can additionally receive module-specific protocols, which can be used to adjust how customized health management modules are displayed on the user device, and/or implement security features that are used to protect personally identifiable information associated with users.

The publishing system 130 also includes a provider manager that monitors activities of multiple providers that are available for each organization. For instance, the provider manager can receive a list of providers for each client organization from the administrator system 110 and then monitor incoming and outgoing transmissions from the program coordinator. For example, the module coordinator can provide information related to a specific treatment program, and the provider manager can then determine the appropriate provider for the treatment program.

The publishing system 130 also includes a decision engine that executes computer-implemented processes based on one or more rules associated with configuration protocols of the health management modules. For instance, the decision engine can extract configuration data from the module specifications 114 transmitted from the administrator system 110, compare the extracted configuration data to a set of business rules specified within the admin portal 112, and execute responsive operations based on the comparison. For example, the decision engine can determine appropriate content to be included within a customized healthcare module, select the appropriate content and transmit the content selection to the content manager. In another example, the decision engine can determine a set of configuration protocols based on information included within the module specifications 114, and transmit the set of configuration protocols to the program coordinator.

The publishing system 130 also includes a content management system (CMS). The CMS stores content items for different modules and specifies how particular content items are used in health management modules. The CMS may store and organize any of the components of a module template or a completed module. For example, the CMS may store text, media, and other content that is used to form module templates made available by the publishing system 130. This stored information may also include descriptions of particular user interactions for a module, user experiences provided by a module, or characteristics of user interfaces. The CMS may also store custom content provided by organizations when they customize module templates to generate a customized module, for example, text, logos, images, videos, and so on. Other examples of content that can be stored by the CMS include messages to be displayed to a user, hyperlinks, files, or email templates.

The content management system can categorize content items according to the type of content or the intended usage of the content. The intended usage can indicate what portion of an interface of a module the content should be displayed, or when the content should be presented during use of a module. Some items may be categorized for display on a main content panel, while other items may be designated for display on a settings panel, a reminder view, a calendar view, or other portion of an interface. Content items in the CMS may be designated for display in response to certain conditions, such as surveys or forms to be provided in response to certain actions. Similarly, the CMS may include preloaded provider messages, such as pre-defined content that a healthcare provider may be able to cause to be displayed when appropriate.

The publishing system 130 also includes form/log manager that maintains a set of customized forms created in the admin portal 112. The forms are used to gather data such as user-submitted information, user preferences, and/or other user inputs that include health-related information associated with the provider or the client organization. For instance, the forms or logs can include patient surveys that request healthcare-related information from patients prior to a medical consult. In other instances, the forms or logs can include module-specific content such as treatment information or prescription dosages. In addition, the forms can include various user interface components that are associated with particular data types entered by the user (e.g., field entry fields for user-submitted text queries, user-specific graphical content, provider-lists populated for a particular client organization, etc.).

The form/log manager can also execute a set of computer-implemented instructions received from the module configurator. For instance, the instruction can include logic for selecting particular user interface components and adjusting the layout of user interface components on a particular user form/log based on the operations performed by the module coordinator. In this regard, the data transmissions between the module coordinator and the format/log manager enables the generation of user forms that can customize the layout of user interface components, transitions between different user interface sections or user interface components, and/or specify one or more conditions for generating specific types of user forms. In one example, in response to determining that the user has an upcoming checkup with a primary care provider, the module coordinator transmits instructions to the form/log manager to generate a user form that includes relevant clinical information and appointment information. In response to receiving the instructions, the form/log manager can generate a patient checkup form that includes the user data received from the module manager. In addition, the form/log manager can customize the display and layout of the user data such that the most vital patient information is displayed in a more central location of the user form than other non-vital patient information.

After processing the data included within the module specifications 114 and the module information 124 and performing the operations described above, the publishing system 130 can store processed data within the repository 134 and generate a set of customized module 136. As described previously with respect to FIG. 1, the repository 134 can include historical user data, templates for stored health management modules for generation on the user device 150 at a later time period, components or rules generating customized health management modules, and/or lists of applicable health management modules for particular user devices based on user, provider, and client organization information.

The customized module 136 can provide a user interface displayed on the mobile application 142 that includes published information based on the module specifications 114 and the module information 124. For instance, as depicted in FIG. 5C, the customized module 136 can include client organization-specific information (e.g., logos and promotional material) and information submitted by a healthcare provider (e.g., clinical information for the user). In some examples, the customized module 136 can displayed on the mobile application 142 by adjusting the display of the interface of the mobile application 142 by publishing information received by the publishing system 130.

After a module 136 has been received from the publishing system 130, the module 136 may be updated in a manner that is seamless and transparent to the user. The mobile application 142 can obtain updates to the module 136 from the publishing system 130 in real-time, e.g., in the background while the user is interacting with the module. The application 142 may incorporate updates to the customized module 136 so that the module 136 and the interface shown at the user device 150 are updated without requiring the user to re-login into the mobile application 142. Similarly, updates may occur without any update to the mobile application 142 from the app store 140. For example, in some instances, the customized module 136 can be locally stored on the user device 150. The user may have the application 142 open and in use, showing the interface of the module 136. While user is interacting with the interface, the application 142 may request an update from the publishing system 130, or the publishing system 130 may push an update to the application 142. When an update is received, the interface and interactivity of the module 136 may be updated, even by changing aspects of the current view shown to the user.

In some implementations, the customized module 136 can also include one or more computer-implemented protocols for generating customized health management modules for display on the user device 150. For instance, the customized module 136 can specify content to be displayed based on user, healthcare provider, and client organization information, designate a layout for the specified content based on user-specific settings, and/or provide user-specific information such as a list of providers for the client organization associated with the user. The data can be provided by a provider entity 102b on the provider portal interface 122.

In some instances, the customized module 136 can also specify a set of conditional rules that enable the user to track health-related information on customized health management modules that are generated on the user device 150. The set of conditional rules can be used to trigger the display of tracking information and reminders associated with a treatment program that the user is registered in, and execution of other actions performed on the user device 150. An example of a conditional rule can be automatically adjusting the list of providers that are displayed on a customized health management module based on determining that the user is scheduled to have a particular procedure performed as a part of a treatment program. In such an example, the list of providers displayed includes providers that support healthcare-related services associated with the particular procedure (e.g., post-operative recovery and monitoring, follow-up procedures, etc.).

After receiving the customized module 136, the user device 150 generates the customized health management modules based on implementing module specifications included within the customized module 136 as described previously.

In some implementations, as depicted in FIG. 2A, the customized health management modules can be generated by the mobile application 142. As described previously, the mobile application 142 can be installed from the app store 140 for the corresponding operating system of the user device 150. The mobile application 142 can initially be configured to include a set of baseline health management modules when the mobile application 142 is first installed on the user device 150. The baseline health management modules include generalized content and content layout that can be adjusted based on the customized module 136. For instance, the generalized content can be basic information associated with the system 100 that is applicable to all providers, client organizations, and users (e.g., user authentication protocols, mobile application infrastructure, system configurations and settings, etc.). In this regard, the customized module 136 can be used to adjust the baseline health management modules to display entity-specific information and exhibit user and provider-specific interaction settings such that the front-end user interface of the mobile application 142 appears unique to each user that operates on a single application framework.

Figure 2B:
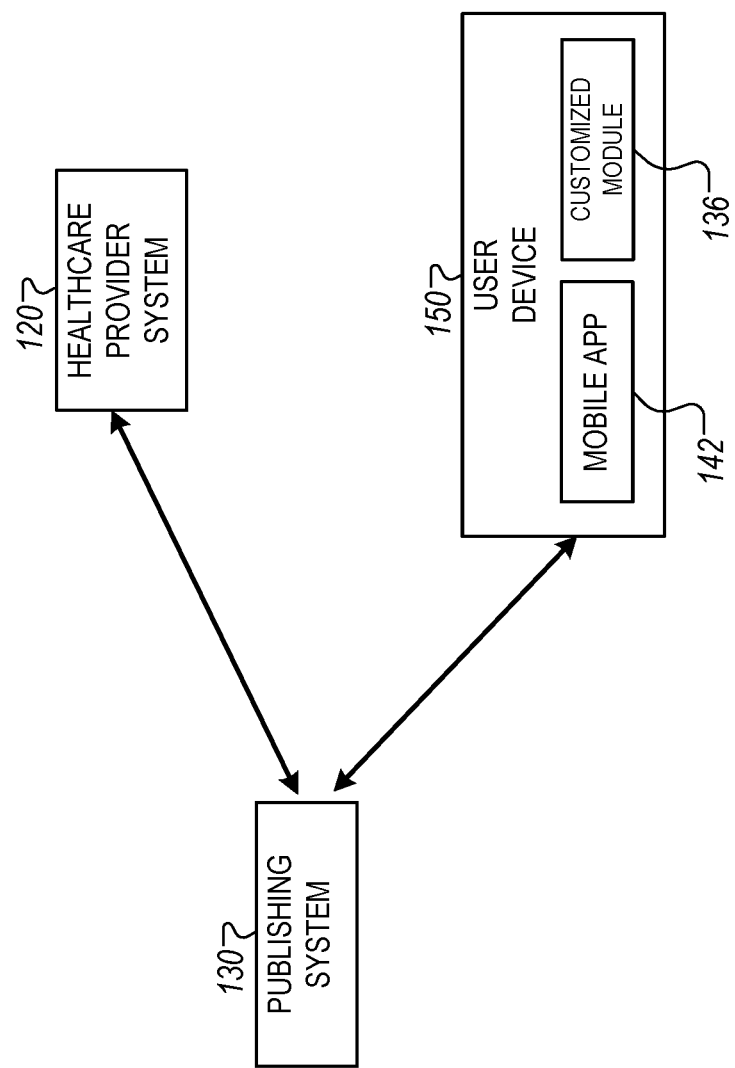
FIG. 2B is a diagram that illustrates communication that a publishing system facilitates between various systems.

FIG. 2A is a diagram that illustrates communication that the publishing system 130 facilitates between various systems. Once the customized module 136 is installed at the user device 150, the publishing system 130 facilitates communication between the user and healthcare providers. The same publishing system 130 from FIG. 2A is shown in FIG. 2B for convenience, but this system may represent multiple server systems or a different server system from the one that generates or provides the customized module 136 in FIG. 2A.

In some implementations, the publishing system 130 enables two-way asynchronous or synchronous communication between users of the module 136 and healthcare providers associated with the module 136. For example, users may submit questions for a doctor through an interface of the module 136, and the doctor may respond through an interface of the module 136, or vice versa. As another example, after a user has entered information, for example, indicating symptoms, exercise activity, or whether medicine was taken, the information may be uploaded to the publishing system 130 and made available to the healthcare provider. As another example, a healthcare provider may send content to be displayed within the interface of a module 136, e.g., educational materials, surveys, a predefined or customized message, and so on. Thus the healthcare provider may encourage or instruct a user of a module 136 remotely through the publishing platform. Messages can be provided through notifications, even when the application 142 and module 136 are not active on the user device 150. As another example, messages can be shown when a user opens the application 142, navigates to a particular view of the module 136, or opens a message inbox of the module 136. In some implementations, a module 136 may permit a live chat or video conference between a user and a healthcare provider.

In some implementations, healthcare providers can use the publishing system 130 to monitor or observe patients on an ongoing basis. These features can facilitate real-time messaging and real-time remote care planning. As noted above, customized modules can include trackers that specify types of information to obtain and provide to the publishing system. The information may be provided periodically or in response to particular triggers or conditions. For example, a module focused on diabetes care may provide periodic updates about a patient's most recent blood sugar tests. As another example, a module supporting fitness may provide a notification when a certain level of activity has been detected by sensors of the user device 150. In some instances, healthcare providers may send requests, to the publishing system 130, for information about their patients on an on-demand basis, and the publishing system 130 communicates with an individual user device 150 to obtain and provide the requested information. In this regard, customized modules may define communications permissions, e.g., to specify what information is permitted to be collected by the module 136, and what healthcare providers can receive the information.

In some implementations, a module specifies how existing functionality of the application 142 is to be used. Unlike application updates, the addition of a module can be done without modifying the actual executable files of the application 142. Instead of altering the application 142, the module can indicate what existing functionality of the application 142 to expose to a user, and in what manner. For example, the application 142 may include functionality for tracking and analyzing various types of sensor data of a device. A module can define, from among the capabilities of the application 142, which data should be collected and at what frequency. Additionally, the module can specify rules for how to process acquired data, as well as actions that the user's device should perform conditioned on the analysis. Thus, a module can change the ongoing or default behavior of the application 142. A module can be persistent at a user's device, for example, stored and active until a user indicates that the module should be removed. In some implementations, modules adjust the initial view or behavior of the application 142, the content and interactions with a user while the application 142 is active, and/or actions performed by the application 142 in the background while a different application is active.

A module may be structured in a number of different formats. In some implementations a module is structured as XML data or other non-executable data, and in some instances excludes executable content. In some instances, a module may include executable or interpretable instructions. In some instances, a module includes references to other content, and instructs the application 142 to download the additional content to support the module. The module may specify that additional content should be downloaded, e.g., when the module is first installed, or that additional information should be obtained or refreshed on a periodic or ongoing basis, or that additional information should be downloaded on-demand when the user accesses certain views or when certain triggering conditions are detected by the application 142.

As discussed above, a module can represent a combination of a template and customization settings. The content of the module may include various different items, including user interface instructions (e.g., defining formatting, size, color, layout, media displayed, etc.), branding (e.g., an organization's name, logo, colors, contact info), organization-specific information (e.g., identifying an applicable health insurance plan). Modules can include tracker components, such as data that defines a trigger or condition to cause a particular type of data to be collected, as well as actions to take when the trigger occurs (e.g., send to a server, store, analyze, notify user, etc.). Modules may define a set of user experiences, such as interaction flows or dialogs for a user, or forms, surveys, games, or other interactions. The module may include media content, and additionally or alternatively include links to media provided by one or more other sources, such as servers. The module can provide educational materials, information about specific medical conditions, and treatment regimens or wellness plans. The information provided through a module, and the interactions that the module instructs the application 142 to provide to the user, can be based on clinically-validated health or treatment information. As noted above, installing a module can configure the application 142 in various ways, including specifying how the application 142 accesses sensor data, provides user interface elements, interacts with an operating system or other applications (e.g., configuring the application 142 to send reminders, messages, notifications at device), and interacts over a network.

In some implementations, modules include information that connects a user device to healthcare providers. For example, the module can configure the application 142 to provide information (e.g., sensor data of the phone, user comments, health plan compliance information) to a physician, coach, or other health care provider. This information may be sent from a user's device through the publishing server to a device of the provider. Similarly, a module may configure the application 142 so that, through the publishing platform, the healthcare provider can send real-time communications or updates to treatment plans or goals. According to the instructions in the module, communications from providers can be displayed or used to modify the interactions of the application 142 with the user.

Figure 3:
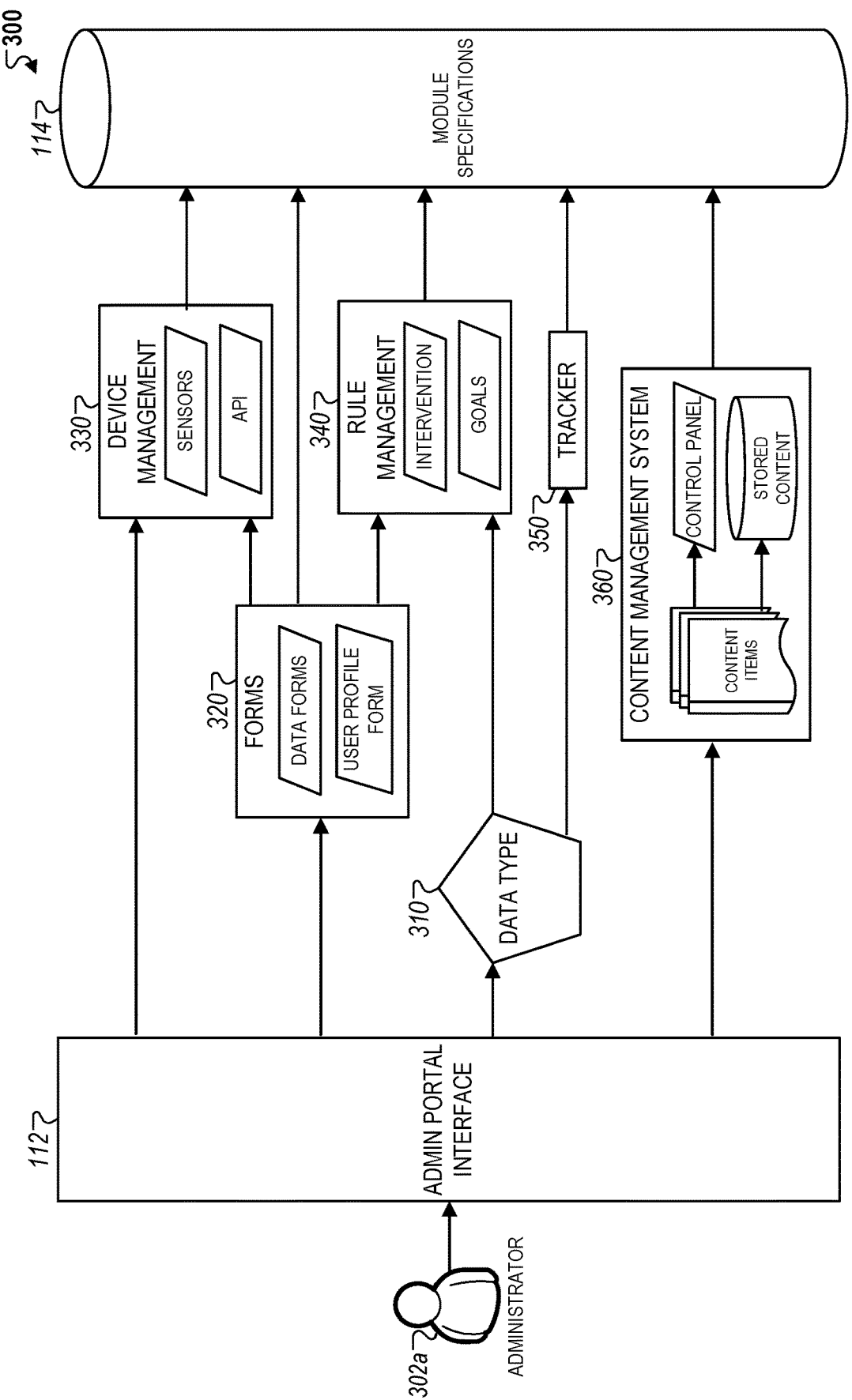
FIG. 3 is a diagram that illustrates examples of data that can be used to generate module specifications for a customized health management module.

FIG. 3 is a diagram that illustrates examples of data that can be used to generate module specifications for a customized health management module. The data can be provided by an administrator 302a on the admin portal 112. Briefly, the data provided by the administrator 302a can include a data type 310, form information 320, device management information 330, rule management information 340, tracker information 350, and/or content information from a content management system 360.

In general, the various types of data provided by the administrator 302a can be processed sequentially or parallel in order to generate the module specifications 114. For instance, aggregation techniques can be used such that data from multiple sources can be cross-correlated to generate a single output (e.g., the module specifications 114). For example, as depicted in FIG. 3, information submitted on forms 320, such as user demographic information submitted on data forms and the user's healthcare plan information on a user profile form be combined to specifically manage a user device associated with the user (e.g., perform specific authentication protocols associated with the user's health insurance provider). The form information 320 can also be used to specify rules related to intervention and wellness goals based on user-submitted information within the user profile form (e.g., utilizing a user's indication of lifestyle choices to adjust the behavior of the system 100 based on detecting wellness data associated with the user activities.

In more detail, the data type 310 is used to keep track of user-submitted information on the mobile application 142. For instance, the data type 310 can include a category associated with the user-submitted information that indicates how the user-submitted information should be processed by the system 100. For example, user inputs indicating a user's health-related information can be categorized as categorical data to determine user privileges whereas user inputs including symptoms can be categorized as treatment-related data that is provided to applicable providers associated with a treatment program that the user is currently enrolled in.

The form information 320 includes user-submitted information on forms such as user registration forms, inpatient forms, or patient surveys. As depicted in FIG. 3, two examples of forms can include data forms where a user submits inputs that are used as activity data associated with the user. For example, data forms can include forms for tracking exercise activity for wellness monitoring purposes. The other example can include a user profile form, which includes demographic information, user preferences, and health-related information such as a healthcare plan, or other clinically relevant information (e.g., medical history, immunization records, etc.).

The rule management information 340 specifies conditions that designate how particular types of user data are processed, and specific actions to be taken by the system 100 based on received user data. As depicted in FIG. 3, two examples of rules can include interventions where user data on forms can be used to predict at-risk conditions associated with the user and provide alerts on the health management modules to provide information related to preventative measures to present the at-risk conditions. For example, a user's medical history indicating risks of high blood pressure can be combined with sensor information from a heart rate sensor to predict the risk of a heart attack. In the second example, user goals can be determined based on a set of user preferences provided by the user on the user profile form. For example, a user can submit information related to an exercise regimen on the user profile form, which can be used to set a set of personal wellness goals that are periodically updated and communicated through notifications on the health management modules.

The trackers 350 are used to monitor user data from multiple sources and transmit signals in response to detecting patterns associated with the monitored user data. For instance, the trackers 350 can be used to monitor specific biometric parameters (e.g., heart rate, blood pressure, oxygen levels) in related to a user's healthcare conditions to adjust the activity of the system 100. For example, as described previously, the health management modules can be customized to display pertinent healthcare-related information. In this example, the trackers 350 can transmit signals to adjust the information displayed on the health management modules based on real-time biometric measurements. The trackers 350 can also designate conditions or contexts that trigger measurement and measuring of particular types of user information.

The content management system 360 is used to specify how particular content items to be displayed on the health management modules are processed by the system 100. As depicted in FIG. 3, the content management system 360 may either process content to adjust settings within a control panel or stored in a repository. For example, the content management system 360 can categorize content items' intended usage by the users or by types of content. In the first instance, the intended usage can be used to adjust particular settings in the control, or generate preloaded messages from providers that are associated with the intended usage. In the second instance, content items can be classified as, for example, messages, hyperlinks, files, or email templates.

The control panel can be used to adjust one or more settings related to the display of content within the health management modules. For example, the control panel can specify which particular content items are associated with particular health management modules, particular users, or rule-based events. In another example, the control panel can specify how content items are presented within a health management module (e.g., design layouts, or transition effects).

Figure 4:
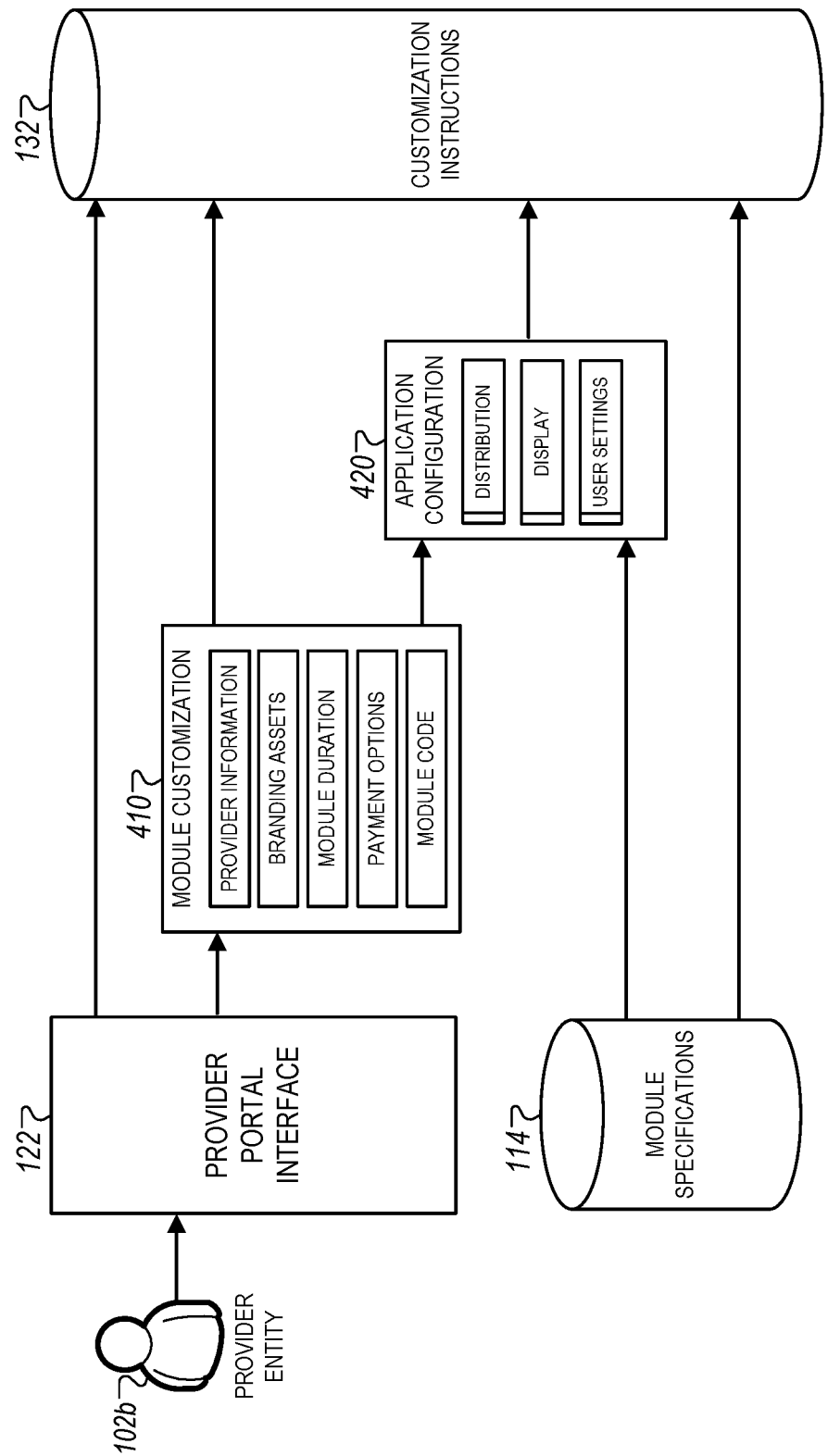
FIG. 4 is a diagram that illustrates examples of data that can be used to generate customization instructions for a customized health management module.

FIG. 4 is a diagram that illustrates examples of data that can be used to generate customization instructions for a customized health management module. The data can be provided by a provider entity 102b on the healthcare provider portal 122. Briefly, the data provided by the provider entity 102b can include module customization information 410 and application configuration 420. The data provided by the provider 102b can further be combined with the module specifications 114, as described previously, in order to generate the customization instructions 132.

In general, provider-specific information can be submitted on the provider portal interface 122 in order to customize the display of the health management modules on user devices of users that are associated with the provider. In some instances, the provider entity 102b can be a client organization such as an employer. In this regard, the module customization information 410 and the application configuration 420 is eventually combined with the module specifications 114 to generate the customization instructions 132.

In more detail, the module customization information 410 includes provider-specific information that are used to adjust the display and layout of content, graphics, and/or other information on the health management modules. As depicted in FIG. 4, examples of module customization information 410 can include provider information, branding assets, module duration, payment information, and module code. Provider information can include areas of practice, types of health insurances accepted, and/or size of healthcare practices. Branding assets can include marketing or promotional content (e.g., logos, advertisements, program incentives, etc.) that are specific to the provider entity 202a.

The module duration specifies how long a health management module will be displayed on the user device 150. For example, health management modules for short-term conditions (e.g., a doctor's appointment) can be accessible for one day whereas modules for chronic disease treatment programs (e.g., a weight management program) can be accessible for extended periods until the user has achieved goals associated with the treatment program. The payment options indicate methods of payment that are accepted by the provider entity 102b and specified amounts charged for procedures performed (e.g., co-pay amounts for checkups). The module code includes provider-specific numbers, associated with procedures, billing codes, and/or other accounting information, used to identify healthcare services provided to users.

The application configuration 420 can be one or more settings associated with the mobile application 142 that adjust how the health management modules 142 are displayed on the mobile application 142. As depicted in FIG. 4, examples of application configurations 420 can include application distribution (e.g., how the mobile application 142 is provided to users), application display (e.g., workflow design of the mobile application 142), and user settings (e.g., user-submitted preferences that configure the mobile application 142). The application configuration 420 is generated based on aggregating the module specification 114 and the module customization 410 using similar techniques as those described with respect to FIG. 3.

Figure 5A:
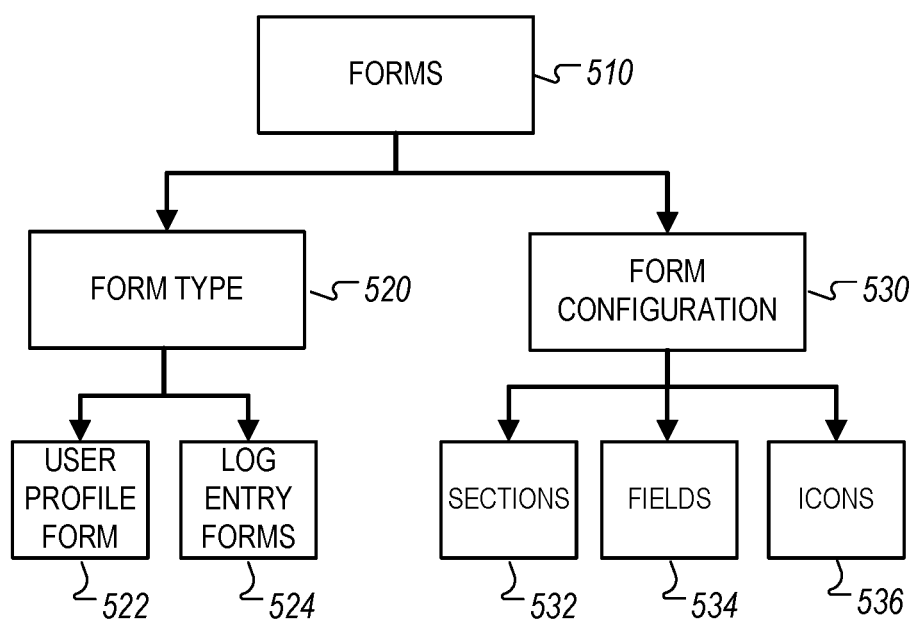
FIGS. 5A-5B are diagrams that illustrate examples of customization instructions for a published customized module.
Figure 5B:
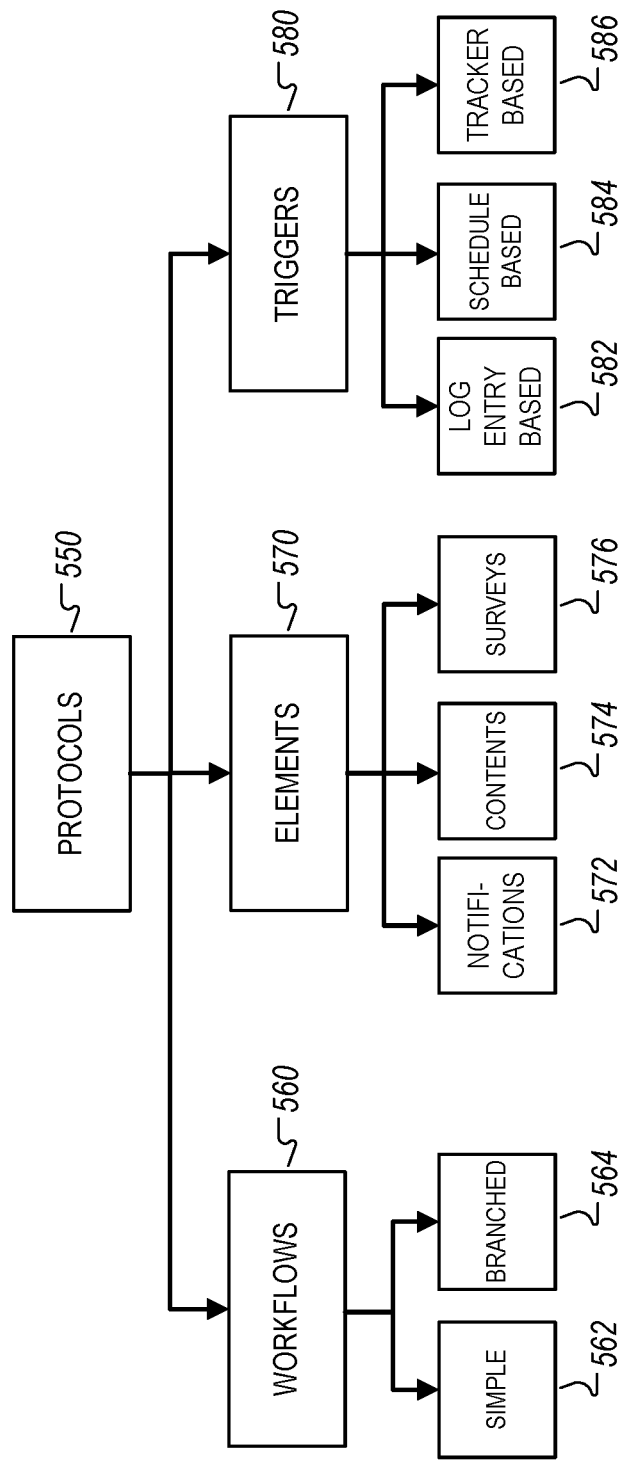
Figure 5C:
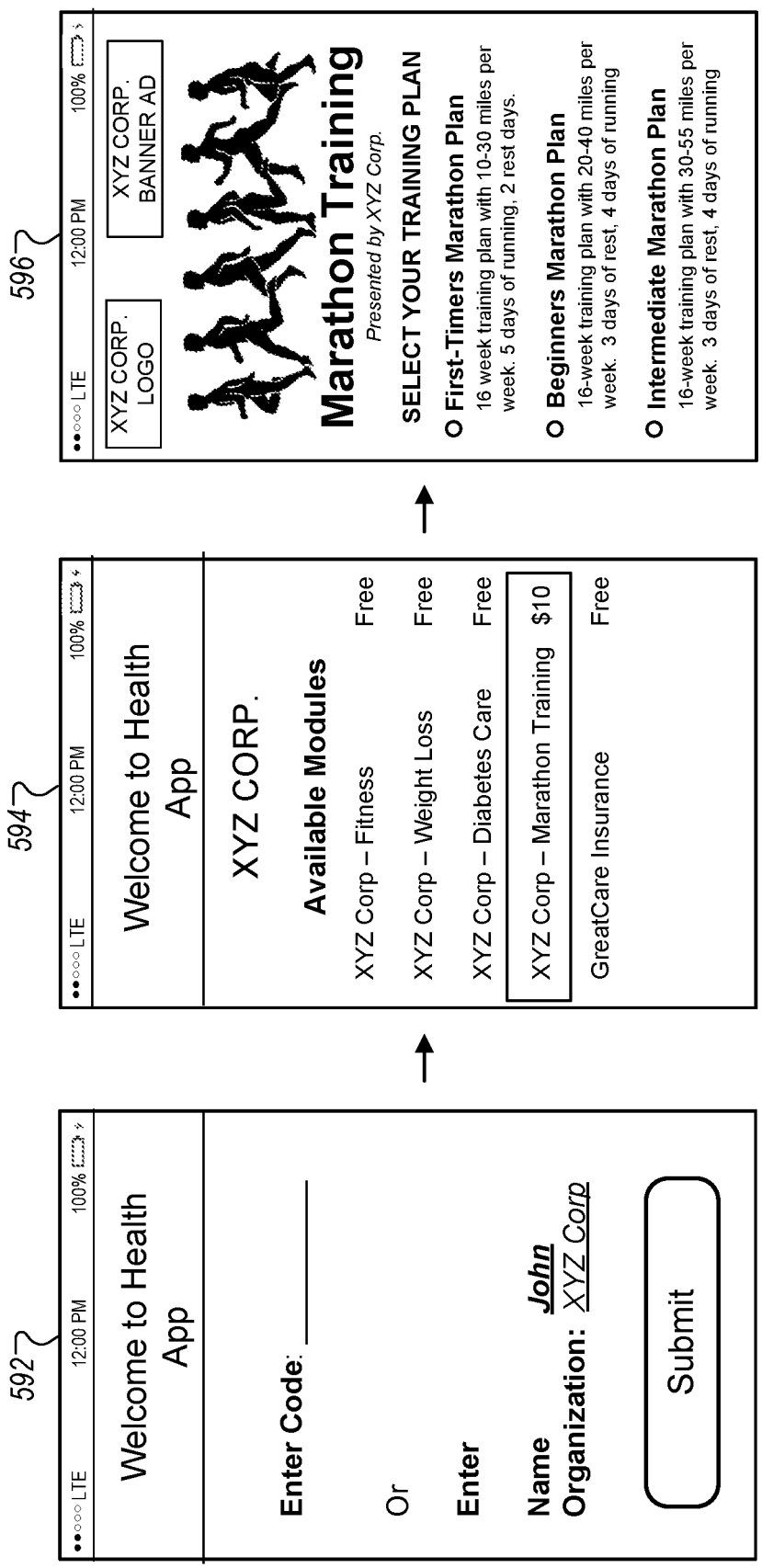
FIG. 5C is a diagram that illustrates an example of user interfaces for selecting a customized module.

FIGS. 5A-5B are diagrams that illustrate examples of customization instructions for generating customized health management modules. FIG. 5A depicts examples of customization instructions that can be generated based on information selected from user forms 510. FIG. 5B depicts examples of customization instructions that can be generated based on different adjustment protocols.

Referring to FIG. 5A, examples of information selected from forms 510 can be form type 520 and form configuration 530. The form type 520 refers to a category assigned to a particular form based on the nature of information included within the particular form. Examples of form types can include a user profile form 522 that requests a user to provide demographic insurance information, and a log entry form 524 that includes data that is used to measure user activity in relation to a treatment program that the user may be registered in. The form configuration 530 refers to an arrangement and presentation of components included within the form 510. Examples of form configurations can include sections 532, fields 534, and icons 536. The sections 532 refer to the individual areas of the form 510 that organize different types of user information. The fields 534 refer to different types of data fields that enable the user to provide field submissions that describe user information. The icons 536 refer to various graphical content that can be associated with providers and client organizations that are associated with the user.

Referring to FIG. 5B, examples of adjustment protocols can be workflows 560, elements 570, and triggers 580. The workflows 560 refer to data aggregation techniques used to propagate user data from multiple sources to generate the customized module 136. Examples of workflows 560 include a simple workflow 562 where user data is aggregated using a linear process using a preconfigured algorithm and a branched workflow 564 where user data is aggregated based on a set of decision points that specify different aggregation techniques for each result of the decision point. For instance, as described previously, rules or conditions can be used to analyze characteristics of user data and perform conditional processes that are designed to be more appropriate for the characteristics of the user data. For example, in some instances, scores representing characteristics of user data can be compared to threshold values to determine the result at a decision point.

The elements 570 refer to different interface elements of the health management modules. Examples of the elements 570 include notifications 572, contents 574, and surveys 576. The notifications 572 can be alerts that are provided to users or providers in response to detecting alarm events associated with detected user data, or periodic updates that provide a user's progress within a treatment program. For example, the notifications 572 can be calorie loss alerts that are associated with a weight loss program). The contents 574 can be user information or data that is included within the health management modules. For example, the contents 574 can be data visualizations for monitored activity data, text fields that include a user's account information, or user input fields that enable a user to submit information that may be relevant to the treatment program. The surveys 576 can be different types of user forms that request information from the user to determine a user's progress within a treatment program. For example, the surveys 576 can include patient response surveys that allow a user to provide pain severity scores during a medical consult to provide information related to symptoms that the user may be experiencing.

The triggers 580 refer to different types of conditions that initiate a set of computer-implemented processes related to the health management modules. Examples of the triggers 580 include log entry based triggers 582, schedule based triggers 584, and tracker based triggers 586. The log entry based triggers 582 initiate processes in response receiving user inputs that match a set of specified conditions. For example, a log entry based trigger can initiate a communication session on the health management modules between a provider and a user based on receiving user input indicating that the user may require emergency medical assistance. The schedule based triggers 584 initiate processes on a reoccurring basis based on a specified schedule associated with user data provided on the health management modules. For example, a schedule based trigger can trigger a display of a daily calorie intake for the user based on times that are associated with the user's exercise regimen. The tracker based triggers 586 initiate processes based on monitoring user data and determining that the monitored user data satisfies one or more condition associated with the monitored data. For example, a tracker-based trigger may track heart rate data and in response to detecting an elevated heart rate above a threshold value, transmit instructions to the update exercise data that is presently displayed on the healthcare management module.

FIG. 5C depicts examples of interfaces 592, 594, and 596 on the mobile application 142. Briefly, the interface 592 displays an initial landing page of the mobile application, which may be displayed after the user installs the application. On interface 592, a user can provide information associated with a particular client organization or customized module to obtain information about available modules. The interface 594 displays a list of available health modules for the particular client organization allowing a user to select an appropriate module. The interface 596 displays a customized health module that has been selected by the user, downloaded to the user's device, and used to customize the experience of the application for a particular client organization.

In more detail, the interface 592 can initially be displayed on the mobile application 142 once the user first runs the mobile application 142 on the user device 150. As depicted, the user can provide information such as a code that is associated with a particular client organization, or identifying information such as a name of the user and the name of the client organization. In these examples, the user-submitted information is provided to the publishing system 130, so that the publishing system 130 can retrieve and return a list of available health modules corresponding to the particular code or the particular client organization that the user indicated. In the example shown, the user indicates that he is an employee of XYZ Corp., and the user submits this information to the publishing system 130.

The interface 594 displays a gallery of available health modules for a particular client organization, e.g., "XYZ CORP" in the example. In addition, the interface 594 presents a list of available modules that are associated with XYZ CORP and with a healthcare provider that is associated with XYZ CORP (e.g., GreatCare Insurance). The available health modules can have pricing options available that are specified by the particular client organization. For example, the module for marathon training includes a ten dollar fee for access. A user can then make a selection of one of the available modules, which then directs the user to the interface 596.

In the example, the user selects the marathon training module on the interface 594, and the module is downloaded to the user's device. As a result, the mobile application customizes its interface to display the information and features specified by the customized module. The interface 596 is an example of an interface of the mobile application after processing the customized health module. The interface 596 can include client organization-specific information such as logos, or marketing and promotional materials. The interface 594 can also display information provided by a healthcare provider associated with the client organization. In the example, marathon training information such as various skill levels for a user, different training regimen for each skill level represents information that is provided by a healthcare provider associated with the XYZ CORP.

In some implementations, instead of entering information about an organization, a user may obtain information about a module by entering a code that is associated a particular module or a particular set of modules. For example, the publishing system 130 may store a table that associates modules with codes corresponding to the modules. An organization may distribute the code for a particular module, e.g., by an e-mail, SMS text message, a web page, or other means. At the interface 592, the user may enter the received code to be taken directly to an interface showing information for a specific module (or specific set of modules). For example, an employer may distribute a code that, when entered into the appropriate field of interface 592 and submitted, brings the user directly to a view describing and making available the customized module for the employer. In some implementations, submitting the code may cause the application 142 to automatically download and install the corresponding module. In some implementations, the code may be provided in a hyperlink or other interactive element that a user can interact with to cause a user device to then automatically open the application 142, submit the code, and either download or show information about a particular module.

In some implementations, the code is used to verify a user's authorization to obtain a module. For example, in addition to providing information associated with the organization on the interface 592, the user can also be asked to provide an authentication code on the interface 594 in order to gain access to an available module for the organization. For example, the authentication code can be provided to users that purchase a subscription service of the organization.

In addition, the available modules that are displayed on the interface 594 can be adjusted based on a permission level associated with the user of the mobile application. For example, the available modules can be associated with age requirements such that if a user attempts to access a particular module with a higher age requirement, the application can restrict access to the particular module. In other examples, the permission levels can also be based on a user classification (e.g., role within an organization) or a different types of purchased subscriptions for healthcare services.

Figure 5D:
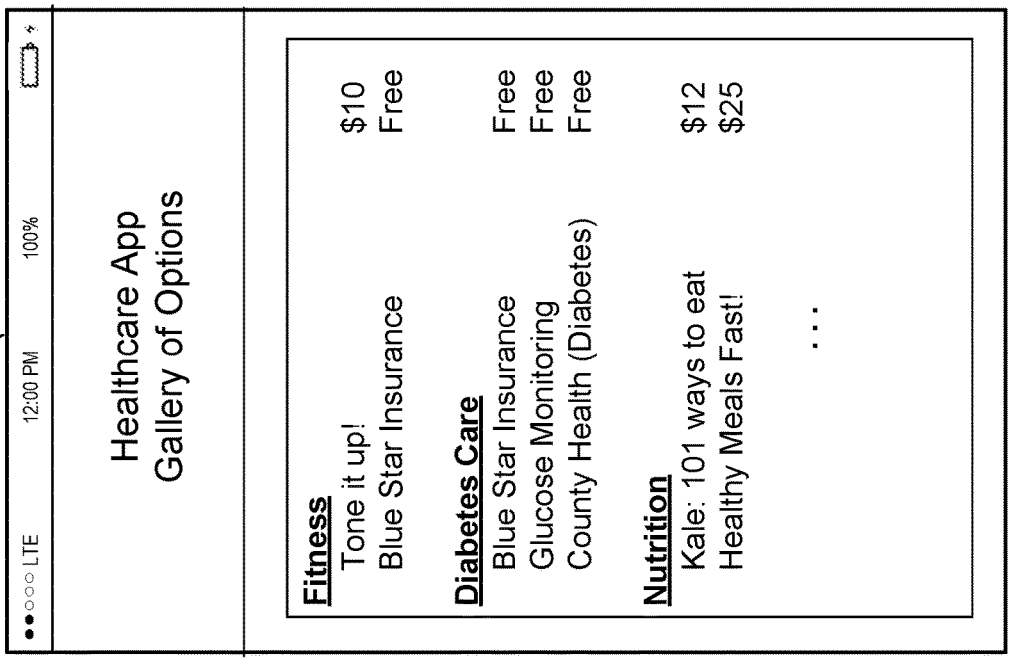
FIG. 5D is a diagram that illustrates an example of a user interface for selecting modules available to a user.

FIG. 5D is a diagram that illustrates an example of a user interface 598 for selecting modules. The interface 598 shows a gallery of different types of modules that are available. For example, the gallery may show a marketplace of modules that are published by the publishing system 130, but which have been customized by various different organizations. These organizations can provide modules that are sold through the publishing platform.

The interface 598 may be shown to any user of the application 142, allowing the user to browse and select one or more modules. As illustrated, the interface 598 may show a gallery or marketplace view showing different categories of available modules. These may be categorized by, for example, medical condition or aspect of wellness addressed by the module, popularity, price, or organization type or organization that is offering the module through the platform.

Figure 6A:
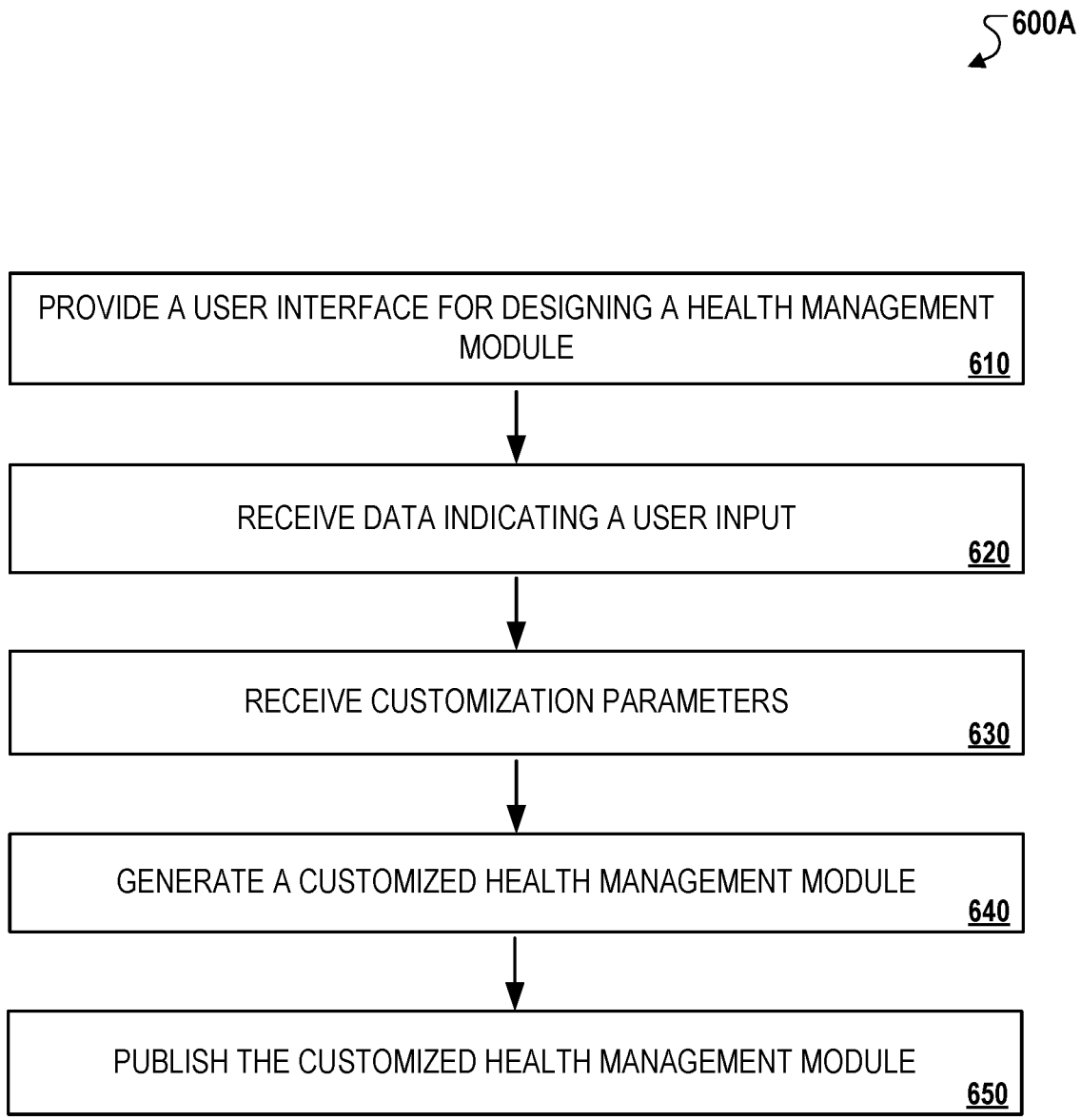
FIGS. 6A-6B are diagrams of examples of processes for publishing a customized module.
Figure 6B:
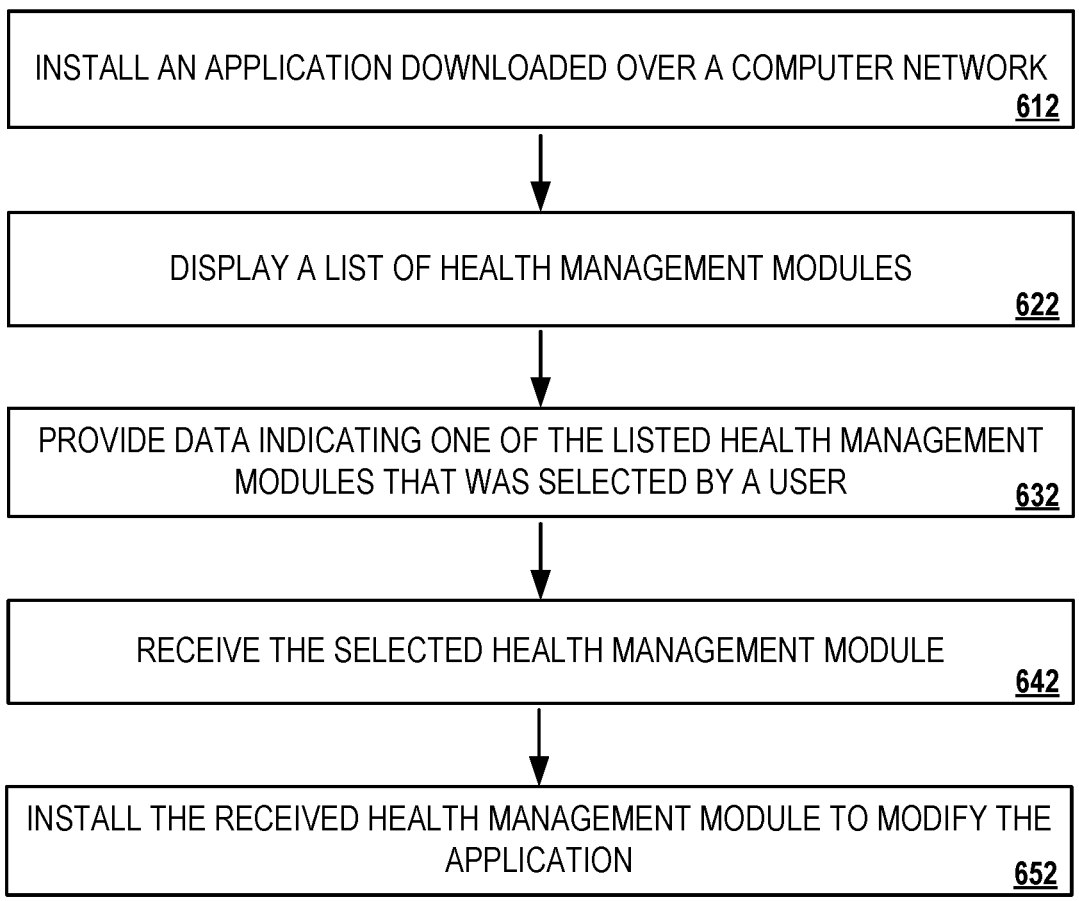

FIG. 6A-6B are diagrams of example of processes 600A-600B for publishing customized health management modules. Referring to FIG. 6A, the process 600A can include providing a user interface for designing a health management module (610), receiving data indicating a user input (620), receiving customer parameters (630), generating a customized health management module (640), and publishing the customized health management module (650).

In more detail, the process 600A can include providing a user interface for designing a health management module (610). For instance, the publishing system 130 can provide the admin portal 112 for designing a health management module. The admin portal 112 can identify a plurality of health management module templates such as the module specifications 114. As described previously, the healthcare management templates can include account information associated with client organizations or user access privileges for particular client organizations or users, and other related information available on the admin portal 112. In addition, the publishing system 130 can also provide the healthcare provider portal 122 for specifying provider information associated with the health management module.

The plurality of health management module templates can include templates corresponding to treatment programs for different treatment programs. For example, as described previously, the plurality of health management module templates can include a set of templates associated with health and wellness programs targeted to improve fitness and another set of templates associated with chronic disease treatment targeted to assist users to recover from treatment procedures. In some instances, the templates indicate treatment recommendations and/or other types of clinically relevant information sent from the provider, tutorials targeted to assist the user, or billing codes associated with specific procedures performed on the user. In other instances, the plurality of templates includes a set of interactivity settings that specify a set of user actions to follow, which types of user forms and surveys to include in the health management module, and when to present the user forms and surveys. In addition, the set of interactivity settings can also define how the mobile application 142 uses the customized health module 136 and a set of instructions that direct how the mobile application 142 interacts with the user.

In some implementations, the user interface for the health management module can be provided as a webpage that includes the user interface. For instance, as described previously, a browsing application on can be used to access the webpage and identify the plurality of health management module templates.

The process 600A can include receiving data indicating a user input (620). For example, the publishing system 130 can receive data indicating a user input from an administrator through the admin portal 112. The user input can include a selection of one of the plurality of health management module templates.

The process 600A can include receiving customization parameters (630). For instance, the customization parameters can initially be generated based on aggregating data included within the module specifications 114 and the module information 124, and then transmitted the customization parameters to the publishing system 130. As described previously, the customization parameters can be used to customize the selected module template for a particular client organization.

In some implementations, the customization parameters can include provider and/or client organization-specific information include links to health insurance networks or lists of healthcare providers that are supported by a client organization that generates the health management module for the user. As described previously, the provider-specific information can include images, names, logos, or other types of marketing and promotional materials associated with a brand of the provider or client organization. In other implementations, customization parameters can update trackers 350 to indicate what information should be transmitted to the user and a time point when the information should be transmitted. The customization parameters can also specify access conditions associated with the information shown in the health management module, or custom health-related goals, initiatives, or contests sponsored by the client organization. The access conditions can specify individuals that can have sufficient privileges to view information shown in the health management module, or specific circumstances where an individual can access the information. For example, the access conditions can provide privileges to view the information that are conditioned upon the occurrence of one or more detected events associated with the individual.

The process 600A can include generating a customized health management module (640). For instance, the publishing system 130 can generate a customized health management module for the particular client organization based on the selected template and the customization parameters.

The process 600A can include publishing the customized health management module (650). For instance, the publishing system 130 can publish the customized health management module on the user device 150 for display to a user. The customized health management module can include the customized module 136 that configures the mobile application 142 on the user device 150. As described previously, the mobile application 142 can be provided by a third-party application store such as the app store 140.

In some implementations, the publishing system 130 may make the customized health management modules accessible over the network 105 for access by the mobile application 142 on the user device 150. As described previously, the mobile application 142 can be installed on the user device 150 from the app store 140 and afterwards the mobile application 142 can receive data transmissions from the publishing system 130 that include the customized health management modules. In some instances, the publishing system 130 can also provide an index of available modules to the mobile application 142 or search results indicating relevant modules for search criteria associated with the modules. For example, a user can provide search criteria for a particular treatment program on the mobile application 142, and in response the publishing system can provide the search results indicating the relevant modules that include one or more features associated with the particular treatment program.

In some instances, in addition to making the customized health management modules accessible over the network 105 for the mobile application 142, the publishing system 130 can also transmit a set of instructions such that the customized health management modules change the operation of the mobile application 142 on the user device 150. For example, the set of instructions can enable the customized health management modules adjust the visual attributes of the mobile application 142, provide notifications associated with the customized healthcare modules, or enable the customized health management modules to interact with existing components of the mobile application 142.

Referring now to FIG. 6B, the process 600B can include installing an application downloaded over a computer network (612), displaying a list of health management modules (622), providing data indicating one of the listed health management modules that was selected by a user (632), receiving the selected health management module (642), and installing the received health management module to modify the application (652).

In more detail, the process 600B can include installing an application downloaded over a computer network (612). For instance, a user can install the mobile application 142 on the user device 150 from the app store 150. The mobile application 142 can be downloaded over the network 105 from a content provider server.

The process 600B can include displaying a list of health management modules (622). For instance, after installing the mobile application 142 on the user device 150, the user device 150 can display a list of health management modules provided by the publishing system 130. As described previously, the publishing system 130 is independent of the content provider server of the app store 140.

The process 600B can include providing data indicating one of the listed health management modules that was selected by a user (632). For instance, the publishing system 130 can provide data to the user device 150 indicating one of the listed health management modules that was selected by the user of the user device 150.

The process 600B can include receiving the selected health management module (642). For instance, the user device 150 can receive the selected health management module. In some instances, the received health management module is the customized health module 136 as depicted with respect to FIG. 2A.

The process 600B can include installing the received health management module to modify the application (652). For instance, the user device 150 can install the received health management module to modify the mobile application 142 to interact with the user according to the received health management module. As an example, the display of the user interface of the mobile application 142 can be adjusted based on the received health management module so that user can view client organization-specific information that is included within the received health management module.

The techniques discussed above may be used for generating, publishing, updating, and managing customized modules for many different purposes. For example, while various examples discussed refer to healthcare management modules, customized modules may be generated and published for uses outside the healthcare area.

Section 2

FIGS. 7A-11 describe a system enables an administrator to customize a set of rules to dynamically adjust the configuration and output of an application provided to users. The rules may include combinations of triggers, evaluation conditions, and system actions, so that satisfying appropriate triggers or evaluation conditions results in the execution of the corresponding system actions. The rules can be configured by the administrator prior to the start of a user engagement program provided through the application, and then subsequently adjusted by the administrator during the user's participation in the program. Adjustments to rules by the administrators can be made in real-time to adapt to and/or accommodate the interaction of users with the application. In this regard, configuration of the rules allows for the creation of various programs available through a single application, where the programs can be applicable for a large user population. Although general sets of rules may apply to many different users, the outcome of the rules can use the context of each user in determining which content and interactions to provide, resulting in a personalized experience tailored for each user even when using the same rule set.

The system includes a decision engine module that periodically processes or evaluates a set of rules configured by the administrator for a program based on data submitted by users while participating in the program. For instance, in response to determining that a trigger and evaluation condition associated with a rule is satisfied, the decision engine module may then execute a set of system actions specified by the rule due to a user's performance on the program. In other instances, the administrator may reconfigure an existing rule, or add a new rule, during the user's participation in the program, which then automatically adjusts the evaluation techniques used by the decision engine module to evaluate the set of rules associated with the program. In this regard, the system provides a dual feedback mechanism, allowing dynamic reconfiguration of an application based on both the input provided by the administrator and input provided by the user.

The selection of the set of rules enables an administrator to control various aspects of the program in a modular fashion. In some instances, different rules may provide complementary configuration settings that are then evaluated in aggregate by the decision engine module. For example, a first rule may specify evaluation conditions for milestones associated with a user's performance within the program, whereas a second complementary rule may specify types of content to be provided to the user in response to a determination that the conditions for the first rule have been satisfied. The administrator may customize a particular group of rules for a particular program to target specific sets of users based on a set of factors associated with the program (e.g., user type, medical treatment type, medical conditions, etc.). In addition, the administrator may further customize the triggers and/or evaluations conditions specified for each rule within a group in order to adjust the evaluation techniques used by the decision engine module. The assignment of rules to groups, programs, and/or user types can enhance the efficiency of the decision engine module. For example, rather than processing the full set of rules for each user, the system can quickly filter the rules to a customized subset of rules applicable to each respective user. This filtering increases responsiveness of the platform and decreases the amount of computation required to support large sets of users.

The system also enables an administrator, such as a healthcare provider or insurer, to monitor the ongoing activity of users and adjust the triggers and conditions of the set of rules to provide content that is directed to increasing the likelihood that users will complete the program or achieve a desired outcome. In this regard, the system can be used as a content delivery platform to a variety of users using different programs that supply different content and user experiences, and also personalize each program for each individual user. As rule sets are used over time, the system can assess the effectiveness of individual rules and combinations of rules in maintaining user engagement and achieving desired outcomes. Through analysis of user inputs and user behavior, e.g., as detected with sensors of user devices, the system can determine which rule components, rules, and/or combinations thereof are correlated with successful outcomes for users. The system can then provide an administrator with suggested new rules, or suggested changes to existing rules, that are determined to improve user engagement and user outcomes.

The architecture of the system provides various improvements in dynamically adjusting output of a program to individual users, which often requires significant computing and storage resources on server systems. For example, in order to generate customized interactions with individual users, server systems often require storage of different application configurations and associated files for implementing the different configurations on individual client devices. The architecture of the present system, however, utilizes a decision engine module that processes a set of rules that configure a program based on specifications of triggers, evaluation conditions, and system actions associated with individual rules, or the composition of a collection of rules that interact with each other to configure a program. For instance, use of the decision engine module reduces the number of manual actions necessary to generate a large number of variations of a particular program. As described below, the architecture can automate system actions based on the satisfaction of triggers and evaluation conditions specified by rules associated with the particular program.

In addition, the architecture of the system enables the system to address various problems that arise in the networked environment of server-based applications. As an example, application configurations that are provided to client devices by servers are often static for significant periods of time and may require major updates to application code for configuration changes to apply. This can be time consuming for application developers and for end-users since it requires periodic manual reconfiguration of applications, and periodic delivery of the reconfigured applications. As described in more detail below, the architecture of the system addresses this problem by, among other techniques, employing a rule-based decision engine that uses a collection of hierarchal rules to automatically adjust application configuration with limited developer intervention. Moreover, processing of these rules by the system can automatically and dynamically alter a user's experience with the application without requiring users to manually download application updates.

Further, the implementations discussed below can provide ongoing customization of user experiences in an efficient manner, reducing computation need, power consumption, and other resource requirements. Processing the rules for a large set of users can be done efficiently by limiting processing of rules for a given user to a particular subset of rules applicable to the user. Even for rules in the subset, processing can be limited by using the trigger as a threshold test, so that further processing of the rule is not performed until and unless the trigger is detected.

Another problem that often arises in networked environments is that applications are often unable to provide effective real-time adjustments that are appropriate for a user's particular circumstances. For example, while some applications can process historical data and provide analyses and recommendations, such applications are often unable to dynamically adjust (i) the content that is provided to the user on the application, and (ii) the arrangement specifications of the application (e.g., types and characteristics of interface elements, color schemes used in style specifications, etc.) without requiring a manual application update. As described in more detail below, the architecture of the system can address this problem with, among other techniques, the use of a collection of rules that associates triggers and conditions with actions to be executed by the system. The scope of each rule can be manipulated based on selections of the triggers, conditions, and system actions by an administrator. In this regard, some rules can be applied to make general adjustments (e.g., providing notification badges, or adjusting content provided), whereas other rules can be applied as context-specific changes that respond to user behavior.

In one general aspect, a computer-implemented method includes: providing, by the one or computers, a configuration interface for setting rules that dynamically adjust output of an application provided to a plurality of users, the configuration interface permitting the rules to be specified using combinations of triggers, conditions, and actions; receiving, by the one or more computers through the configuration interface, data indicating one or more rules and, for each of the one or more rules, data that specifies (i) at least one trigger or condition, and (ii) one or more system actions to be performed in response to a satisfaction of the at least one trigger or condition; receiving, by the one or more computers and from multiple client devices, activity data indicating user interaction with the application or sensor data for at least some of the plurality of users of the application; determining, by the one or more computers, that the activity data for a first subset of the plurality of the users satisfies the at least one condition or trigger and that the activity data for a second subset of the plurality of the users does not satisfy the at least one condition or trigger; and communicating, by the one or more computers, with client devices associated with the users in the first subset to adjust output of the application according to the one or more system actions of the one or more rules, while not adjusting the output of the application for the users in the second subset based on the one or more rules.

One or more implementations can include the following optional features. For example, in some implementations, dynamically adjusting the output of the application includes adjusting an arrangement of content specified by the rules, where the content is provided for display at the client devices associated with the users in the first subset of the plurality of the users for which the activity data satisfies the at least one condition or trigger.

In some implementations, the system action specified by the rule includes an action to provide content for display in the application; and communicating with client devices associated with the users in the first subset includes providing, by the one or more computers and to the client devices associated with users in the first subset, the content specified by the rule to the client devices associated with the users in the first subset.

In some implementations, the method includes obtaining, by the one or more computers, data indicating historical information indicating the satisfaction of triggers or conditions over a particular period of time; and providing, on the configuration interface, a user-selectable option on the configuration interface to adjust one or more existing rules.

In some implementations, the method further includes: obtaining, by the one or more computers, data indicating historical information indicating received activity data that has satisfied one or more triggers or conditions over a particular period of time; providing, on the configuration interface, a user-selectable list of preconfigured rules that are identified based on the received activity data; and adding, based on a user selection from the user-selectable list, a particular rule of the preconfigured rules to a program provided through the application.

In some implementations, the application provides access to a plurality of programs that each provide different sets of interactive content through the application; the rules that dynamically adjust output of the application include (i) one or more global rules that are associated with each of the plurality of programs and (ii) one or more program rules associated with only a particular program of the plurality of programs.

In some implementations, the method includes providing, by the one or more computers and for output on the configuration interface, a user-selectable option to: (i) adjust a collection of rules associated with a particular program that includes at least one rule, or (ii) adjust the combination of the triggers, conditions, and actions for the at least one rule.

In some implementations, the configuration interface includes a set of filters that each provide selections of program criteria for a particular program; and providing the configuration interface for setting rules that dynamically adjust output of the application includes providing a user-selectable list of preconfigured rules that are predetermined to associated with the selections of program criteria for the particular program.

In some implementations, the configuration interface is provided to a plurality of administrators that are each associated with a different organization; and the one or more rules are each associated with respective programs provided by the different organizations.

In some implementations, the configuration interface provided to the plurality of administrators is associated with a single application provided to the plurality of users.

Figure 7A:
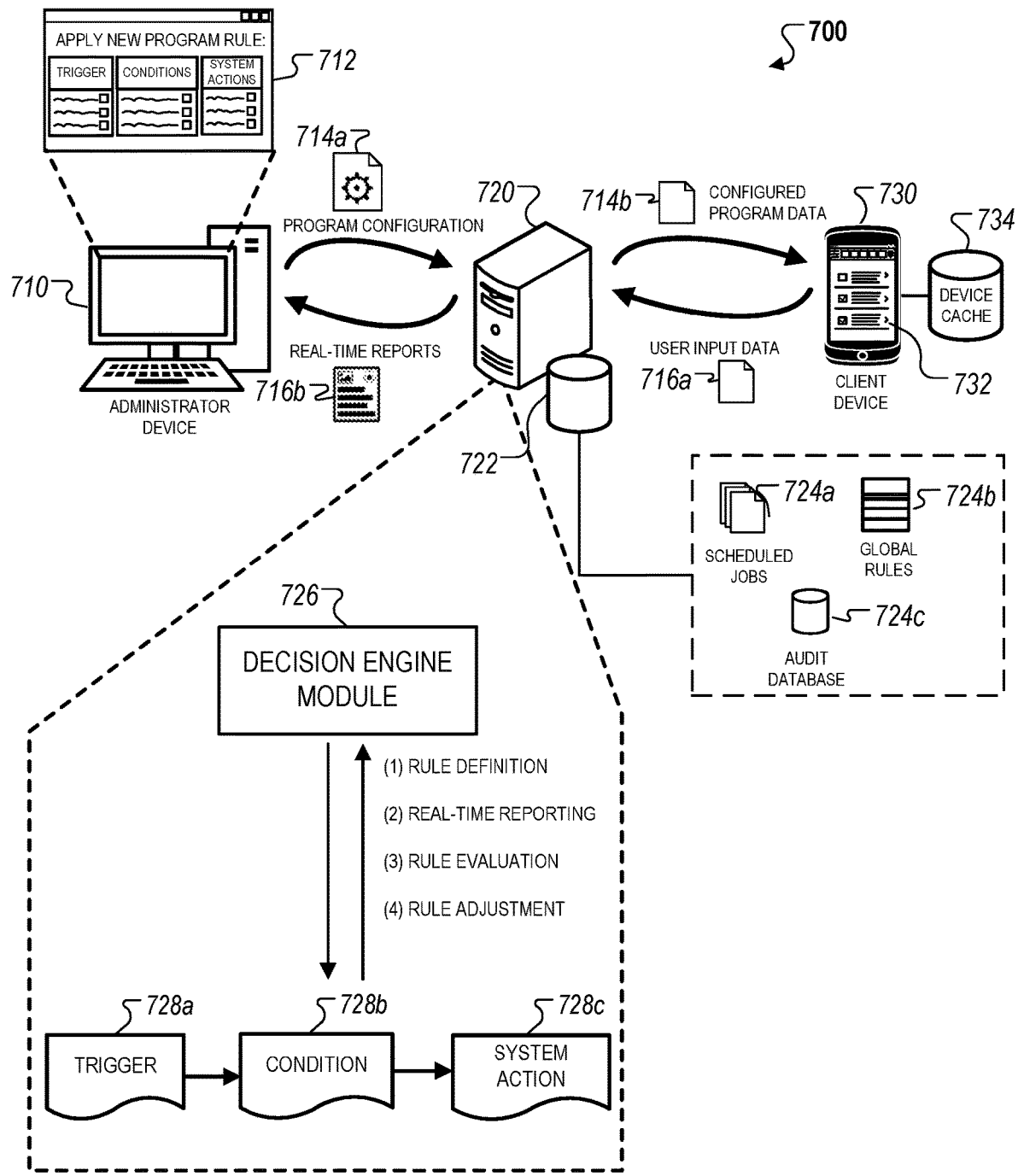
FIG. 7A is a diagram that illustrate an example of an electronic system that is capable of configuring rules that dynamically adjust application behavior.
Figure 7B:
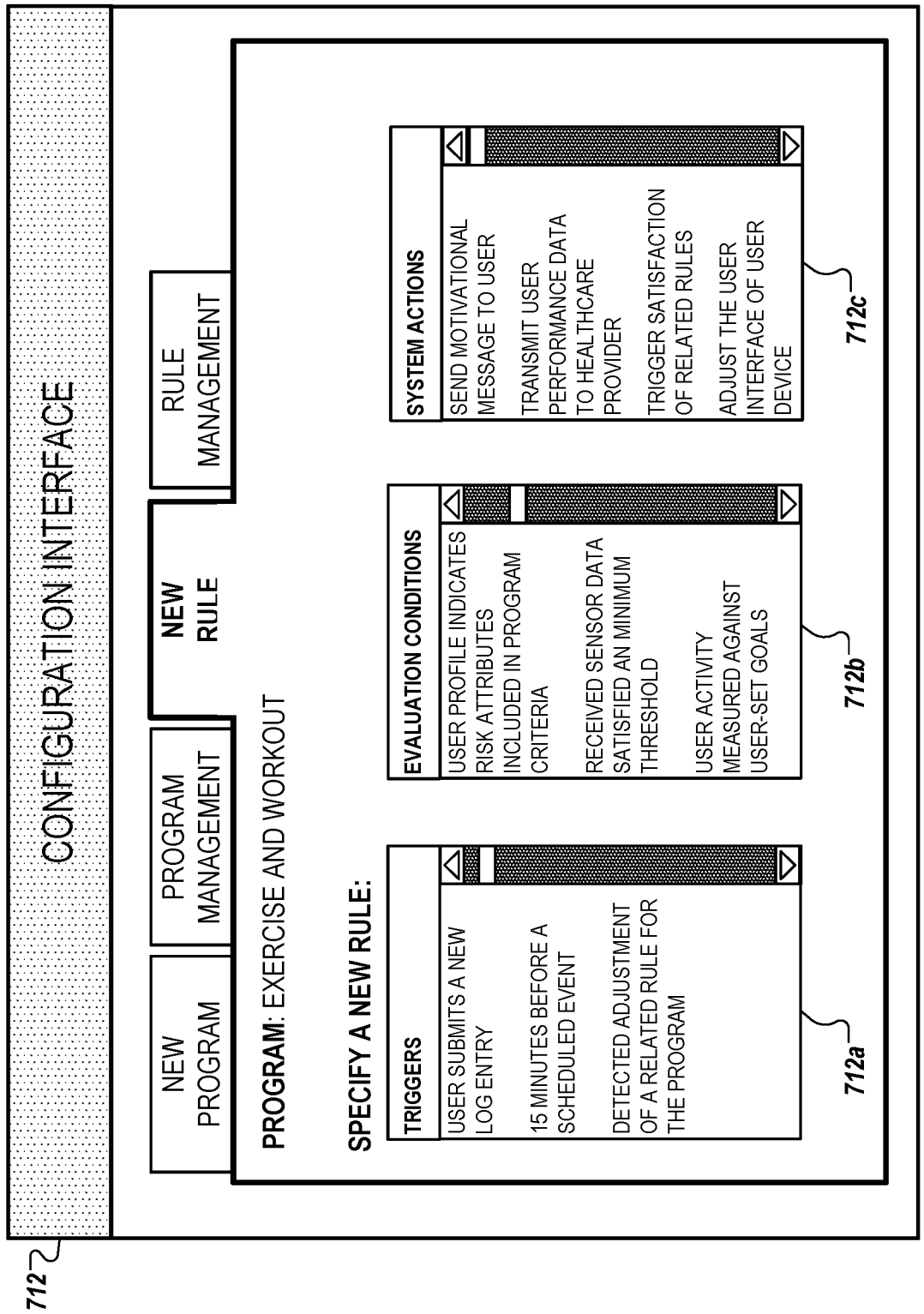
FIG. 7B is a diagram that illustrates an example of a user interface that may be used to configure rules for a program.

FIG. 7A is a diagram that illustrates an example of an electronic system 700. The system 700 generally includes one or more administrator devices 710, a server 720, and one or more client devices 730 connected over a network 705. The administrator device 710 provides a configuration interface 712 that enables an administrator to configure a set of rules 732 that dynamically adjust output of the application 732 provided to users associated with the client devices 730. The server 720 includes a decision engine module 726, which generates and adjusts configuration of a set of rules based on input provided by an administrator on the interface 712. FIG. 7B illustrates a diagram of the decision engine module 726 in greater detail.

In general, a system enables an administrator to customize a set of rules that dynamically adjust the configuration and output of an application provided to users. The rules may include sets of triggers, evaluation conditions, and system actions. When certain triggers or evaluation conditions are satisfied, the system actions specified by the rules are executed. The rules can be configured by the administrator prior to the start of a program on the application, and then subsequently adjusted by the administrator during the user's participation in the program. The system acts as a platform that allows third parties, such as administrators of different programs, to easily fine-tune their rules to adjust the user experiences provided through their programs.

Adjustments to rules by the administrators can be implemented in real-time to change the way an application interacts with users. In this regard, configuration of the rules allows for the creation of various programs on a single application that are applicable for a large user population. Although general sets of rules may apply to many different users, the outcome of the rules can use the context of each user in determining which content and interactions to provide, resulting in a personalized experience tailored for each user even when using the same rule set. At any given time, the actions performed by combinations of the rules will be different for different users, providing each user a unique experience tailored to his or her unique circumstances.

As used with respect to FIGS. 7A-11, an "administrator" refers to an entity or individual that interacts with a configuration interface of the system to manage a program. This can include specifying a set of triggers, evaluation conditions, and system actions for individual rules, and/or a collection of individual rules that are to be associated with a particular program. As an example, the administrator may use the configuration interface to specify the definitions (e.g., triggers, evaluation conditions, system actions) of five individual rules, and then further specify that three of the five rules are associated with a first program and that the two remaining rules are associated with a second program. In some instances, a single rule may be associated with multiple programs, whereby the multiple programs have overlapping collections of associated rules. The administrator may also use the configuration interface to identify a list of users that are eligible to receive the program, data indicating applicable healthcare providers or insurance plans, access privileges associated with particular features of the programs, or custom content that is provided on the program.

As used with respect to FIGS. 7A-11, a "program" refers to a set of rules or instructions that define a user experience provided through an application. A single application can make multiple different programs available to a user, and different programs may be managed and provided by different organizations. As discussed below, a program can include collections of interactive content and rules that define when and how content should be delivered through an application. Although a program can include executable software, it is not required to be defined in this manner. Rules that define a program may be processed or interpreted by multiple devices, including user devices and server systems, to create the customized user experiences that a program provides. In some implementations, at least part of a program is implemented as a service, with one or more server systems dynamically selecting and delivering at least some of the program content to a client device, customized for a specific user.

As used with respect to FIGS. 7A-11, a "healthcare provider" refers to any of various individuals, institutions, or organizations that provide healthcare services to users. In some instances, the healthcare provider can be an individual health professional such as a physician, or an entity such as a hospital that provides preventative, curative, or rehabilitative programs for users, or a health insurance provider. Healthcare providers can use a provider portal to interact with the system, both to submit information that is accessed through appropriate modules and to receive information from users of certain modules to use in enhancing treatment. As an example, healthcare providers may submit health-related information such as electronic health records, treatment program information, or promotional material. This information may be general for a group of users (e.g., for all users who have a particular insurance plan) or specific to individual users.

As used with respect to FIGS. 7A-11, a "user" or "patient" refers to an individual that uses a mobile application and one or more programs provided through the application. In some instances, the user receives healthcare-related services from the healthcare provider. For instance, the user can use a mobile application that provides a customized experience using a healthcare program created by or on behalf of the user's employer, the user's insurance company, or another entity.

As used with respect to FIGS. 7A-11, a "trigger" refers to a pre-specified event or situation that signals when a rule is applicable. For example, an individual rule may have a trigger that indicates when an associated condition should be evaluated, or the occurrence of which causes the system to perform a corresponding system action specified for the event or condition. Examples of triggers include exceeding a threshold value associated with a particular user data metric (e.g., maximal heart rate for exercise condition), receiving data that is flagged for system action (e.g., receiving an email from a healthcare provider including an updated treatment regimen), among others. Other examples of triggers are discussed below.

As used with respect to FIGS. 7A-11, "evaluation conditions" generally refer to criteria for determining whether a list of actions associated with a rule should be performed. These conditions can be expressed as logical expressions that specify a set of comparisons (e.g., greater than, less than, equal to, etc.) of data values to expected values in order to evaluate whether a condition has been satisfied. For instance, the data may include log entry data provided by users as input on the application, data indicating a program status associated with users, and/or data indicating input provided by the administrator on the configuration interface. The evaluation conditions may include multiple conditions that are each associated with specific categories of data. For example, different conditions may each be associated with a data type category, a data property, or a data property mapping.

The evaluation conditions can be used to measure a user's performance within the program against a set of program criteria specified by the administrator. For instance, the evaluation conditions can be used to determine a user's adherence to one or more treatment goals associated with a program. As an example, an evaluation condition may specify a target daily calorie loss for an exercise program, and in response to determining that the measured calorie loss for the user is greater than the target daily calorie loss, the system may determine that the evaluation condition has been satisfied. As described with respect to FIGS. 7A-11 regarding triggers, the evaluation conditions may also be adjusted by the administrator after an initial configuration of the program.

As used with respect to FIGS. 7A-11, an "action" (or "system actions") refer to one or more automatic actions performed by the system in response to a satisfaction of at least one trigger and/or evaluation condition specified by an individual rule. Examples of actions may include transmitting push notifications to various devices associated with the program (e.g., administrator device, client devices, provider device, etc.), escalating a status of a particular user's account associated with the program, delivering content to a particular user device, transmitting prompts to enable a user to provide information on a user interface of the application, among others.

In general, the architecture of the system 700 enables the server 720 to perform data processes that would otherwise be resource-intensive, such as dynamically processing configurations and concurrently adjusting program outputs for many different users of the mobile application 732 on different user devices, using minimal resources. For example, the server 720 periodically exchanges communications with the administrator device 710 and the user device 730 such that updated program configurations transmitted by the administrator device 710 are automatically transmitted to the user device 730 without a manual request to update the mobile application 732 on the user device 730 (e.g., by an update processed through an app store). In some implementations, the server 720 provides instructions, on an on-going basis, that adjust the interface of the application 732 in different ways for different users, according to the context and characteristics of each user.

In addition, the server 720, the administrator device 710, and the user device 730 periodically exchange data operations that enable automatic configuration and adjustment to the output of the mobile application 732 to the user device 730. For example, in each data communication with the administrator device 710 and the user device 730, the server 720 transmits a set of instructions that cause the administrator device 710 and the user device 730 to delete application data that is no longer determined to be relevant or useful to the progress of the user through the software program (e.g., outdated or satisfied rules). Instead, the server 720 transmits instructions to install additional program data that are to be specified for display on either the configuration interface 712 or the mobile application 732. In this regard, the periodic exchange between the server 720, the administrator device 710, and the user device 730 enables both the administrator device 710 and the user device 730 to utilize less storage to execute processes related to outputting the mobile application 732 based on the rules specified on the configuration interface 712.

Referring initially to the components of the system 700, the administrator device 710 may be any type of electronic computing device that is capable of providing a user interface to accept input from an administrator. For example, the administrator device 710 may be smartphone, a tablet computing device, a wearable computing device, or any other type of electronic computing device.

The configuration interface 712 can be an interface associated with an administrator portal where an administrator provides input to configure programs associated with the application 732. For instance, as depicted in the example, the configuration interface 712 enables an administrator to specify a new rule associated with a particular program provided through the application 732. The configuration interface 712 also enables the administrator to provide real-time adjustments to rule definitions and/or collections of rules associated with a particular program in order to dynamically adjust output of the application 732 on the user device 730.

The configuration interface 712 may be presented on the administrator device 710, for example, as a webpage or through an administrator application associated with the application 732. In some implementations, the administrator application may be a mobile or desktop application from an organization that provides the application 732. In other implementations, the configuration interface 712 may be a separate interface on the application 732 that is provided only to administrators. In such implementations, the administrator may use specific user credential data to obtain access to the configuration interface 712.

The server 720 may be one or more electronic computing devices located remotely from the user device 730. The server 720 monitors and controls the data transmissions between the administrator device 710 and the user device 730. For instance, the server 720 can process data that is periodically exchanged between the administrator device 710 and the user device 730 in order to dynamically adjust output of the application 732 to the user device 730. The server 720 includes a database 722 that stores program data. The stored program data can include scheduled jobs 724$a$, global rules 724$b$, and audit logs 724$c$.

The scheduled jobs 724$a$ can be a queue of actions and/or processes to be executed on the user device 730 based on satisfaction of triggers and/or evaluation conditions of individual rules since the prior data exchange between the server 720 and the user device 730. For instance, the content of the scheduled jobs 724$a$ can be adjusted based on the operations of the decision engine module 726 such that, at each instance when the decision engine module 726 determines that the trigger or an evaluation condition for a particular rule has been satisfied, the corresponding system action to be performed is then added to the scheduled jobs 724$a$. In this regard, the scheduled jobs 724$a$ specifies a set of instructions that are included within the configured program data 714$b$ during the next data exchange between the server 720 and the user device 730.

The global rules 724$b$ can be a set of configuration rules associated with protocols for various programs that are provided on the mobile application 732. The global rules 724$b$ can be used to trigger the display of specific user-selectable content based on the data in the user input data 716$a$ satisfying one or more triggers or evaluation conditions specified by the global rules 724$b$. An example of a global rule is that access to new content should be provided if a user action has satisfied a trigger for a particular program. Another example of global rule is that a notification on the application 732 should be provided if received user input data 716$a$ indicates that as a daily minimum level of physical activity has not been met by the user.

The audit logs 724$c$ may be a repository that tracks information associated related to the satisfaction of triggers and/or evaluation conditions specified by individual rules associated with a program. For instance, the audit logs 724$c$ may include timestamps indicating when a particular trigger or evaluation condition was satisfied by activity of the user on the application 732, and other associated information such as, for example, a classification of the type of user activity satisfying the trigger or condition, a rule identifier corresponding to the applicable rule, user data within a particular time window before or after the satisfaction of the trigger or condition. The audit logs 724$c$ essentially provide performance-related information associated with condition evaluation such that an administrator can then evaluate the effectiveness of previously configured rules given the information indicated by the audit logs 724c. In some instances, the data included within the audit logs 724c may be repackaged and transmitted for display on the configuration interface 712 as data reports, e.g., in the form of data visualizations, output of decision support algorithms, or performance summaries.

The server 720 also includes a decision engine module 726 that performs a set of operations generally including rule definition, real-time reporting, rule evaluation, and rule adjustment. Briefly, rule definition refers to a configuration of a program based on the data included within the program configuration 714a received from the administrator device 710. Real-time reporting refers to dynamic processing of the user input data 716a and generation of real-time reports 716b concurrently with the execution of a configured program on the application 732. Rule evaluation refers to automated processing and analysis of the user input data 716a in relation to rules in the program configuration 714a. Rule adjustment refers to the processing of a set of rule adjustments, received from the administrator device 710, for an already configured program based on the transmitted real-time reports 716b. More particular descriptions of operations performed the decision engine module 726 are provided with respect to FIGS. 8A-8B.

The user device 730 can be any of the various types of electronic devices that are capable of providing a user interface. Although FIG. 7A depicts the user device 710 as a smartphone, in other implementations, the device 710 can be, for example, a tablet computing device, a laptop computing device, a desktop computing device, or a wearable device (e.g., a smart watch, glasses, or a bracelet). In addition, the user interface of the application 732 provided on the user device 730 may include information provided through a visual display, but may additionally or alternatively provide information through, for example, audio output, haptic output, or other output, which may be dynamically configured based on information associated with the user.

Referring now to the example depicted in FIG. 7A, the administrator device 710 initially transmits a program configuration 714a to the server 720. The decision engine 726 then generates a set of configured program data 714b to transmit to the user device 730 based on the triggers 728a, conditions 728b, and system actions 728c included within the program configuration 714a, and program data stored on a database 722 (e.g., scheduled jobs 724a, global rules 724b, audit logs 724c). The user device 730 then generate and provide the application 732 for display to users based on the configured program data 714b.

After the application 732 is provided for output on the user device 730, the server 720 then periodically monitors user activity data 716a describing user interaction with the application 732. The user activity data 716a is collected and transmitted to the server 720, which then evaluates the effectiveness of the program configurations 714a. The results of the evaluation are then aggregated and packaged into a set of real-time reports 716b, which are then transmitted back to the administrator device 710 for rule assessment and adjustment. As described more particularly below, this process may be iteratively performed to dynamically adjust the output of the application 732 on the user device 730 without any intervention or action by the user.

In more detail, the program configuration 714a specifies a set of rule definitions provided by the administrator through the configuration interface 712. For example, an administrator may define a rule by associating one or more triggers and/or evaluation conditions with one or more system actions. In another example, the administrator may also specify that a collection of rules that are associated with a program that is provided on the application 732. In this regard, the program configuration 744a specifies definitions for individual rules (e.g., administrator-specified associations of triggers, evaluation conditions, and system actions), and a collection of rules to be associated with a particular program.

The configured program data 714b includes instructions for the user device 730 to execute a set of operations related to the output of the application 732. For example, the configured program data 714b may include instructions to execute the scheduled jobs 724a which were previously stored on the database 722. As another example, the configured program data 714b may instruct performance of system actions specified by rules which have triggers and/or evaluation conditions that have been determined to be satisfied by the decision engine 726. This can include providing customized content specified by rules that are determined to be satisfied, arranging content in a particular arrangement specified by rules that are determined to be satisfied, and so on. Of course, some system actions may be performed by the server 720 while other system actions may be performed by the client device 730.

In some instances, when program rules are processed by the client device 730, the configured program data 714b includes data indicating adjustments to rules that are provided by the administrator on the configuration interface 712. In such instances, the configured program data 714b is used to dynamically adjust the output of the application 732 on the user device 730.

The user input data 716a may include data indicating user interactions with the application 732, and/or sensor data generated or received by the user device 730. For instance, the user input data 716a may include survey response data submitted by the user on the mobile application 732, user selections in response to requests for information, among other types of user input data. The user input data 716a can also include sensor data received by the user device 730 and provided by the user while participating in activities associated a particular program. For example, sensor data can include heart rate measurements of a user during an exercise-related activity, a picture of the user and/or a region of the body of the user undergoing treatment, or physiological measurements made by external devices that exchange data communications with the user device 730 during a specified period of a particular program.

With respect to FIGS. 7A-11, a program can be structured based on different configurations of applicable rules by the administrator. In some instances, a program can be varied based on combinations of triggers, conditions and system actions for each individual rule. In other instances, a program can be varied based on the composition of a collection of rules where individual rules interact with one another to configure the program. In each instance, an administrator can configure rules that alter the experience provided to users of a program.

The program can also be adjusted after configuration by the administrator. For instance, an administrator may adjust the specifications of individual rules or adjust the composition of individual rules within a collection of rules for a particular program in order to adjust the program after initial configuration. The program adjustment may be processed by the system in substantially same manner as an initial configuration so that adjustments can be dynamically provided to users without requiring any additional actions from the user. The adjustments to rules can, in turn, change various aspects of the program. For example, adjustments can specify (i) different collections of content items to provide as part of a program, (ii) different interactivity settings that coordinate the presentation of content items on an interface of the application, (iii) different arrangements of previously provided content items, among others.

To minimize the computational resources requirements necessary to provide personalized content, the system utilizes a set of global rules that enable a server to perform a smaller number of processing steps to provide personalized experience for all users while providing varied user interfaces. For instance, the rules can be used to adjust types of content provided for each individual user using a set of common adjustment and distribution schemes to allow for use shared resources in providing personalized content for groups of users that are predetermined to be similar to one another. For example, the server may be capable of clustering content data based on prior activity within a program, similar demographic information, by similar programs, among other types of classifications.

The set of rules associated with a program can vary in scope and in hierarchy to enable the system to select particular rules from the set of global rules to adjustably execute aspects associated with the data processing of the personalized content. In this regard, the system may select applicable rules to guide data processing in order to maximize resource allocation efficiency. For example, rule selection may be based on the different types of content to be provided, the size of the content to be provided, and/or the number of users that are associated with particular types of content to be provided.

The rules associated with a program can also have an assigned scope of applicability. Different rules may be designated to apply for only specific segments, tracks, or levels within a program. Rules may be defined for combinations of these program elements. For example, a rule may be defined to apply only during a particular segment or time period of a program and also only for a particular track and level within the track. The data for each rule may include a value or code that indicates its applicability, allowing the appropriate rules for any given portion of a program to be efficiently identified. In some implementations, the rules are arranged in a hierarchy, with some rules being applicable to a program in its entirety, some rules being applicable only for specific time periods, and others being applicable in more specific situations. Also, the computer systems that allow administrative users to build programs can provide user interfaces that allow the administrative users to alter a program by adjusting the applicability of the rules, to efficiently adjust the user experiences provided by the program.

Multiple triggers may be specified for an individual rule. In some instances, a rule may specify triggers that are each associated with different system events, but are all associated with the same system action to be performed upon the single occurrence of one of the system events specified by the triggers. In other instances, system actions may be associated with combinations of triggers such that the system action is performed after occurrences of a specified subset of triggers. In such instances, multiple system actions can be associated with different subsets and/or combinations of trigger events to further specify performance of specific actions in relation to the occurrence of particular combinations of events.

Programs can be created and administered for a wide variety of topics and purposes. Some examples below describe ways that a program may be used to encourage and assist a user to improve health, e.g., by establishing better habits or helping to deal with a medical condition. The techniques of generating, delivering, and using programs is not limited to healthcare, however, and the same techniques can be used to provide customized user experiences to many other types of applications.

FIG. 7B is a diagram that illustrates an example of the configuration interface 712 that can be used by the administrator 702 to configure rules to dynamically adjust output of the application 732. For instance, the configuration interface 712 enables an administrator to configure a new rule by associating one or more triggers, one or more evaluations, and a system action from a list of available options for each selection. While the descriptions below are provided for exemplary purposes, more particular descriptions related to the different types of triggers, evaluations, or system actions are provided with respect to FIG. 9.

The configuration interface 712 provides a list of triggers 712a, a list of evaluation conditions 712b, and a list of system actions 722c. The list of triggers 712a identifies events that initiate the rule evaluation techniques performed by the decision engine module 726 described previously with respect to FIG. 7A. For example, a first trigger may be satisfied when a user submits a new log entry that includes user-submitted data to the application 732. In another example, a second trigger may also be satisfied based on the start of a time window associated with a program schedule such as a scheduled exercise event. In yet another example, a third trigger may also be satisfied for a rule if the administrator has recently adjusted a related rule for the same associated program.

The list of evaluation conditions 712b identify expressions that are used to evaluate whether the system should initiate the selected system action from the list of system actions 712c. For example, the first evaluation condition may be satisfied if the user's medical history includes a risk condition that is also identified as risk condition for a particular program (e.g., risk of heart attack associated with an exercise program). In another example, the second evaluation condition may be satisfied if received sensor data indicates that a particular measurement parameter satisfies a threshold specified for the program (e.g., total calories burned for an exercise event). In yet another example, the third evaluation condition may be satisfied if measured user activity over a time period on the application 732 meets a set of goals associated with the program (e.g., user-set goal to lose fifteen pounds within a three-month time frame).

The list of system actions 712c identify actions that may be performed in response to a satisfaction of the triggers 712a or the evaluation conditions 712b. For example, the first system action specifies the transmission for a motivational message to improve user performance within the program. In another example, the second system action specifies the transmission of user performance data to a healthcare provider for the program in order to improve subsequent instances of the program. In yet another example, the third system action specifies the automatic satisfaction of related rules for the same program.

In some implementations, the administrator 702 can use the configuration interface 712 to test the execution of configured rules on a test environment of the application 732 prior to transmitting the program configuration 714a to the server 720. For instance, the administrator 702 may specify different rules for a particular program and then compare predicted performance differences between the execution of each rule on the application 732. Different rules can be evaluated using split testing techniques to determine the preferable configuration of the rules given a set of computed performance metrics. As an example, alternate configurations of a rule that is focused on improving user interaction can be compared based on predicting a likelihood that each rule configuration will result in the user providing a positive user input on the application 732. In this example, historical user input information obtained from the real-time reports 716b can be used to estimate the impact of the alternative rule comparisons on subsequent user activity on the application 732.

In some instances, the administrator 702 can use the configuration interface 712 to configure rules that are not associated with a particular trigger. In such instances, rules can be configured to be manually triggered either by an administrator 702 or triggered in conjunction with the triggering and/or execution of another associated rule. In other instances, the administrator 702 can configure rules that specify null conditions for the evaluation condition. In such instances, rules can be configured to always enable the automatic execution of a specified system action in response to a satisfaction of the trigger. In this regard, the selection of triggers and/or conditions by the administrator 702 can be used to adjust the sensitivity by which rule execution is initiated and/or completed.

Although FIG. 7B illustrates rule configuration on the configuration interface 712 as a selection of user-selectable options from the list of triggers 712a, the list of evaluation conditions 712b, and the list of system actions 712c, the configuration interface 712 may provide other means of configuring rules. For example, the configuration interface 712 may additionally or alternatively provide a text field to allow the administrator 702 to input a logical expression such as a structured query language (SQL) for setting evaluation conditions for a configured rule. In some instances, such complicated configuration interfaces can be provided as a customizable option that enables the administrator 702 with greater flexibility in configuring rules.

Figure 8A:
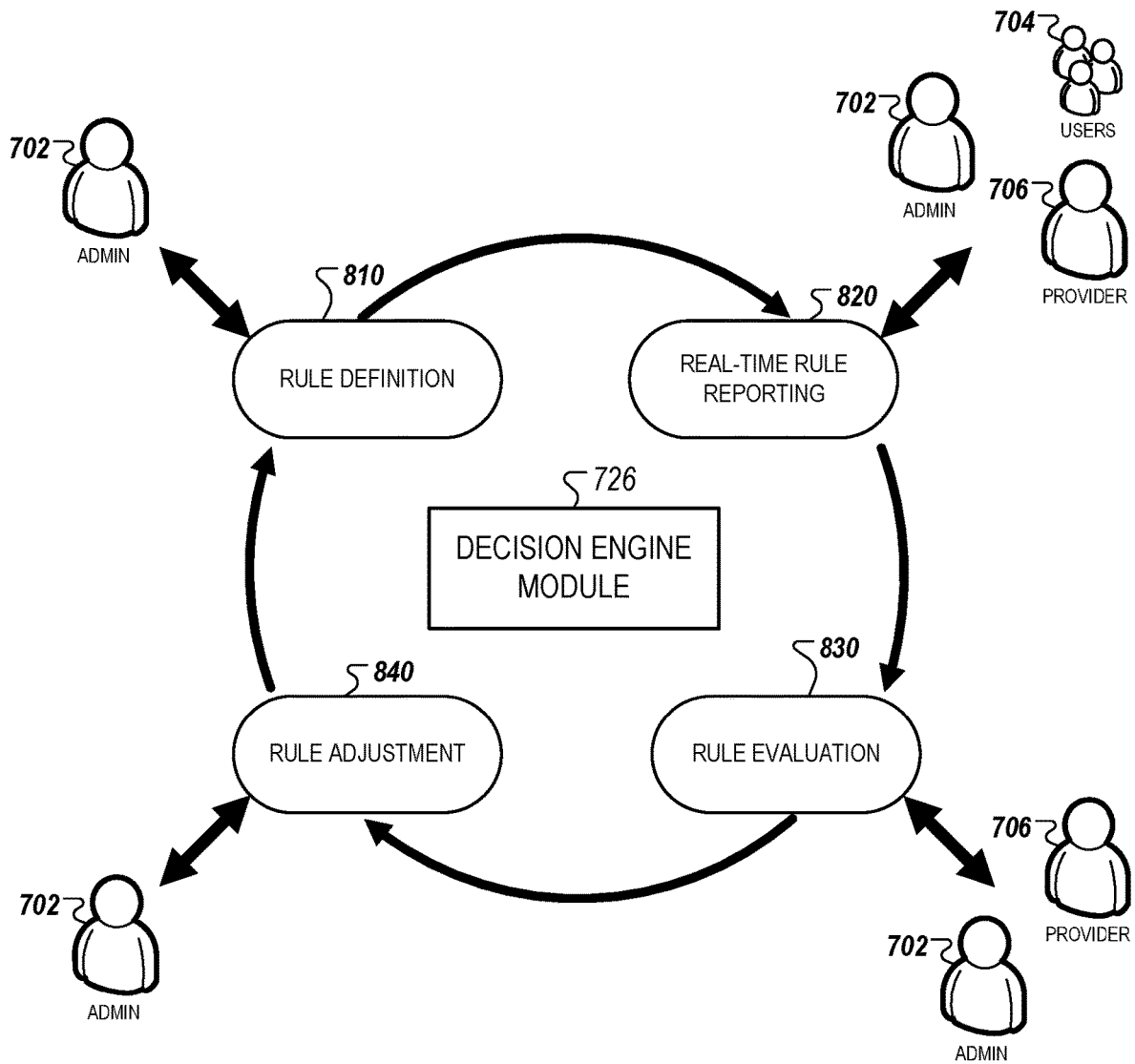
FIG. 8A is a diagram that illustrates examples of rule configuration and adjustment operations performed by a decision engine module.

FIG. 8A is a diagram that illustrates examples of rule configuration and adjustment operations performed by the decision engine module 726 of the server 720. The operations generally include rule definition (210), real-time rule reporting (220), rule evaluation (230), and rule adjustment (240).

In general, the decision engine module 726 may iteratively perform the operations 810-840 on a reoccurring basis so that each iteration results in training the decision engine module 726 to become more responsive to program requirements associated with each of the administrator 702, the users 704, and the provider 706. For example, during each operation, the decision engine module 726 exchanges data transmissions with devices associated with the applicable entities in order to obtain and transmit data and/or feedback related to the applicability of rules that are processed by the decision engine module 726 in relation to the users' real-time participation in the application 732 (e.g., progression through a fixed time period program).

Referring initially to 810, the rule definition operation relates to the decision engine module 726 receiving data from the administrator device 710 that specifies one or more rules for configuring the application 732. For instance, the received data may include rule specifications, provided by the administrator 702, that associate a particular trigger or condition and one or more system actions to be performed in response to a satisfaction of the particular trigger or condition. As an example, the administrator 702 may use the configuration interface 712 to specify a rule that associates a selection of one or more triggers, one or more evaluation conditions, and system actions.

Referring now to 820, the decision engine module 726 may generate real-time reports 716b based on data received from each of the administrator 702, the users 704, and the provider 706. For instance, the real-time reports 716b may be generated based on comparing data included in the user input data 716a to program criteria specified within the program configuration 714a, and evaluating the relevance and/or effectiveness of the rules associated with the by the administrator 704 on the configuration interface 712.

Referring now to 830, the decision engine module 726 may provide the real-time reports 716b for output to the administrator device 710 and/or systems associated with provider 706. The decision engine module 726 may also generate audit logs 724c based on the user input data 716a received from the user device 730. As described previously with respect to FIG. 7A, the audit logs 724c may provide data that represents analyses related to the satisfaction of triggers and/or evaluation conditions of rules associated with programs. The audit logs 724c provided for output include information that assists the administrator 704 and/or healthcare provider 706 adjust program criteria based on the user's performance within the program indicated by the user input data 716a.

Referring finally to 840, the decision engine module 726 may receive adjustment specifications provided on the configuration interface 712 in response to data output to the administrator device 710 in step 830. For example, as described previously with respect to FIG. 7A, the adjustment specifications can include adjustments to specifications to an individual rule (e.g., changes to triggers, evaluation conditions, or system actions), or adjustments to collection rules associated with a particular program. In this regard, the adjustment specifications provided can then be used to redefine a particular rule and re-initiate the process at the step 810.

Figure 8B:
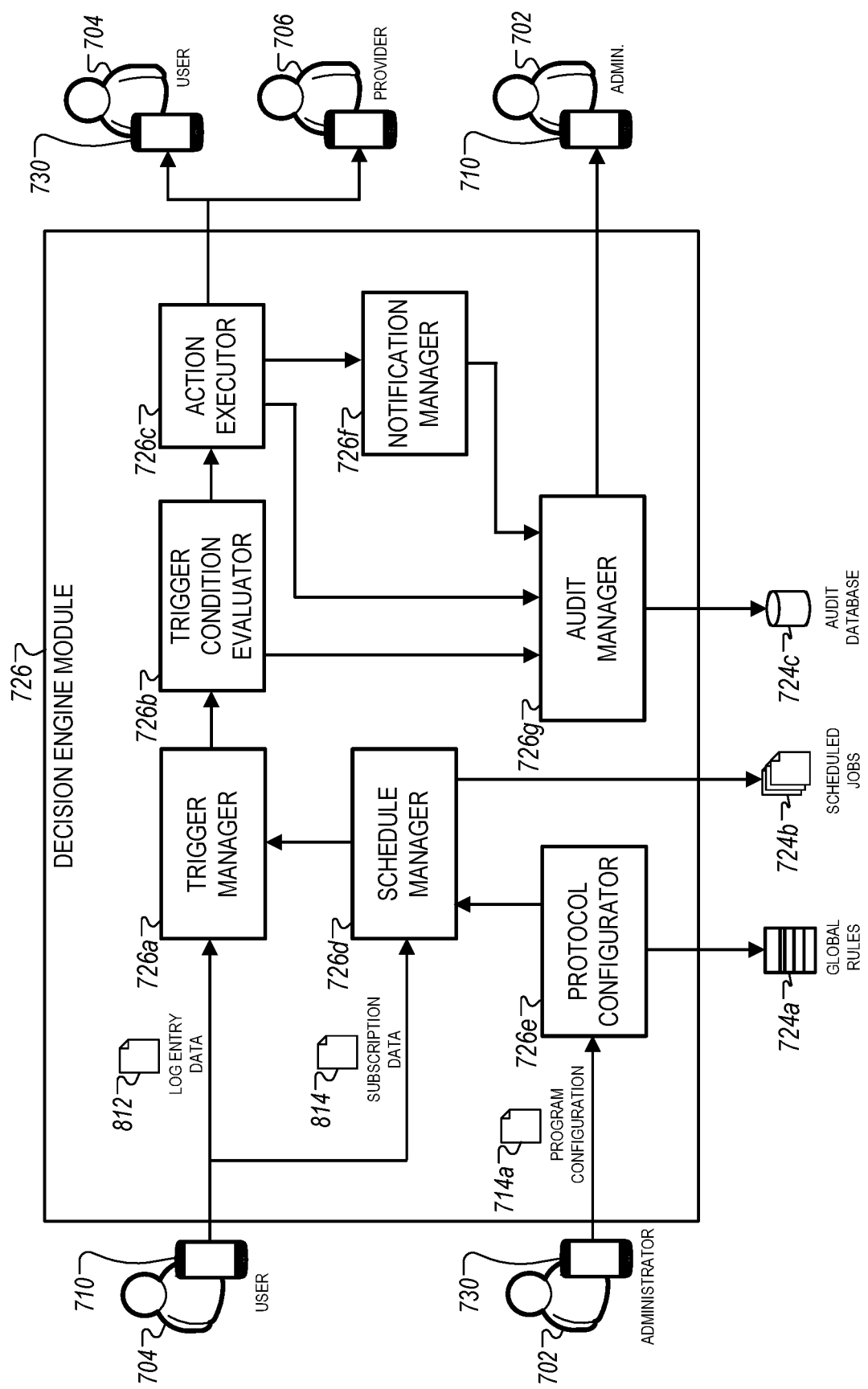
FIG. 8B is a diagram that illustrates an example of a decision engine module.

FIG. 8B is a diagram that illustrates examples of subcomponents of the decision engine module 726. The components of the decision engine module 726 generally analyze data received from the administrator device 710 and the client devices 730 using a set of predetermined processes, and then provides the output of the processes to the administrator device 710, the client devices 730, and the provider device 740. Descriptions of each of the components of the decision engine module 726, and the processes executed by the components are described below.

The components of the decision engine module 726 include a trigger manager 726a, a trigger condition evaluator 726b, an action evaluator 726c, a schedule manager 726d, a rule configurator 726e, a notification manager 726f, and an audit manager 726g. Each of these components perform a set of individual actions, and execute a set of coordinated processes in order to perform the functions of the decision engine module 726.

Referring initially to the data received from the user devices 730, the decision engine module 726 processes log entry data 812 and subscription data 814 using two different processes.

The first process relates to analyzing rules associated with a program based on the specifications previously provided by the administrator 704 on the configuration interface 712 as depicted in FIG. 7B. For instance, log entry data 812 included within user input data 716a, provided by a particular user 704 on the application 732, is initially analyzed by the trigger manager 726a. The trigger manager 726a initially determines whether triggers 728a of rules associated with a particular program have been satisfied. The received log entry data 812 is then transmitted to the condition evaluator 726b to determine whether any of the evaluation conditions 728b of the rules have been satisfied.

If either at least one trigger 728a or evaluation condition 728b is determined to be satisfied, then the trigger manager 726a and the condition evaluator 726b may collect data that is respectively associated with the satisfied condition or the satisfied evaluation condition. As described previously with respect to FIG. 7A, the collected data may include user activity data within a particular time period prior to or after a timestamp associated with satisfaction, associated data or information related to use interactions on the application 732, or other types of information that may be used to evaluate the effectiveness of the associated rules. This collected data may be handled by the audit manager 726g and stored within the audit logs 724c as described previously with respect to FIG. 7A.

In addition to storing satisfaction data collected by the trigger manager 726a and the condition evaluator 726b, the first process may also include transmitting a signal that identifies the rules with satisfied triggers and/or evaluation conditions to the action executor 726c. The action executor 726c determines system actions associated with the identified rules, and then transmits data including the determined system actions to either the user 704 or the provider 706. In some instances, this data includes a set of instructions to automatically perform the determined system actions on the user device 730 associated with the user 704. In other instances, corresponding data is transmitted to systems associated with the provider 706. As an example, if a system action specifies charging a copayment to a user for receiving a particular treatment procedure, the data transmitted by the action executor 726 can include an instruction to user device 730 (or the application 732) to charge a payment method associated with the user 704, and a corresponding instruction to provider system to record the copayment transaction for the particular procedure in a user account corresponding to the user 704 within the provider system.

The action executor 726c may also generate notifications associated with the system actions to be executed on the user device 730, and then transmit the generated notifications to the notification manager 726f, which then forwards the generated notifications to the audit manager 728g, and ultimately provided for display on the administrator device 710. For example, as described previously with respect to FIG. 7A, the notifications can include the real-time reports 716b that provide an analysis on data associated with system actions to be performed to the administrator device 710. In other instances, the notification manager 728g may directly provide the generated notifications for output on the administrator device 710 without initially transmitting the notifications through the audit manager 728g. The transmitted notification can be used by the administrator 704 to either adjust specifications for an individual rule associated with a particular program, or adjust the composition of a collection of rules associated with a particular program.

The second process performed by the decision engine module 726 for data received from the client device 710 includes processing subscription data 814 and transmitting the processed data to the schedule manager 726d. The subscription data 814 may include information relation to selections of available programs that the user 704 wishes to enroll into. For example, the subscription data 814 may include enrollment information that includes the user's medical history, log entries related to a user's goals within the selected program, among other types of information.

The schedule manager 816 then processes the information included within the subscription data 814 in order to identify scheduled jobs that the trigger manager 726a should perform in response to an initial enrollment by the user 704. For example, the schedule manager 816 may identify jobs related to initial content generation for the content to be displayed within the selected program, or updates to be set to the provider 706 or the administrator 704 indicating that the user has opted to enroll into a particular program. The identified jobs may then be stored in the scheduled jobs 724b for subsequent execution.

Referring now to the data received from the administrator device 710, the decision engine module 726 processes the program configuration 714a, described previously with respect to FIG. 7A, using the rule configurator 726e. The rule configurator 726e identifies new rule definitions within the program configuration 714a, and adds the new rule definitions to the repository of global rules 724a. For example, each time the administrator 702 defines a new rule on the configuration interface 712, the new rule definitions are then included within the program configuration 714a transmitted from the administrator device 710 to the server 720 and then stored in the global rules 724a by the rule configurator 726e. In this regard, the repository of global rules 724a expands over time to include new rule configurations associated with a particular program.

The program configurator 726e also processes changes to existing rule definitions, indicating that prior definitions may either be inapplicable to the output of the application 732. In some instances, the rule configurator 726e processes rule adjustments by generating additional instances of the pre-existing rules within the repository of global rules 724a in order to keep a track record of rule adjustments. Alternatively, in other instances, the rule configurator 726e instead replaces preexisting rule definitions with newer rule definitions in order to conserve storage capacity.

Figure 9:
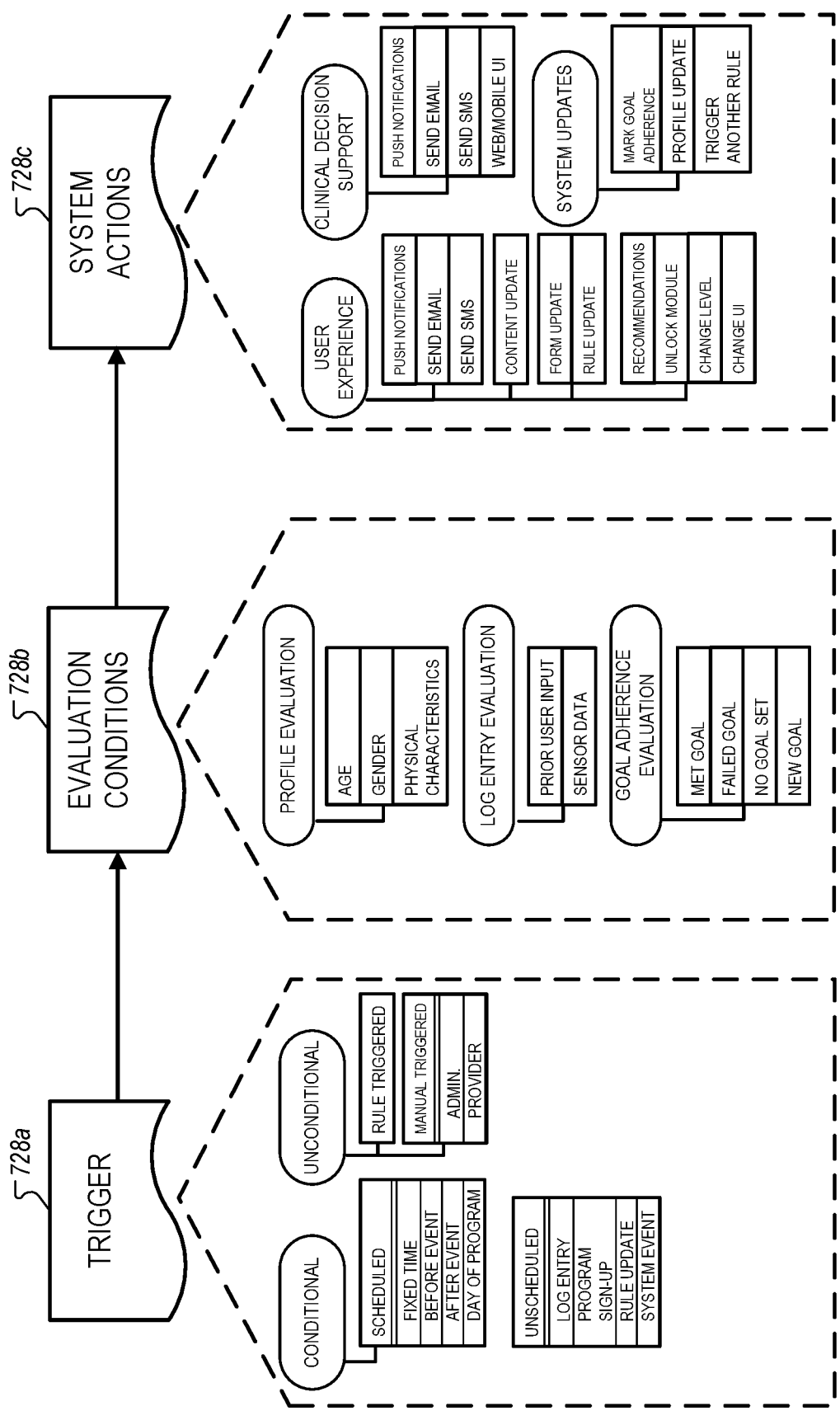
FIG. 9 is a diagram that illustrates an example of an architecture for rule configuration.

FIG. 9 is a diagram that illustrates an example of an architecture for rule configuration that relates triggers 728a, evaluation conditions 728b, and system actions 728c. As described with respect to FIGS. 7A-11, rule definitions can be specified by the administrator 702 on the configuration interface 712 depicted in FIG. 7B. Each rule definition associates selected triggers 712a, selected evaluation conditions 712b, and selected system actions 712c on the configuration interface 712. The rules are then periodically evaluated by the decision engine module 726 to identify a satisfaction of at least one the selected triggers 712a and/or the selected evaluation conditions 712b, and in response to an identified satisfaction, the system 700 may perform the selected system actions 712c.

As depicted in FIG. 9, the architecture for rule configuration can include different categories and sub-categories of triggers 728a, evaluation conditions 728b, and system actions 728c in order to vary the scope and applicability of different rules to dynamically adjust the output of the application 732. For example, the triggers 728a may generally include conditional triggers that specify events the occurrence of which are related to satisfaction of the evaluation conditions 728b, and unconditional triggers that specify events the occurrence of which are unrelated to the evaluation conditions 728b.

Conditional triggers may be sub-categorized into scheduled triggers or unscheduled triggers. For instance, scheduled triggers refer to triggers that specify events that are related to an anticipated time period (e.g., fixed time period for response), or related to the occurrence of a particular event that takes place on reoccurring basis (e.g., before event, after event). As an example, an event may that satisfies a scheduled trigger may include the daily submission of a log entry by a user 704 (e.g., submission of self-reported patient data collected on the application 732). Unscheduled triggers refer to triggers that specify events that may take place on an ad hoc basis (e.g., initial program sign-up, or a general rule update).

Unconditional rules may be sub-categorized into rule-based triggers or manual triggers. Rule-based triggers may specify events that indicate a satisfaction of an associated or related rule (e.g., satisfaction of another rule within a collection of rules that are each associated with a particular program). Manual triggers refer to triggers that specify events related to the actions performed by administrators or providers associated with the system 700. As an example, an unconditional trigger may be satisfied based on the submission of a rule adjustment by the administrator 704 on the configuration interface 712. In another example, an unconditional trigger may be satisfied based on the submission of updated clinical treatment criteria for a particular program by the provider 706.

The evaluation conditions 728b may generally include a set of conditional expressions that are evaluated as either "true" or "false" in order to determine a satisfaction of a specified evaluation condition. The evaluation conditions 728b may generally include profile evaluation conditions, log entry evaluation conditions, and goal adherence evaluation conditions. The profile evaluation conditions generally refer to a set of expressions that analyze attributes or characteristics specified within a user profile (e.g., age, gender, physical characteristics). As an example, a profile evaluation condition may specify an age range for an at-risk population for a potential health condition that is satisfied when a user account indicates that he/she falls within the age range.

Log entry evaluation conditions refer to a set of expressions that analyze user input or data associated with user activity provided by the user on the application 732 (e.g., prior user input, sensor data). As an example, a log entry evaluation condition may specify a minimum calorie burn goal for a particular exercise program that is satisfied when received heart rate data is used to indicate that the user has completed the specified goal.

Goal adherence evaluation conditions refer to a set of expressions that analyze a user's performance throughout a program in relation to a set of performance goals specified for the user (e.g., met goal, failed goal, no goal set, new goal, etc.). As an example, a goal adherence evaluation condition may specify a target level of physical activity over a period of time (e.g., amount of steps over a month) that is satisfied when a wearable device that exchanges data with the application 732 indicates that the user's calculated steps exceeds the target level.

The system actions 728c generally refer to a set of actions to be performed by the system 700 in response to a satisfaction of at least one trigger 728a and/or evaluation condition 728b. In some instances, satisfaction of triggers 728a and evaluation conditions 728b may both be a prerequisite to perform a particular system action 728c (e.g., dual satisfaction of the trigger and evaluation condition). In other instances, the triggers 728a and the evaluation conditions 728b may instead be unrelated such that a satisfaction of either results in the performance of the specified system action 728c. System actions 728c can generally be related to patient experience, clinical decision support, and system updates.

System actions related to patient experience refer to system actions that are directed to improving the user's experience and/or performance in the program provided on the application 732. For example, such actions can include providing push notifications to improve the interactivity of the program, sending emails or SMS messages that include updates and/or other motivational information to the user. In other examples, such actions include dynamically updating the content provided on the application 732 in order to improve the user's performance associated with a particular program (e.g., adjusting content based on the user's content consumption preference).

System actions related to clinical decision support refer to system actions that are directed to informing the providers 706 of the user's performance within a program in order to further improve clinical criteria associated with the program (e.g., patient adherence to treatment conditions, improvements in post-operative recovery, etc.). For examples, such actions can include providing notifications of the user's performance and/or other associated information to providers that create the program.

System actions related to system updates refer to system actions that are directed to updating internal processes performed by the system 700 in order to more efficiently and dynamically adjust the output of the application 732. For example, such actions can include marking a goal adherence program complete so that the decision engine module 726 may subsequently process rules associated with other programs. Other examples can include updating data associated with the user in order to ensure that user account information accurately reflects the present condition of the user, or determining that the trigger of an associated rule has been satisfied in order to enhance evaluation of related conditions.

Figure 10:
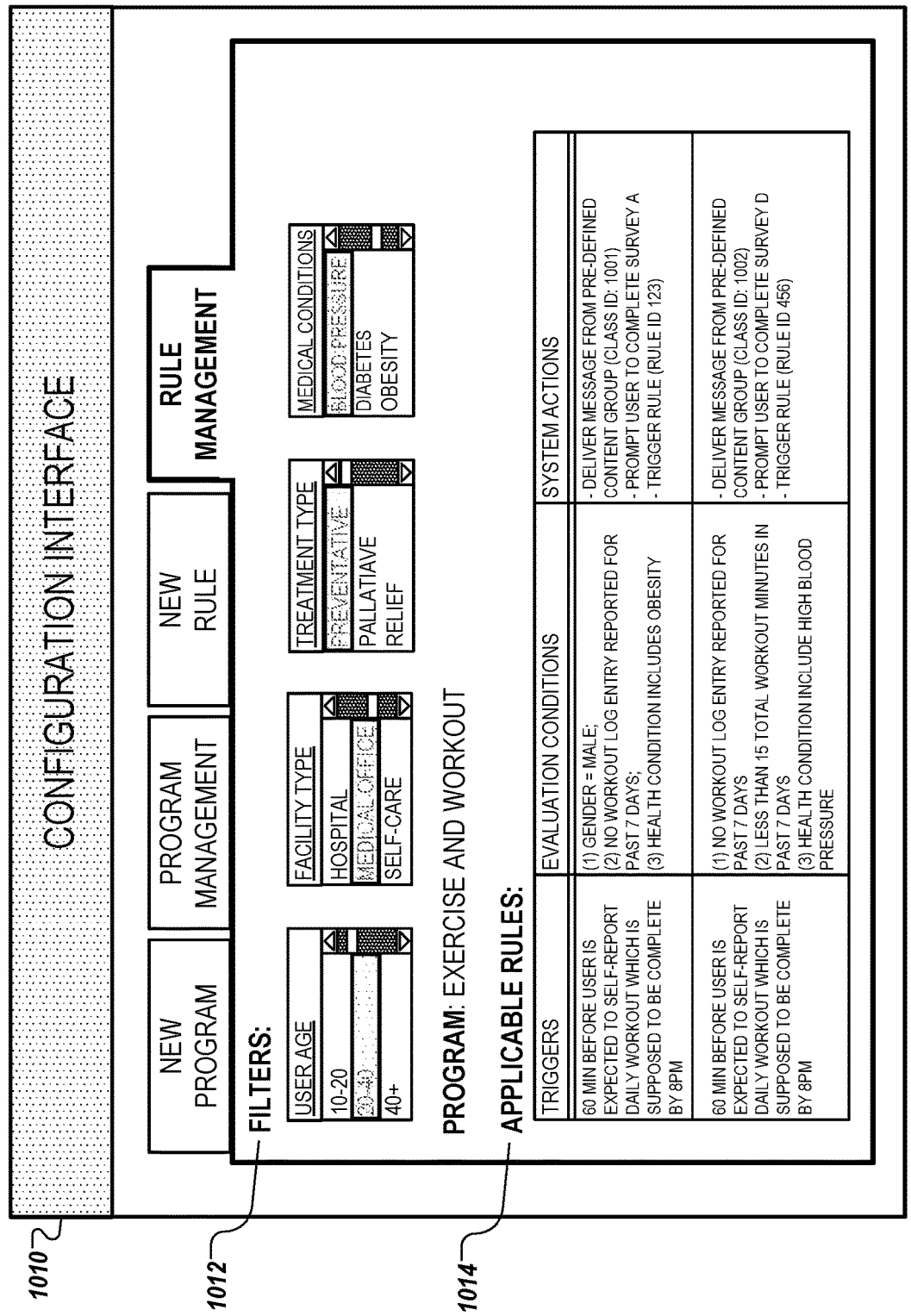
FIG. 10 is a diagram that illustrate an example of a user interface that may be used to identify applicable rules for a set of program criteria.

FIG. 10 is a diagram that illustrates an example of a configuration interface 1010 that may be used by the administrator 702 to identify a list of predetermined rules 1014 that are determined to be responsive to a set of filters 1012 for specified program criteria. In some implementations, the interface 1010 may be a different page within the interface 712 depicted in FIG. 7B that provides the administrator 702 with a different set of features to configure or reconfigure the output of the application 732 on the client devices 730.

The interface 1010 enables the administrator 702 to use a set of filters 1012 to provide program criteria. For example, the filters may include a target user age range, a facility type, a treatment type, medical conditions associated with a program, among other types of filters. Selections for each of the filters enable the system to filter the repository of global rules 724b and identify rules that may be applicable to the administrator 702. In this regard, the list of predetermined rules 1014 enables the administrator 702 to easily access related rules rule adjustment for an existing program, or rule selection for creating a new program.

In the examples depicted in FIG. 10, an administrator selects "20-40 years" for user age, "MEDICAL OFFICE" for facility type, "PREVENTATIVE" for treatment type, and "BLOOD PRESSURE" for medical conditions. In response to these selections, the configuration interface 1010 automatically identifies a program category of "EXERCISE AND WORKOUT" based on the selections related to preventative care and blood pressure. The configuration interface 1010 also provides a set of applicable rules that are determined to be associated with the selections.

The two applicable rules provided both indicate a trigger that specifies a self-reporting event by the user and two conditions associated with the event (e.g., time period before self-reporting event, and completion time for the event). The two applicable rules also provide different respective evaluation conditions to cover different conditions associated with the trigger event. For example, the first rule is directed towards inactive male patients that are predisposed to obesity, whereas the second rule is directed towards patients of both genders who are obtaining insufficient exercise and are predisposed to having high blood pressure. As described previously with respect to FIG. 7A, the difference in evaluation conditions of each of the rules allows for varying scopes of applicability to users (e.g., the first rule is only applicable to men, and the second rule is applicable to both genders).

The two applicable rules also provide different system actions based on the different evaluation conditions. For example, each of the rules specify the delivery of a message from different content groups, prompt users to complete different surveys, and triggering of different rules. In this regard, the different evaluation conditions can be used to direct different adjustments to the application 732 in response to satisfaction of the trigger and/or evaluation condition of the applicable rule.

Figure 11:
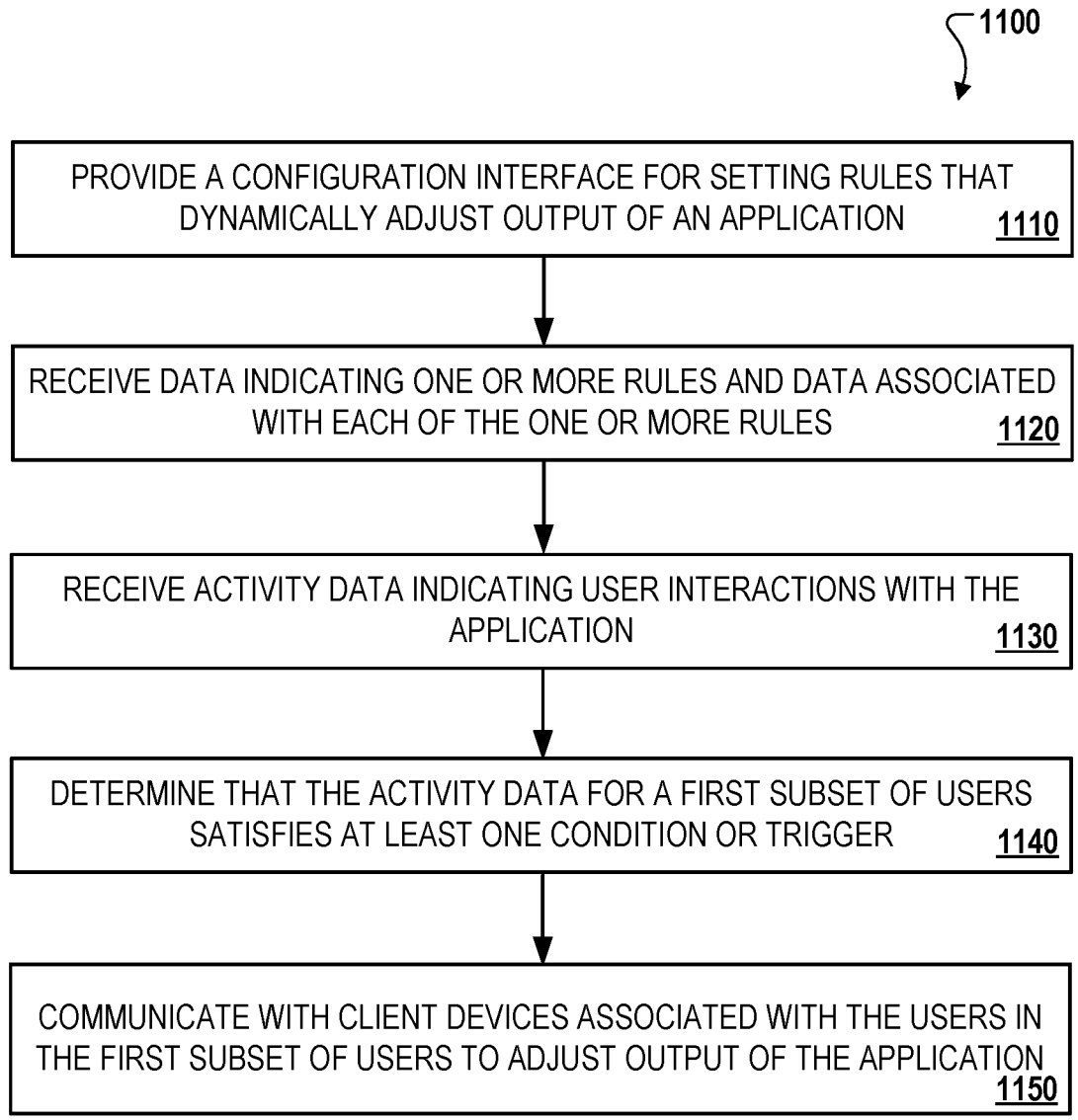
FIG. 11 is a diagram of an example of a process for dynamically adjusting output of an application provided to users.

FIG. 11 is a diagram of an example of a process 1100 for dynamically adjusting a configuration of a program provided to users. Briefly, the process 1100 may include providing a configuration interface for setting rules that dynamically adjust output of an application (1110), receiving data indicating one or more rules and data associated with each of the one or more rules (1120), receiving activity data indicating user interactions with the application (1130), determining that the activity data for a first subset of users satisfies at least one condition or trigger (1140), and communicating with client devices associated with the users in the first subset of users to adjust output of the application (1150).

In more detail, the process 1100 may include providing a configuration interface for setting rules that dynamically adjust output of an application (1110). For instance, the administrator device 710 may provide the configuration interface 712 for setting rules that dynamically adjust output of the application 732 provides to a plurality of users. The configuration interface 712 permits the rules to be specified using combinations of input triggers 728a, conditions 728b, and actions 728c.

As described above, the application 732 can be used to provide users with access to a plurality programs that each provide different sets of interactive content through the application 732. For example, programs can be designed for the treatment of specific health conditions experienced by a population of users (e.g., chronic illnesses). In this regard, rules that dynamically adjust the output of the application 732 can include global rules 724b that are associated with each of the programs that are provided on the application 732, and program rules that are specifically associated only with a particular program. For example, global rules can be used to dynamically change content that is provided across all programs, whereas program rules can be used only to dynamically change content that is provided on a specific program.

In some implementations, dynamically adjusting the output of the application 732 provided to the plurality of users includes adjusting the content to be displayed on the application 732 or an arrangement of content to be displayed. For example, a change to an arrangement can be used to reflect changes to prioritizations of different types of content based on user activity, whereas changes to the content to be displayed can be used to adjust what the user is able to view and interact with on the application 732. In these examples, content can be displayed can be determined based on comparing user activity data for different users against triggers and/or conditions specified by the configured rules. User devices of users whose activity data satisfies at least one condition or trigger, can be provided the content for display whereas user devices of users whose activity data does not satisfy at least one condition or trigger are prevented from receiving the content. In this regard, the system can utilize rules to adjust how content is transmitted to different subsets of users within a population of users.

In some implementations, the configuration interface 712 is provided to different administrators that are each associated with a different organization. In such implementations, rules configured by the different administrators on the configuration interface 712 are associated with respective programs provided by the different organizations. For example, healthcare providers associated with different medical insurance companies can provide specific programs that are only accessible by users that have supported medical insurance plans. In this regard, the configuration interface 712 can be used to enable multiple organizations to use the same means to provide independent content through the same application (e.g., the application 732).

The process 1100 may include receiving data including one or more rules and data associated with each of the one or more rules (1120). For instance, the administrator device 710 may receive data through the configuration interface 712 that indicates one or more rules. The administrator device 710 may also receive data for each of the one or more rules that specifies at least one selected trigger 712a or condition 712b, and one or more selected system actions 712c to be performed in response to a satisfaction of the at least one selected trigger 712a or condition 712b.

In some implementations, the server 720 may additionally receive data indicating historical information indicating the satisfaction of triggers or conditions over a period of time. For example, as described above, the administrator device 710 may receive real-time reports 716b from the server 720 that include user input data 716a received on the application 732 over a particular period of time.

The administrator device 710 can then provide various user-selectable options on the configuration interface to adjust one or more existing rules. As illustrated in FIG. 7B, the administrator 702 can use historical information to adjust the triggers and/or rules associated with an existing rule of the historical user input data indicates that the existing rule has been ineffective in achieving its intended purpose. As examples, the administrator 702 can be provided with a user-selectable to adjust a collection of rules associated with a particular program that includes a particular rule, or adjust the combination of triggers, conditions and/or actions of the particular rule.

In addition, the obtained historical information can be used to determine whether the received user input data 716a satisfies one or more triggers or conditions over a particular period of time. In some instances, as illustrated in FIG. 10, in response to determining that the historical information satisfies one or more triggers or conditions, the administrator device 710 may provide a user-selectable list of preconfigured rules that are identified based on the received user input data 716a. Once the user has modified a preexisting rule displayed on the configuration interface 1010, the modified rule can then be added to a list of preconfigured rules for a program provided through the application 732. As depicted in FIG. 10, the configuration interface 1010 includes a set of filters that each provide selections of program criteria such as user age, facility type, treatment type, or medical conditions for a particular program (e.g., exercise and workout).

The process 1100 may include receiving activity data indicating user interactions with the application (1130). For instance, the server 720 may receive activity data indicating user interaction with application or sensor data for at least some of the plurality of users of the application 732 from multiple client devices 730.

The process 1100 may include determining that the activity data for a first subset of users satisfies at least one condition or trigger (1140). For instance, the server 720 may determine that the activity data for a first subset of the plurality of users satisfies the at least one selected condition 712a or trigger 712b. The server 720 may also determine that the activity data for a second subset of the plurality of the users does not satisfy the at least one selected condition 712a or the trigger 712b.

The process 1100 may include communicating with client devices associated with the users in the first subset of users to adjust output of the application (1150). For instance, the server 720 may communicate with the client devices 730 associated with the users in the first subset to adjust output of the application 732 according to the one or more system actions of the one or more rules, while not adjusting the output of the application 732 for the users in the second subset based on the one or more rules.

Section 3

FIGS. 12A-17 show an application architecture uses a server system that interacts with client devices to dynamically provide personalized content in mobile applications. The server system can store and update program data that defines multiple different programs that are each available to users through the same single application. The program data can divide each program into a sequence of multiple segments corresponding to different time periods. The program data can also define different tracks that represent different types of content or functionality within the program, as well as different levels within each track. These tracks and levels can span many or all of the segments, allowing a user to transition between different experiences while maintaining a consistent progression through the segments of the program over time.

In some instances, mobile applications can be used to deliver healthcare content to electronic devices of users. However, some applications can be under-inclusive because they are designed to target a specific patient population affected by a complex medical condition that is not prevalent among the general population. For example, an application focused on the needs of patients receiving chemotherapy is generally inapplicable to users who are not affected by cancer. Other applications can be over-inclusive because they are designed to target a large population but fail to adequately provide a personalized experience for an individual user. For example, mobile applications that target a broad user audience by providing general services often fail to provide the necessary personalized experience to keep users engaged and meet their specific needs. As a result, many health-related mobile applications are often unable to be used to treat a variety of disease conditions while also being relevant to a broad spectrum of patient populations.

To address these concerns, programs can designed with modular features to provide individual users within a general population with different groups of content that are each personalized for the specific needs of the individual users. For instance, such modularized features can include different time period segments within a single program, and different groups (or arrangements) of content to be provided for each time period. In this regard, the overall program can be applicable for the general population whereas individual modules can be used to segment specific user groups and provide personalized groups using the modular features. In some implementations, a system stores program data for a program that provides interactive content over a series of multiple time periods. In some instances, the transitions between the multiple time periods can be used to represent different milestones associated with an individual user's progress through the program. In other instances, the transitions can simply represent the passage of time since a user has enrolled into a program. Each time period also includes a set of user-selectable tracks that provide different categories of personalized content to analyze the progress of the individual user through the program. For example, a performance level for the user can be measured based on the individual user's activity within each track.

As the user progresses through the different time periods of the program, the system can periodically adjust the content displayed on a mobile device associated with the individual user based on the user's activity within the different tracks. For instance, the system uses a set of rules that specify the content to be displayed on the mobile device based on satisfying corresponding conditions and triggers. This content can be of a variety of types, including, for example, notifications, media (e.g., images, animations, videos, audio, text), interactive elements including surveys and assessments, and so on. The triggers and conditions can be specified for the different time periods, tracks and performance levels such that the content provided to the program is adaptive to the user's ongoing activity throughout the program.

The system enables an administrator such as a healthcare provider or insurer to monitor the ongoing activity of the individual user and adjust the triggers and conditions of the set of rules to provide content that is directed to increasing the likelihood that the individual user will complete the program. In this regard, the system can be used as a content delivery platform to a variety of users using different programs that supply different content and user experiences, and also personalize each program for each individual user.

In some implementations, a computer-implemented method includes: storing, by the server system, program data for a program that provides interactive content to an application that runs on mobile computing devices, the program comprising a sequence of multiple segments each corresponding to different time periods, the program comprising multiple selectable tracks and multiple levels within each track, the program data indicating rules for the program that vary the interactive content provided to different users according to at least the respective tracks, levels, and segments of the program associated with the different users; receiving, by the server system, activity data from a mobile computing device indicating interaction of a particular user with the mobile computing device during a particular segment of the multiple segments of the program; accessing, by the server system, data indicating that the particular user is associated with the program, and data indicating a current segment, a current track, and a current level for the particular user in the program; identifying, by the server system and from among the rules indicated by the program data, a rule that corresponds to the current segment, the current track, and the current level in the program for the particular user; determining, by the server system, that a trigger of the identified rule is satisfied and that one or more conditions specified by the identified rule are satisfied; and in response to determining that the trigger of the identified rule is satisfied and that the one or more conditions specified by the identified rule are satisfied, providing, by the server system, content specified by the identified rule for display in the application of the mobile computing device associated with the particular user.

Other versions of these and other aspects disclosed herein include corresponding devices, systems, and computer programs encoded on computer-readable storage devices that are configured to perform the actions of the methods. These and other aspects may include one or more of the features discussed below.

In some implementations, providing the content specified by the identified rule for display at the client device associated with the particular user includes providing access to a new track not included among the multiple selectable tracks within the program data of the program of the particular user.

In some implementations, providing the content specified by the identified rule for display at the client device associated with the particular user includes providing an interactive assessment that is selected based at least on the accessed data indicating the current segment, the current track, and the current level for the particular user in the program.

In some implementations, determining that the trigger of the identified rule is satisfied includes determining that the accessed data indicates that the particular user transitioned from a previous segment of the program to the current segment of the program within a particular range of time.

In some implementations, providing the content specified by the identified rule for display at the client device associated with the particular user includes: in response to determining that the accessed data indicates that the particular user has been associated with the current segment, selecting, by the server system, one or more user-selectable tracks from among the multiple selectable tracks within the program data that are associated with the current segment; and providing data identifying the selected one or more user-selectable tracks for display at the client device associated with the particular other user.

In some implementations, determining that the one or more conditions of the identified rule is satisfied includes determining that the current level for a particular track is greater than a predetermined threshold level specified by the identified rule.

In some implementations, providing the content specified by the identified rule for display at the client device associated with the particular user includes: in response to determining that the current level for a particular track is greater than a predetermined threshold level for the particular track specified by the identified rule, selecting a plurality of tracks from among the multiple selectable tracks within the stored program data that are determined to be similar to the current track; and providing the selected one or more tracks for display at the client device associated with the particular other user.

In some implementations, the identified rule that corresponds to the current segment, the current track, and the current level in the program for the particular user includes an arrangement specification for the content specified by the identified rule for display at the client device associated with the particular user.

In some implementations, the method further includes: adjusting the arrangement of the content specified by the identified rule for display at the client device associated with the particular user based at least on arrangement specification of the identified rule.

In some implementations, the method further includes: in response to determining that the trigger of the identified rule is satisfied and that the one or more conditions specified by the identified rule are satisfied, generating, by the one or more computers, an instruction for the application of the mobile computing device associated with the particular user indicating a new time period in the program for the particular user; and providing the instruction indicating the new time period in the program for the particular user to the client device associated with the particular user.

In some implementations, the server system performs operations including: providing, to a third party system, an interface for an administrator of the third party system; receiving, from the third party system and through the interface, program data that alters the rules for the program that vary the interactive content provided to different users according to at least the respective tracks, levels, and segments of the program associated with the different users; and applying the altered rules for the program to adjust interaction of the application of the mobile computing device with the particular user.

In some implementations, the data identifying the selected one or more user-selectable tracks for display at the client device associated with the particular other user includes: a data package including content for the current segment, the current track, and the current level in the program for the particular user; an instruction for the mobile computing device associated with the particular user to clear a program data cache of the application of the mobile computing device; and a set of rules corresponding to the current segment, the current track, and the current level in the program for the particular user, the set of rules specifying adjustment techniques used by the application of the mobile computing device to customize the content for the current segment, the current track, and the current level in the program for the particular user.

In some implementations, the rules for the program include one or more global rules and one or more rules that apply to each program.

In some implementations, the activity data received from the mobile computing device includes data collected by one or more sensors that exchange communications with the mobile computing device.

FIGS. 12A-17 illustrate a system that stores program data for a program that provides interactive content over a series of multiple time periods. The transitions between the multiple time periods can be used to represent different milestones associated with an individual user's progress through the program. Each time period also includes a set of user-selectable tracks that provide different categories of personalized content to analyze the progress of the individual user through the program. For example, a performance level for the user can be measured based on the individual user's activity within each track.

As the user progresses through the program sequence of the program, the system uses a set of rules with triggers and conditions associated with the time period, track, and performance level to dynamically provide content within the program. For instance, the triggers of the rules can be used to detect when the user transitions between time periods or when changes in the user's performance level with respect to particular tracks takes place, and the conditions of the rules can be used to determine when the user's progress and/or performance level satisfies the requirements to transition between different periods of the program sequence.

The technical architecture of the system further provides various improvements in administering personalized content to individual users, which often require significant storage resources on client devices. In some implementations, the technical architecture of the system enables a client device to provide administering personalized content to individual users without using significant storage with the use of a dynamic application cache. For instance, techniques for data processing and analysis associated with the program can be performed by a remote server so that the client device automatically receives personalized content for the individual user instead of having to store different content items that are manually requested by user over time. For example, instead of the client device requesting content from the remote server, the server can automatically determine the content to provide to the mobile application. In this regard, the remote server can periodically transmit data packages including content items to be provided to the individual user, instructions to install and display the content included in the transmitted data packages, or instructions to caching or removing old content items that are no longer relevant to the program from the storage of the client device, instructions to reconfigure the display of the interface on the mobile application. This periodic data exchange between the remote server and the client device enables the client device to utilize fewer computational resources such as memory or storage in operating the mobile application to provide the individual user with a personalized experience. In some instances, the remote server may receive data from a third party system that adjusts the operations performed by the remote server.

To minimize the computational resources requirements necessary to provide personalized content, the system utilizes a set of global rules that enable a server to perform a smaller number of processing steps to provide personalized experience for all users while providing varied user interfaces. For instance, the rules can be used to adjust types of content provided for each individual user using a set of common adjustment and distribution schemes to allow for use shared resources in providing personalized content for groups of users that are predetermined to be similar to one another. For example, the server may be capable of clustering content data based on prior activity within a program, similar demographic information, by similar programs, among other types of classifications.

The set of global rules can vary in scope and in hierarchy to enable the system to select particular rules from the set of global rules to adjustably execute aspects associated with the data processing of the personalized content. In this regard, the system may select applicable rules to guide data processing in order to maximize resource allocation efficiency. For example, rule selection may be based on the different types of content to be provided, the size of the content to be provided, and/or the number of users that are associated with particular types of content to be provided.

With respect to FIGS. 12A-17, a "program" refers to a set of rules or instructions that define a user experience provided through an application. As discussed below, a program can include collections of interactive content and rules that define when and how content should be delivered through an application. Although a program can include executable software, it is not required to be defined in this manner. Rules that define a program may be interpreted by multiple devices, including user device and server systems, to create the customized user experiences that a program provides. In some implementations, at least part of a program is implemented as a service, with one or more server systems dynamically selecting and delivering at least some of the program content to a client device, customized for a specific user.

A program can be structured with a variety of divisions. For example, programs can be defined to include a sequence of segments, where each segment lasts for a fixed or variable time period. Users who begin a program progress consistently through a segment as time passes, and then progress from one segment of the program to the next. For example, a program defined to last for a year could be divided into 52 week-long segments or 12 one-month segments. Each segment may involve the different user experiences, content, and rules. In some implementations, a user moves from one segment to the next purely by passage of time, while in other implementations, a user may be required to satisfy additional criteria to progress to the next segment. In addition to the segments, programs can also be divided into different tracks and different levels, discussed further below.

The program can indicate specific features of an application that an organization selects to provide to the user. When downloaded and stored on a user device, program data may configure an associated mobile application to provide custom content and interactions for a particular user. When the user subsequently runs the application, the application retains the configuration, appearance, and interactivity specified by the previously downloaded program data. The mobile application can provide a user with a customized user experience of a native mobile application without the need for the client organization to code and register an application with an app store (e.g., the Apple App Store, or Google Play for Android Apps, etc.). For wellness-related programs, the program enables the user and the organization that provides the program to perform specific types of data tracking and reporting according to a user's specific medical needs, or the priorities of the client organization (e.g., to encourage and reward exercise, or to promote quitting smoking, etc.). In this regard, the program can be customized to the goals of the user.

Programs can be created and administered for a wide variety of topics and purposes. Some examples below describe ways that a program may be used to encourage and assist a user to improve health, e.g., by establishing better habits or helping to deal with a medical condition. The techniques of generating, delivering, and using programs is not limited to healthcare, however, and the same techniques can be used to provide customized user experiences to many other types of applications.

With respect to FIGS. 12A-17, a "program sequence" refers to a set of user milestones that are used to indicate a user's progress within the program. The program sequence generally includes a set of time-variable periods that can represent different iterative stages within the program sequence. For example, a program sequence may specify psychological user conditions that are commonly associated with a particular treatment program, physical conditions associated with a post-operative recovery period, or a set of intermediate requirements that a user must satisfy to advance through the program. The program sequence can also be used to customize the arrangement of content to be provided on the program for each user. For example, survey data obtained from the user can be used to adjust the program sequence of each program such that the progress milestones are designed around a user's specific medical history, demographic information, among other types of information.

With respect to FIGS. 12A-17, a "period" refers to a defined time segment that indicates a user's progress within a program. For instance, multiple periods of different specified time lengths can be sequentially arranged to represent different clinical treatment stages associated with a medical condition of the program. The period can be used to specify a progress measure indicating a user's performance within the program. The progress measure can be calculated based on, for example, amount of time spent on specific content provided on the program, overall amount of time spent within the program, or amount of time spent by the user compared to an expected level of time for based on data obtained from similar users within the same program. The period can also be used to adjust content to be provided to a user. For example, the program can be configured such that targeted content for a specific period is provided on the program once the progress measure indicates that the user has transitioned into a particular period. Likewise, content previously displayed on the program can also be removed once a user transitions to a new period where the previously displayed content is determined to be no longer relevant.

With respect to FIGS. 12A-17, a "track" refers to user-selectable collections of content to be provided on the program. In some implementations, the tracks are alternatives, and only one track is active at a time. In other implementations, a user may be able to have multiple tracks of a program active simultaneously. Different tracks can represent different topics or categories of content that can be provided to a user based on, for example, the current period the user is in within the program, medical conditions or procedures associated with the user, or demographic information associated with the user. In this regard, the arrangement of content tracks within a program can be used to customize the program for each individual user by providing a user with access to certain tracks that are predetermined to the relevant to the user. In some instances, particular tracks may be track may be designated as period-specific such that these tracks are only provided to the user when the user is in a particular period of the program. In other instances, tracks may be grouped together by similarities in content provided on the program.

With respect to FIGS. 12A-17, a "level" refers to a determination of a user's performance within a particular track. For instance, a single track may include various levels that are each associated with a set of user performance requirements. A user may be designated to a particular level based on the types of user input provided on the program. For example, a track associated with exercise may have different levels that each correspond to different levels of user fitness. In this example, measured sensor data provided by the user can be used to estimate a user fitness and designate a corresponding level for the user's performance within the exercise track. Level designations for the user can also be used to adjust the display of content on the program. For instance, a particular track may have prerequisites such as a minimum level within an associated track, and once the user is designated to the minimum level, the particular track may be provided for display on the program.

With respect to FIGS. 12A-17, an "arrangement specification" refers to the collection of tracks that are provided for selection by a user. For instance, the arrangement specification can be specified based on a particular period such that each period within the program sequence includes a different arrangement specification to assist with the user's progress through the various periods of the program. In other instances, the arrangement specification can be specified on the attributes of an individual user (e.g., age, gender, location, etc.) such that the arrangement specification can be used to personalized a collection of tracks that are provided to each individual user.

With respect to FIGS. 12A-17, a "performance level measure" refers to a designation of a user's current level within a particular track. The performance level measure can be used as an indicator of the user's performance within the particular track. For example, a high performance level measure can indicate that the user has been designated to higher levels of difficulty within the particular track, which can then be used to infer that the user has achieved a minimum level of proficiency to successfully satisfy the requirements associated with the particular track. In addition, individual performance level measures for each tracks can be aggregated to compute a user's overall performance within a particular period. For example, if a particular period provides a user with three tracks, then the performance level measures for each of the three tracks can be aggregated to represent the user's overall performance within the particular period.

With respect to FIGS. 12A-17, a "progress measure" refers to a user's current status within the program, which can be used to indicate the user's overall performance within the program. In some instances, the progress measure can be an aggregated score of the individual performance level measures for each track. In other instances, the progress measure may be further augmented with additional metrics such as a time spent within a particular period relative to the overall time spent within the entire program, a comparison of the time spent within the current period and the time spent within the previous period, among others. The progress measure can also be used to determine when a user should be transitioned to a subsequent period within the program sequence of the program.

With respect to FIGS. 12A-17, an "administrator" refers to an entity or individual that interacts with an administrator portal of the content distribution system to designate specific tracks to provide to a user on program. In some instances, the administrator is an employee or representative of the client organization that manages and updates the customized module. For instance, the administrator can use an administrator portal of the publishing system to select from various options and provide specifications for a desired module. Additionally, the administrator may identify a list of users that are eligible to receive the module, data indicating applicable healthcare providers or insurance plans, access privileges associated with particular features of the health management modules, or custom content for health management modules.

With respect to FIGS. 12A-17, a "healthcare provider" refers to individuals, institutions, or organizations that provide healthcare services to users. In some instances, the healthcare provider can be an individual health professional such as a physician, or an entity such as a hospital that provides preventative, curative, or rehabilitative programs for users, or a health insurance provider. Healthcare providers can use a provider portal to interact with the publishing system, both to submit information that is accessed through appropriate modules and to receive information from users of certain modules to use in enhancing treatment. As an example, healthcare providers may submit health-related information such as electronic health records, treatment program information, or promotional material. This information may be general for a group of users (e.g., for all users who have a particular insurance plan) or specific to individual users. In some instances, the information submitted on the provider portal can be compiled into a set of module information that is used to personalize the display and operation of the customized health management modules to the provider.

With respect to FIGS. 12A-17, a "user" or "patient" refers to an individual that uses a mobile application and one or more customized modules. In some instances, the user receives healthcare-related services from the healthcare provider. For instance, the user can use a mobile application that is customized using a healthcare module created on behalf of the user's employer, the user's insurance company, or another entity.

Figure 12A:
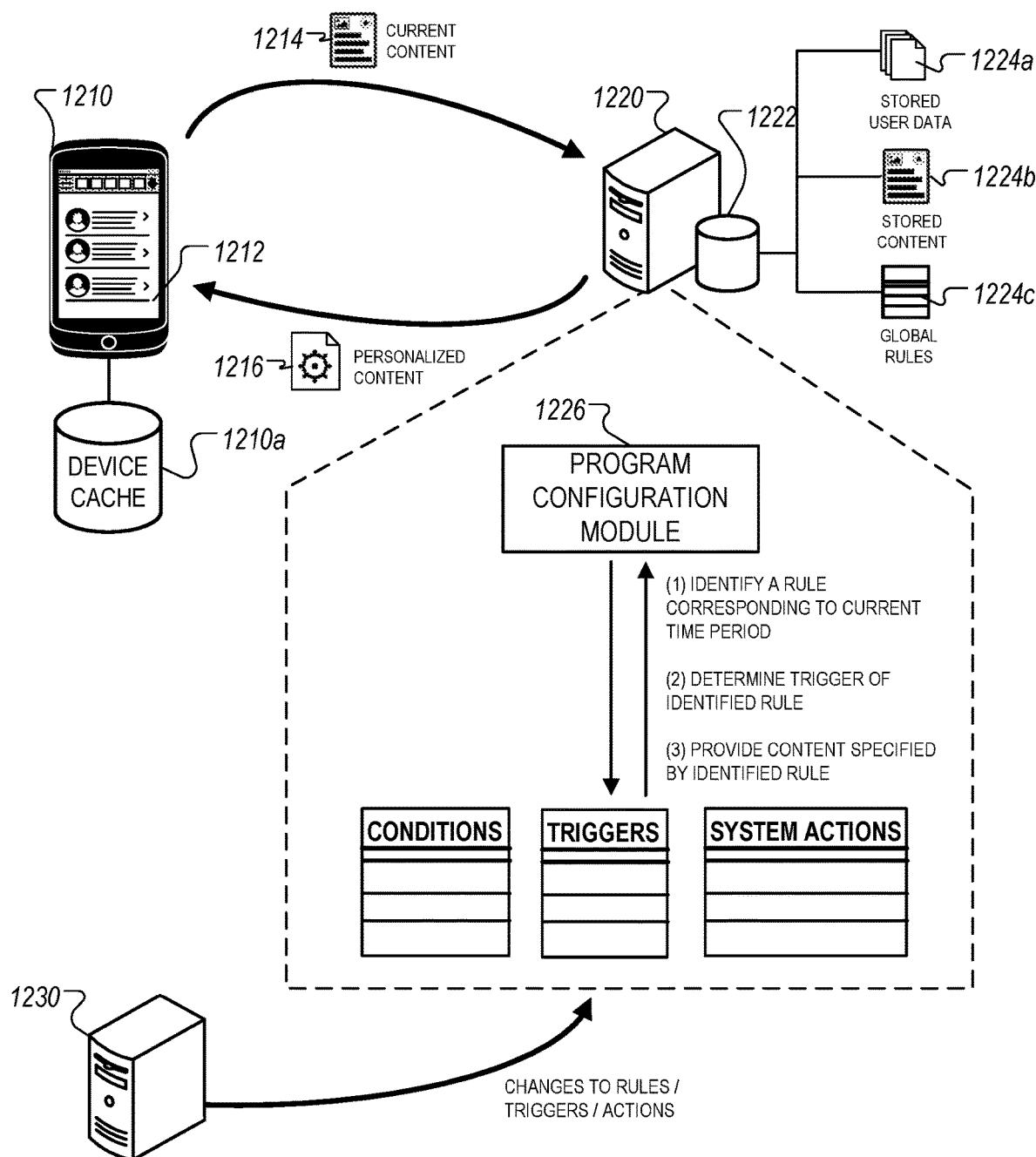
FIGS. 12A-12C are diagrams that illustrate examples of a content distribution system.
Figure 12B:
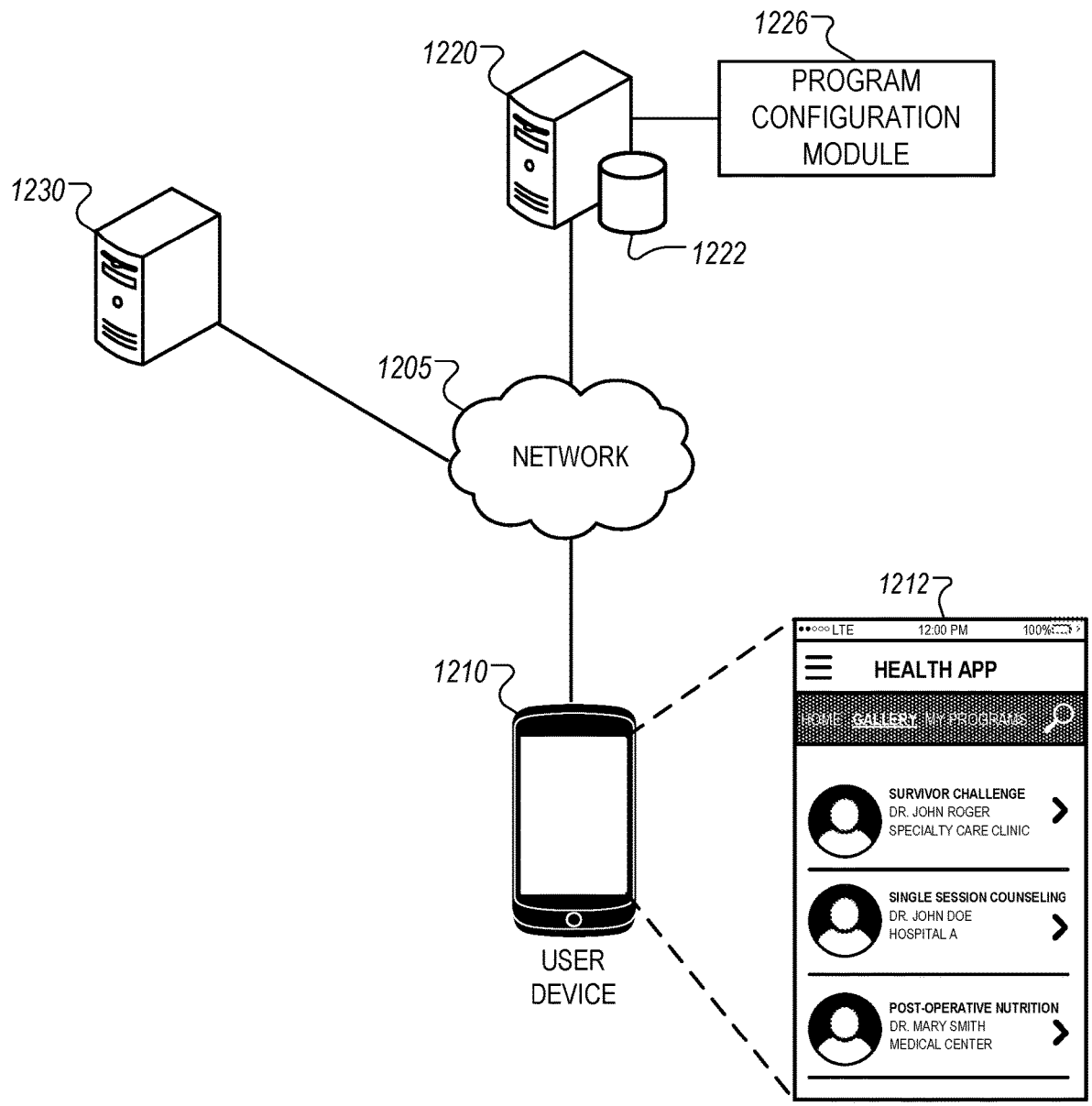
Figure 12C:
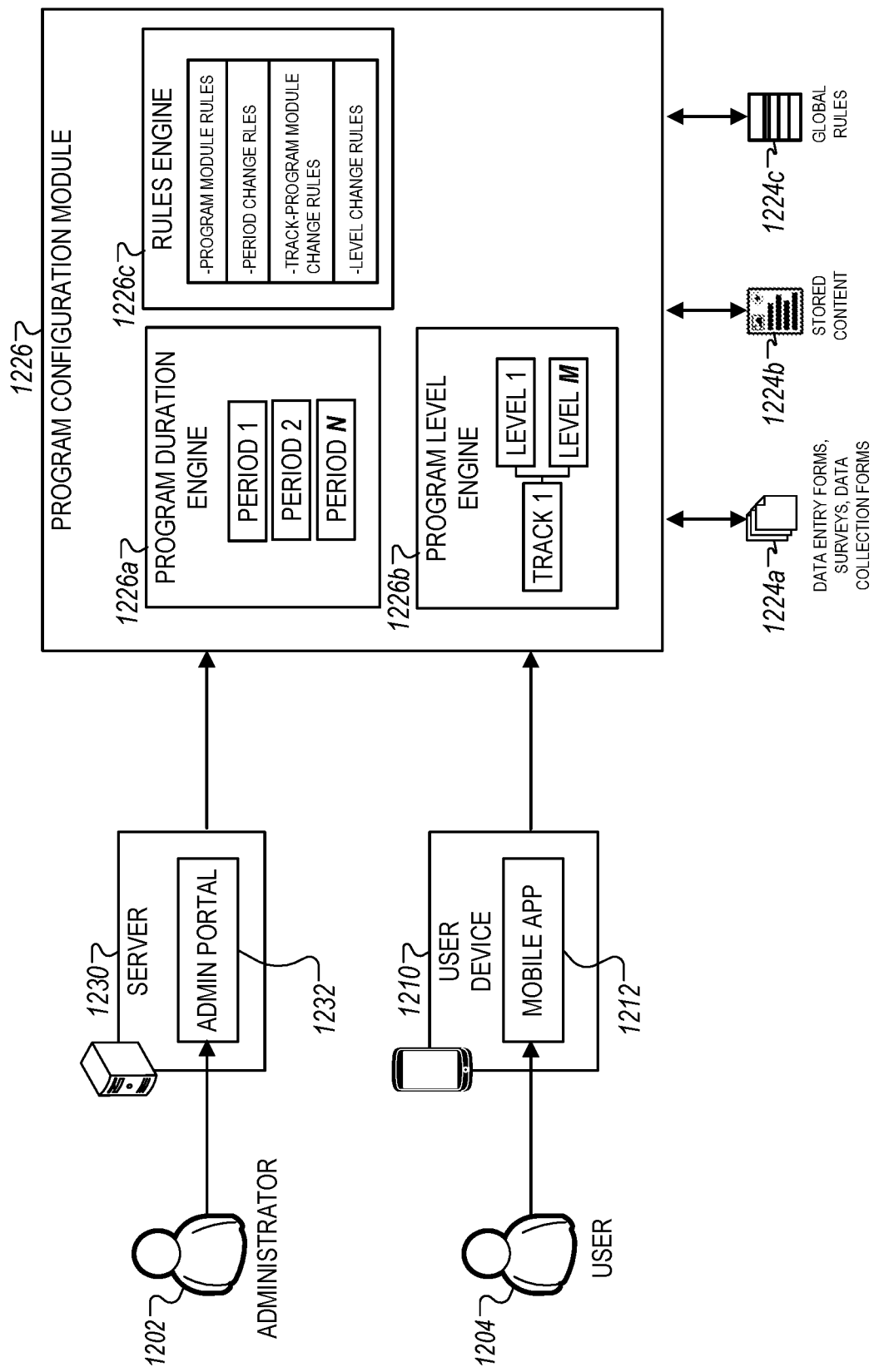

FIGS. 12A-12C are diagrams that illustrate examples of a content distribution system 1200. FIG. 12A illustrates a diagram of an example of personalized content generation processes performed by the system 1200. FIG. 12B illustrates a block diagram of the system 1200, which generally includes a user device 1210, a server 1220, and an administrator system 1230 connected over a network 1205. The server 1220 includes a program configuration module 1226, which generates and adjusts configuration and generation of content to be provided on a mobile application 1212 on the user device 1210. FIG. 12C illustrates a diagram of the program configuration module 1226 in greater detail.

In general, the technical architecture of the system 1200 enables the server 1220 to perform resource-intensive data processes such that the resources necessary to operate the mobile application 1212 on the user device 1210 to provide a personalized user experience is minimal. For example, the server 1220 periodically exchanges communications with the user device 1210 such that updated content is automatically transmitted to the user device 1210 without a manual request from content being transmitted by the user (e.g., an update). The periodic exchange between the server 1220 and the user device 1210 also enables automatic updating of content to be provided on the mobile application 1212 without requiring the client device 1210 to download and store additional content while also storing prior content in storage. For example, in each data communication with the client device 1210, the server 1220 transmits a set of instructions that cause the client device 1210 to delete content items that is no longer determined to be relevant or useful to the progress of the user through the software program, and instead install additional content items that are to be provided for display on the mobile application 1212. In this regard, the periodic exchange between the user device 1210 and the server 1220 enables the client device 1210 to utilize less storage to execute the mobile application 1212 to provide the user with a personalized experience.

Referring to FIG. 12A, the user device 1210 and the server 1220 may periodically exchange communications to update content provided to a user on the mobile application 1212. In general, the user device 1210 initially transmits current content 1214 to the server 1220. The server 1220 then performs a set of operations based on program data stored on a database 1222 of the server 1220, e.g., stored user data 1224a, stored content 1224b, global rules 1224c, and then determines personalized content 1216 to be provided to the mobile application 1212 based on a set of program rules, conditions and triggers.

In more detail, current content 1214 may be data generated by the mobile application 1212 indicating a current time period, a current track, and a current level for the user associated with the user device 1210. For instance, for a particular program within the mobile application 1212, the current content 1214 may specify a list of tracks that are presently available to the user, and for each track, user performance level data indicating a current level, and a user progress measure indicating a current time period within the particular program. In some instances where a user participates in multiple programs within a certain time period, the current content 1214 also includes data for each of the multiple programs.

The current content 1214 can include user input data including, for example, survey response data submitted by the user on the mobile application 1212 while interacting with user-selectable content associated with a particular track, user selections in response to requests for information provided within a track, among other types of user input data. The current content 1214 can also include sensor data received by the user device 1210 and provided by the user while participating in activities associated a particular track. For example, sensor data can include heart rate measurements of a user during an exercise-related activity, a picture of the user and/or a region of the body of the user undergoing treatment, or physiological measurements made by external devices that exchange data communications with the user device 1210 during a specified period of a particular program.

The current content 1214 is received by the server 1220, which then compares the data included within the current content 1214 to program data stored in the database 1222. The program data can include stored user data 1224a, stored content 1224b, and global rules 1224c. The user data 1224a represents historical and demographic information associated with the user. For example, the user data 1224a can include registration information that is submitted by the user after initially installing the mobile application 1212 and/or enrolling in a particular program. Such information can include identifying information (e.g., name, age, sex, and social security number) as well as medical history, and ongoing medical conditions (e.g., current prescriptions, treatment schedules, and recent operations).

The stored content 1224b can include prior data received by the server 1220 during an earlier transmission from the user device 1210. For example, the user data 1224a can include data indicating prior programs that the user participated in, and for each prior program, the prior tracks accessed by the user. The stored content 1224b can also include statistical information associated with the prior user activity data. For example, the statistical information for a particular program can include percentage of tracks successfully completed, average time period for track completion, number of level advancements for various tracks, average performance level measures for a particular time period, among others. In each of these examples, the stored content 1224b may include data that is reflective of user activity within a particular program, a particular period within a particular program, and/or for a particular track within the particular time period. In this regard, the accumulated data within the stored content 1224b can be used to derive data trends that can be analyzed to prepare automated recommendations to either provide to the user in subsequent programs, or to generate custom content to be provided to a user during subsequent programs.

The global rules 1224c can be a set of configuration rules associated with protocols for various programs that are provided on the mobile application 1212. The global rules 1224c can be used to trigger the display of specific user-selectable context based on the data in the current content 1214 satisfying one or more rules conditions specified by the global rules 1224c. An example of a global rule can be providing access to new tracks based on determining, based on the current content 1214, that the user has advanced to a new time period within the program sequence of a particular program. Another example of global rule can be providing a notification on the user on the mobile application 1212 based on determining that the user has advanced to a new level within the track.

In general, the rules of a program can have an assigned scope of applicability. Different rules may be designated to apply for only specific segments, tracks, or levels within a program. Rules may be defined for combinations of these program elements. For example, a rule may be defined to apply only during a particular segment or time period of a program and also only for a particular track and level within the track. The data for each rule may include a value or code that indicates its applicability, allowing the appropriate rules for any given portion of a program to be efficiently identified. In some implementations, the rules are arranged in a hierarchy, with some rules being applicable to a program in its entirety, some rules being applicable only for specific time periods, and others being applicable in more specific situations. Also, the computer systems that allow administrative users to build programs can provide user interfaces that allow the administrative users to alter a program by adjusting the applicability of the rules, to efficiently adjust the user experiences provided by the program.

The stored server 1220 includes a program configuration module 1226 that compares the received current content 1214 and compares the data included within the current content 1214 to the stored data within the database 1222 to perform a variety of tasks that are described more particularly below. However, for simplicity, FIG. 12A depicts an example of an operation where the program configuration module 1226 generates personalized content 1216 based on comparing the data included within the current content 1214 against a set of program rules, conditions, and triggers associated with a particular program.

In the example depicted in FIG. 12A, the program configuration module 1226 identifies a rule corresponding to a current time period within the current content 1214, determines an applicable trigger of the identified rule, and provides custom content 1216 from the database 1222 that is specified by the identified rule. A greater description of the program rules, conditions, and triggers are provided with respect to FIG. 14.

The program rules, conditions, and triggers used by the program configuration module 1226 may be adjusted over time based on ongoing user activity on the mobile application 1212 such that, as a user progresses through multiple periods within a program, the program configuration module 1226 is capable of dynamically adjusting the techniques used to generate the personalized content 1216. In this regard, as the user progresses through a particular program, feedback provided on the mobile application 1212 can be augmented and adjusted by the program configuration module 1226 based on adjustments made to the program rules, conditions, and triggers associated with the particular program. More particular descriptions of such adjustments are provided with respect to FIG. 12C.

The personalized content 1216 provided to user device 1210 can include adjustments to programs provided on the mobile application 1212. The adjustments can include providing additional content to be displayed on the program, providing access to content that was previously displayed but inaccessible to the user, and/or removing content that is no longer determined to be relevant or necessary to the user's progress through the program. For example, where program configuration module 1226 determines that the current content 1214 indicates that a user has satisfied the requirements for a particular period, the personalized content 1216 may include data for a subsequent period within the program. In another example, where the program configuration module 1226 determines a user's performance level measure within a particular track has substantially increased, data for additional tracks within a particular time period can be included to provide the user with different tracks to advance through the particular time period. Other examples of the personalized content 1216 are provided in the descriptions below.

In some implementations, the personalized content 1216 includes instructions from the server 1220 adjust a device cache 1210a associated with the mobile application 1212 on the client device 1210. The device cache 1210a may store data associated with the mobile application 1212 (e.g., application configuration data, computer-implemented instructions to operate the mobile application 1212) or program data associated with a user associated the client device 1210. For example, the device cache 1210a can include user data from prior tracks, content previously transmitted from the server 1220, among other types of data used by the mobile application 1212. In such implementations, the instructions included in the personalized content 1216 may specify instructions to add or remove content from the device cache. For example, the instructions can specify removal of data associated with a prior track or period of the program to reduce the storage space on the user device 1210 necessary to execute the personalized content 1216. As another example, the user device 1210 can determine which cached data no longer corresponds to the current period, level, or track of the user in the program, and may delete the unneeded content as a result.

The caching of data at the user device 1210 allows shared processing of program rules by the user device 1210 and the server 1220. The data cached at the user device 1210 can include subsets of program rules dynamically selected by the server 1220, in some instances, a customized subset of rules selected for a particular user. For example, the server 1220 may determine the current period, track, and level of a user in a specific program, and send a data package that includes only the rules that define behavior affecting the user for that portion of the program. The server 1220 may further filter the rules according to the characteristics of the user (e.g., the user's personalized goals or history of use of the program) exclude rules that are not applicable, to limit the amount of data transferred to and stored at the user device 1210. The user device 1210 receives the data package including the rules, stores it, and processes the subset of rules locally, allowing for quick response times for user interaction and continuation of the program when the user device 1210 may not have a network connection to communicate with the server 1220.

In some implementations, the operations performed by the program configuration module 1226 may be updated and/or changed based on a set of instructions received from the administrator system 1230. For instance, the changes can include alterations to the conditions, triggers, and/or system actions used to determine the content to include within the personalized content 1216, addition of new rules that impact the selection of content to be provided within the personalized content 1216, among other types of adjustments. In some instances, the administrator system 1230 can be monitored and operated a third party organization (e.g., a healthcare provider, a health insurer) that is separate from the organization that operates the server 1220.

FIG. 12B is a block diagram that illustrates an example of the system 1200 for distributing custom content for a program. As depicted, the user device 1210, the server 1220, and the administrator system 1230 can be connected over a network 1205. The server 1220 additionally includes the program reconfiguration module 1226 for generating personalized content 1216 based on receiving data transmissions from the administrator system 1230 and the user device 1210. The personalized content 1216 is then transmitted over the network 1205 for display on a user interface of the mobile application 1212.

The server 1220 can periodically exchange data with the user device 1210 over the network 1205. For example, the server 1220 can receive user input data and user behavior data associated with a user's participation in a program from the user device 1210. The program configuration module 1226 can be a module of the server 1220 that processes the received data transmissions from the device 1210 and the server 1230 and determines the personalized content 1216 to be provided on the mobile program 1212a. For example, as described more particularly with respect to FIG. 14, the program configuration module 1226 may determine whether one or more conditions associated with a rule indicated by program stored on the server 1220 are satisfied.

In some implementations, the program configuration module 1226 can be a component that is executed on the user device 1210. The program configuration module 1226 may be configured to operate based on a set of computer-implemented instructions stored locally on the user device 1210. Other arrangements can also be possible. For example, the functions of the program configuration module 1226 may be split between the server 1220 and the user device 1210. In another example, the server 1220 may periodically provide updates to rules and other program data stored on the user device 1210, and application the user device 1210 may apply the rules and provide the personalized content 1216.

The user device 1210 can be any of various types of electronic devices that are capable of providing a user interface. Although FIGS. 12A-12C depict the user device 1210 as a smartphone, in some implementations, the device 1210 can be a tablet computing device, a laptop computing device, a desktop computing device, or a wearable device (e.g., a smart watch, glasses, or a bracelet). In addition, the user interface provided on the user device 1210 may include information provided through a visual display, but may additionally or alternatively provide information through, for example, audio output, haptic output, and electroshock, which may be dynamically configured based on information associated with the user.

The personalized content 1216 to be provided on the mobile application 1212 may be based on various user actions on the user interface of the mobile application 1212. For example, depending on a user's responses to visual notifications, audible notifications, electroshock stimulations and haptic notifications such as vibrations of the user device 1210. For example, if notifications requiring user action are dismissed, the performance level metric of the user can be reduced to indicate inactivity, which is then used to provide personalized content 1216 that is more interactive for the user. In addition, the personalized content 1216 may adjust the appearance of visual notifications, as well as the sound, volume, or length for audio notifications, and the intensity, pattern, or type of haptic outputs.

In some implementations, the system 1200 includes one or more other servers or systems 1230 or other devices that provide information that is used to reconfigure the program. For example, a mobile application may communicate with independent, third-party systems operated by a user's healthcare provider, health insurance provider, or employer. The mobile application 1212 may display additional user-selectable content on the program in response to receiving information from these third-party systems. Similarly, information from these third-party systems may be used to select which content should be presented and determine how prominently the content should be displayed (e.g., at what size or ranking in a list the content should be shown). For example, the mobile application 1212 may access electronic medical records (EMR) from a user's physician to determine or verify a user's care plan, and then configure the program to include information corresponding to that care plan. As a result, mobile application 1212 can be automatically updated to provide, for example, physician appointment reminders, medication reminders, encouragement for health plan compliance, instruction and information, and surveys related to the care plan. Similarly, when an employer's health plan options and incentives change, the server 1220 can be notified and the interface reconfiguration module 1226 can reconfigure the interface to inform the user.

FIG. 12C is a diagram that illustrates the types of data transmissions received and processed by the program reconfiguration module 1226 to generate personalized content 1216. Briefly, an administrator 1202 and a patient (e.g., user) 1204 may provide input on the admin portal 1232 and the mobile application 1212, respectively, which is then transmitted to program reconfiguration module 1226 by the administrator system 1230 and the user device 1210. As described previously with respect to FIG. 12B, the administrator system 1230 can be associated with one or more organizations that either administer or monitor a user's progress on a program (e.g., a primary healthcare provider or a health insurance company), or an entity that generates, maintains, or provides content to be access by the user (e.g., a healthcare content provider or a specialty treatment clinic). In addition to the data received from the administrator system 1230 and the user device 1210, the program configuration module 1226 can also receive data stored on the server 1220, for example, stored user data 1224a, stored content 1224b, and global rules 1224c as described previously with respect to FIG. 12A.

The program configuration module 1226 includes a set of sub-modules for determining whether conditions and/or triggers associated with the program are satisfied based on the data received from the administrator system 1230 and the user device 1210 and the program data stored on the database 1222. For instance, the program configuration module 1226 includes a program duration engine that computes a user progress measure, a program level engine 1226b that computes a user performance level measure, and a rules engine 1226c that compares the information included in the received data to determine if the triggers and/or conditions associated with a set of program-specific rules have been satisfied.

The program duration engine 1226a enables the program configuration module 1226 to track the overall progress of the user 1204 through the program sequence of the program. For example, the program duration engine 1226a is capable of extracting data from the current content 1214 as depicted in FIG. 12A and identify the current time period of the user 1204. The program duration engine 1226a also compares the current time period of the user 1204 and the prior time periods indicated within the stored content 1224b to determine the progress of the user 1204 between the present condition and the last received content from the user device 1210.

In one example, the program duration engine 1226a computes a progress measure for a particular period based on a set of requirements associated with the period. The value of the progress measure is then used to represent a user's progress through the particular period. In this example, the value of the progress measure can be compared between successive data transmissions from the user device 1210 to measure a user's development through the period. In another example, the program duration engine 1226a performs a set of tests to detect when the user 1204 has transitioned between successive periods. In this example, the program duration engine 1226a can aggregate the values for a set of performance level measurements for each of the multiple tracks within a particular period, and determine that the user has satisfied the requirements for the particular period based on determining that the aggregate performance level measurement exceeds a threshold value. In yet another example, the program duration engine 1226a uses a combination of techniques to both measure the progress of the user 1204 within a particular period and determine if the user 1204 has satisfied the requirements to transition to a successive period after a data exchange with the user device 1210.

The program level engine 1226b enables the program configuration module 1226 to determine a level that indicates performance of the user 1204 within a particular track. For instance, the program level engine 1226b may extract track-specific data associated with each current track within the current content 1214, and compare the track-specific data against a set of criteria to designate a level to the user 1204 for each current track. In one example, where the data within a particular track includes quantitative data (e.g., heart rate measurements, breathing rate measurements), the program level engine 1226b measures a performance level measure for each current track based on sensor data associated with user activity data. In another example, where the data within a particular track includes qualitative data (e.g., user survey information), the program level engine 1226b estimates an intensity score based on a set of user attributes associating with well-being (e.g., depression, anxiety, psychological condition) and assigns a level based on where the intensity score falls within a range of scores associated with each level.

The rules engine 1226c enables the program configuration module 1226 to identify applicable rules that are associated with the program and determine whether one or more conditions for the applicable rules have been satisfied. For instance, the rules engine 1226c may extract the data included in the current content 1214 and initially select a subset of applicable rules from among the global rules 1224c.

After selecting the applicable rules, the rules engine 1226c then compares the extracted data against requirements for each of the applicable rules to determine if a trigger associated with the applicable rules or one or more conditions associated with the applicable rules have been satisfied. For example, such criteria can include a minimum measurement value for a particular user parameter as described throughout, or a presence of specific event within the current content 1214 indicating that the user 1204 associated with a milestone of the program (e.g., data indicating that the user 1204 is able to walk in a rehabilitative physical therapy treatment program). In this example, a trigger may be used to enable the program configuration module 1226 to transmit a set of instructions within the personalized content 1216 for the mobile application 1212 to adjust the display of content related to the program. Likewise, the satisfaction of one or more conditions can be used to determine transitions associated with the current data (e.g., upgrades to a new level within a track, determining that the user has advanced to a new period). In this regard, techniques used by rules engine 1226c with respect to triggers and conditions associated with applicable rules enable the program configuration module 1226 to produce variations of content to provided based on prior user activity on the mobile application 1212.

Figure 13:
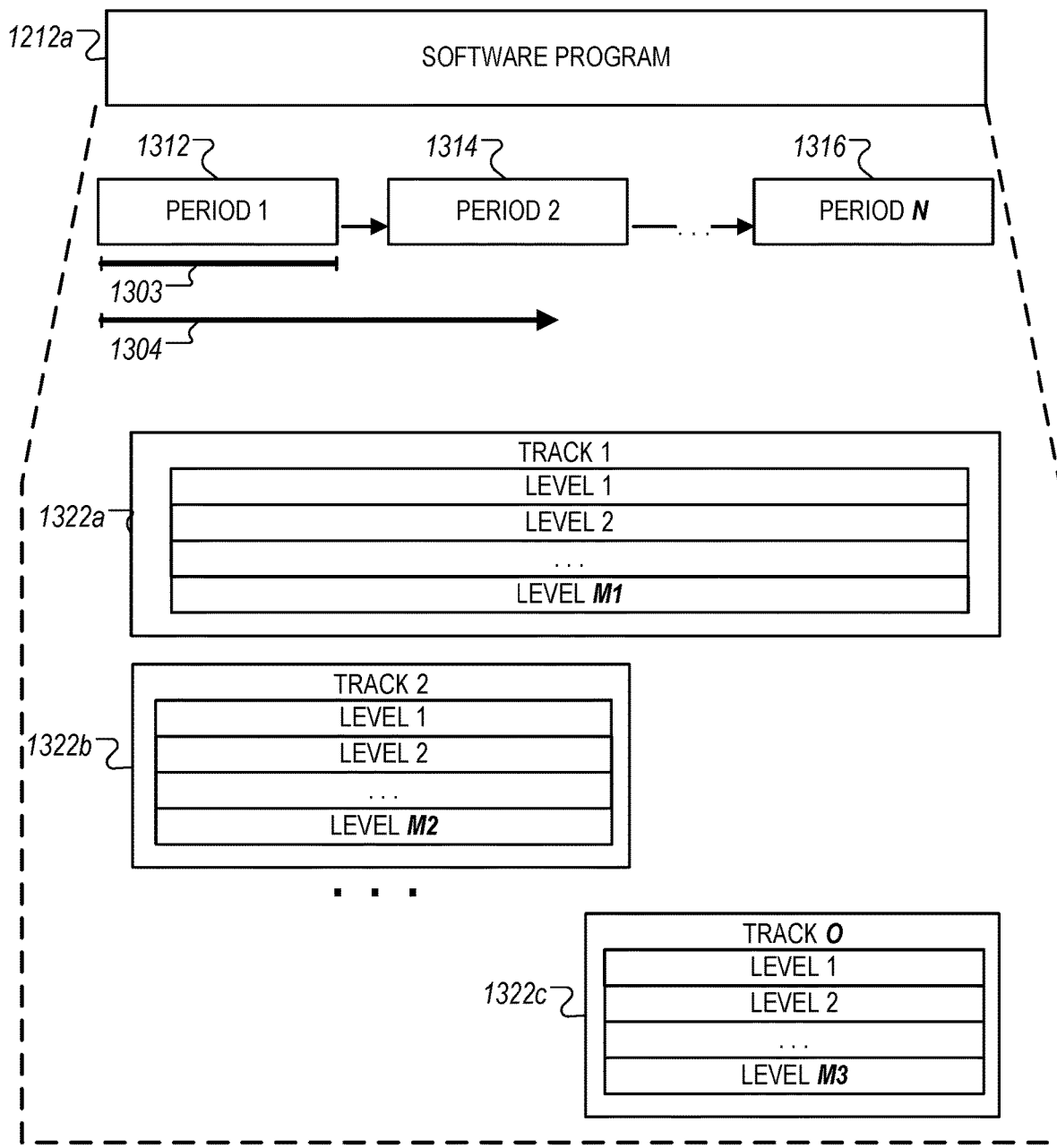
FIG. 13 is a diagram that illustrates an example of a multi-level content architecture.

FIG. 13 is a diagram that illustrates an example of a multi-level content architecture 1300. In general, a program 1302 includes a program sequence defined by a series of periods with defined time lengths including periods 1312, 1314, and 1316. For example, the period 1312 has a corresponding time length 1303. As described previously with respect to FIG. 12A, each of the periods 1312, 1314, and 1316 may have corresponding requirements indicative of a user's progress within the program 1302. As an example, the periods 1312, 1314, and 1316 can represent different stages or phases of a clinical treatment plan (e.g., diagnosis, disease control, restorative, and maintenance).

Although FIG. 13 depicts the program 112a as having multiple periods 1312, 1314, and 1314, each with multiple tracks 1322a, 1322b, and 1322c, in some implementations, the program 112a includes a single period with either a single track and/or multiple tracks. In addition, as depicted in FIG. 13, the different tracks within the program 1212a can have different corresponding lengths within the program sequence specified by the arrangement of the periods.

A progress measure 1304 can be used to indicate a user's development through respective periods (e.g., periods 1312, 1314, and 1316) and through the overall program 1302. In some instances, the progress measure 1304 can be computed based on comparing user activity data received on the mobile application 1212 to requirements associated with each of the respective periods to determine if the user has satisfied the requirements to transition between sequential periods. For example, exercise measurements (e.g., heart rate, calories burned, blood pressure) indicating a user fitness level submitted on the mobile application 1212 can be used to compared against a minimum fitness level for different periods of a physical therapy program to determine an appropriate time to transition the user between successive periods.

As depicted in FIG. 13, each period also includes a set of user-selectable tracks 1322a, 1322b, and 1322c. Each of the tracks 1322a, 1322b, and 1322c represent alternative content that can be provided for display on the mobile application 1212 based the data included within the current content 1216, and the program data stored on the database 1222. For instance, as described previously with respect to FIG. 12A, the program configuration module 1226 can processes user information (e.g., current tracks, current period) included within the current content 1216 to identify rules associated with the current tracks, and compares the data included in the current content 1216 against stored content 1224 to determine whether a trigger associated with the identified rule has been satisfied, and/or if one or more conditions specified by the identified rule are also satisfied. More particular descriptions related to the comparison techniques used by the program configuration module 1226 are described below with respect to FIG. 14.

Each track includes a set of levels that are used to indicate a user performance level measure representing a user's activities within a particular track. In some instances, the different levels can represent different difficulties associated with activities performed by the user during the track. For example, different levels within an exercise track that determines a user fitness level can represent exercise regimen of varying intensities (e.g., a relaxing walk, a mild jog, a sprint), or varying time lengths of activities (e.g., a five-minute warm-up walk, a half-mile jog, a half-marathon run). In other instances, the different levels can severities of user performance measurements across a predetermined spectrum. For example, an anxiety track may include different levels that represent measured anxiety levels associated with the user based on the user's submitted responses to surveys presented on the program. In both of these examples, the levels can be used as indicators for a user's performance level within a particular track such that period measurements of the user's current level over a period of time can be used to represent a user's progress within the track as the user progresses through the period that includes various tracks.

Figure 14:
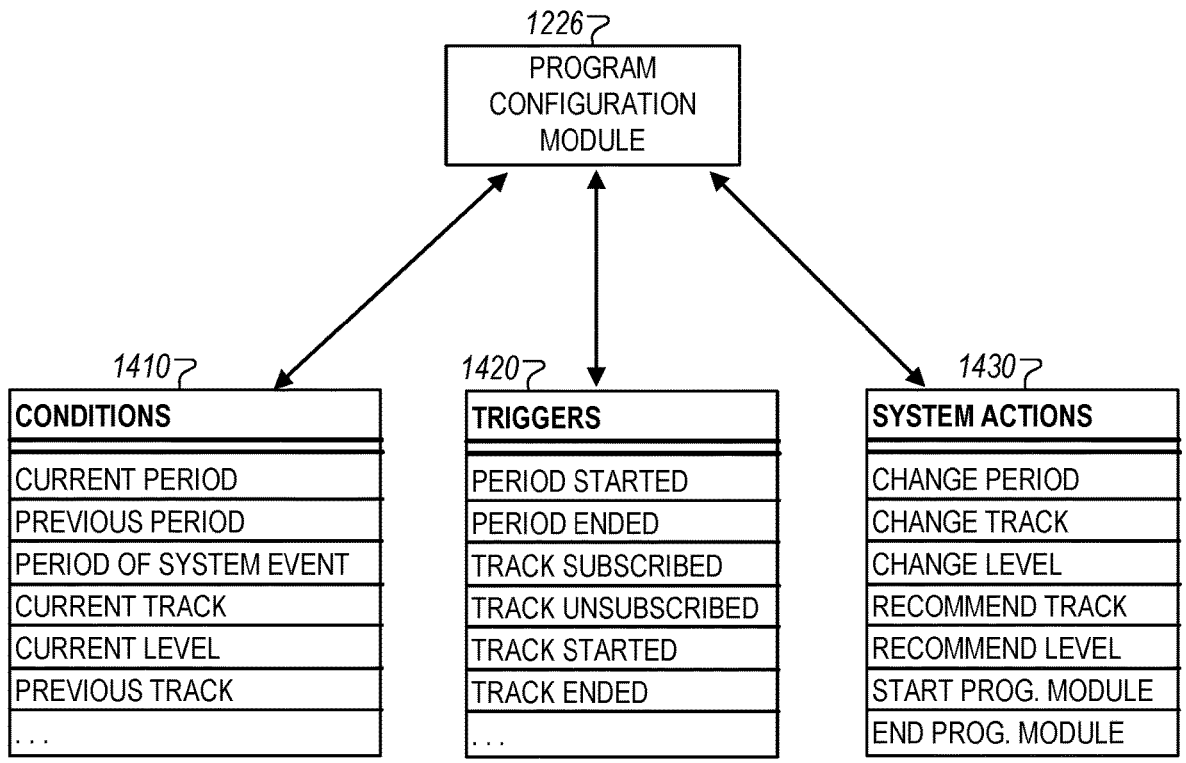
FIG. 14 is a diagram that illustrates examples of data that can be used to generate content adjustments.

FIG. 14 is a diagram that illustrates examples of different types of data that can be used to generate provide personalized content in. The program configuration module 1226 can use a set of conditions 1410, triggers 1420, and system actions 1430 to both identify applicable rules, from among the global rules 1224c, for the current content 1214 of the program. As described previously, the current content 1214 may specify a current period indicating the progress of the user 1204 within the program, the current available tracks within the current period, and the measured level for each of the current tracks associated with the user.

The applicable rules selected by the program configuration module 1226 using a variety of selection techniques. In some instances, the rules within the global rules 1224c can be predetermined to be associated with specific types of programs (e.g., preventative care programs vs. palliative care programs). In such instances, the program configuration module 1226 may determine a program category associated with the program, and filter the global rules 1224c based on the determined program category. In other instances, the rules within the global rules 1224c can be selected based on other factors such as attributes of the data included within the current content 1214 (e.g., qualitative vs. quantitative data), the particular tracks selected to participate in by the user, the arrangement of tracks within the current period, among other factors.

In some implementations, the applicable rules selected by the program configuration module 1226 can be based on relationships between historical data for the user associated with the program (e.g., prior content accessed) and the data included within the current content 1214. For example, a rule associated with a particular track may be selected if the comparison suggests that the user has repeatedly selected the particular track over multiple periods within the program sequence of the program. In another example, a transitional rule that describes actions to be performed as a result of a transition (e.g., between levels within a track, between periods within the program sequence) if the comparison suggests that either the level within the tracks have changed, the arrangement of the available tracks within a particular period has changed, or if the user has advanced or digressed to a different period than the last period.

The program configuration module 1226 also uses data within the current content 1214 to determine if triggers or conditions associated with the applicable rules have been satisfied. FIG. 14 illustrates of certain types of data that can be used to determine whether triggers or conditions have been satisfied. For example, if a rule includes a condition that specifies the user 1204 to be in a particular period within the program sequence of the program, then the program configuration module 1226 may compare the current period indicated by the current content 1214 and determine whether the current period corresponds the particular period specified by the rule condition.

In other examples, the rule can include other conditions that associate specific system events and a particular period within a program sequence. For instance, a system event can include backend processes performed by the servers 1220 and 1230 (e.g., initiating a data transmission with the user device 1210, storing the current content 1214 within the database 1222, generating the personalized content 1216 to transmit to the user device 1210). In these examples, if the current content 1214 specifies a current period that satisfies the rule, the program configuration module 1226 determines that the rule has been satisfied. For example, satisfaction of the rule can be used to coordinate the execution backend processes that adjust the selection of content to be provided on the mobile application 1212, or adjust the comparison techniques between the current content 1214 and the stored content 1224.

The satisfaction of the rules selected by the program configuration module 1226 can also be based on triggers. For instance, the program configuration module 1226 may compare the data within the current content 1214 against the historical data within the stored content 1224b to determine changes that correspond to changes specified by triggers. In one example, if the current content 1214 indicates that the user 1204 has initiated a new period within the program sequence since the last data transmissions, the program configuration module 1226 determines that a trigger for a rule that controls the display of notifications on the mobile application 1212 is satisfied, and in response, transmits an instruction to display a notification on the mobile application 1212 congratulating the user in beginning a new period. In other examples, the triggers associated with the selected rules can be associated when a user subscribes, unsubscribes, starts, or completes an available track within a period or when a user completes a track within the period.

FIG. 15 is a diagram that illustrates examples of rules that can be used by the program configuration module 1226 to adjust content associated with a program. As depicted, rule list 1510 includes four rules that are each associated with a "dog walking" track within a program focused on improving a user's physical fitness. Each period within this program corresponds to different stage of physical fitness, which may be monitored based on the frequency of activities performed by the user. Each track corresponds to a different physical activity (e.g., walking the dog, going for a jog, weight lifting), which can be used to monitor different aspects of physical fitness (e.g., endurance, stamina, strength, flexibility). Each track also includes a level indicating the intensity of the activity performed by the user.

The rules included in the list 1510 can be used to perform certain system actions based on determining whether the data transmitted from the user device 1210 satisfies one or more conditions or triggers associated with each rule. In some instances, the different rules can be used to perform alternate content delivery actions. For example, the triggers and conditions for program rules 1 and 2 can be used to perform different system actions (e.g., assessment 1 or assessment 2) and deliver different categories of content (e.g., video 1 and email 1, or video 2 and email 2). In this example, the different conditions between the rules can be used to perform the specific content delivery action based on the specific level within the current track (e.g., moderate vs. vigorous). In other instances, the different rules can be used to provide different categories of content to the mobile application 1212. For example, in response to satisfying either program rule 3 or program rule 4, a content item from either category A or category B can be provided for display on the mobile application. In this example, satisfaction of the condition is based on the user's progress within the track (e.g. no change in level, increase in the level, or decrease in the level).

Although FIG. 15 illustrates different rules that are used to provide alternate content delivery actions, in some implementations, different sets of discrete rules can be used in combination to customize the content provided to the mobile application 1212. For example, the different sets of rules can be based on the user's progress within the program (e.g., using a set of rules directed to the period), a user's performance with a single track (e.g., using a set of rules directed to the levels of the single track), a user's performance within multiple tracks within the period (e.g., using a set of rules directed to comparing user's enrollment and subscription into different tracks), and time-based changes in the user's activities within the program sequence (e.g., using sets of rules directed to detecting changes in period, track, and level). In such implementations, the triggers and conditions associated with the different rules can be used to identify certain changes that are likely to impact a user's experience within the program.

Figure 16A:
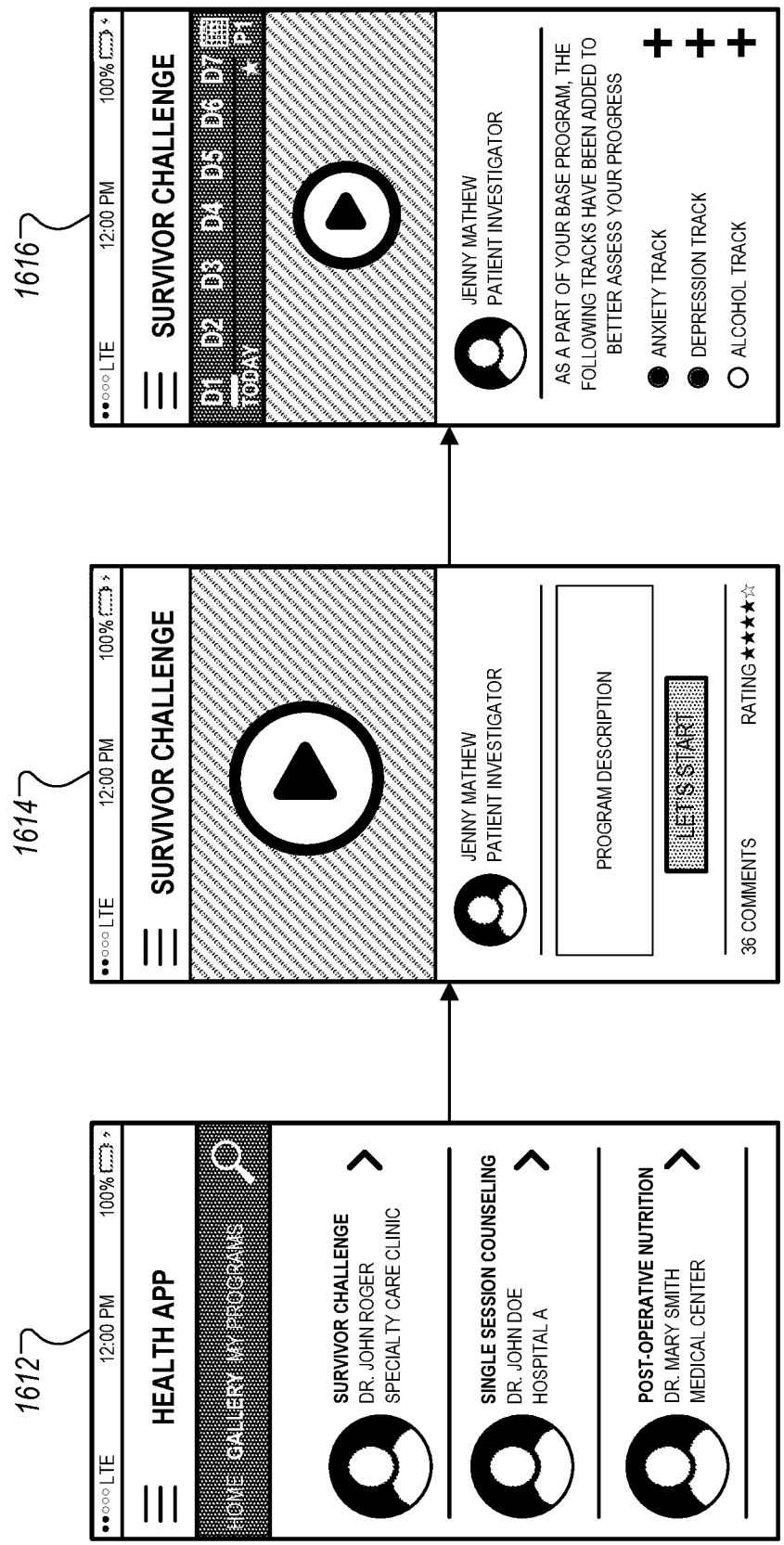
FIGS. 16A-16C are diagrams that illustrate examples of user interfaces for providing personalized content.
Figure 16B:
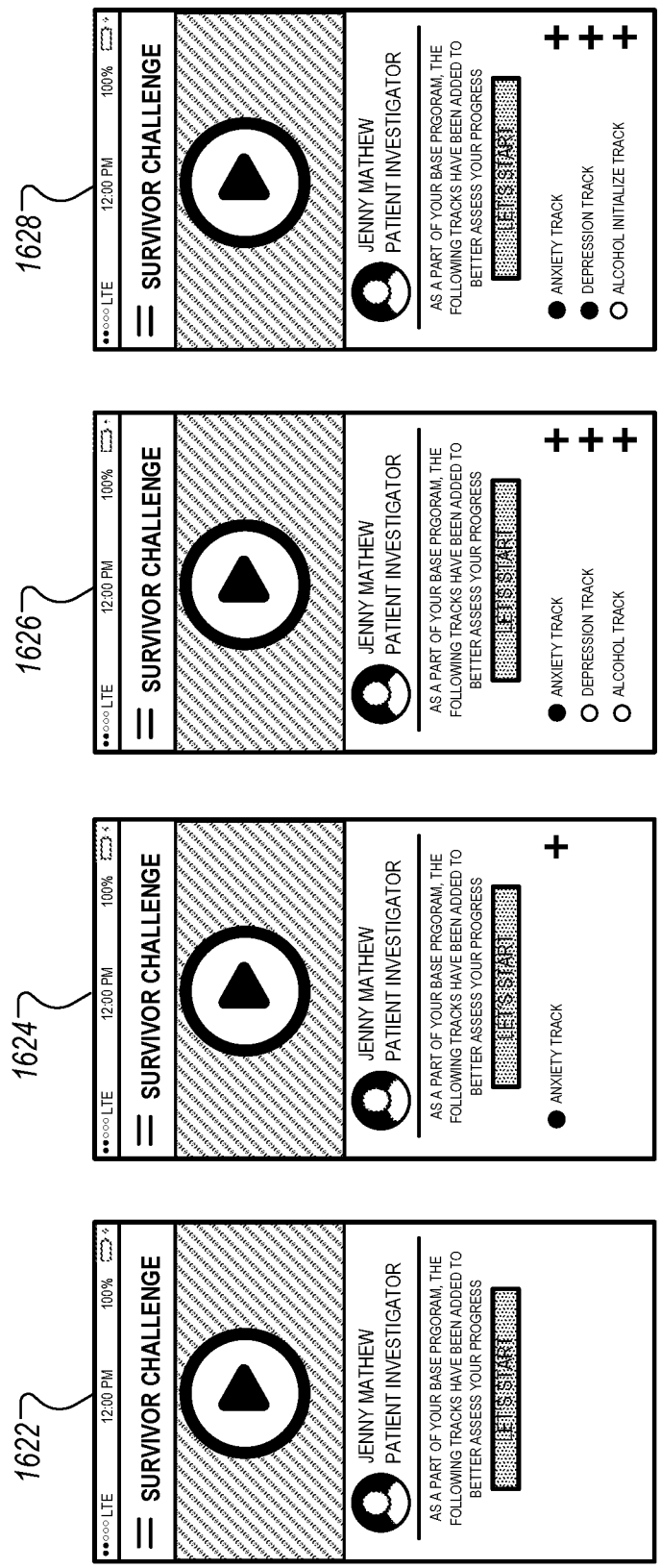
Figure 16C:
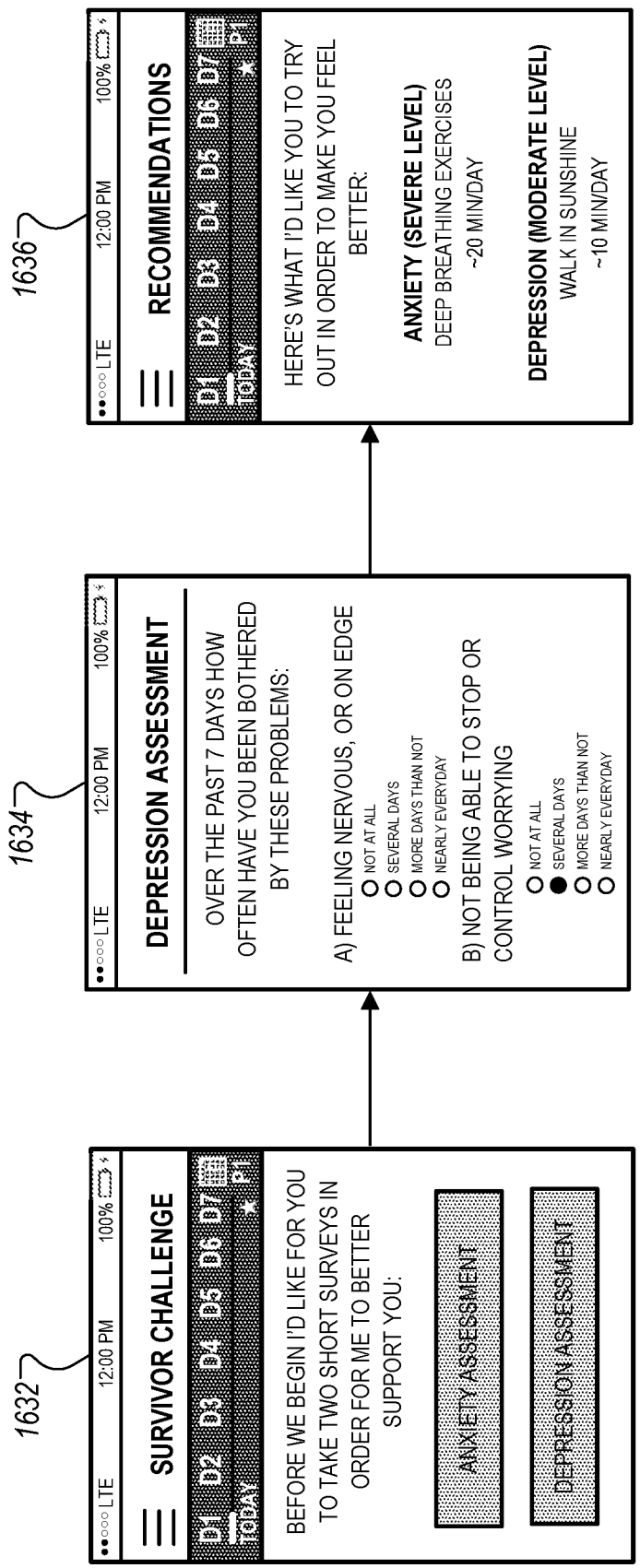

FIGS. 16A-16C are diagrams that illustrate examples of user interfaces for providing personalized content. FIG. 16A illustrates an example of user interfaces that enable to enroll into a program. FIG. 16B illustrates various user interfaces that represent different instances of the mobile application 112 based on the content transmitted from the server 1220. FIG. 16C illustrates interfaces that are used to collect information from a user, assess the collected information, and provide recommendations for tracks and levels based on the assessments.

Referring to FIG. 16A, the user 1204 may initially be presented with a list of different programs on a gallery interface 1612. In the examples illustrated in FIG. 16A, the programs include "Survivor Challenge," "Single Session Counseling," and "Post-Operative Nutrition." The interface 1612 additionally includes information associated with each program such as the healthcare provider and the related institution. Such information is provided to assist a user to select an appropriate program that is relevant to the user.

In some implementations, the list of programs provided on the interface 1612 may be selected for the user 1204 based on user-specific information. For example, the user 1204 may be requested to complete an initial registration survey when the user 1204 installs the mobile application 1212 on the user device 1210. The survey can include request for a user's primary healthcare provider, health insurance company, medical history, and other types of user-identifying information. The information submitted on the survey can then be used by the server 1220 to determine the programs that are determined to be relevant to the user 1204.

In some implementations, the list of available programs provided on the interface 1612 can be periodically updated by the server 1220 based on the user data submitted on the mobile application 1212. For instance, if a user enrolls into a particular program focused on post-operative recovery, then the server 1220 may determine other programs that are associated to the enrolled program (e.g., similar programs enrolled into by other patients who have enrolled into post-operative recovery programs, other programs that are complementary to post-operative recovery programs). The other programs can then be provided on the interface 1612 as the user 1204 progresses through the post-operative recovery program.

In the example in FIG. 16A, the user 1204 selects the "Survivor Challenge" program on the interface 1612 and is then directed to the interface 1614. The interface 1614 is a program-specific interface that provides program information to the user 1204. For example, the interface 1614 can provide information for a healthcare provider such as a patient investigator, a program description providing an overview of the program sequence, and/or media content associated with the program. The interface 1614 can also display user-submitted feedback such as reviews and ratings from other users that have previously participated in the program.

Once the user 1204 enrolls into program on the interface 1614, the user 1204 is then directed to the interface 1616. The interface 1616 provides program-related information such as the period information (indicated as P1 in the interface 1616), track information (e.g., available tracks and unavailable tracks) and options for the user to subscribe to available tracks. The interface 1616 may also provide media content that overviews the entire program and provides the user 1204 with a comprehensive view of the program sequence of the program.

In some implementations, the initial tracks available for access to the user may be predetermined based on a set of baseline tracks that are available to all users that initially enroll into the program. In such implementations, the user can be provided with access to the baseline tracks (e.g., Anxiety Track and Depression Track in the FIG.), but not provided with access to additional tracks (e.g., Alcohol Track) until the user has either completed or achieved a certain performance level with the baseline tracks. For example, the Alcohol Initialize Track may become available to the user 1204 based on either the user completing one or both of the Anxiety Track and Depression Track, the user 1204 achieving a minimum performance level within each of these tracks to satisfy the criteria for the Alcohol Track. In each of these examples, access to the additional tracks may be governed with the use of rules to determine whether the user 1204 has satisfied a set of conditions or triggers as described previously with respect to FIGS. 14-15.

Referring now to FIG. 16B, the interface 1616 can be adjusted at different time points to alternate configurations specified by different rules as described previously with respect to FIG. 15. The configurations of the interfaces 1622, 1624, 1626, and 1628 can be adjusted based on a user's progress through the program. For instance, the interface 1622 represents an example of an interface when the user 1204 initially enrolls into the program. In this example, relatively simple configuration of the interface provides the user 1204 with access to a base track without any additional tracks. This interface can be used to improve user experience when the user 1204 has limited experience with the program to prevent confusion and/or ease the user 1204 into the program.

The interface 1624 illustrates an example of an interface where the user 1204 may be provided with access to an optional "Anxiety Track" in addition to the baseline track for the program. In some implementations, the optional track is automatically provided based on determining that it is commonly associated with the program. For instance, the optional track may be provided because historical data associated with the program indicates that other users who have previously participated in the program have enrolled into the track from a list of optional tracks. In other implementations, the optional track may be provided based specifically on user-specific information associated with the user 1204. For instance, the user may complete an initial survey when enrolling into the program, which can then be used to determine a set of baseline attributes used to determine optional tracks of interest. In such instances, the decision to provide an optional track can be used to customize the program for the user 1204.

The interface 1626 illustrates an example of an interface that provides optional tracks that are not presently accessible (e.g., Depression Track and Alcohol Track). In this example, access to the optional tracks may be controlled using the rule satisfaction techniques described throughout this disclosure. For example, access to the optional tracks may be restricted to provide the user 1204 with an incentive to increase participation in the presently available tracks (e.g., the baseline track and the Anxiety Track) until the progress or performance level of the user 1204 exceeds a minimum value specified by one or more associated rules. In one example, access to the restricted tracks may be provided after the user progresses to a certain period within the program sequence of the program. In this example, the user 1204 may progress through the period based on the passage of time (e.g., a seven-day period), or based on the performance level measure of the user 1204 within each of the available tracks (e.g., achieving higher levels within the baseline track and the Anxiety Track). In another example, access to the restricted tracks may be manually provided by the administrator 1202 after reviewing user data (e.g., survey information, performance on tracks) submitted on the mobile application 1212. In this example, the interface 1626 enables the administrator 1202 to use the program configuration module 1226 dynamically provide content that is directed to improving the experience and progress of the user 1204 through the program.

The interface 1628 illustrates an example of an interface that provides the user 1204 with the ability to select from a list of optional tracks. In this example, the tracks included in list of optional tracks are initially selected to be provided on the interface 1628 based on a variety of factors described above with respect to the interface 1622. This enables the user 1204 to select a customized experience within the program based on the selections from the list of optional tracks. In addition, as described throughout, the selections of the optional tracks can then be used to adjust the techniques used by the program configuration module 1226 to both identify the applicable rules and determine whether the conditions and rules of the applicable rules have been satisfied after receiving data transmissions from the user device 1210.

Although the interfaces 1622, 1624, 1626, and 1628 are described as alternative interfaces, in some instances, the interfaces 1622, 1624, 1626, and 1628 can be different instances of the mobile application 1212 over a period of time. In such instances, the interface 1622 is presented to the user at time point t1, and the interfaces 1624, 1626, and 1628 are subsequently presented to the user at time points t2, t3, and t4, respectively. The transition between time point t1 and t4 reflects the addition of supplemental content and various access settings on the program as the user progress through different periods of the program sequence of the program.

Referring now to FIG. 16C, interfaces 1632, 1634, and 1636 can be used to collect information from the user 1204, assess the collected information, and provide recommendations for tracks and levels based on the assessments. For instance, the interface 1632 may present the user 1204 with the option to participate in assessment surveys related to subscribed tracks within the program.

The user can select an assessment and then be directed to the interface 1634 to answer questions that are relevant to the selected track. For instance, the interface 1634 requests the user to provide answers to questions related to the selected track. In the example, the questions are directed to determine a depression level of the user based on questions related to the user's feelings of nervousness and lack of control.

After user 1204 completes the assessment survey on the interface 1634, the collected data may be analyzed by either the user device 1210 or the server 1220. For instance, the user responses included within the collected data may be analyzed against previously submitted responses by the user, prior responses submitted by other users who have completed similar survey assessments, or other types of statistical data models. The server 1220 can then determine a level associated with the user responses and then provide the level determinations on the interface 1236.

The interface 1636 can also provide recommendations to the user 1204 based on the determined levels for each of the tracks. In the examples illustrated, the interface 1636 provides a recommendation to perform deep breathing exercises in response to determining a severe anxiety level, and a recommendation to walk in sunlight in response to determining a moderate depression level. In this regard, the user-submitted information can be used to automatically provide the user 1204 with feedback on improving his/her performance within the available tracks within the program.

In some implementations, the level determinations can be used to further adjust the content displayed to the user 1204 on the program. For example, as described throughout this disclosure, in response to determining the track levels and generating user recommendations, the program configuration module 1226 may also identify additional tracks that are associated with the recommendations and provide the additional tracks for display on the program. In other examples, the program configuration module 1226 may perform other system actions such as providing additional notifications and/or messages to the user to improve motivation of the user 1204, adjusting the layout of the content within the program, or enable the user to subscribe into other tracks that are more suitable to the recommendations than the currently available tracks.

Figure 17:
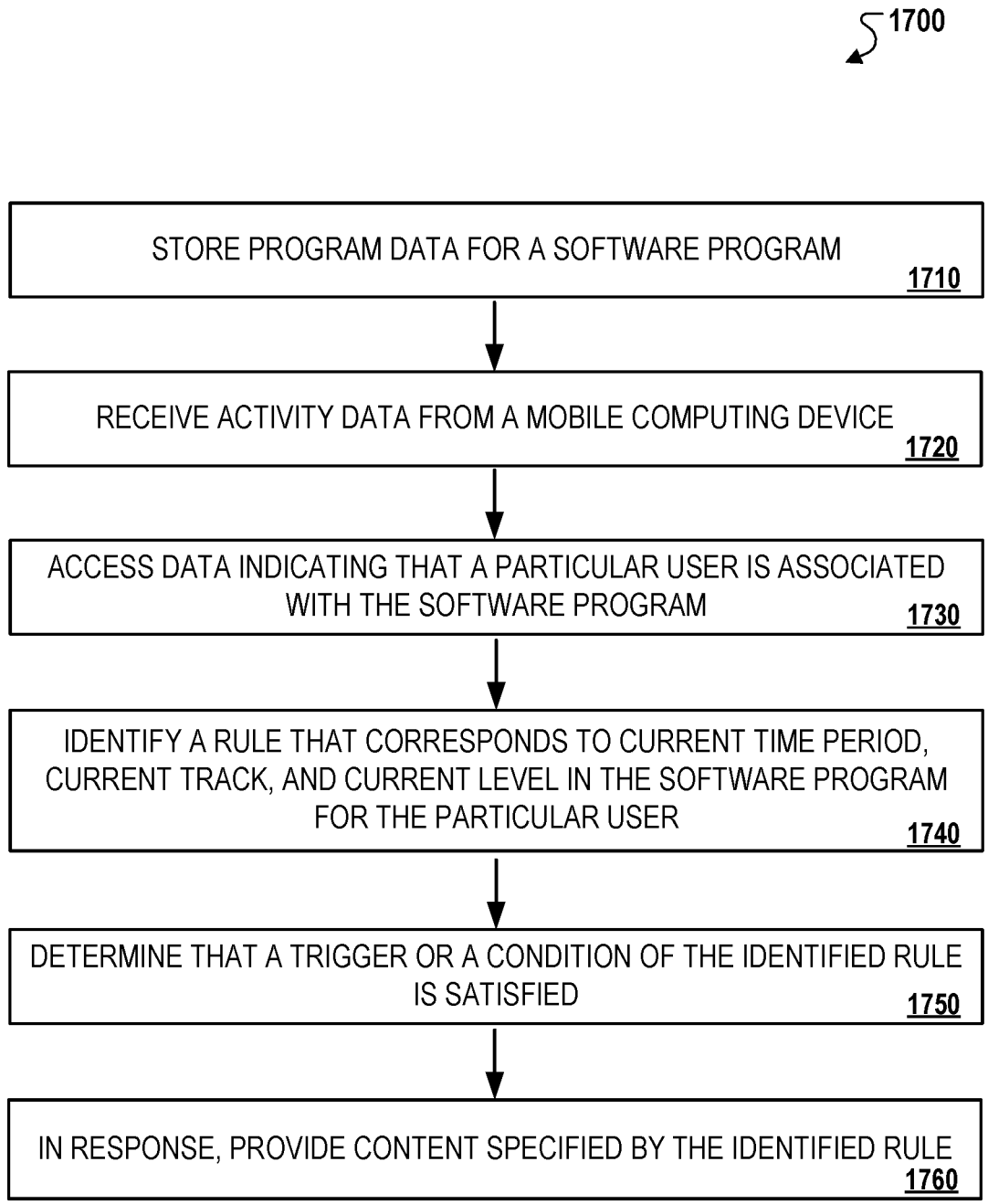
FIG. 17 is a diagram of an example of a process for providing personalized content based on an identified rule.

FIG. 17 is a diagram of an example of a process 1700 for providing personalized content based on an identified rule. Briefly, the process 1700 can include storing program data for a program (1710), receiving activity data from a mobile computing device (1720), accessing data indicating that a particular user is associated with the program (1730), identifying a rule that corresponds to a current time, current track, and current level in the program for the particular user (1740), determining that a trigger or a condition of the identified rule is satisfied (1750), and in response, providing content specified by the identified rule (1760).

In more detail, the process 1700 can include storing program data for a program (1710). For instance, the server 1220 stores program data for a program 1212a such as the stored user data 1224a and the stored content 1224b. The stored program data provides interactive content over a program sequence that includes a series of multiple time periods such as periods 1312, 1314, and 1316. As described previously with respect to FIG. 13, the program 1212a includes multiple selectable tracks 1322a, 1322b, and 1322c, and multiple levels within each track. The program data also indicates global rules 1224c for the program that vary the interactive content provided to different users according to at least the respective tracks, levels, and time periods of the different users in the program.

The process 1700 can include receiving activity data from a mobile computing device (1720). For instance, the server 1220 can receive activity data from the user device 1210 that indicates interaction of the user 1204 during a particular period of the multiple time periods 1312, 1314, and 1316 of the program 1212a. As described previously with respect to FIG. 12A, the data can include user inputs provided by the user on the mobile application 1212, selections of particular tracks that the user 1204 decides to subscribe to, or responses to assessment surveys provided on the mobile application 1212.

The process 1700 can include accessing data indicating that a particular user is associated with the program (1730). For instance, the server 1220 can access the current content 1214 from the mobile application 1212 that indicates that the user 1204 is associated with the program on the user device 1210. The current content 1214 can include a current time period, a current track, and a current level for the user 1204 in the program. As described previously with respect to FIG. 12A, the server 1220 can periodically access the current content 1214 over intervals of time to determine the progress of the user 1204 through the program, and other changes in the current content over time.

The process 1700 can include identifying a rule that corresponds to a current time, current track, and current level in the program for the particular user (1740). For instance, the server 1220 can identify an applicable rule from among the global rules 1224c that corresponds to the current time period, the current track, and the current level in the program for the user 1204. As described previously with respect to FIG. 14, the applicable rule can be selected based on comparing the current content 1214 to the program data stored on the database 1222.

The process 1700 can include determining that a trigger or a condition of the identified rule is satisfied (1750). For instance, the server 1220 can determine that the trigger and the condition of the identified rule is satisfied based on determining that portions of the current content in the database 1222 correspond to the requirements specified by the identified rule.

The process 1700 can include providing content specified by the identified rule in response to determining that the trigger or the condition of the identified rule is satisfied (1760). For instance, in response to determining that the trigger or the condition of the identified rule is satisfied, the server 1220 can transmit the personalized content 1216 to user device 1210 for display on the mobile application 1212. As described previously with respect to FIG. 12A, the personalized content 1216 can include additional content (e.g., new tracks) that the user 1204 did not previously have access to, instructions to adjust the display of content (e.g., removing access to tracks completed by the user 1204), notifications and/or messages to be displayed on the interface of the mobile application 1212 (e.g., a user survey provided in response to user performance within a certain track), among other types of content.

Section 4

FIGS. 18A-22 show a system capable of improving user engagement with an application by individually personalizing the communication between the application and each user. For example, the application, and an associated server system, can implicitly learn a user's preferences for engagement through user responses periodically sent to the user on the application. Additionally, the system can determine which types of communications and timing are most effective in supporting the user in achieving appropriate performance targets.

With respect to FIGS. 18A-22, "user engagement" refers generally to user's activity on the application. In some instances, "user engagement" refers to the input received on the application that is related to user activity on the application (e.g., user input provided on an application interface, or sensor data associated with user activity). In other instances, "user engagement" refers to the user's performance on a program that is provided on the application. The user's performance can be measured relative to a set of program criteria that describes the objective or purpose of the program (e.g., physical activity goals, lowering cholesterol). In this regard, the system can measure "user engagement" in order to identify communications to both improve a user's interactions on the application (e.g., number of user inputs provided on the application) and improve the user's performance on a program provided on the application.

With respect to FIGS. 18A-22, "performance category" refers to a particular aspect of user activity on the application that is evaluated by the system in order to improve user engagement on the application. As an example, a performance category can represent goal adherence, where the system monitors user input data received on the application (e.g., a manual input indicating user cholesterol level), and compares the user input data relative to a particular performance goal (e.g., target cholesterol level). In this example, the comparison is used to adaptively adjust communications to maximize the user's ability to achieve the performance goal (e.g., through different types of communications that suggest different user behaviors directed towards goal adherence). As another example, a performance category can also represent a level of user interactivity, where the system monitors the number of user interactions on the application over a specified period of time. In this example, the number and regularity of user interactions on the application can be used to determine user interactivity on the application. The system can then adaptively determine, based prior user interactions on the application, the user's preferences for certain communications in relation to specific user contexts. The system then adjusts the communications provided on the application based on the user's present context in order to improve user interactivity on the application.

Applications are often unable to enable maintain consistent and meaningful engagement with users. For instance, users often use an application frequently when it is new, then reduce or discontinue use over time. In the case of healthcare support applications, failing to use an application can be detrimental to the user, since the user may fail to reach his potential for physical and mental wellbeing.

In some implementations, a system is capable of improving engagement with an application by individually personalizing the communication between the application and each user. For example, the application, and an associated server system, can implicitly learn a user's preferences for engagement through user responses periodically sent to the user on the application. Additionally, the system can determine which types of communications and timing are most effective in supporting the user in achieving appropriate performance targets.

For example, different users can respond differently to communications. Some users respond well to a single reminder for taking medicine, given at the time the medication is needed. However, other users respond better to a reminder at the beginning of the day, or a reminder thirty minutes beforehand, or a reminder in a particular location.

As another example, some users respond to a direct instruction, while others respond to a more indirect communication, such as praise for taking the medication the day before. The system can start with a set of standard reminders, and adjust the timing and type of interactions with the user based on the user's performance with respect to certain metrics.

To individually personalize the communications with the application, the system initially determines how different aspects of communication affect a specific user's performance on the application with respect to a set of performance categories. For example, such performance categories can include the level of user interactivity on the application (e.g., number and type of user responses after receiving communications), adherence to specified program criteria (e.g., taking medications as instructed in accordance with a treatment plan), or patterns of passively determined user behaviors that indicate engagement or lack of engagement (e.g., consistency of periodic user input that reflects a user's participation), among others. Measurements relating to the user's performance with respect to such performance categories are then used to determine a user's preferences for receiving information. This enables the system to determine the type of content to send to the user during specific circumstances, and an optimal time period in which to send the content responsive to a particular user context.

The system utilizes the user's preferences to provide specific communications that are responsive to a particular user context and targeted to improve the engagement of the user on the application. For example, the system may receive context data indicating a particular location associated with the user, prior applications used by the user, or other types of information indicating external circumstances beyond the user's activity on the application. The system then determines a set of responsiveness scores indicating a respective likelihood that a particular communication type and/or content type will improve the user's engagement in the application with respect to a particular performance category.

As an example, a performance category can be to improve the user's adherence to a user-defined fitness goal by engaging the user to participate in specified fitness exercises. In response to receiving context data indicating the location of the user, current activity of the user and the user's current performance relative to the fitness goal, the system can transmit different types of communication that engage the user in different ways based on the user's current context. For instance, if the user's current context indicates that he/she has limited availability to interact with the application and that his/her performance is below the specified fitness goal for a specified period of time, the system sends a text-based message to encourage the user to improve performance to adhere to the goal. In another instance, if the user's current context indicates that he/she has greater ability to interact with the application, the system may instead send a video message that is directed to improving user performances. In these two scenarios, the user's availability to interact is used to compute respective responsiveness scores associated with each type of content (e.g., text or audio content), and automatically send the most appropriate content indicated by the values associated with the respective responsiveness scores.

Additional advantages result from the ability to eliminate unnecessary interactions that are not likely to assist the user. By eliminating these unhelpful outputs, the system conserves battery power, processing cycles, and network bandwidth.

In some implementations, a method performed by one or more computers includes: identifying a performance category for which performance is tracked for a user of an application; receiving, from a client device associated with the user, context data indicating a current context of the user; determining one or more responsiveness scores indicating actions of the user with respect to the performance category following the previous communications through the application; selecting a communication, from among communications of multiple types, based on the context data for the user and the one or more responsiveness scores for the user; determining a time to provide the communication to the user based on the context data; and providing the selected communication for output by the client device at the determined time.

In some implementations, at least one of the one or more responsiveness scores indicates a likelihood that the selected communication will improve the performance of the user with respect to the identified performance category.

In some implementations, at least one of the one or more responsiveness scores reflects a context-specific likelihood that the selected communication will improve the performance of the user with respect to the identified performance category when the user is presently in the current context.

In some implementations, determining one or more responsiveness scores comprises: receiving historical context data indicating a prior context associated with the user; identifying prior actions of the user with respect to the performance category when the user was determined to be in the prior context; determining a prior performance of the user with respect to the performance category; determining that the prior context associated with the user corresponds to the current context of the user; and determining the one or more responsiveness scores based at least on the prior performance of the user with respect to the performance category.

In some implementations, identifying the performance category performance category comprises determining a user-specific target metric for the user; and determining one or more responsiveness scores comprises determining one or more responsiveness scores indicating performance of the user with respect to the target context-specific metric following previous communications through the application.

In some implementations, selecting the communication comprises: selecting a type of content to be included within the selected communication; and selecting a type of user interaction to be specified by the selected communication.

In some implementations, the method includes periodically adjusting the values of the one or more responsiveness scores based at least on the tracked performance for the user with respect to the identified performance category over a particular period of time.

In some implementations, the method includes determining that one or more communications are not likely to improve performance of the user with respect to the identified performance category based on the received context data and the one or more responsiveness scores for the user.

In some implementations, the method includes generating a user profile based at least on an analysis of (i) user interactions on the application after the selected communication is for output by the client device, and (ii) performance of the user after the selected communication is for output by the client device.

In some implementations, the performance of the user is determined based at least on receiving sensor data indicating one or more user physical activity metrics.

Figure 18A:
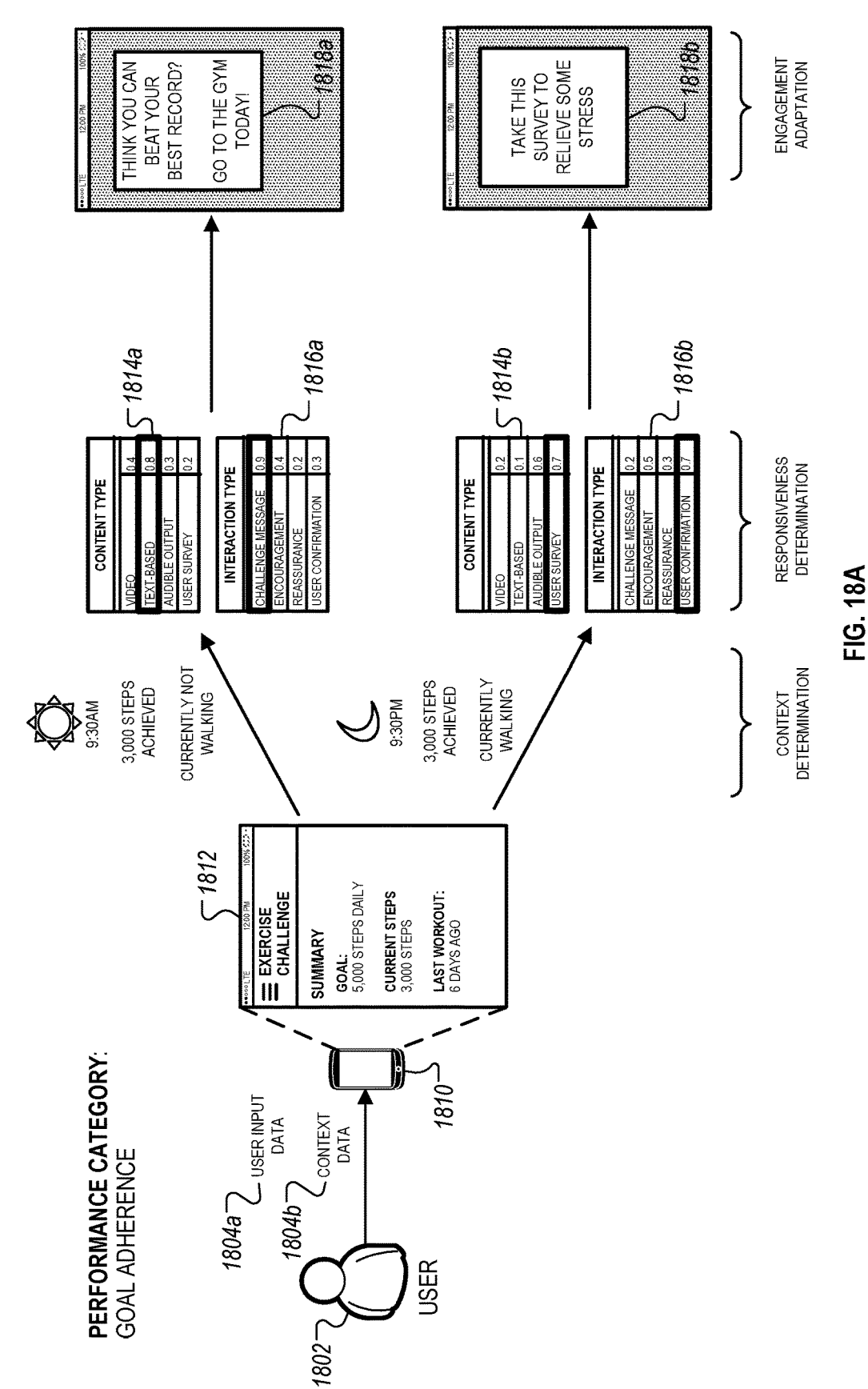
FIG. 18A is a diagram that illustrates examples of different context-based engagement adaptations for a performance category.

FIG. 18A is a diagram that illustrates examples of different context-based engagement adaptations for a performance category. In the example, a user 1802 participates in an exercise challenge program through an application 1812 that runs on a client device 1810. The exercise challenge program allows the user 1802 to set a performance goal (e.g., 5,000 steps daily). The measured user performance, based on the user interactions on the application 1812, are then compared to the performance goal. This comparison is used to adaptively improve user engagement on the application to improve goal adherence based on the user's present context.

The client device 1810 initially receives user input data 1804*a* from a user 1802, and context data 1804*b* associated with the user input data 1804*a*. The user input data 1804*a* can include manual input provided by the user on an application interface, or sensor data that is associated with user activity related to the application. The context data 1804*b* can include various types of data indicating a present context of the user 1802 (e.g., user location, time of day, prior user activity on other applications on the client device 1810, etc.). In the example, the user input data 1804*a* specifies a number of steps achieved by the user 1802, and the context data 1804*b* indicates a time of day and present user activity at the time when the user input data 1804*a* is received by the client device 1810.

Upon receiving the user input data 1804*a* and the context data 1804*b*, the application 1812 updates the performance tracking data associated with the exercise challenge. For example, the application 1812 provides a summary that specifies the target performance goal of 5,000 daily steps, a present user performance indicating 3,000 steps achieved for the present day, and the last identified workout for the user.

The system then adaptively adjusts the user engagement based on the present context indicated by the context data 1804*b*. This is accomplished by initially performing a context determination to identify the present context associated with the user 1802, determining a set of responsiveness scores that indicate respective likelihoods of the user 1802 responding to a type of content provided and a type of interaction included within a communication, and then providing a specific communication based on the values of the responsiveness scores. In the examples depicted in FIG. 18, different communications 1818*a* and 1818*b* are provided to the user based on the different present contexts identified for the user 1802.

In the first instance, the system initially determines that the context data 1804*b* indicates that the time of day is morning (e.g., 9:30 AM), the user performance is below the target performance (e.g., 3,000 steps achieved with a goal of 5,000 daily steps), and that the user is not presently walking. The system then computes a set of respective responsiveness scores for a type of content and a type of interaction to be included within a subsequent communication, which are specified by the tables 1814*a* and 1816*a*, respectively.

The table 1814*a* specifies that the responsiveness score is the greatest for text-based content based on determining that the time of day specified by the context data 1804*b* indicates that the attention of the user 1802 may be occupied because he/she may presently be travelling to work. In calculating the responsiveness scores, the system may also consider prior user activity or user interactions at the time of day specified by the context data 1804*b*. Therefore, because text-based content is the least intrusive compared to the other types of content included within the table 1814*a* (e.g., video content, audible output, user survey), the system calculates the highest responsiveness score for text-based content.

In addition, the table 1816*a* specifies that the responsiveness score is the greatest for a challenge message based on determining that that user's current performance, in relation to the early time of day, indicates that the user is likely to exceed the daily target goal. In addition, because the context data 1804*b* indicates that the user 1802 is not presently walking, the system may determine a communication may be necessary to motivate the user to continue walking throughout the day. In calculating the responsiveness scores, the system considers the type of user interaction that is likely to improve user activity. Therefore, because the present user performance indicates that the user has outperformed the performance goal for the time of day, the challenge message is determined to have the highest responsiveness score.

The system then provides the communication 1818*a* for output on the application 1812. As depicted, the communication 1818*a* is a text-based challenge message that is targeted to motivate the user 1802 to go to the gym later in the day in order to exceed the target performance goal. The communication 1818*a* is generated based on the highest responsiveness scores indicated by the tables 1814*a* and 1816*a*.

Referring now to the second instance, the system initially determines that the context data 1804*b* indicates that the time of day is night (e.g., 9:30 PM), the user performance is below the target performance (e.g., 3,000 steps achieved with a goal of 5,000 daily steps), and that the user is presently walking. The system then computes a set of respective responsiveness scores for a type of content and a type of interaction to be included within a subsequent communication, which are specified by the tables 1814*b* and 1816*b*, respectively.

Compared to the first instance, the table 1814*b* instead specifies that the responsiveness score is the greatest for a user survey based on determining that the time of day specified by the context data 1802 and the user activity level indicates that the user 1802 may be tired and/or exhausted from a long day. In this situation, the system determines that the user is highly unlikely to achieve the performance goal for the program. In addition, because of present user activity indicating that the user is presently walking, the system may determine that the user may be trying to superficially accomplish the target goal, which may potentially cause detrimental impacts to his/her mental well-being. Therefore, the user survey is determined to have the highest responsiveness score within the table 1814*b* to prepare the user to improve performance the following day.

In addition, the table 1816*b* specifies that the responsiveness score is the greatest for a user confirmation based on determining that the user's performance for the present day is deficient in relation to the performance goal for the program. In addition, because the user has not worked out in the last six days, the system determines that the user's interaction level on has fallen below a threshold level and a user confirmation may be necessary to re-evaluate the user's fitness goals and/or expectations from participating in the exercise challenge program.

The system then provides the communication 1818*b* for output on the application 1812. As depicted, the communication 1818*b* is a request for the user to particulate in a stress relieving survey. The survey requests the user to answer questions related to his/her performance on the exercise challenge program, whether he/she has faced any anxiety or stress during participation in the program, and/or other information. The questions or information included within survey is based on the responsiveness scores indicated by the tables 1814*b* and 1816*b*.

In the two instances described in FIG. 18A, the system utilizes the context data 1804*b* indicating a present user context of the user 1802 and data related to the user's prior interactions on the application 1812, to determine the most appropriate communication to send to the user 1802 in order to improve and/or maximize goal adherence. In this regard, the selected performance category (e.g., goal adherence) is used to calculate values of the responsiveness scores for content type and interaction type to improve the user's performance with respect to the particular performance category.

Figure 18B:
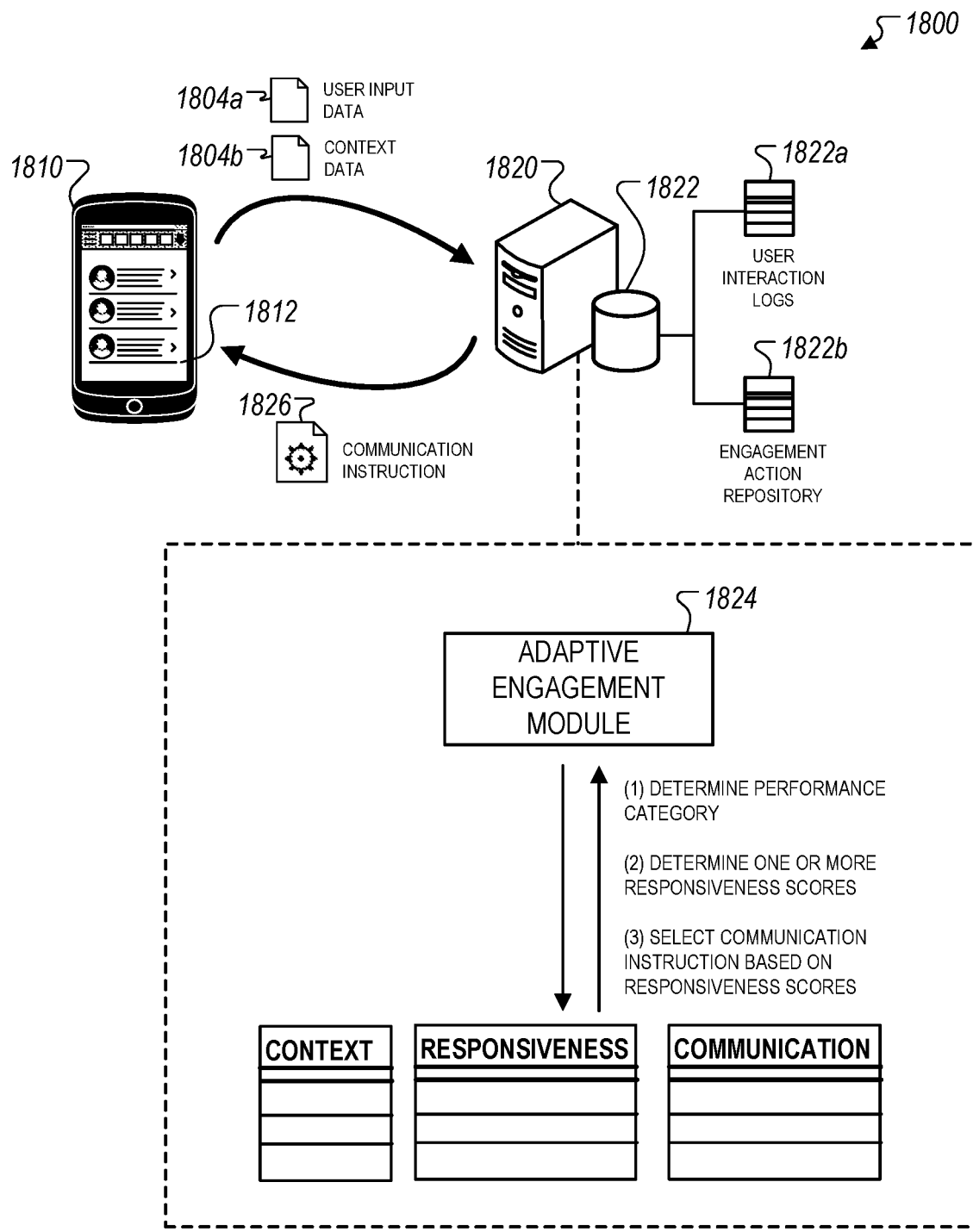
FIG. 18B is a diagram that illustrates an example of a system that is capable of adaptively performing personalized engagement.

FIG. 18B is a diagram that illustrates an example of a system 1800 that is capable of adaptively adjusting user engagement on an application. The system 1800 generally includes the client device 1810 and a remote server 1820, which exchange communications over a network. The server 1820 includes a database 1822 that stores user interaction logs 1822*a* and engagement action repository 1822*b*. The server 1820 further includes an adaptive engagement module 1824 that determines the most appropriate communication to provide to the client device 1810.

In general, during an engagement adaptation process, the client device 1810 initially transmits the user input data 1804*a* and the context data 1804*b* to the server 1820. The adaptive engagement module 1824 then identifies an applicable performance category to evaluate the received data, determines one or more responsiveness scores based on the received data, and then selects a communication instruction based on the values of the one or more responsiveness scores. The adaptive engagement module 1824 uses a rule engine analyzes a set of rules that are each specified by associated conditions, triggers, and system actions. The server 1820 then generates a communication instruction 1826 that includes the communication selected by the adaptive engagement module 1824, and transmits the communication instruction 1826 for output on the client device 1810.

The client device 1810 can be any type of electronic computing device that is capable of executing an application and providing a user interface. For instance, although the client device 1810 is depicted as a smartphone, in some implementations, the client device 1810 may be a tablet computing device, a laptop computing device, a desktop computing device, or a wearable device (e.g., a smart watch, smart classes, a bracelet, etc.). In addition, the user interface provided on the client device 1810 may be outputted through a visual display, but may additionally or alternatively provide information through, for example, audio output, haptic outputs, and electroshock which may be dynamically configured based on information about the user.

The server 1820 can be any type of remote electronic computing device that is capable of exchanging data transmissions with the client device 1810 over a network. The server 1820 stores data received from the client device 1810 (e.g., the user input data 1804*a* and the context data 1804*b*) in the database 1822. For example, after each data transmission between the client device 1810 and the server 1820, the data received by the server 1820 may be stored in the database 1822 as historical data stored included within the user interaction logs 1822*a*. This data can then be used in selecting the most appropriate communication in a subsequent adaptive engagement adjustment operation.

The user interaction logs 1822*a* include historical data related to user activity and/or performance on the application 1812. For example, the user interaction logs 1822*a* can include mappings between a prior user context, a prior communication provided to the user, and a user's prior response to the communication. The user interaction logs 1822*a* can also include prior responsiveness score calculations made by the adaptive engagement module 1824. In this regard, the user interaction logs 1822*a* enable the adaptive engagement module 1824 to utilize historical information associated with the user to make personalized adjustments in communication that are likely to be responsive to user when he/she is associated with a particular context. In addition, because the user interaction logs 1822*a* are periodically updated with each data transmission, the data included within the user interaction logs 1822*a* can be used to slowly adapt the communications to the inherent preferences of the user.

The engagement action repository 1822*b* includes a list of prior communications that were provided to the user in a prior engagement adjustment operation. For instance, the engagement action repository 1822*b* can specify a prior context associated with the user 1802, the respective responsiveness scores predicted for the user 1802 given the prior context, and the selected communication that was provided to the user 1802. In this regard, during a subsequent engagement adjustment operation, the data included within the engagement action repository 1822*b* can be used to provide a user 1802 with a similar communication if the user's present context is determined to be similar to a prior context that is associated with a previously submitted communication. For example, the data included within engagement action repository 1822*b* can be used to transmit quick-response communications that are associated with a set of predetermined reoccurring contexts for the user (e.g., when the user is at work, when the user is at home, etc.).

The adaptive engagement module 1824 may be a software module that selects a communication to be included within the communication instruction 1826 based on comparing the user input data 1804*a* and the context data 1804*b* received from the client device 1810 to the data stored on the database 1822 (e.g., the user interaction logs 1822*a*, the engagement action repository 1822*b*). In some instances, the adaptive engagement module 1824 selects an appropriate communication based on comparing the present user context indicated by the context data 1804*b* to prior user contexts included within the user interaction logs 1822*a*, and selects an appropriate communication for output from the engagement action repository 1822*b*. The adaptive engagement module 1824 is described more particularly below with respect to FIG. 189.

While the example of FIG. 18B shows the client device 1810 communicating with the server 1820 to obtain a communication instruction, in some implementations, a user device such as the client device 1810 can generate and provide communications as discussed with respect to FIGS. 18A-22 independently. For example, in some implementations a user device receives context data, determines responsiveness scores, and then selects and provides communications at an appropriate time without an instruction from a server. Indeed, the user device may locally store software that provides the algorithm for generating responsiveness scores and generating appropriate communications. This software may be part of an application, application module, or Internet resource downloaded by the user device. Similarly, the user device may store a history of user interactions (e.g., with the user device or with another device) or other data used to generate the responsiveness scores. Thus, a user device may perform the techniques discussed with respect to FIGS. 18A-22, and communication with a server system may be optional in such implementations.

Figure 19:
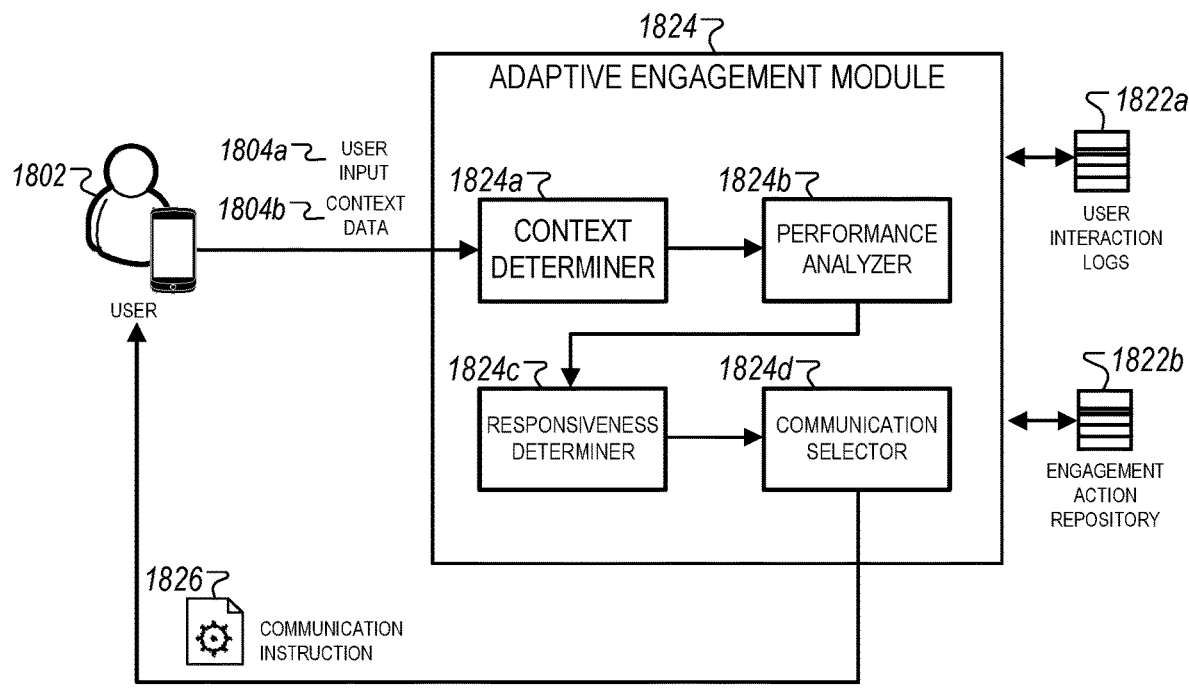
FIG. 19 is a diagram of an example of an adaptive engagement module.

FIG. 19 is a diagram of an example of an adaptive engagement module 1824. The adaptive engagement module 1824 includes a context determiner 1824a, a performance analyzer 1824b, a responsiveness determiner 1824c, and a communication module 1824d. The adaptive engagement module 1824 processes the user input data 1804a and the context data 1804b associated with the user 1802 in order to generate and output the communication instruction 1826 that used to adjust the user engagement on the application 1812 with respect to a particular performance category.

The context determiner 1824a initially predicts a current context of the user 1802 indicated by the context data 1804b. For example, as described previously with respect to FIG. 18, the context data 1804b can include location information associated with the client device 1810, user activity on applications besides the application 1812 (e.g., web search data, prior voice and text queries, etc.), and/or sensor data indicating a current user activity.

The context determiner 1824a predicts a current context of the user 1802 by comparing the information included within the context data 1804d to the information included within the user interaction logs 1822a. For example, in some instances, the context determiner 1824a predicts a current context of the user 1802 based on identifying similarities to information related to a prior context of the user 1802. In this regard, historical context data included within the user interaction logs 1822a is used to identify the current context of the user 1802. In other instances, the context determiner 1824a may use various clustering techniques to determine a current context of the user 1802 based on identifying similarities to context data associated with other users within a cluster of users. In such instances, the cluster includes the user 1802 and other users that are determined to be similar to the user 1802 (e.g., users that are enrolled in the same program, or users within the same demographic).

After predicting the current context of the user 1802, the performance analyzer 1824b determines a performance category to evaluate the received user input data 1804a associated with the current context of the user 1802. In some instances, the performance category may be determined based on performance criteria associated with a program provided on the application 1812. For instance, in the example depicted in FIG. 18, the selected program category (e.g., goal adherence) is based on the exercise challenge program being provided on the application 1812 since goal adherence has a determinative impact on user performance with respect to the objectives of the program. In other instances, the program category can be selected based on improving particular aspects of the user activity on the application 1812 (e.g., increasing the amount and/or regularity of user interaction).

After selecting the program category, the responsiveness determiner 1824c computes a set of responsive scores with respect to the selected program category. As described previously with respect to FIG. 18A, the responsiveness scores reflect respective likelihoods that particular types of content and/or particular types of interactions will increase engagement between the user 1802 and the application 1812.

The respective values of the responsiveness scores are calculated based on prior interactions of the user 1802 on the application 1812. For instance, the responsiveness determiner 1824c accesses the user interaction logs 1822a to determine how the user 1802 has responded to the particular types of content and/or the particular types of interaction when user 1802 was in a prior context that is similar to the current context predicted by the context determiner 1824a. In other instances, the user interaction logs 1822a may specify a set of general user preferences, which are then used to up-weight or down-weight the computed responsiveness scores for different types of content and the different types of interactions. In such instances, the user 1802 may indicate user preferences during a program enrollment process, which is then used to adjust the calculation of the responsiveness scores.

The communication selector 1824d then selects an appropriate communication from among communications of different types based on the values of the responsiveness scores. For instance, the communication selector 1824d identifies the particular content type and the interaction type with the greatest responsiveness score, and then selects a communication that is associated with the identified content type and interaction type. In some implementations, this is accomplished by selecting a communication from a list of predetermined communications that are included within the engagement action repository 1822b, which specifies a content and interaction classification for each communication within the list. In such implementations, the communication selected uses the content type and interaction type to filter the list of predetermined communications and ultimately selects the appropriate communication based on additional information (e.g., type of input specified by the user input data 1804a, the user's progress within the program, among others).

Alternatively, in other implementations, the communication selector 1824d dynamically generates a communication by using the responsiveness scores as building blocks for data and/or information to include within the generated communication. For example, the responsiveness score for the content type can be used to identify the most applicable stored content in the database 1812, whereas the responsiveness score for the interaction type can be used to generate a format for presenting the stored content. In such implementations, after the communication selector 1824d dynamically generates the communication, the generated communication is then added to the engagement action repository 1822b.

The communication selected and/or generated by the communications selector 1824d is then packaged into the communication instruction 1826. The adaptive engagement module 1824 then determines an appropriate time to transmit the communication instruction 1826 to the client device 1810. The time to transmit the communication may be determined based on the current context of the user 1802. For example, if the current context indicates that user 1802 is presently occupied, the adaptive engagement module 1824 may wait to transmit the communication instruction 1826 at a later time when the user 1802 is available. In another example, if the communication instruction 1826 includes a context-specific communication, then the adaptive engagement module 1824 may transmit the communication instruction 1826 when the user 1802 is determined to be in the particular context associated with the context-specific communication.

In some implementations, the adaptive engagement module 1824 uses a rule-based decision engine to select a communication to provide a user in response to receiving the user input data 1804a and the user context data 1804b. For instance, each rule may associate one or more triggers, one or more evaluation conditions, and one or more corresponding communications to provide in response to a satisfaction of at least one of the one or more triggers and/or evaluation conditions. The rules may have varying scopes and hierarchies. For example, some rules can be associated with a reoccurring context as a trigger and used to specify the output of a general communication when the user is determined within the reoccurring context (e.g., providing a general reminder to workout when the user arrives home from work). These rules are associated with multiple programs that are provided on the application 1812. Alternatively, other rules can be program-specific and associated with a program-specific program metric as an evaluation condition. These rules are used to enable the output of tailored communications used to specifically improve user engagement with respect to a particular program-specific performance category (e.g., improving the number of daily calories burned).

Figure 20A:
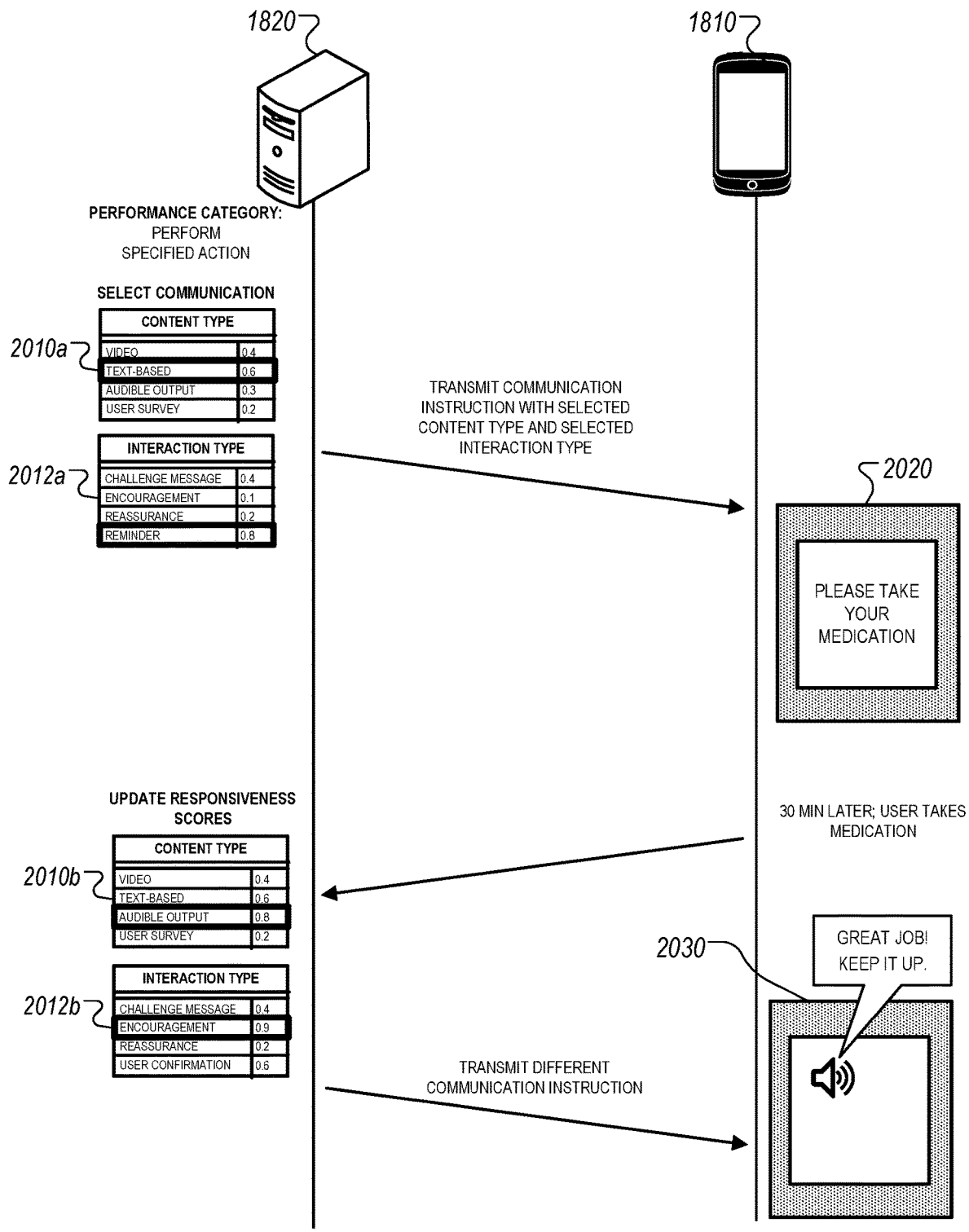
FIG. 20A is a diagram that illustrates an example of a set of interactions for adaptively transmitting communications to a client device.

FIG. 20A is a diagram that illustrates an example of a set of interactions for adaptively transmitting communications between the server 1820 and the client device 1810. In the example, the server 1820 transmits communications related to a long-term treatment adherence program. In this example, the system adjusts the user engagement in order to improve a user's compliance with the treatment criteria such as, for example, taking a prescribed medication according to a predetermined schedule.

The adaptive engagement module 1824 of the server 1820 initially determines that the performance category is for the user to perform a specified action (e.g., take a prescribed medication associated with the treatment adherence program). The adaptive engagement module 1824 then computes a set of responsiveness scores for the specified performance category using the techniques described with respect to FIGS. 18A-22.

As depicted, the tables 2010a and 2012a specify a set of respective responsiveness scores that are computed for different types of content and different types of interaction. The adaptive engagement module 1824 then selects a text-based reminder for output based on the highest values indicated by the tables 2010a and 2012b and transmits a selected communication 2020 to the client device 1810. The selected communication 2020 is provided for output on the application 1812 in order to remind the user to take a medication.

Once the user provides a user input indicating that he/she has taken the medication (e.g., through a manual input on the application 1812), the adaptive engagement module 1824 then re-calculates the previously calculated responsiveness scores in review of the recently received user input data. For instance, the updated responsiveness scores within the tables 2010b and 2012b reflect higher scores for audible input and encouragement relative to the scores within the tables 2010a and 2012b. This increase reflects a change in user performance because the user has performed the action that is indicated by the performance category (e.g., taking the prescribed medicine).

In the example, the adaptive engagement module 1824 determines that an audible output that provides encouragement to the user 1802 for taking the prescribed medication will improve subsequent user participation in the treatment adherence program. The adaptive engagement module then transmits a different communication instruction that includes the communication 2030 for output to the client device 1810.

Figure 20B:
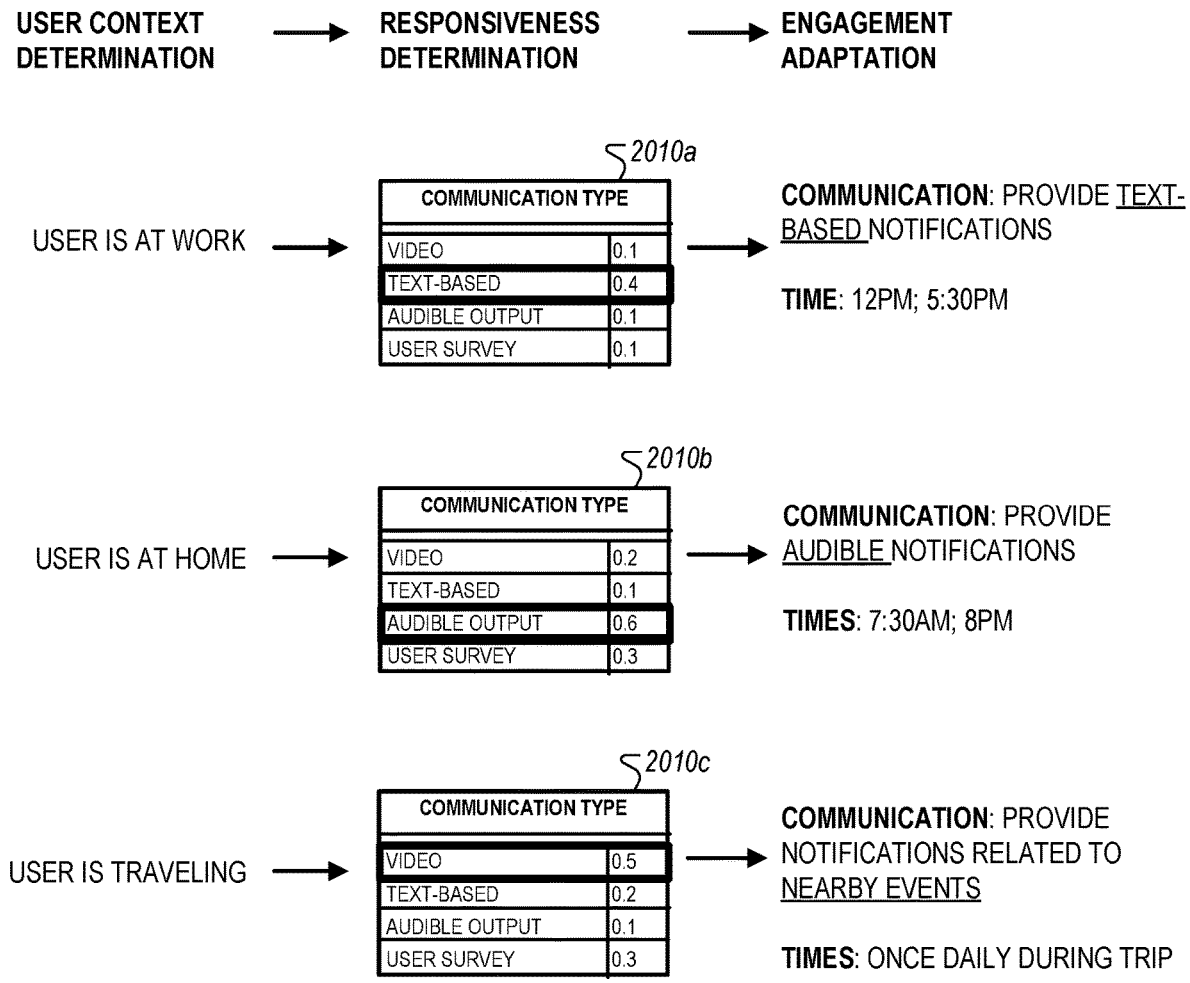
FIG. 20B is a diagram that illustrates examples of context-specific engagement adaptations.

FIG. 20B is a diagram that illustrates examples of context-specific engagement adaptations. In the examples depicted, the engagement adaptation performed by the system is varied based on the particular context for the user 1802.

The adaptive engagement module 1824 initially performs a context determination to identify a current context of the user 1802. The adaptive engagement module 1824 then predicts the responsiveness of the user 1802 to different communications with respect to the determined context, and finally selects the appropriate communication to provide for output during an adaptive engagement adjustment operation.

In the first example, the current context of the user 1802 indicates that he/she is presently at work. This may be determined based on, for example, location data associated with the client device 1810, user activity on applications on the client device 1810, or information from user data stored on the client device 1810. In this context, the system determines that the user's ability to interact on the application 1812 may be limited to non-intrusive communications, and in response, computes a set of responsiveness scores in table 2010a that reflects the user's ability to respond to each type of communication. As depicted, the text-based communication type is determined to have the highest responsiveness score because it is the least intrusive.

The adaptive engagement module 1824 also determines times to provide the communication based on the current context associated with the user 1802. For example, the adaptive engagement module 1824 determines that 12 PM and 5:30 PM are appropriate times to provide the selected communication because these times are associated with lunch break and when the user 1802 is finished with work. These times are selected based determining that the user 1802 has greater availability to interact on the application 1812 while he/she is presently the current context. The adaptive engagement module 1824 then provides a text-based notification based on determining that the responsiveness score for text-based communications has the highest value.

In the second example, the current context of the user 1802 indicates that he/she is presently at home. In this context, the system determines that the user's ability to interact on the application 1812 may be greater than other contexts (e.g., being at work), including more interactive forms of communication. Thus, in this example, the adaptive engagement module 1824 computes a set of responsiveness scores in table 2010b based on the communication and interaction preferences of the user based on the user's responsiveness to prior communications. As depicted, the audible output communication type is determined to have the highest responsiveness score because the user prefers audible output compared to other communication types. The adaptive engagement module 1824 then selects 7:30 AM and 8:00 PM as the times to send the communication based on determining that these are times when the user is likely to be home.

In the third example, the current context of the user 1802 indicates that he/she is traveling and not presently located near frequent locations such as home or work. In this context, the system determines that the user's focus and/or attention may be directed to information that is related to the travel location. Thus, in this example, the adaptive engagement module 1824 computes a set of responsiveness scores in table 2010c based on the types of content that are more likely to provide the user 1802 with a greater amount of information related to the travel location. As depicted, the video content is determined to have the highest responsiveness score because the user is more likely to take in interest in videos related to nearby events of the travel location. In addition, the adaptive engagement module 1824 provides a daily update during the trip because the user 1802 is likely to have limited availability compared to normal situations when the user is not traveling.

FIG. 21 is a diagram that illustrates examples of different communications that are provided in response to user actions on an application. As depicted, the communications 2110a, 2110b, and 2110c represent alternative communications that can be presented to a user enrolled within a program available on the application 1812. The adaptive engagement module 1824 selects the particular communication to provide based on a combination of the prior performance of the user and the length of time the user has been enrolled into the program.

In the example, the user is a middle-aged woman that participates in a marathon preparation program that provides guidance on training exercises and best practices to prepare for a novice runner to run a marathon. The program is intended to be interactive and providing training exercises for the user with a set of associated performance targets. In this regard, the program periodically measures the user's running performance and compares the measured performance to a set of predetermined performance targets to determine if the user's performance is progressing according a set of program goals. This can be measured in, for example, the time that it takes the user to finish running a certain distance, the number of breaks that the user takes within a certain distance, among other types of performance metrics.

The adaptive engagement module 1824 initially determines that the performance criteria for the program is to increase the user's adherence to program criteria. This is determined based on the program objective to prepare the user to train to achieve a physical state that enables him/her to complete the marathon. A secondary program objective may be to help the user achieve a specific time for completing the marathon.

The adaptive engagement model 1824 then periodically monitors the user activity and performance on the program, and selects communications to improve user engagement based on the monitored user activity and performance. For instance, the adaptive engagement module 1824 determines a set of responsiveness scores based on the monitored user activity and performance, and then selects a communication that includes a content type and communication type with the highest responsiveness scores.

With respect to the communication 2110a, the adaptive engagement module 1824 determines that, because the prior performance indicates deficient performance relative to the target performance (e.g., +15 minutes per running exercise) and that the user is repeatedly stopping during exercises, the user may be using improper running form and techniques that are likely the cause of increased fatigue. This determination is also supported by the indication that the user has only been enrolled in the program for two days, indicating that he/she may not be familiar with proper running techniques (her demographic indicates no history of performance running). In this example, the adaptive engagement module 1824 determines that the most appropriate communication to provide for output is a video that explains the best running techniques for marathon runners. This determination is based on the responsiveness score for video content being the highest (e.g., the most instructive relative to other types of content), and the responsiveness for encouragement being the highest (e.g., to motivate the user to stay on track with the program guidelines).

With respect to the communication 2110b, the adaptive engagement module 1824 determines that, because the user's performance exceeds the target performance of the program, the user is performing exceptionally well compared to the expected performance for a user at the particular period of the program. In this example, the adaptive engagement module 1824 determines that the most appropriate communication to provide for output is a challenge message that pushes the user to improve even further to maximize his/her outcome from the program. This determination may also be based on comparing the performance of the user to other users who are co-enrolled into the program (e.g., friends and/or co-workers participating in the same marathon). In response, the adaptive engagement module 1824 transmits a text-based communication that challenges the user to outperform his/her current performance in an effort to further improve the user's performance in the program.

With respect to the communication 2110c, the adaptive engagement module 1824 determines that, because the user has not participated in any exercises in an extended period of time and has reduced the overall level of interactions on the application, the user may likely to be feeling discouraged about his/her physical ability to complete the marathon. In this example, the adaptive engagement module 1824 determines that the most appropriate communication to provide for output is one that reassures the user's mental state and requests feedback to improve the user's level of interactivity to try to get the user back on track. Thus, the adaptive engagement module 1824 transmits a user survey that requests the user to complete a set of questions that are related to an anxiety assessment. This allows the program to gather additional information related to the user's present mental state, which can subsequently be used as user input data and/or context data in a subsequent adaptive engagement adjustment operation.

Figure 22:
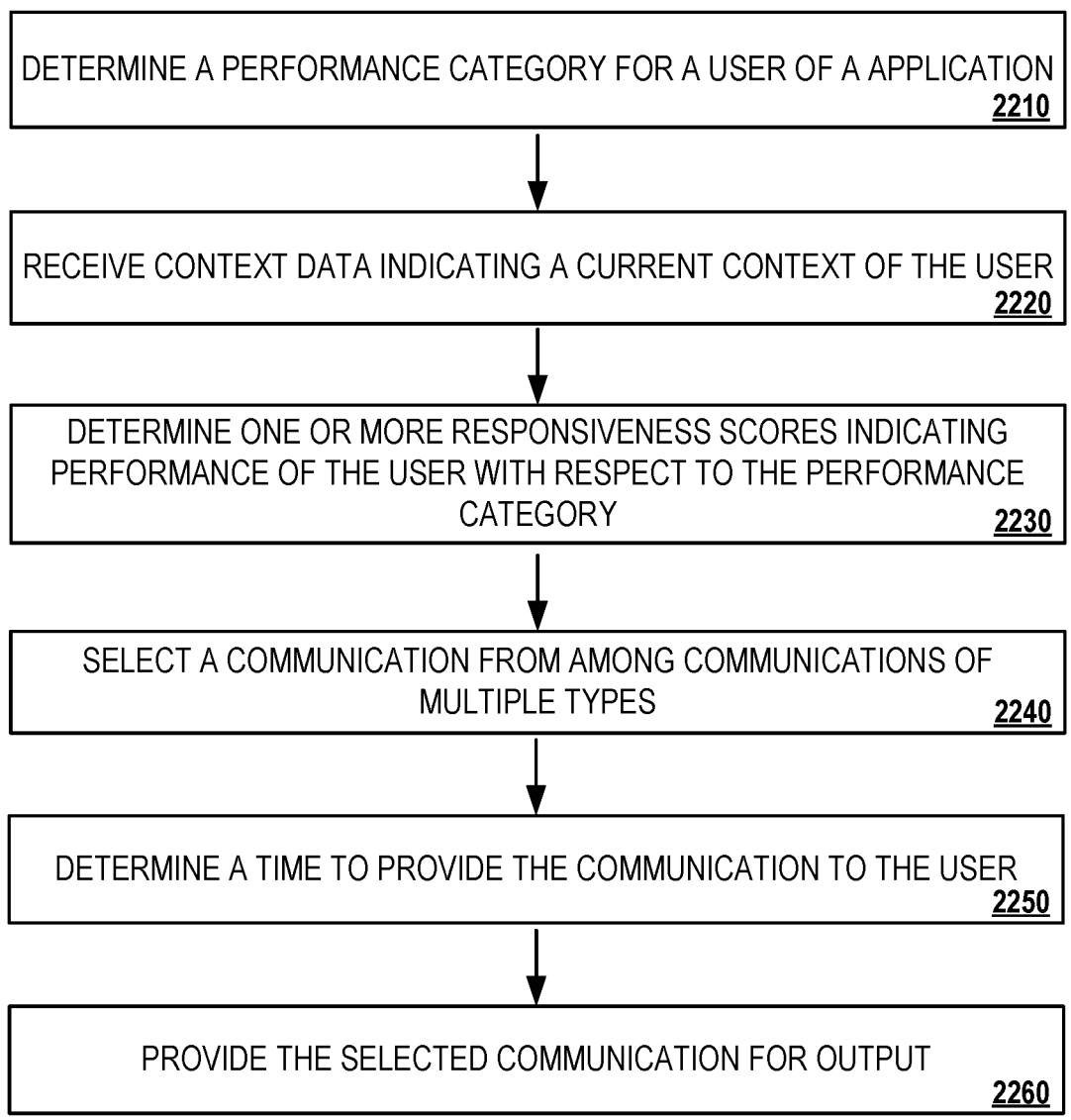
FIG. 22 is a diagram that illustrates a process for adaptively performing personalized engagement.

FIG. 22 is a diagram that illustrates a process 2200 for adaptively performing personalized engagement. In some implementations, the process is performed by one or more computers of a server system, such as server 1820. In some implementations, the process 2200 is performed by a user device, such as client device 1810. For example, a user device, such as a mobile phone, a tablet computer, a laptop computer, a desktop computer, or a wearable electronic device such as a watch, may obtain software that permits the user device to generate responsiveness scores and generate appropriate communications for a user. The user device may obtain the software that causes the user device to perform the process in any of a variety of ways, such as downloading an application, downloading a module of an existing application, obtaining a web page or code of an Internet resource, or through communication of an application with a server system.

Briefly, the process 2200 may include determining a performance category for a user of an application (2210), receiving context data indicating a current context of the user (2220), determining one or more responsiveness scores indicating performance of the user with respect to the performance category (2230), selecting a communication from among communications of multiple types (2240), determining a time to provide the communication to the user (2250), and providing the selected communication for output (2260).

In more detail, the process 2200 may include determining a performance category for a user of an application (2210). For instance, the adaptive engagement module 1824 may identify a performance category for which performance is tracked for the user 1802 on the application 1812. The identified performance category relates to a particular aspect of user performance which is evaluated to improve the engagement between the user 1802 and the application 1812.

The process 2200 can include receiving context data indicating a current context of the user (2220). For instance, the server 1820 may receive the context data 1804*b* indicating a current context of the user 1802 from the client device 1810. In some instances, the received context data 1804*b* can include, for example, a location associated with the client device 1810, user activity on other applications besides the application 1812 on the client device 1810, and/or other data associated with the user that indicates an interest of the user 1802 (e.g., recent search results, voice queries submitted, etc.).

The process 2200 can include determining one or more responsiveness scores indicating actions of the user with respect to the performance category (2230). For instance, the adaptive engagement module 1824 computes responsiveness scores with respect to the identified performance category following previous user communications through the application 1812. For example, the adaptive engagement module 1824 may access the user interaction logs 1822*a*, which include mappings between a prior user context, a previously selected communication that was provided to the user when he/she was in the prior user context, and a user response to the previously selected communication. The adaptive engagement module 1824 may analyze the prior responses of the user to determine whether the previously submitted communication was responsive. This can be determined based on measuring, for example, the type of response provided by the user, the number of follow-up queries submitted by the user, time period for user response to the previously submitted communication, among others. The adaptive engagement module 1824 then uses this analysis of prior communications to compute a responsiveness score that predicts the response of the user to a set of candidate communications.

The process 2200 can include selecting a communication from among communications of multiple types (2240). For instance, the adaptive engagement module 1824 may select a communication based on the received context data 1804*b* for the user 1802 and the one or more responsiveness scores. In some instances, responsiveness scores can be calculated for different content types (e.g., video content, text content, audible output, etc.) and different interaction types (e.g., encouragement, reassurance, user challenge, user survey, etc.). The adaptive engagement module 1824 then identified the particular content type and the particular interaction type with the greatest responsiveness score and then selects a communication based on the identified content type and interaction type. In this regard, the received context data 1804*b* and the values of the responsiveness scores are used to select the most appropriate communication that has the greatest likelihood of increasing the engagement between the user 1802 and the application 1812.

The process 2200 can include determining a time to provide the communication to the user (2250). For instance, the adaptive engagement module 1824 may determine a time to provide the selected communication based on the current context indicated by the context data 1804*b* of the user 1802*b*. In some instances, the current context may indicate that the user 1802 is present unavailable (e.g., being at work), which reduces the likelihood that the communication will cause an increase in the engagement between the user 1802 and the application 1812. In such instances, the adaptive engagement module 1824 may determine a more appropriate time to provide the communication based on a predicted availability of the user (e.g., determining to provide the communication at 6 PM when the user 1802 is likely to be home from work). In other instances, the adaptive engagement module 1824 may also consider the next time when the user 1802 is likely to be in the current context indicated by the context data 1804*b* (e.g., the following day at work). In such instances, the communication can be provided as a context-specific reminder when the user 1802 is determined to be within a particular context.

The process 2200 can include providing the selected communication for output (2260). For instance, the server 1820 can provide the selected communication for output to the client device 1810 as the communication instruction 1826. As discussed previously, the communication instruction 1826 can include specify a content type to provide for output, and an interaction type that adjusts the language and/or technique in which the content type is provided to the user. The communication instruction 1826 can also include an identified time to provide the communication for output.

While the process 2200 is described with examples involving both server 1820 and client device 1820, the process may additionally or alternatively be done by a user device, such as the client device 1820 alone. Of course, when performing the process 2200, a user device may optionally communicate with other devices, including remote server systems over a network, to obtain information used in the process. For example, a user device may query a server system for information regarding a log of user actions, prior responsiveness scores, content options for communications, and so on, and use the received information in generating personalized communications.

Section 5

FIGS. 23-29B relate to a system that allows customized forms to be dynamically provided through an application. The system can include an interface for an administrator to create a form, and then remotely make adjustments to the form that take effect automatically and in real time on user devices. The forms that an administrator creates can also be dynamically customized for each user. As a result, the same form definition can cause different interfaces to be shown to different users. Similarly, the same form definition can cause a different view to be shown to the same user at different times, due to differences in the context of the user. These features and others discussed below give administrators the flexibility to provide multiple variations of a form through a single form definition and easily update the form for a large number of users. Similarly, the customizations for individual users can increase user engagement with the application and reduce the burden on users to enter data in the form.

Conventional applications often do not allow remote adjustment of electronic user forms or customization for individual users. As a result, these forms have often failed to maintain consistent and meaningful engagement with users. For instance, electronic forms of applications are often defined by client-side instructions that are pre-defined for a general population of users. In the case of healthcare support applications, electronic forms that are provided to a large population of users often need to be adjusted for different users to be effective. For example, forms may need to collect different types of information at different precision levels in order to effectively monitor the individual physical and mental wellbeing across different health conditions.

In some implementations, a system is capable of variably and dynamically adjusting electronic forms provided to users on an application in order to improve collection of information related to different user-specific factors. For example, different configurations of an electronic form can be customized for users with different conditions or users with different attributes. The use of customized electronic forms can then allow for precise control over the type of data collected, techniques used to collect data, and the content provided on the customized electronic form based on user attributes. As a result, engagement between users and the application are improved by individually personalizing electronic forms provided on the application.

The server can customize the electronic forms by updating a form definition that configures the electronic form. The form definition specifies characteristics of the electronic form such as display properties, interactive elements to be included, and/or rules that vary content of the electronic form for different users or user types. The form definition can also specify different data types to be collected on the user form (e.g., user input provided on the electronic form, data obtained from third party APIs, data collected by devices wirelessly connected to the user device, or data collected by sensors of the user device). In addition, the form definition can also specify validation rules that specify types of valid or invalid input by the user.

The architecture of the system generally includes a user device that has the application installed, and an associated system where an administrator can create and update a form definition for an electronic form that is provided to the user through the application. The administrator can design the electronic form using a configuration interface that allows for customization of the electronic form by specifying data types to collect using the electronic form and/or layout parameters for displaying the electronic form on the application. An application server can then process the administrators design in order to generate a form definition that includes rules for generating the electronic form on the user device. The generated form definition is then transmitted to the user device so that the user device can dynamically generate the electronic form within the application without any intervention by the user.

The rules specified within the form definition can be used to dynamically adjust the content provided on the electronic form. A client device can interpret the form definition to adjust individual views of the electronic form, e.g., by changing the interface elements that are included within an electronic form, or adjusting the precision level of information provided on an electronic form. Adjustments can also be made to multiple electronic forms such as adjusting the arrangement of multiple forms that are displayed on a single user interface.

Adjustments to electronic forms can be carried out in real-time without requiring application updates (e.g., without altering the executable code of the application). For example, the server may periodically provide form definition updates to adjust an electronic form within the application without requiring a full application update. The application can then process the updated form definition to adjust the electronic form while the user is using the application. In this regard, the system can automatically update electronic forms responsive to data received on the user device.

If a user provides an invalid input into an electronic form, then the electronic form can be updated to restrict submission of additional information. In another example, if the application receives sensor data that reflects user performance (e.g., pedometer data), then an electronic form that requests the user to submit the number of steps may be dynamically deactivated to reduce data redundancy.

In addition, the server can adjust the form definition based on data that is received by the user device over a period of time. As an example, a form definition adjustment can include rules that specify updates for specific user activities, user behaviors, and/or user actions on the user device, and how these actions vary over time. After the server generates an initial form definition, the form definition can then be adjusted based on monitoring the user's real-time activity on the application. In this regard, adjustments can either be reactive to recent changes in a user's actions, or proactive in using pattern recognition analysis of historical user activity to anticipate subsequent changes in user activity.

In one general aspect, this specification describes a method performed by one or more computing devices. The method includes receiving, by the computing device and over a computer network, form data that specifies characteristics of an electronic form, the form data including one or more rules configured to vary the content of the electronic form that is presented for different users; obtaining, by the computing device, user data indicating characteristics or activities of a user of the computing device; selecting, by the computing device, an interactive element from among a set of multiple interactive elements based on the user data and the rules in the received form data; customizing, by the computing device, a view of the electronic form for the user of the computing device by including, in the customized view, the interactive element selected based on the user data and the rules in the received form data; and displaying, by the computing device, the view of the electronic form that is customized for the user of the computing device.

One or more implementations can include the following optional features. For example, in some implementations, the form data is configured to cause the computing device obtain (i) user input to the electronic form, and (ii) additional data from one or more additional data sources, the additional data including passively-sensed sensor data, actively-sensed sensor data, data from a sensor of the computing device, data from a device wirelessly connected to the computing device, or data from a third-party API.

In some implementations, the one or more rules include a first rule, and where the first rule specifies one or more triggers for application of the first rule, one or more conditions to evaluate for the first rule, and one or more actions to be performed based on a satisfaction of at least one of the one or more conditions.

In some implementations, the electronic form includes multiple sections displayed in a sequence, where the one or more rules customize the content of the sections or the sequence of the sections based on user input provided to the electronic form.

In some implementations, the form data defines at least one validation rule that specifies requirements for user input to a portion of the electronic form; where the method further includes: receiving an a user input through the electronic form; determining that the user input does not satisfy the at least one validation rule; and restricting submission of data through the electronic form based on determining that the user input does not satisfy the at least one validation rule.

In some implementations, the form data specifies a data type for user input collected through the electronic form; where the method further includes: selecting, by the computing system, an interactive element to receive user input of the specified data type, the interactive element being selected from among multiple different interactive elements that each receive input of the specified data type; and including, by the computing system, the selected interactive element in the customized view of the electronic form.

In some implementations, selecting the interactive element includes selecting the interactive element from among multiple different interactive elements that each receive user input of the specified data type at a different level of precision.

In some implementations, the form data is provided to an application that runs on the computing device, and the view of the electronic form is provided by the application; where the method further includes: receiving an updated form data over a network after displaying the view of the electronic form that is customized for the user of the computing device, the updated form data indicating a change to the electronic form; and displaying an updated view of the electronic form through the application in response to receiving the updated form data before restarting the application or updating executable code of the program.

In some implementations, customizing the view of the electronic form includes: determining a level of difficulty required for a user to complete data entry to the electronic form; determining that the level of difficulty exceeds a threshold level of difficulty; and in response to determining that the level of difficulty exceeds the threshold level of difficulty, adjusting the content in the customized view of the form to reduce the level of difficulty below the threshold level of difficulty.

In some implementations, customizing the view of the electronic form includes: determining that the form data instructs collection of data of a particular data type; obtaining, from the computing device, the data of the particular type based at least in part on sensor data from the computing device; based on obtaining the data of the particular type, customizing the view of the electronic form to omit a region for requesting data of the particular type from the user.

In another general aspect, this specification describes a different method is performed by one or more computers. The method includes: providing, by the one or more computers, a user interface for designing an electronic form for collecting data about a user; receiving, by the one or more computers, data indicating user input through the user interface, the user input indicating one or more data types for data to collect using the electronic form and one or more layout parameters for the electronic form; generating, by the one or more computers, form data that specifies one or more rules for customizing the electronic form; and providing, by the one or more computers, the form data to a computing device, the form data being configured to cause different versions of the electronic form to be presented to different users.

In some implementations, the method further includes: receiving, from devices of multiple users, data collected by the electronic form associated with the form data, the received data including information of a particular data type that was collected in different data formats from different users; converting the received information of the particular data type to a common data format; and storing the converted data.

In some implementations, converting the received information includes: accessing data indicating a hierarchy of categories; identifying different categories in the hierarchy that correspond to the different data formats; and converting the information of the particular data type using relationships of the categories in the hierarchy that correspond to the different data formats.

In some implementations, providing the form data to the computing device includes: providing the form data to the computing device such that the form data updates a form definition in an application installed at the computing device without any action by the user of the computing device In some implementations, the form data includes one or more state rules for the electronic form, where the one or more state rules cause the computing device to select, from among multiple assessment algorithms, a particular assessment algorithm according to data collected using the electronic form.

In some implementations, providing the user interface includes providing a user interface that indicates a set of pre-defined database fields; where receiving the data indicating the user input includes receiving data indicating selection of a particular database field; and where generating the form data includes including, in the form data, an element of the form that is personalized for a viewer of the electronic form using data for the viewer from the particular database field.

In some implementations, providing the user interface includes providing a user interface that enables a user to (i) update the form data to change characteristics of the electronic form and (ii) publish the updated form data to cause an application installed on remote computing devices to update the characteristics of the electronic form in real time.

In some implementations, the electronic form includes multiple sections shown in different views; where receiving data indicating the user input includes receiving data indicating rules configured to cause different transitions among the sections of the electronic form based on data collected by the electronic form.

In some implementations, generating the form data includes generating the form data to direct a computing device presenting the electronic form to capture data from one or more additional data sources that includes at least a device wirelessly connected to the computing device, a third-party API, and a sensor of the computing device.

In some implementations, providing the user interface includes providing a user interface that permits a user to specify one or more validation requirements for data entered into the electronic form.

Other embodiments of these aspects include corresponding systems, apparatus, and computer programs, configured to perform the actions of the methods, encoded on computer storage devices. A system of one or more computers can be so configured by virtue of software, firmware, hardware, or a combination of them installed on the system that in operation cause the system to perform the actions. One or more computer programs can be so configured by virtue having instructions that, when executed by data processing apparatus, cause the apparatus to perform the actions.

The techniques described with respect to FIGS. 23-29B can provide a number of advantages and benefits. For example, a single form definition can be provided to multiple user devices and include embedded rules. The rules may customize the display of an electronic form each time it is displayed. Similarly, the rules may allow an application to customize the form for each user and each device, so the same form definition provides significantly different presentations depending on the attributes of the user, the capabilities of the device, and/or different user inputs to the form. By maintaining and distributing form data in this manner, the storage requirements and complexity of distribution can be significantly reduced. In addition, the system can permit transmit updated form definitions to cause the forms displayed on user devices to be updated remotely and in real time or near real time. Additional advantages result from the ability to eliminate unnecessary interactions that are not likely to assist the user. By eliminating these unnecessary outputs, the user devices conserves battery power, processing cycles, and network bandwidth.

In general, a system allows customized forms to be dynamically provided through an application. The system can include an interface for an administrator to create a form, distribute it to various user devices, and then remotely make adjustments to the form that take effect automatically and in real time on the user devices. The forms that an administrator creates can provide a dynamically customized view for each user. As a result, the same form definition can cause different interfaces to be shown to different users. Similarly, the same form definition can cause a different view to be shown to the same user at different times, due to differences in the context of the user. These features and others discussed below give administrators the flexibility to provide multiple variations of a form through a single form definition and easily update the form for a large number of users. Similarly, the customizations for individual users can increase user engagement with the application and reduce the burden on users to enter data in the form.

As described throughout, form definitions can be used to configure and adjust an electronic form provided by the application. The form definition is initially specified by a system administrator on a configuration interface that allows the administrator to customize, for example, data types to collect using the electronic form and/or layout parameters for the electronic form. The specified form definition is then transmitted to the user device to either dynamically generate or adjust the electronic form of the application without any intervention by the user.

The architecture of the system provides various improvements in dynamically configuring an application to provide customized electronic forms to individual users, which often requires significant computing and storage resources on client devices. For example, in order to generate a new electronic form to be displayed on an application, a software update for the entire application is usually necessary because form data is often pre-configured within application code. The architecture of the present system, however, utilizes configurable form definitions that process a set of rules that dynamically configures an electronic form based on data collected on the application. For instance, the client device may process form definition data to generate multiple customized electronic forms without requiring an application-wide update from the server. As described below, this enables the application to utilize less storage space on the client device and less network bandwidth since the entire application does not require an update each time a new version of an electronic form is to be generated.

In addition, the architecture of the system enables the system to address various problems that arise in the networked environment of client-based applications. As an example, application configurations provided by servers are often static for significant periods of time and may require major updates to application code. This can be time consuming for application developers and end-users since it requires periodic manual reconfiguration of applications, and periodic delivery of the reconfigured applications. As described in more detail below, the architecture of the system addresses this problem by, among other techniques, employing the use of form definition data that uses a collection rules to automatically adjust electronic forms to be provided on an application without requiring changes to the entire application configuration. This enables an administrator or a developer to adjust the information collected by the application with limited intervention. Moreover, processing of these rules by the system can automatically and dynamically alter a user's experience with the application without requiring users to manually download application updates.

Further, the implementations discussed below can provide ongoing customization of user experiences in an efficient manner, reducing computation needs, power consumption, and other resource requirements. Processing rules within form definition data for a large set of users can be done efficiently by limiting processing of rules for a given user to a particular subset of rules applicable to the user. Even for rules in the subset, processing can be limited by using the trigger as a threshold test, so that further processing of the rule is not performed until and unless the trigger is detected.

Another problem that often arises in networked environments is that applications are often unable to provide effective real-time adjustments that are appropriate for a user's particular circumstances. For example, while some applications can process historical data and provide analyses and recommendations, such applications are often unable to dynamically adjust (i) the content that is provided to the user on the application, and (ii) the arrangement specifications of the application (e.g., types and characteristics of interface elements, color schemes used in style specifications, etc.) without requiring a manual application update. As described in more detail below, the architecture of the system can address this problem with, among other techniques, the use of a collection of rules that associate triggers and conditions with actions to be executed by the system. The scope of each rule can be manipulated based on selections of the triggers, conditions, and system actions specified by an administrator. In this regard, some rules can be applied to make general adjustments (e.g., providing notification badges, or adjusting content provided), whereas other rules can be applied as context-specific changes that respond to user behavior.

Yet another problem that often arises in networked environments is that third-party organizations that create content to be provided on an application developed by a separate entity often have limited ability to control as to how a user interacts with their content. For example, third-party organizations often have to adjust content creation to satisfy application requirements set forth by application developers that provide updates to an application. As described in more detail below, the architecture of the system can address this problem, by providing a configuration interface to an administrator associated with a third-party organization that enables the customization of forms to be provided in third-party application modules accessible on the application by a user. The configuration interface enables the administrators to make adjustments using a user-friendly interface rather than having to adjust the application code directly. In addition, because the system architecture enables the creation of multiple third-party application modules to be provided within the same application, different third-party organizations can configure and adjust the content to be displayed within their respective application modules.

Figure 23:
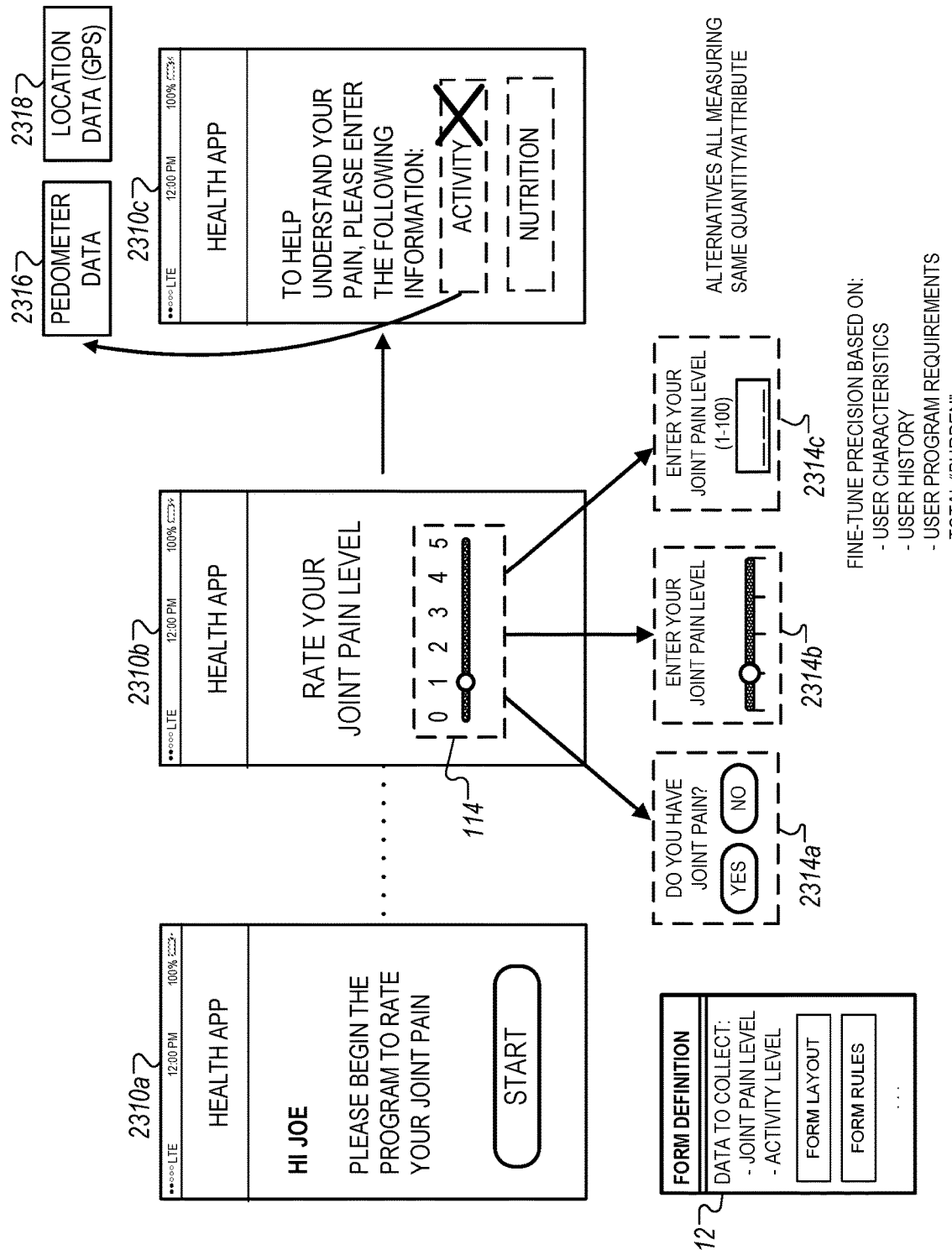
FIG. 23 is a diagram that illustrates an example of a process for dynamically generating an electronic form based on a form definition.

FIG. 23 is a diagram that illustrates an example of a process 2300 for dynamically generating an electronic form based on a form definition. The form generation techniques described in this document can be used for any appropriate application. For clarity in illustration, examples of forms related to healthcare management are provided and discussed, but the technology is not limited to those uses or data types.

In the example depicted in FIG. 23, a health application on a user device is used to periodically monitor joint pain experienced by a user of the user device in relation to activity level of the user. The health application accesses a form definition 2312 that describes characteristics of an electronic form to collect data about the user. The form definition 2312 includes information that allows the application to provide user interfaces that request certain data from the user. The form definition 2312 can also cause the application to obtain other information about the user, for example, actively-sensed sensor data, passively-sensed sensor data, information through third-party application programming interfaces (APIs), and so on. Based on the form definition 2312, the application in the example of FIG. 23 provides user surveys for the user to provide input about pain levels experienced by the user. The user surveys include different views or user interfaces that accept user input. Input received on the electronic forms can then be collected, analyzed, sent to a server system, and used by the application to assist the user.

The user is initially directed to a start a user survey on an interface 2310a. Upon receiving a user input to initiate the survey, the system dynamically generates a user interface 2310b that includes a form element 2314 to enable the user to rate a joint pain level. The form element 2314 is generated based on a configuration specified by the form definition 2312. For example, the form definition 2312 may specify a type of data to be gathered, such as joint pain level, and may also specify layout parameters about how the user interface 2310b should appear. In addition, the application can customize one or more elements of the user interface 2310b for the specific user. In some instances, the form definition 2312 itself describes different variations of an interface that can be provided through rules embedded in the form definition 2312. In addition, or as an alternative, the application that generates a view of the form may apply customizations that are not specifically indicated by the form definition 2312.

In the user interface 2310b, the application determines which of several form elements 2314a, 2314b, or 2314c to display based on a set of rules governing the configuration of the electronic form. Each of the form elements 2314a, 2314b, or 2314c can be used to obtain data about a joint pain level. However, the different form elements 2314a, 2314b, or 2314c obtain the information at a different level of precision, and different elements may be appropriate for different users. The form element 2314a represents an example of a low-precision element that only accepts binary input from the user (e.g., "Yes" for experiencing joint paint or "No" for not experiencing joint paint). The form element 2314b represents a medium-precision element with a slider element that allows a user to specify a value within a finite spectrum of values (e.g., a value along a range as illustrated in FIG. 23). The form element 2314c represents a high-precision element that allows the user to provide a numerical value within a specified integer range (e.g., 0 to 100).

The application may select one of the electronic form elements 2314a-2314c to display on the interface 2310b based on rules specified by the form definition 2312. The form definition 2312 may specify various rules that specify a selection of a particular visual format based on user characteristics, user history, requirements for a health program that the user participates in (e.g., program objectives, milestones, etc.), and a total burden imposed on the user, and other factors. As an example, a user profile may indicate that the user has previously had difficulty answering questions on electronic surveys, or that the user had a low rate of completing surveys. The form definition 2312 may specify that for users with low completion rates, the form element 2314a should be selected since this form has the lowest complexity with a binary selection. In another example, the user history may indicate that a user's joint pain level, indicated by the previous user inputs, has varied greatly. The form definition may specify that if the variation in prior inputs exceeds a certain level, then the form element 2314c should be selected to provide the user with greater precision in providing a pain assessment. In other examples, the selection may also be based on user preferences, the type of medical condition monitored for the user, among other factors.

When customizing a user interface for a user, the application may apply any of a variety of rules. Some rules may be general or default rules, such as an application-level rule that attempts to maintain a consistent visual style or to keep the complexity of a form below a maximum level. Other rules may be specific to individual forms, as indicated in specific form definitions. The form-level rules may be used in addition to the general rules, and may override the general rules for the purposes of presenting specific forms.

A variety of customizations can be made to personalize a view of an electronic form for a particular user. For example, the application can also determine whether or not to request certain information from a user. Based on the data available, or information about the current context of the user, the application may omit certain form elements from the user survey. This determination can be based on different types of data that are received by the application. For example, an application can obtain data from sources other than user input, such as sensor data or stored data from the user's device. This additional data can be used to meet the data collection requirements indicated by the form definition 2312, and can also adjust the view of the form.

In FIG. 23, the application receives pedometer data 2316 indicating the user's current number of steps taken and location data 2318 indicating the user's current location. The form definition 2312 may direct the application to provide an interface to collect activity data and nutrition data from the user. However, the application can determine that the pedometer data 2316 provides the activity level information needed, and so the user does not need to enter input. Because the pedometer data 2316 already indicates the activity level of the user, the application no longer requires user input to identify a measured activity level. The application generates the user interface 2310c to exclude the "activity level" form element, thus simplifying the view shown to the user. In this this regard, data received from external sources (e.g., wearable devices wirelessly connected to the user device, third party application programming interfaces (APIs), and sensors of the user device) can be used to dynamically generate electronic forms to minimize unnecessary user input. If the pedometer data 2316 or other data were not available to the application, then a different user interface including a request for activity level data would be provided. The form definition 2312, may indicate that the application should acquire information from certain data sources. In addition, or as an alternative, the form definition 2312 may indicate certain types of data to acquire, and the application may include data separate from the form definition 2312 that specifies sources from which to acquire that data, such as a mapping between data types and data sources.

As shown in FIG. 23, a single form definition 2312 can define the characteristics of multiple user interfaces 2310a-2310c. Together, these user interfaces 2310a-2310c can provide a multi-stage form with multiple views presented sequentially. According to the rules in the form definition 2312, the content of each individual view, the sequence of the views, and whether certain views will be shown to a user can vary from one user to the next. Similarly, the rules in the same form definition 2312 may cause differing views to be provided to the same user at different times.

As described throughout, rules embedded within the form definition can be used to customize an electronic form for a particular user. Each rule can be associated with one or more triggers, one or more evaluation conditions, and one or more specified actions to be automatically performed by the system. Satisfaction of the triggers of a rule can be used to automatically initiate an evaluation of associated conditions of that rule. The system then performs the corresponding system actions in response to determining that at least one of the conditions has been satisfied. The embedded rules can thus be used by an application to determine, for example, which of multiple forms should be provided, when a form should be displayed, the content and appearance of a form, which data should be requested through a form, what level of precision or complexity should be used in the form, and other form characteristics. Some embedded rules may be used generally to select or schedule a form for display, while other rules may be used specifically to customize a form for an individual user. This technique can be used selectively perform system actions related to the electronic form based on the triggers and conditions specified by individual rules within a repository of rules.

The repository of rules may include different types of rules that adjust form generation in various ways. For instance, the individual rules within the repository of rules can vary in scope and in hierarchy to enable an application to adjustably generate an electronic form. As an example, certain rules can be "state rules," which enable the system to select an appropriate assessment algorithm from among multiple assessment algorithms based on the data collected using an electronic form. In this example, each state rule may specify the use of a different assessment algorithm as a system action based on the satisfactions of different triggers and/or conditions. In another example, other rules can be "validation rules," which enable the system to determine whether a user input on the electronic form is valid based on the data type associated with the conditions specified by each validation rule. While state rules and validation rules are two examples of different types of rules, other examples are also possible.

State rules can be defined in any of various ways. As an example, a state rule can have one or more triggers organized in an unordered list. If any of the specified triggers occurs, the state rule is executed. Similarly, a state rule can have one or more conditions organized in an ordered list. The conditions can be evaluated in sequence, until the one of the condition expressions evaluates to "true," indicating that the condition is satisfied. The application can then cause the action associated with the satisfied condition to be performed. Each condition may have a single condition expression. In some instances, a condition can have a "null" value or "true" value indicating that the condition is always satisfied and always evaluates to true. For each condition, one or more actions are defined. These actions can be organized in an ordered list or be prioritized in another manner. When a condition is selected as being satisfied (e.g., is the first in an ordered list that evaluates to true), each of the actions will be performed, in the sequence defined by ordered list of actions.

Other variations of state rules can be used. For example, in some implementations, certain actions may have additional conditions that must additionally be satisfied before the action is performed. As another example, some state rules may be defined so that each condition is evaluated after a trigger is detected, and the actions specified for each condition that is satisfied can be performed. In some instances, actions may set, clear, or adjust values for parameters of a form being displayed. The actions may change various display configuration properties. The various values or properties can be specified by a type, an identifier, and/or a path through the hierarchy of elements specified in the form data.

As described throughout, a customized electronic form can be used for different types of health management applications. For example, in some implementations, form customization enables the system to provide risk assessment forms that provide directed questions to obtain information about a user's present health condition. The information obtained through the customized electronic form can then be used to evaluate health risks associated with a known medical condition of the user. The types of customized forms can typically be used to improve a user's progress through a particular health module. In another example, form customization enables the system to obtain user feedback data on the effectiveness of the actual health module. For instance, electronic forms can be provided to request a user's feedback on a treatment programs specified by a health module they are presently participating in. The two examples above illustrate that form customization can be used to both gain information relating to a user's performance within a health program, as well as the effectiveness of the health program. The obtained information can be enable an administrator to identify changes to either a user's individual treatment plan (e.g., an adjustment of individual user's goals or actions), or changes to the way in which a health program is provided to a collection of users (e.g., adjusting a care plan for users that are diagnosed with the same medical condition).

Figure 24:
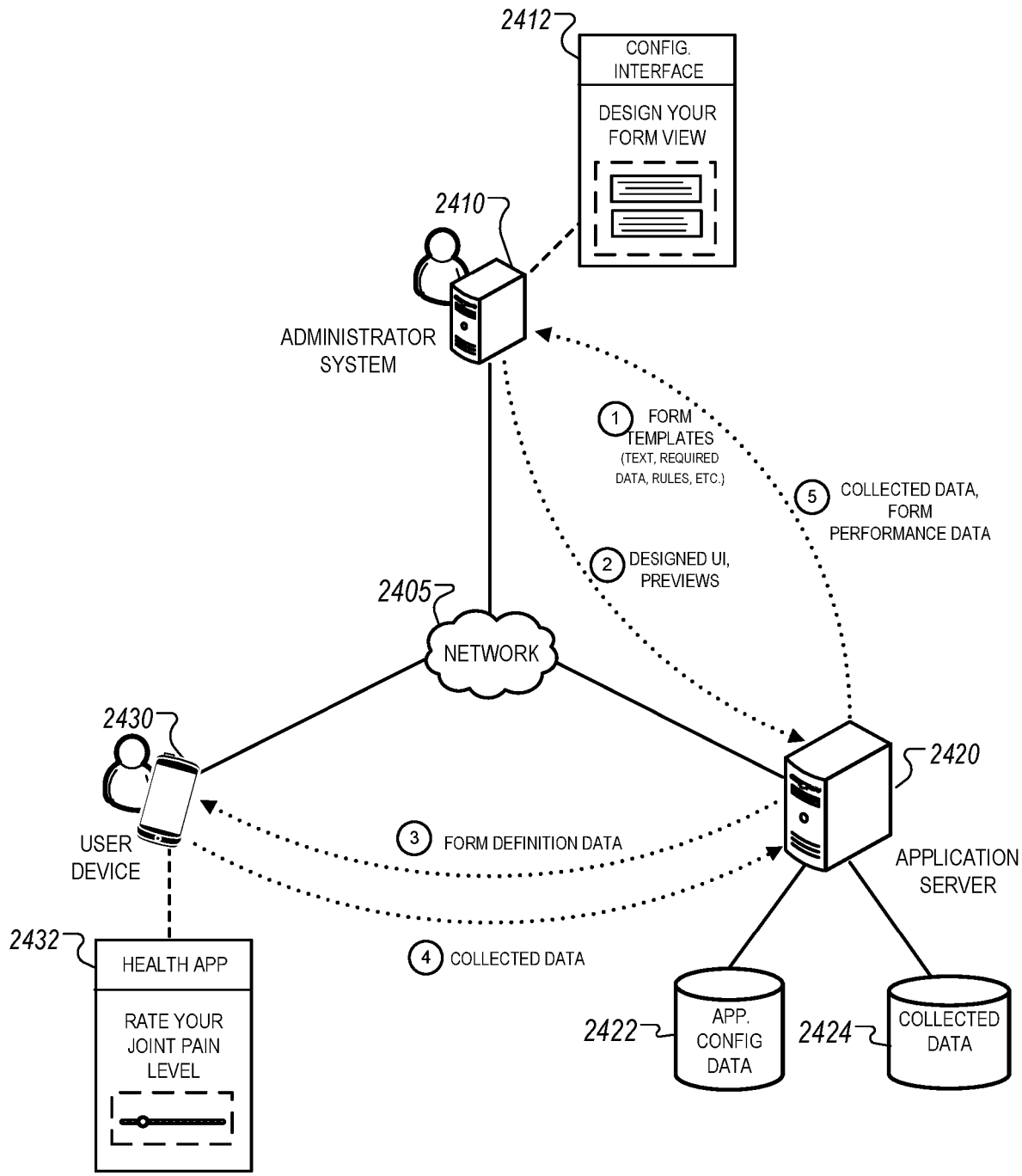
FIG. 24 is a diagram that illustrates an example of a system that is capable of generating dynamic electronic forms.

FIG. 24 is a diagram that illustrates an example of a system 2400 that is capable of generating dynamic electronic forms. The system 2400 generally includes an administrator system 2410, an application server 2420, and a user device 2430 connected over a network 2405. The administrator system 2410 provides a configuration interface 2412 that allows an administrator to design electronic forms that are provided for output on an application 2432 running on the user device 2430. As described above, the system 2400 enables data exchange between the administrator system 2410, the application server 2420, and the user device 2430 such that electronic forms displayed on the applications 2432 can be dynamically constructed and adjusted based on forms designed by the administrator using the configuration interface 2412.

In general, the application 2432 can support multiple program modules provided by different third-party organizations separate from the organization associated with the application server 2420. The various program modules can include health modules. A health module can represent any type of program to measure, maintain, or enhance a person's physical and/or mental wellbeing. Health programs can be used for monitoring, treatment, research, coaching, teaching, and other purposes. Each program can provide a user experience that benefits the user through the use of the application. A user can enroll in multiple health modules within the application 2432 that are provided by different organizations. In this regard, the system 2400 enables administrators from different organizations to design customized electronic forms that are provided within different programs of the same application.

In step (1), the administrator system 2410 initially receives form design data from the application server 2420. As noted above, the administrator system 2410 can be a client device of a third-party administrator that creates or maintains a program provided through the application server 2420. The design data may include pre-generated form design templates that specify text, required text, and/or associated rules. The design templates may be specified by a particular medical condition, a particular health program in which a group of users have participated in, or an entity or organization that provides healthcare services to a group of patients. For example, design templates for an employer may include form data that relates to specific health programs or initiatives supported by the employer. In another example, design templates for a particular medical condition may include form data for collecting patient information in relation to treatment of the particular medical condition.

The administrator may then use the configuration interface 2412 to design customized electronic forms to be provided for output on the application 2432. The customized electronic forms may include a customized selection of interface elements, content to be provided to the users, and different data types to be collected on the electronic forms. More specific descriptions related to the configuration application are provided below with respect to FIG. 25.

The administrator to configure many permutations of form experiences with a single form definition. This allows for a high degree of personalization and engagement tailored for individual users. Depending on the choices that a particular user makes when viewing the form, and the data that is entered in the form, the appearance and behavior may change. For example, the state rules discussed above can define different combinations of content and input fields to display, depending on the user's responses and other user information obtained from other sources besides the input fields of the form. In some implementations, an administrator may define a set of rules that provide a condition-based survey with branching logic or cascading user input fields, where the entry in first field governs the presentation of a second field in the form.

In step (2), the customized electronic forms designed by the administrator are then transmitted to the application server 2420. The customized electronic forms may include designed user interfaces that include the customized electronic forms, rules that indicate the behavior of forms or variations of the forms for different users or scenarios, or various types of instructions that cause the application 2432 to display the customized forms on the application 2432. The data received from the administrator system 2410 may then be aggregated and packaged by the application server 2420 based on a set of stored application configuration data 2422.

In step (3), the packaged data can then be transmitted from the application server 2420 to the user device 2430 as form data that configures the application 2432 to provide the customized electronic forms designed by the administrator for display to the user. The updated definitions in the form data are provided automatically and remotely to the user devices, substantially in real time. In some implementations, when the form data for a program module is updated, the packaged data can be pushed to each user device associated with a user who has subscribed to that program module. In some implementations, the application on the user device periodically requests updates to form data for the programs that are subscribed.

The dissemination of form data to the user devices requires no action on the part of the subscriber, e.g., there is no need for application updates, re-login to an application, or even restarting of the application. Once form data is received at a user device, a new or updated form can be provided as soon as display of the form is triggered according to the rules in the form data.

This ability to almost instantly provide form updates also assists administrators to preview and test form configurations. The administrator may cause the an updated form definition to first be provided only to certain devices designated for testing, or to be active on only certain devices. This limited distribution phase allows an administrator to see the results of updated forms, on the actual types of devices where the forms will be seen, before disseminating the updated form to subscribers. With these techniques, administrators can conduct rapid prototyping of forms for user experience and usability testing. For example, form updates can be rolled out to small groups, assessed, updated, and then provided to a broader set of users.

The form data can include form definitions that allow user devices that receive the form data to customize views of the forms for specific users, as described above, and rules that specify triggers and conditions in which the customized forms are provided for display to the user.

In some instances, the form data may also include instructions that cause the user device 2430 to obtain information through the user input of the customized electronic forms, through other devices that are wireless connected to the user device 2430 (e.g., wearable devices), third-party application programming interfaces (APIs), or sensors of the user device 2430. For health-related forms, this allows a single form to collect objective, un-biased information about a user in addition to self-reported data obtained as user input to the form. In other instances, the form data may include specifications that configure or adjust the content of the customized forms, or the arrangement of customized forms on the interface of the application 2432. For example, the form data may specify multiple sections for a particular electronic form, and rules included within the form data may customize the content of each section or the sequence of the sections based on user input provided on the electronic form.

In some implementations, the sections of a form can be nested. For example, the form data may specify different views or portions of a form, and groupings or other relationships of the different views. For example, form data may specify that different sections of a form should be shown, depending on a user's responses to a first section of a form. For example, an initial view of a form may ask a user to input information about exercise. The form data may specify that if the user enters a type of exercise that is typical for that user, then the form should then proceed to display the next section, e.g., asking about nutrition. The form data may specify that if the user enters a type of exercise that is new for the user, one or more nested sections related to exercise should be provided, e.g., congratulating the user for trying something new, asking about how the user liked the new activity, and so on. The form data may organize form sections into groups or hierarchies that specify different nested elements that are selectively displayed according to the current information about the user. Different views can be displayed in sequence as indicated by the form data.

In other examples, the form data may define validation rules that specify requirements for user input to portions of the customized electronic forms. For instance, the form data may specify a specific data type for a particular electronic form (e.g., numerical input, or input in a particular numerical range). The form data may include instructions to adjust the configuration of the customized form in response to determining that a user's input is invalid or does not satisfy the requirements set forth by the validation rules. As an example, an electronic form for physical pain level measurement may request that a user may provide a description of the pain experienced by the user. In this example, a validation rule may indicate common terms that are related to physical pain measurement, which would represent acceptable input in a free-form text input area. Inputs that do not satisfy the criteria in the validation rules, such as a user input relating to depression (e.g., emotional pain), can be identified as inappropriate. In this instance, the user may have misunderstood the question presented on the initial form. In response to detecting the inappropriate input, the application 2432 may prompt the user to correct the answer, or may prevent the user from continuing or submitting the form.

In step (4), data collected by the application 2432 through forms is provided to the application server 2420. The collected data 2424 can include user input (e.g., data indicating user responses or interactions with a view of the form) as well as other information that a form definition directs the application 2432 to obtain. The application 2432 may periodically collect user input data provided to the customized electronic forms (e.g., text submitted, user selections from a list of presented options, etc.) and other input data that is associated with the user's participation in the electronic form (e.g., total time taken to complete the electronic form, other background applications used by the user while completing the electronic form, etc.). The application 2432 may also collect other data separate from user input, as directed by the form definition. For example, the application 2432 may collect passively-sensed sensor data or actively-sensed sensor data. The data can be obtained from additional data sources such as the sensors of the user device 2430, a wearable device wirelessly connected to the user device 2430 (e.g., through Bluetooth), or from a third-party API. The collected data for each electronic form is then transmitted to the application server 2420 for storage and analysis.

In step (5), the application server 2420 then generates performance reports for the customized electronic forms based on the user input data collected on the application 2432. The performance reports may include summary information indicating user patterns while completing the customized electronic forms (e.g., amount of time spent on the customized electronic forms), or analytical determinations based on the user patterns (e.g., effectiveness of the customized electronic forms). More particular descriptions related to the performance reports that are generated for the customized electronic forms are provided below with respect to FIG. 28.

The performance reports generated by the application server 2420 are then transmitted to the administrator system 2410 for analysis. In some instances, the performance reports may be used to adjust form definitions for customized electronic forms in order to improve the engagement of the user on the customized electronic forms. Adjustments to the electronic forms may be made manually by the administrator on the configuration interface 2412, or automatically by either the administrator system 2410 or the application server 2420 based on the information indicated by the performance reports. In the first example, the administrator can adjust the form definition by providing input on the configuration interface 2412 (e.g., adding or removing interface elements of an existing form definition, adjusting the content to be displayed, etc.). In the second example, automatic adjustments to the form definitions can be processed based on the identification of specific types of user input data (e.g., not receiving any user input on a particular electronic form for a long period of time, indicating that it may no longer be relevant to the user). In addition, as described above, adjustments can be processed in real-time such that an existing electronic form may be adjusted as the user is providing user input on the electronic form.

In some implementations, the administrator can use the configuration interface 2412 to configure an entire health risk assessment (HRA) for the user. The HRA can evaluate health assessments and recommendations based on data collected through the application 2432 (e.g., passively or actively sensed data, data obtained from third-party APIs, etc.) in addition to self-reported user input data on the electronic form. Because the configuration interface 2412 enables the creation of different types of electronic forms, the administrator may configure different HRA forms for a single health module that is run within the application 2432. A health module can represent any type of periodic monitoring or treatment program that the user can participate in through the use of the application. For example, a user can enroll in multiple health modules within the application 2432. In addition, the administrator can configure form definitions to specify rules that direct the selection of different HRAs based on the data collected on the application 2432.

In other implementations, other types of clinical assessments can be incorporated into the content of the electronic forms. For example, the administrator may configure clinical outcome assessments (COA), patient reported outcomes (PRO), among other types. As described above, rules specified within the form definition can be utilized to provide specific types of output in response to receiving different types of user data. In this regard, the administrator can customize the electronic form to the specific needs of a particular healthcare provider or entity in order to perform a large variety of patient monitoring functions.

In some implementations, the administrator can also use the configuration interface 2412 to configure an entire diagnostic tool (EDT) with the use of customized electronic forms. For instance, the administrator may create a diagnostic form with a form definition that specifies rules for predicting a diagnosis for a user based on input provided on the user. As described above, the particular diagnostic evaluation applied can be varied based on the different types of data collected on the diagnostic form.

In other implementations, the administrator can configure automated clinical decision support features into the electronic forms using the form definitions configured on the configuration interface 2412. For example, the configured form definition can include rules that automatically provide clinical recommendations for display on the electronic form based on the contents of the data collected by the user. The rules can associate different types of input data that are associated with particular medical conditions with the corresponding clinical recommendations that are often provided as solutions to types of symptoms experienced by the user. As an example, if a user submits on the electronic form that he/she is experiencing pain, a rule can be configured to automatically provide a recommendation to take a pain relieving medication in response to receiving the user input.

Figure 25:
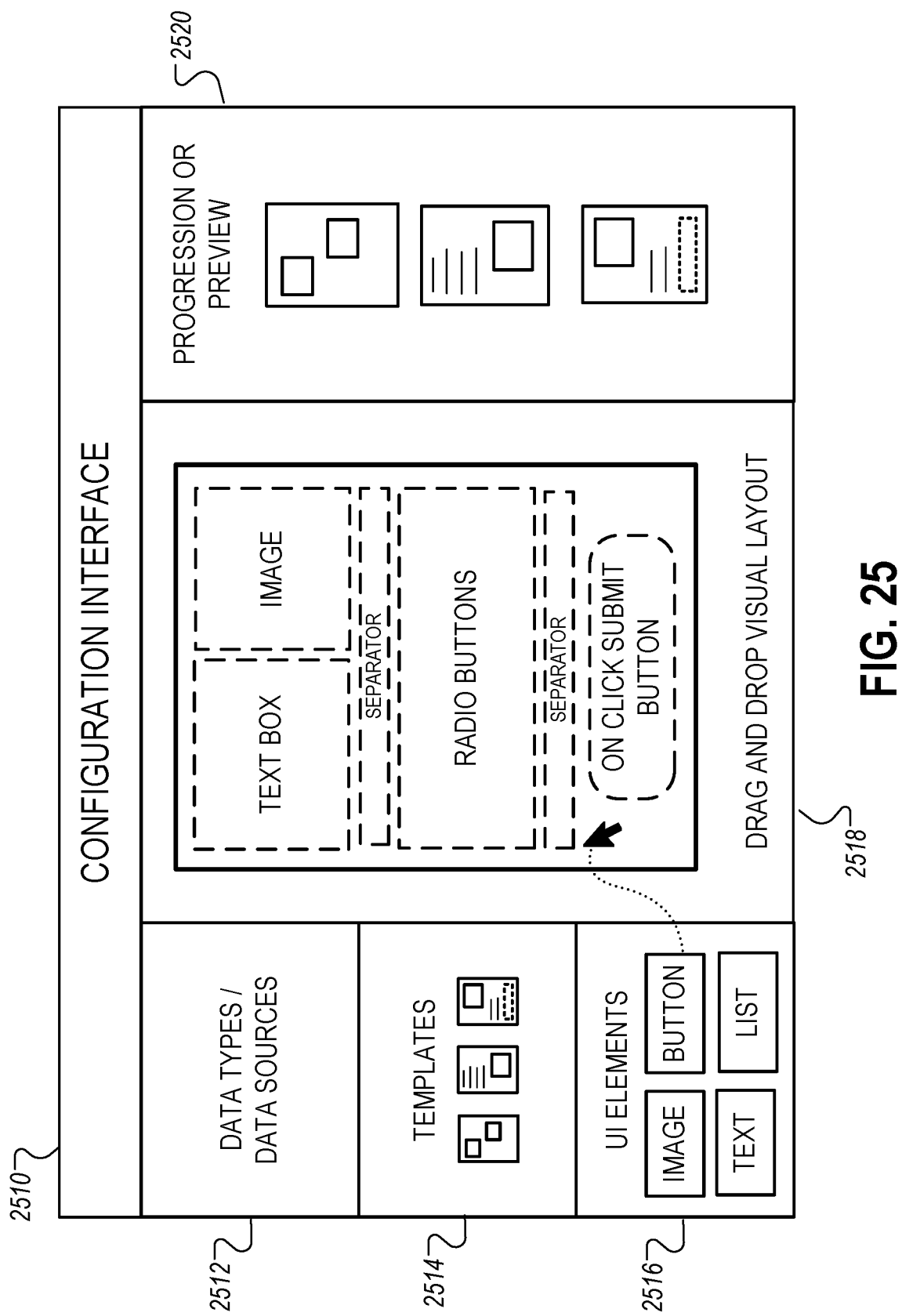
FIG. 25 is a diagram that illustrates an example of a configuration interface for customizing form definitions.

FIG. 25 is a diagram that illustrates an example of a configuration interface 2510 for customizing form definitions for electronic forms. The interface 2510 may be presented to the administrator on the configuration interface 2412 described above. The interface 2510 allows an administrator to have fine-tuned control over various aspects of an electronic form. For instance, in region 2512, the administrator may select a data type for the user input to be received on the electronic form (e.g., text input, voice input, etc.), and a data source for the user input to be received on the electronic from (e.g., user input data received through the keyboard of the user device 2430, input data received from other devices wirelessly connected to the user device 2430, input data received from third party APIs, input data received from sensors of the user device 2430). In some instances, the administrator may also specify whether the input data to be collected is passively sensed data, actively sensed data, or a combination of both.

In region 2514, the administrator may select from among a set of pre-generated templates for the electronic form. The pre-generated templates may be obtained from prior configurations of other customized electronic forms that are stored locally on the administrator system 2410, or other configurations that are stored remotely on the application server 2420, e.g., configurations made by other users. As an example, the administrator may select a form template from a repository of form templates that categorizes the templates across various categories (e.g., health program, affiliated entities/organizations, associated medical conditions, etc.). After importing a form template, the administrator may also make additional updates to customize the electronic form that is being designed. For example, an administrator may begin with a standard template to quickly obtain a functional form for acquiring data of a needed type. The administrator may then customize the appearance and behavior of the form, e.g., selecting the color scheme, logos, and other information. In this manner, the administrator can quickly design an entire form, with appropriate customized branding to set it apart from others available through the application 2432, without writing any computer code.

In region 2516, the administrator may select the user interface elements to be included within the electronic form to be designed. For example, the administrator may include images, buttons, text boxes, lists, and radio buttons, among other types of common interface elements. The administrator may also specify ways in which the user interacts with each interface element. For example, the administrator may configure rules that adjust the availability of certain interface elements based on the satisfaction of specified triggers or conditions associated with the interface element. As an example, a particular interface element may only be available once the user has provided a valid user input to a preceding user interface element within the electronic form.

In region 2518, the administrator may adjust the arrangement of interface elements and/or the interaction rules of interface elements within the electronic template through a drag and drop visual layout. For example, as depicted in FIG. 25, the administrator can configure locations in the electronic form where the selected user interface elements should be placed, specify field values for certain elements, or provide interactive elements that helps the user transition between different parts of the same electronic form, or different electronic forms. In some instances, the administrator may also specify embedded conditional logic into interface elements for performed pre-determined calculations based on the user input provided on other interface elements (e.g., calculating a body mass index based on the mass and height submitted by the user on two preceding fields).

In region 2520, the administrator may adjust the presentation of the electronic form. For example, the administrator may adjust the size of interface elements, colors of the interface elements, fonts of text to be displayed, and/or other graphical attributes associated with the interface elements (e.g., shadows, line thickness, padding, margins, orientation, etc.). An administrator may also adjust the timing associated with when the electronic forms are provided on the application. For example, the administrator may adjust time delays between a designated user input that initiates a display of an electronic form, specify triggered events that either cause an electronic form to be displayed or removed from display, among other types of settings.

The configuration interface 2510 may additionally include a progression or preview tab that enables the administrator to view progressive changes made to the draft electronic form (e.g., history of changes made from a pre-existing template) and/or a preview of electronic form within the user interface of the application 2432.

The administrator may specify various user-specific customizations that should occur. For example, the configuration interface 2510 may provide a list of database fields from which data may be obtained at the time of form presentation. These fields may represent characteristics that can be obtained from a user profile, e.g., a field [Subscriber_Name] or [Subscriber_Profile_Image]. When a view of the form is generated, the application 2432 obtains the current information from the user's profile, or other data source referenced, to generate a custom view of the form. The database fields may also provide information that helps motivate and engage a user. For example, the form could include a sentence such as "[Supporter] thinks it's important for your cancer treatment to complete this survey," where the [Supporter] field is replaced by a name of friend of note from that person could also be obtained and presented in the view of the form.

The present techniques can facilitate efficiently and effectively conducting large-scale data collection projects through surveys. Other systems that use hard-coded forms often lack the flexibility to control to edit the survey or add new survey questions after deployment. With the techniques described with respect to FIGS. 23-29B, a versioning technique can be used to allow multiple versions of a form. When the administrator edits an existing data collection form, validation rules automatically determine whether there are a subscriber has utilized this form to submit data. If not, then the form is edited and saved as the same form version in the database. If a user has submitted the form previously, then a new version of the form is automatically saved. Any subscriber presented with the form will automatically be presented with the newer version of the form. However, if an existing subscriber edits or views a form that they saved using the older version, the system correctly presents the older version of the form. This allows seamless updates for users that have not yet used a form, while preserving the entered data and progress of users who have invested time in filling out the form already. This solves a business problem for large survey projects, which frequently need updates and additions. As a result, a correction to a spelling error, rephrasing a question, or adding sections to a survey can be done easily by a remove administrator for all users. The administrator simply edits the form and it is automatically enabled for anyone already using the administrator's module through the application 2432.

Figure 26:
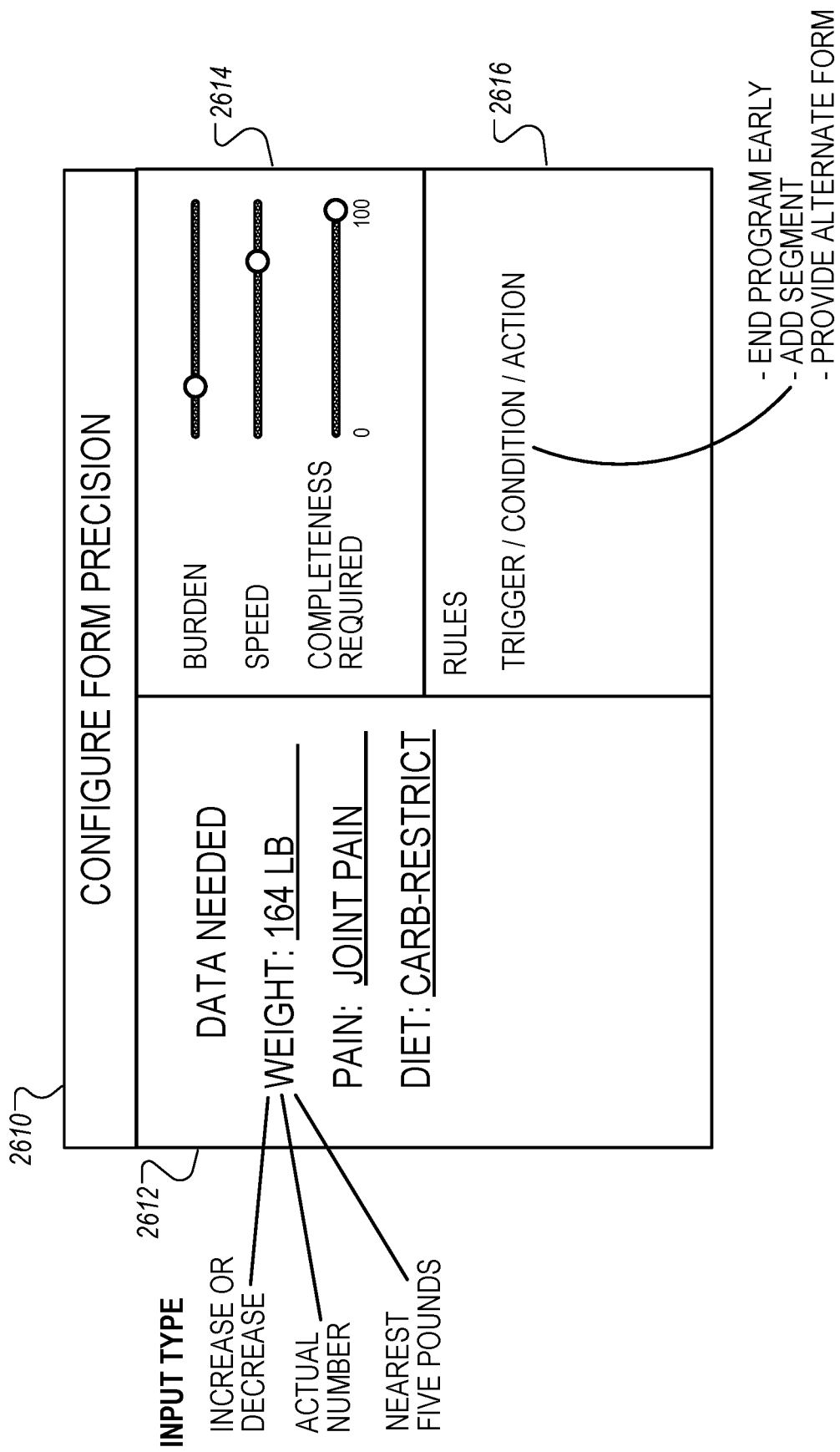
FIG. 26 is a diagram that illustrates an example of a configuration interface for customizing precision levels for data to be collected on an electronic form.

FIG. 26 is a diagram that illustrates an example of a configuration interface 2610 for customizing precision levels for data to be collected on an electronic form. The configuration interface 2610 enables the administrator to configure different precision levels of information shown on a customized electronic form. As described previously with respect to FIG. 23, such configurations can be used to cause the customized electronic form to dynamically adjust to one of the specified precision levels as the user is interacting with the electronic form.

In the example depicted, the configuration interface 2610 allows the administrator to specify the data that is requested from the user (e.g., weight, pain, diet information). In region 2612, the administrator can specify the level of precision for the information requested on the electronic form. For example, the electronic form may request an increase or decrease in weight, the actual number corresponding to the user's weight, or an estimate of the user's weight to the nearest pounds.

In region 2614, the administrator may specify a set of requirements that customize the electronic form for a particular user or a particular group of users. For example, an administrator may specify a target level for the burden imposed on the user (e.g., the difficulty for the user in providing the information requested on the electronic form). As another example, the administrator may indicate a target level for a completion speed (e.g., the time it takes for the user to complete the electronic form), and a requirement for how complete responses need to be in order to be considered a satisfactory or valid user input.

The set of requirements provided on the configuration interface 2610 may then be used to automatically and dynamically configure and adjust the electronic form on the application 2432 based on data associated with the user. Because the requirements are different for each user, the application 2432 may variably adjust the electronic form based on the data associated with each individual user. For example, an administrator may use the configuration interface 2610 to create an electronic form with a "low burden" requirement. When the electronic form is generated on the application 2432, the low burden requirement for a younger user may be higher than the low burden requirement for an older user with disabilities or potential memory loss. Thus, in this example, the application 2432 may use demographic information associated with the user to variably construct a similarly configured electronic form to provide different user experiences.

In region 2616, the administrator can configure specific rules that coordinate the configuration and/or adjustment of an electronic form in relation to specified triggers and conditions associated with the electronic form. For example, the configuration interface 2610 may provide a drop-down list that allows the administrator to select from a list of triggers and a list of conditions. Examples of triggers include receiving sensor data indicating that the user has recently fallen, receiving user input data indicating an abnormally high pain level measurement, and/or data from a wearable device indicating insufficient physical activity. Examples of conditions may include determining that the user's historical activity pattern is below an anticipated goal specified by a treatment program, data indicating that the user has failed to sufficiently complete the last four electronic forms, among others.

The administrator can then specify actions to be performed by the application 2432 in response to a satisfaction of the triggers and/or the conditions. The administrator can either specify application-specific actions (e.g., ending a program early), or actions to be performed in relation to a particular electronic form (e.g., adding a new segment to the electronic form, providing an alternative form, etc.). In this regard, the associated rules of the electronic form can be used to dynamically adjust the content provided on the electronic form and/or the presentation of the electronic form in relation to present conditions associated with the user based on recent data received on the application 2432.

The application 2432 may customize the content and appearance of a form for a particular user based on, for example, a language or dialect of the user, a reading level of the user, a health literacy of the user, impairments of the user (color blindness, etc.), a technology fluency of the user, operating system conventions, a current context of the user or the user device, and other factors. For example, the application 2432 may store, or access from the application server 2420, a user profile for the user to obtain scores for any or all of the factors indicated above. The application 2432 may use the scores for these user-specific factors to apply rules embedded in the received form definitions. A form definition may include a rule that selects among different text prompts to provide based on a language of the user and a reading level of the user, thus providing an understandable instruction to each user despite the widely varying characteristics among the user base. The application 2432 itself may apply general rules separate from form definitions, for example, to adjust form appearance according to user preferences in the application 2432, to adjust form presentation for the characteristics of a user device (e.g., screen size, resolution, etc.), to select content that is in the user's language, and so on. Additional changes that can be made, based on rules in form definitions or by the application 2432, include presenting text in the user's language, setting different font sizes depending on a user's age, phrasing questions differently depending on the user's gender, and phrasing questions differently depending on a user's age and/or reading level. A form definition may provide multiple different variations, such as multiple phrasings of a question, with rules indicating when each version is appropriate. The application 2432 applies those rules to select and present the content most appropriate for the user each time a view of the form is displayed.

Figure 27:
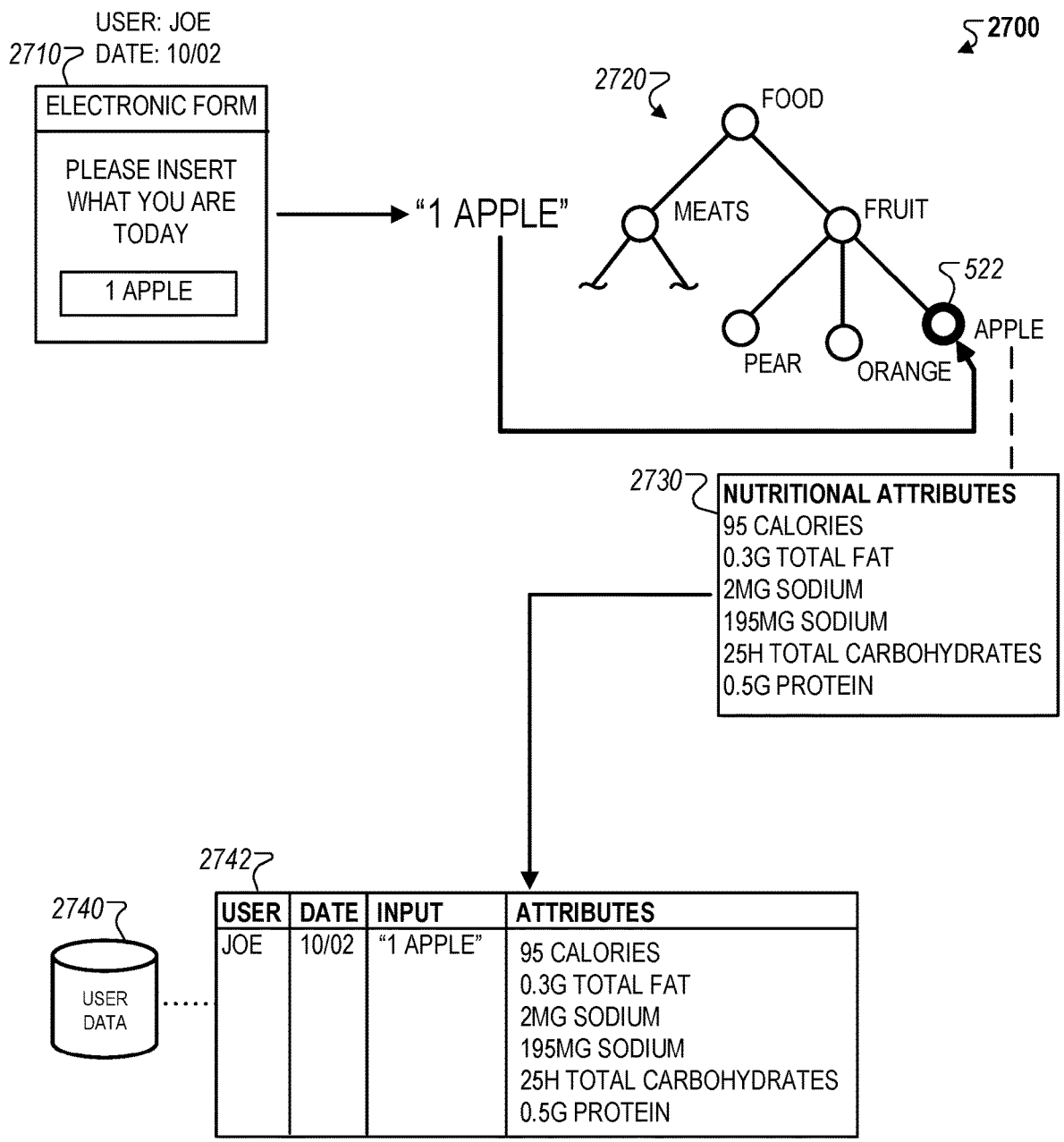
FIG. 27 is a diagram that illustrates an example of a process for processing user input on an electronic form in relation to a set of hierarchal data attributes.

FIG. 27 is a diagram that illustrates an example of a process 2700 for processing user input to an electronic form in relation to a set of hierarchical data attributes. The process 2700 is generally used to standardize different types of user inputs provided on the customized electronic forms in order to enable the system to track patterns associated with user activity, user behavior, and/or user patterns. For instance, different electronic forms can be configured to collect different types of information. As an example, one form can be used to evaluate user activity level by collecting exercise data submitted by the user, whereas another form can be used to track caloric intake by collecting dietary information submitted by the user. The process 2700 can be used to standardize the data collected by different electronic forms, or different parts of a single electronic form so that the system can then make diagnostic inferences and/or determinations based on the collected data across multiple forms.

In general, collected data is standardized categorizing different data types within hierarchies of information, and then obtaining attributes that can be then be analyzed by the system in relation to attributes of another type of input. For example, a user's exercise journal can include text segments corresponding to different exercises performed by the user. The system can then identify the average number of calories burned by performing each exercise in order to standardize the textual input in a number of calories burned by the user as a result of performing the exercises. In another example, a user's dietary journal with foods consumed can be standardized by identifying the number of calories consumed by the user. The system can finally then relate the different types of user input provided on the exercise journal and on the dietary journal by relating the calories consumed and the calories burned.

In the example depicted in FIG. 27, the electronic form 2710 is initially presented to a user to request information relating to his diet. The user provides a text query of "1 APPLE" into a text field to indicate that he has eaten an apple. The application 2432 then processes the received text in relation to a hierarchy 2720 of categories. For instance, the application 2432 may use natural language processing techniques to identify the query "APPLE" as corresponding to an element 2722 within the hierarchy 2720.

Each element within the hierarchy 2720 includes a set of attributes that are generated based on the categories represented within the hierarchy. In the example, the hierarchy categorizes different of food groups, such as meats and fruit, and further categorizes each food groups into different constituent that fit within the same category (e.g., different types of fruit). Each element within the hierarchy 2720 is associated with a set of nutritional attributes that relate to, for example, the estimated number of calories, total fat, sedum, total carbohydrates, and protein are included in one serving of each element.

In response to determining that the text submitted by the user corresponds to the element 2722, the application 2432 then obtains the information included within the set of attributes 2730. The application then generates a table 2742 that includes information related to the user input (e.g., user and date), the input provided by the user, and the set of attributes associated with the corresponding element within the hierarchy 2720. The table 2742 is then stored in user data 2740, which stores user input data for analyzing user input on the electronic form 2710.

The conversion to a common data format, or the assignment of a category or data type to an input, can be done by the user device and/or by the server. In some implementations, there are multiple databases available for administrators to select data types and category hierarchies from, e.g., a food database, a medication database, a fact database, and so on.

In some implementations, individual data types can be defined, and each data type can have a number of data type properties defined. The data type properties may represent an amount or other value obtained through user input, sensor data, or other sources. The data type properties can be assigned values based on the acquired information, e.g., to represent a number food servings, a number of caplets for medication, a body weight, and so on. A data type can have other properties defined, for example, pre-programmed information about a typical calorie content, sugar content, etc., of a food can be stored in association with that food's data type, to provide information for all instances of the data type. A data type may have a conversion parameter, a unit specification (e.g., milligrams, meters, calories, etc.), and/or other information associated with it. Other information may be associated with a data type, such as an identifier for obtaining external information, e.g., a record in another database, a URL for an image file representing the item corresponding to the data type, and so on. Groups of one or more data types can be organized into data type categories (e.g., fruit, pain medication, body vitals, etc.), and groups of one or more data type categories can be organized into data type root categories (e.g., food, medication, measurement, etc.). These hierarchies can provide consistency across the data gathered from different versions of electronic forms and across electronic forms used by different organizations.

Each entry can be associated with one or more higher-level data type categories, such as food, medication, body vital information, and so on.

The processing technique depicted in FIG. 27 illustrates how the application 2432 can obtain information related to a user input provided on an electronic form, identify how the related information is categorized within a corresponding hierarchy, and store the information using relationships of categories. In this regard, user inputs of different data formats can be converted to a common data format based on using different hierarchies coincide with specific data formats. For example, input relating to a user's diet, as illustrated in FIG. 26, can be converted based on nutritional attributes of food included in the user's diet, whereas input relating to a user's activity level can be converted based on the calorie loss associated with exercises performed by the user. The converted information can then be compared and/or evaluated in order to make diagnostic inferences and/or determinations relating to the user's progress in relation a particular health condition.

As another example, an administrator that creates an electronic form can define a data type of "weight." Weight data type can be collected from many different electronic forms, in a variety of formats. In one form, a user may be prompted to manually enter a weight value via a keypad. In another form, a user may be prompted to manually select their weight from a scrollable wheel. In both cases, the form definition will specify that the collected value should be stored as a "weight" data type. The client device and/or the server system it communicate with can also convert varied inputs (e.g., text, button selection, keypad entries, etc.) to a consistent standard format. In this manner, the user-facing experiences can be customized for the audience, while retaining a clean, concise data structure. In addition, by abstracting the user-facing layer of the experience from the underlying data structure, the system can provide an essentially unlimited personalization capability while retaining the ability to perform disciplined data science at the server.

FIG. 28 is a diagram that illustrates an example of a performance analysis report 2810 for an electronic form. The report 2810 provides the administrator with information relating to how a user or a collection of users performed on a particular electronic form (e.g., referred to as "Form A"). In the examples depicted, the report 2810 includes a region 2812 representing overall completion rate, a region 2814 representing an average time spent completing the form, and a region 2816 representing suggested form updates across all users that completed the form.

The report 2810 includes additional performance information for users of two age demographics (e.g., younger than 50 years, and older than 50 years old) and compares the performance with respect to the performance categories provided. As illustrated, users that were older than 50 years had greater difficulty completing Form A compared to users that were younger than 50 years (e.g., 62% compared to 96%). In addition, users that were older than 50 years old spent 8 more minutes on Form A on average compared to users that were younger than 50 years old (e.g., 11 minutes compared to 3 minutes).

As described above with respect to FIG. 24, the performance data relating to the electronic forms can be used to provide automated recommendations within a performance report. In the example, because users that were older than 50 years had a lower rate of completion and a higher time spent on Form A, the system determines that the current configuration of the form may be too complex for users within this age demographic. Thus, the report 2810 includes a recommendation to reduce the form complexity in order to improve performance of users within this age demographic on the form. In comparison, due to high completion rate and low amount of time spent on the form by users that were younger than 50 years, the report 2810 includes a recommendation to maintain the current form for users within this demographic.

Performance reports such as the report 2810 can be generated by the application server 2420 or the administrator system 2410 in order to provide administrators with feedback on customized electronic forms that are designed on the configuration interface 2412 and displayed to users through the application 2432. In this regard, information included within the performance reports can be adjust the form definitions of the customized electronic forms in order to improve user engagement on the application 2432. As described above, in some instances, the performance information can be used to allow manual adjustment by the administrators through the configuration interface 2412, whereas in other instances, the performance information can be used in automated algorithms to dynamically update the form definitions without any intervention by the administrators. In the second instance, periodic automatic adjustments to a customized electronic form can be used to fine-tune or tailor the electronic form specifically towards the needs of an individual user or a collection of users based on prior user input data received on prior instances of the electronic form.

In general, the performance reports can indicate measures (e.g., scores, charts, graphics, etc.) that indicate the feasibility, validity, usefulness, and usability of forms that an administrator has designed.

Figure 29A:
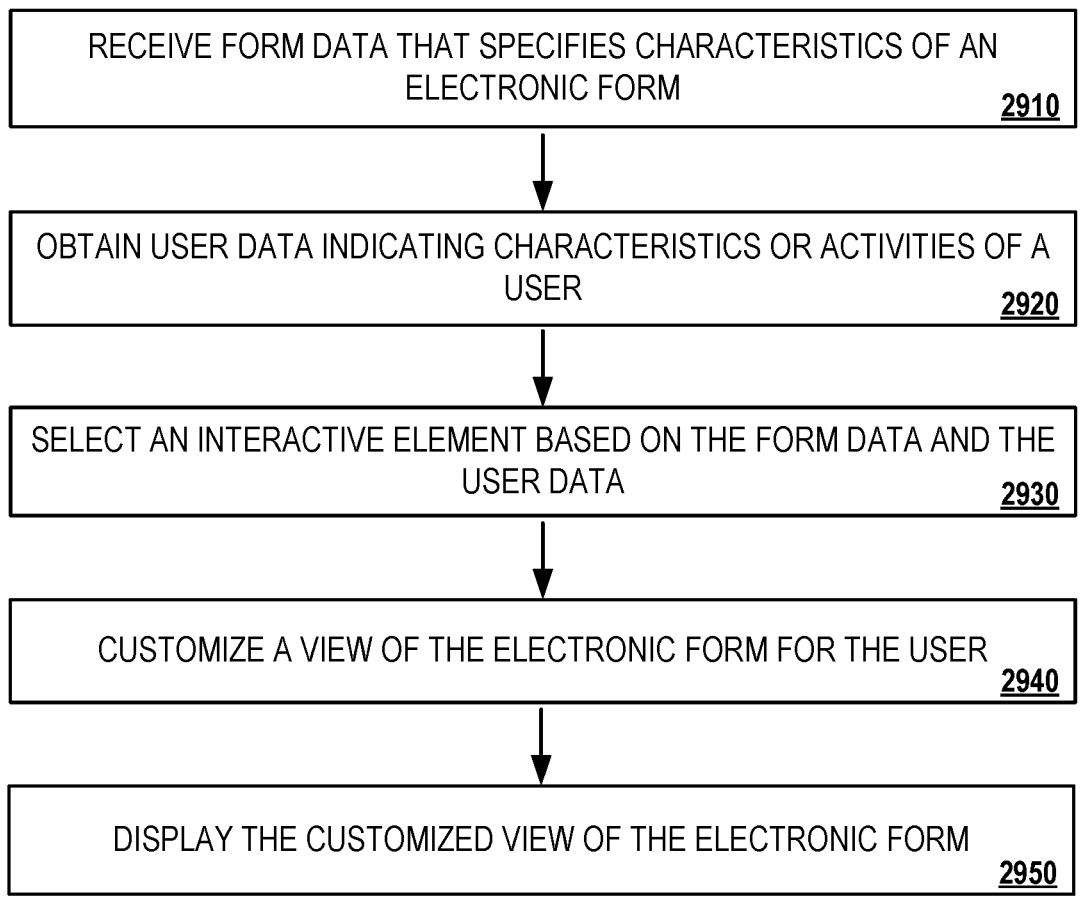
FIG. 29A is a diagram that illustrates an example of a process for displaying a customized electronic form to a user.

FIG. 29A is a diagram that illustrates an example of a process 2900A for displaying a customized electronic form to a user. Briefly, the process 2900A may include receiving form data that specifies characteristics of an electronic form (2910), obtaining data indicating characteristics or activities of a user (2920), selecting an interactive element based on the form data and the user data (2930), customizing a view of the electronic form for the user (2940), and displaying the customized view of the electronic form (2950).

In more detail, the process 2900A may include receiving form data that specifies characteristics of an electronic form (2910). For instance, the user device 2430 may receive form data that specifies characteristics of an electronic form over the network 2405. As described above, the form data can include rules configured to vary the content of the electronic form that is presented for different users. The characteristics of the form can include a desired level of precision for information presented on the electronic form, the way in which input data is received by the electronic form, actions to be performed in response to a satisfaction of triggers and/or conditions specified for the rules, the sequence of sections within the electronic form, and/or the content that is provided on the electronic form. In some instances, the form data may also define validation rules that specify requirements for user input on the electronic form.

In some implementations, the form data is configured to cause the user device 2430 to obtain user input to the electronic form, and additional data from additional sources (e.g., passively-sensed sensor data, actively-sensed sensor data, data from a sensor of the user device 2430, data from a device wirelessly connected to the user device 2430, or data from a third-party API). As described above the form data can be used to direct the user device 2430 to obtain such data in response to certain conditions and/or triggers specified by rules included within the form data.

The form data includes various types of rules as described above. In one example, a rule can specify one or more triggers to initiate system actions specified by the rule, one or more conditions to evaluate for the rule, and one or more actions to be performed based on the condition. In some instances, the rules can include a validation rule that specifies requirements for user input to a portion of the electronic form. As described above, the validation rules can be used to determine that a user input does not satisfy a set of requirements indicated by the validation rule, and in response, the application 2432 may restrict submission of data through the electronic form based on determining that the user input does not satisfy the validation rule. As an example, if an electronic form requests a user to complete an assessment, and the user provides incorrect and/or insufficient responses, the application 2432 may automatically restrict further input from the user based on determining, based on the failure of the user input to satisfy a validation rule, that the user is probably confused by the way in which the electronic form is displayed on the application 2432.

In some implementations, the form data specifies a data type for user input collected through the electronic form. The form data can then be used to select an interactive element to receive user input of the specified data type. In such implementations, the interactive element can be selected from among different interactive elements that each receive input of the specified data type. The selected interactive element can then be included within a customized view of the electronic form. As an example, the form data can indicate the collection of numerical data for a weight assessment form. The application 2432 can then select from among different types of data entry fields that each collect numerical input from the user but with different levels of precision as illustrated in FIG. 23. In this example, the application 2432 may select a data entry field that represents the appropriate level of precision based on variety of factors such as, for example, demographic information of the user or previous inputs from the user indicating a level of comprehension relating to the electronic form.

In some implementations, the electronic form includes multiple sections displayed in a sequence. The content provided in the sections can be customized based on the rules that included within the form definition for the electronic form. For example, the rules may specify the display of types of content on a particular section in response to receiving user input on the application 2432 in relation to the particular section.

The process 2900A may include obtaining data indicating characteristics or activities of a user (2920). For instance, the user device 2430 may receive user data indicating characteristics or activities of the user. As described above, user characteristics can include demographic information associated with the user, a medical history/condition associated with the user, and/or user preferences for engagement through the application 2432. Examples of user activities can include input data received from devices wirelessly connected to the user device 2430 (e.g., pedometer data, sleep pattern data), user inputs provided on the application 2432 (e.g., prior text queries, submitted search queries, prior user selections), data received from third party APIs (e.g., list of background apps used by the user while completed the electronic form, data associated with a social media profile), or data obtained from sensors of the user device 2430 (e.g., accelerometer data, location data, microphone data).

The process 2900A may include selecting an interactive element based on the form data and the user data (2930). For instance, the application 2432 may select an interactive element from among a set of multiple interactive elements based on the user data and the rules in the received from data. For example, this may refer to selecting a particular interaction element from a set of alternative interaction elements based on the user's preferences for engagement on the application 2432 (e.g., selecting a slider interface over a text input box based on a user data indicating greater frequency of usage of the former over the later. In another example, this may refer to selecting an optimal precision level for information to be provided on the electronic form based on requirements set forth by the administrator (e.g., maximal user burden, requested completion rate, speed of completion). In this example, the application 2432 may dynamically identify an optimal level of precision based on the information indicated by the user data, and select from among alternative form configurations of different precision levels.

The process 2900A may include customizing a view of the electronic form for the user (2940). For instance, the user device 2430 may customize a view of the electronic form for the user by including, in the customized view, the interactive element selected based on the user data and the rules in the received form data. For example, the selected interactive element may be used to dynamically construct or adjust the display the electronic form on the application 2432. As described above, in some instances, this process may be performed in real-time such that the customization of the electronic form may be performed while the user is presently using the application 2432 without requiring an additional application-wide update from the application server 2420.

The process 2900A may include displaying the customized view of the electronic form (2950). For instance, the user device 2430 may display the view of the customized electronic form on the application 2432.

Figure 29B:
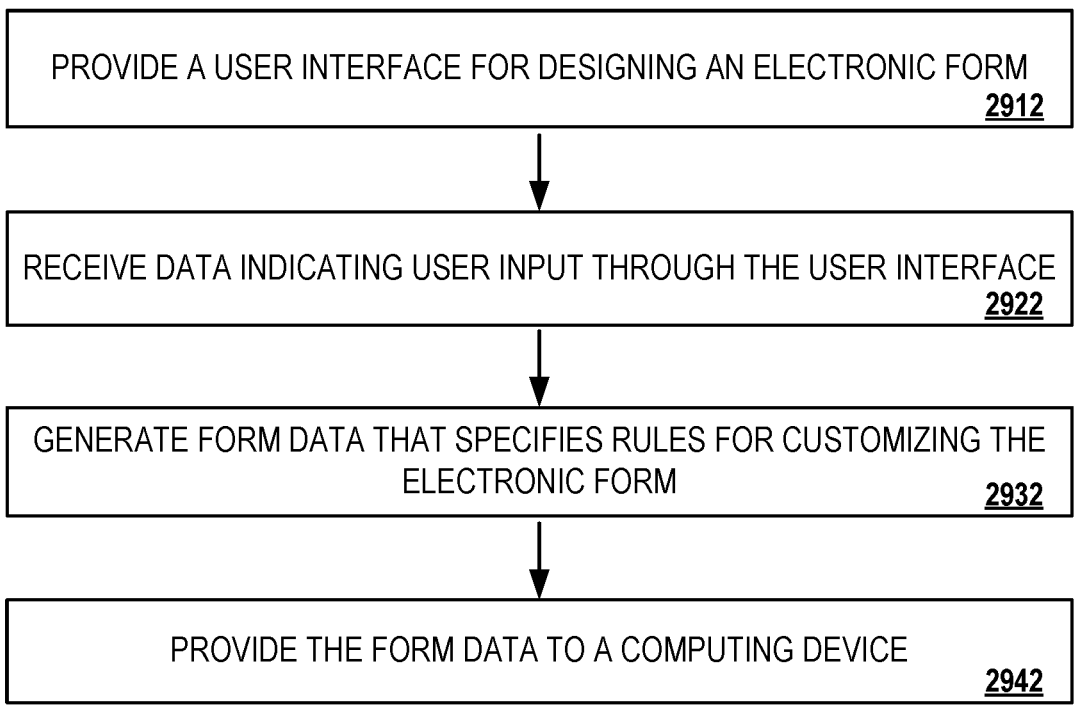
FIG. 29B is a diagram that illustrates an example of a process for generating a form definition for customizing an electronic form.

FIG. 29B is a diagram that illustrates an example of a process 2900B for generating a form definition for customizing an electronic form. Briefly, the process 2900B may include providing an interface for designing an electronic form (2912), receiving data indicating user input through the user interface (2922), generating form data that specifies rules for customizing the electronic form (2932), and providing the form data to an electronic computing device (2942).

In more detail, the process 2900B may include providing an interface for designing an electronic form (2912). For instance, the administrator system 2410 may provide a configuration interface 2412 for designing an electronic form for collecting data about the user of the user device 2430. As described previously with respect to FIGS. 25 and 26, the configuration interface 2412 enables the administrator to customize a form definition that configures or adjusts the display of the electronic form on the application 2432.

The process 2900B may include receiving data indicating user input through the user interface (2922). For instance, the administrator system 2410 may receive data indicating user input by the administrator through the configuration interface. The user input may indicate data types for data to collect using the electronic form and layout parameters for the electronic form. As described above, the administrator may specify data types for user input (e.g., numerical input, textual input, voice input) based on the purpose of the electronic form. The administrator may also specify layout parameters that adjust the presentation of the electronic form and/or the interactivity of the electronic form with the user through the application 2432. For example, the administrator may select interactive elements to include within the electronic form, adjust the adjustment of the selected interactive elements in a particular layout, and/or configure other graphical attributes associated with the electronic form.

The process 2900B may include generating form data that specifies rules for customizing the electronic form (2932). For instance, the administrator system 2410 may generate form data that specifies rules for customizing the electronic form. As described above, the form data includes a form definition that includes, among other types of specifications, rules that adjust the configuration of the electronic form based on the satisfaction of associated triggers and/or conditions that are specified by the administrator. As an example, a rule can be used to change the content provided on the electronic form based on the satisfaction of triggers and/or conditions that are each associated with different types of users. In this regard, the rules specified by the form definition can be used to vary content provided on the same electronic form that are provided to different users.

The process 2900B may include providing the form data to an electronic computing device (2942). For instance, the administrator system 2410 or the application server 2420 may transmit the form data to the user device 2430 to configure or adjust the display of the electronic form on the application 2432. As described above with respect to FIG. 24, the form data that is provided can be used to initially configure a new electronic form to be displayed within the application 2432, or adjust the configuration of an existing electronic form that has been previously displayed to the user. In the second instance, the transmitted form data can be processed by the user device in real-time in order to dynamically adjust the existing electronic form in real-time without any intervention by the user. This technique can be used to automatically adjust the electronic form in response to user input data received on the application 2432, or manually adjust the electronic forms in response to updates to the form definition provide by the administrator on the configuration interface 2412.

CONCLUSION

Various implementations of the systems and methods described can be realized in digital electronic circuitry, integrated circuitry, specially designed ASICs (application specific integrated circuits), computer hardware, firmware, software, and/or combinations of such implementations. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium," "computer-readable medium" refers to any computer program product, apparatus and/or device, e.g., magnetic discs, optical disks, memory, Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device, e.g., a CRT (cathode ray tube) or LCD (liquid crystal display) monitor for displaying information to the user and a keyboard and a pointing device, e.g., a mouse or a trackball by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The systems and techniques described herein can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the systems and techniques described here, or any combination of such back end, middleware, or front end components. The components of the system can be interconnected by any form or medium of digital data communication, e.g., a communication network. Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

A number of embodiments have been described. Nevertheless, it will be understood that various modifications can be made without departing from the spirit and scope of the invention. In addition, the logic flows depicted in the figures do not require the particular order shown, or sequential order, to achieve desirable results. In addition, other steps can be provided, or steps can be eliminated, from the described flows, and other components can be added to, or removed from, the described systems. Accordingly, other embodiments are within the scope of the following claims.

What is claimed is:

1. A method performed by one or more computers, the method comprising:
   providing, by the one or computers, a configuration interface for setting rules to adjust output of an application provided to a plurality of users, the configuration interface permitting the rules to be specified using combinations of triggers, conditions, and actions;
   receiving, by the one or more computers through the configuration interface, data indicating one or more rules that adjust behavior of the application, including receiving, for each of the one or more rules, data that specifies (i) at least one trigger or condition, and (ii) one or more system actions to be performed in response to a satisfaction of the at least one trigger or condition;
   receiving, by the one or more computers and from a client device of a user, activity data indicating (i) user interaction with the application by the user or (ii) sensor data collected for the user of the application;
   in response to receiving the activity data, evaluating, by the one or more computers, applicability of rules for the application based on the activity data for the user, including:
      determining that a first condition of a first rule for the application is satisfied based on the activity data for the user, wherein the first rule is configured to trigger processing of a second rule for the application when the first condition is satisfied; and
      in response to determining that the first condition of the first rule is satisfied, processing the second rule to determine whether a second condition of the second rule of the application is satisfied based on the activity data for the user; and
   adjusting, by the one or more computers, interaction of the application with the user through the client device to selectively perform an action specified by the second rule based on whether the second condition of the second rule is satisfied based on the activity data for the user.

2. The method of claim 1, further comprising:
   receiving, by the one or more computers, activity data for each of plurality of users;
   determining, by the one or more computers, that the activity data for a first subset of the plurality of the users satisfies the at least one trigger or condition and that the activity data for a second subset of the plurality of the users does not satisfy the at least one trigger or condition; and
   communicating, by the one or more computers, with client devices associated with the users in the first subset to adjust output of the application according to the one or more system actions of the one or more rules, while not adjusting the output of the application for the users in the second subset based on the one or more rules.

3. The method of claim 2, wherein:
   the system action specified by the rule comprises an action to provide content for display in the application; and
   communicating with client devices associated with the users in the first subset comprises providing, by the one or more computers and to the client devices associated with users in the first subset, the content specified by the rule to the client devices associated with the users in the first subset.

4. The method of claim 1, further comprising:
   obtaining, by the one or more computers, data indicating historical information indicating the satisfaction of triggers or conditions over a particular period of time; and
   providing, on the configuration interface, a user-selectable option on the configuration interface to adjust one or more existing rules.

5. The method of claim 1, further comprising:
   obtaining, by the one or more computers, data indicating historical information indicating received activity data that has satisfied one or more triggers or conditions over a particular period of time;
   providing, on the configuration interface, a user-selectable list of preconfigured rules that are identified based on the received activity data; and
   adding, based on a user selection from the user-selectable list, a particular rule of the preconfigured rules to a program provided through the application.

6. The method of claim 1, wherein:
   the application provides access to a plurality of programs that each provide different sets of interactive content through the application; and
   the rules that adjust behavior of the application comprise (i) one or more global rules that are associated with each of the plurality of programs and (ii) one or more program rules associated with only a particular program of the plurality of programs.

7. The method of claim 6, further comprising:
   providing, by the one or more computers and for output on the configuration interface, a user-selectable option to:
      (i) adjust a collection of rules associated with a particular program that includes at least one rule, or
      (ii) adjust the combination of the triggers, conditions, and actions for the at least one rule.

8. The method of claim 6, wherein:
the configuration interface includes a set of filters that each provide selections of program criteria for a particular program; and
providing the configuration interface for setting rules that adjust output of the application comprises providing a user-selectable list of preconfigured rules that are associated with the selections of program criteria for the particular program.

9. The method of claim 6, wherein:
the configuration interface is provided to a plurality of administrators that are each associated with a different organization; and
the one or more rules are each associated with respective programs provided by the different organizations.

10. The method of claim 9, wherein the configuration interface provided to the plurality of administrators is associated with a single application provided to a plurality of users.

11. The method of claim 1, wherein the application has a set of rules in which:
one or more of the rules specifies for a server system to perform an action in response to a corresponding trigger or condition; and
one or more of the rules specifies for a client device to perform an action in response to a corresponding trigger or condition.

12. The method of claim 1, wherein the rules for the application are configured so that individual rules interact with one another to configure interactions of the application with users, and wherein carrying out the system action for at least one of the rules comprises creating an event that is designated as a trigger for processing another of the rules.

13. The method of claim 1, wherein the rules for the application include (i) one or more rules that are configured to be processed by a server system to adjust interactions presented to users and (ii) one or more rules that are configured to be processed by client devices to adjust interactions presented to users.

14. A system comprising:
one or more computers; and
one or more storage devices storing instructions that, when executed by the one or more computers, cause the one or more computers to perform operations comprising:
providing, by the one or computers, a configuration interface for setting rules that adjust output of an application provided to a plurality of users, the configuration interface permitting the rules to be specified using combinations of triggers, conditions, and actions;
receiving, by the one or more computers through the configuration interface, data indicating one or more rules that adjust behavior of the application, including receiving, for each of the one or more rules, data that specifies (i) at least one trigger or condition, and (ii) one or more system actions to be performed in response to a satisfaction of the at least one trigger or condition;
receiving, by the one or more computers and from a client device of a user, activity data indicating (i) user interaction with the application by the user or (ii) sensor data collected for the user of the application;
in response to receiving the activity data, evaluating, by the one or more computers, applicability of rules for the application based on the activity data for the user, including:
determining that a first condition of a first rule for the application is satisfied based on the activity data for the user, wherein the first rule is configured to trigger processing of a second rule for the application when the first condition is satisfied; and
in response to determining that the first condition of the first rule is satisfied, processing the second rule to determine whether a second condition of the second rule of the application is satisfied based on the activity data for the user; and
adjusting, by the one or more computers, interaction of the application with the user through the client device to selectively perform an action specified by the second rule based on whether the second condition of the second rule is satisfied based on the activity data for the user.

15. The system of claim 14, wherein the operations further comprise:
receiving, by the one or more computers, activity data for each of plurality of users;
determining, by the one or more computers, that the activity data for a first subset of the plurality of the users satisfies the at least one trigger or condition and that the activity data for a second subset of the plurality of the users does not satisfy the at least one trigger or condition; and
communicating, by the one or more computers, with client devices associated with the users in the first subset to adjust output of the application according to the one or more system actions of the one or more rules, while not adjusting the output of the application for the users in the second subset based on the one or more rules.

16. The system of claim 12, wherein:
the system action specified by the rule comprises an action to provide content for display in the application; and
communicating with client devices associated with the users in the first subset comprises providing, by the one or more computers and to the client devices associated with users in the first subset, the content specified by the rule to the client devices associated with the users in the first subset.

17. The system of claim 14, wherein the operations further comprise:
obtaining, by the one or more computers, data indicating historical information indicating the satisfaction of triggers or conditions over a particular period of time; and
providing, on the configuration interface, a user-selectable option on the configuration interface to adjust one or more existing rules.

18. A non-transitory computer-readable storage device encoded with computer program instructions that, when executed by one or more computers, cause the one or more computers to perform operations comprising:
providing, by the one or more computers, a configuration interface for setting rules that adjust output of an application provided to a plurality of users, the configuration interface permitting the rules to be specified using combinations of triggers, conditions, and actions;
receiving, by the one or more computers through the configuration interface, data indicating one or more rules that adjust behavior of the application, including receiving, for each of the one or more rules, data that specifies (i) at least one trigger or condition, and (ii) one or more system actions to be performed in response to a satisfaction of the at least one trigger or condition;

receiving, by the one or more computers and from a client device of a user, activity data indicating (i) user interaction with the application by the user or (ii) sensor data collected for the user of the application;

in response to receiving the activity data, evaluating, by the one or more computers, applicability of rules for the application based on the activity data for the user, including:

determining that a first condition of a first rule for the application is satisfied based on the activity data for the user, wherein the first rule is configured to trigger processing of a second rule for the application when the first condition is satisfied; and in response to determining that the first condition of the first rule is satisfied, processing the second rule to determine whether a second condition of the second rule of the application is satisfied based on the activity data for the user; and adjusting, by the one or more computers, interaction of the application with the user through the client device to selectively perform an action specified by the second rule based on whether the second condition of the second rule is satisfied based on the activity data for the user.

19. The non-transitory computer-readable storage device of claim 18, wherein the operations further comprise:

receiving, by the one or more computers, activity data for each of plurality of users;

determining, by the one or more computers, that the activity data for a first subset of the plurality of the users satisfies the at least one trigger or condition and that the activity data for a second subset of the plurality of the users does not satisfy the at least one trigger or condition; and communicating, by the one or more computers, with client devices associated with the users in the first subset to adjust output of the application according to the one or more system actions of the one or more rules, while not adjusting the output of the application for the users in the second subset based on the one or more rules.

20. The non-transitory computer-readable storage device of claim 19, wherein:

the system action specified by the rule comprises an action to provide content for display in the application; and communicating with client devices associated with the users in the first subset comprises providing, by the one or more computers and to the client devices associated with users in the first subset, the content specified by the rule to the client devices associated with the users in the first subset.

\* \* \* \* \*

UNITED STATES PATENT AND TRADEMARK OFFICE
CERTIFICATE OF CORRECTION

PATENT NO. : 12,217,036 B2  
APPLICATION NO. : 17/947064  
DATED : February 4, 2025  
INVENTOR(S) : Praduman Jain et al.

Page 1 of 1

It is certified that error appears in the above-identified patent and that said Letters Patent is hereby corrected as shown below:

In the Specification

Column 1, Line 47 (Approx.), delete "is a is a" and insert -- is a --.

In the Claims

Column 107, Line 36, In Claim 1, after "or" insert -- more --.

Column 109, Line 48, In Claim 14, after "or" insert -- more --.

Column 110, Line 38, In Claim 16, delete "claim 12," and insert -- claim 15, --.

Signed and Sealed this  
Twenty-fifth Day of March, 2025

Coke Morgan Stewart  
*Acting Director of the United States Patent and Trademark Office*